US012247018B2

(12) United States Patent
Scherrer et al.

(10) Patent No.: US 12,247,018 B2
(45) Date of Patent: Mar. 11, 2025

(54) ARYL-N-ARYL DERIVATIVES FOR TREATING A RNA VIRUS INFECTION

(71) Applicants: ABIVAX, Paris (FR); CENTRE NATIONAL DE LA RECHERCHE SCIENTIFIQUE, Paris (FR); UNIVERSITE DE MONTPELLIER, Montpellier (FR); INSTITUT CURIE, Paris (FR)

(72) Inventors: Didier Scherrer, Castelnau-le-Lez (FR); Jamal Tazi, Clapiers (FR); Florence Mahuteau-Betzer, Saint Remy-les-Chevreuse (FR); Romain Najman, L'Hay-les-Roses (FR); Julien Santo, Grabels (FR); Cécile Apolit, Grabels (FR)

(73) Assignees: ABIVAX, Paris (FR); CENTRE NATIONAL DE LA RECHERCHE SCIENTIFIQUE, Paris (FR); UNIVERSITE DE MONTPELLIER, Montpellier (FR); INSTITUT CURIE, Paris (FR)

( * ) Notice: Subject to any disclaimer, the term of this patent is extended or adjusted under 35 U.S.C. 154(b) by 903 days.

(21) Appl. No.: 17/259,370

(22) PCT Filed: Jul. 9, 2019

(86) PCT No.: PCT/EP2019/068461
§ 371 (c)(1),
(2) Date: Jan. 11, 2021

(87) PCT Pub. No.: WO2020/011812
PCT Pub. Date: Jan. 16, 2020

(65) Prior Publication Data

US 2022/0356175 A1 Nov. 10, 2022

(30) Foreign Application Priority Data

Jul. 9, 2018 (EP) .................................... 18305911

(51) Int. Cl.
*C07D 401/12* (2006.01)
*A61P 31/12* (2006.01)
(Continued)

(52) U.S. Cl.
CPC ........... *C07D 401/12* (2013.01); *A61P 31/12* (2018.01); *C07C 233/65* (2013.01);
(Continued)

(58) Field of Classification Search
CPC ................ C07D 401/12; C07D 205/04; C07D 213/38; C07D 213/74; C07D 213/75;
(Continued)

(56) References Cited

U.S. PATENT DOCUMENTS 9,827,237 B2 11/2017 Tazi et al.
10,718,770 B2 7/2020 Scherrer et al.
(Continued)

FOREIGN PATENT DOCUMENTS

CN 101142208 A 3/2008
JP 2011-026251 A 2/2011
(Continued)

OTHER PUBLICATIONS

Dardonville et al., "Bisguanidine, Bis(2-aminoimidazoline) and Polyamine Derivatives as Potent and Selective Chemotherapeutic Agents against Trypanosoma brucei rhodesiense. Synthesis and in vitro evaluation", J. Med. Chem. 2004, 47, 2296-2307.
(Continued)

*Primary Examiner* — Andrew D Kosar
*Assistant Examiner* — John D McAnany
(74) *Attorney, Agent, or Firm* — Oliff PLC

(57) ABSTRACT

A compound of formula (Ic)

(Ic)

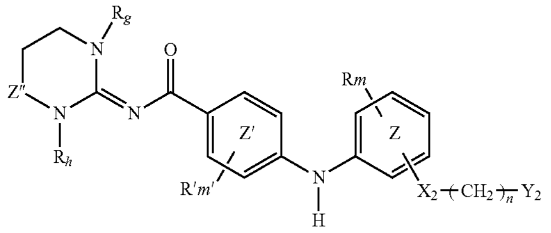

wherein $X^2$ represents a —CO—$NR_k$— group, wherein $R_k$ represents a hydrogen atom or a methyl group, a —NH—CO—NH— group, a —$OCH_2$— group, a —CH(OH)— group, a —NH—CO— group, a —O— group, a —O—$(CH_2)_s$—O—, a —CO— group, a —$SO_2$— group, a divalent 5-membered heteroaromatic ring comprising 1, 2, 3 or 4 heteroatoms, a —NH—$SO_2$— or a —$SO_2$—NH— group; $Y^2$ represents a hydrogen atom, a halogen atom, a hydroxyl group, a $(C_1$-$C_4)$alkoxy group, a

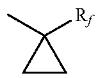

, a (Continued)

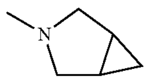

group, a

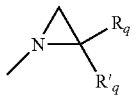

group, a morpholinyl group, optionally substituted by a ($C_1$-$C_4$)alkyl group, a piperazinyl group, a piperidinyl group, or a —$CR^1R^2R^3$ group, or any of its pharmaceutically acceptable salt.

17 Claims, No Drawings

(51) Int. Cl.

| | |
|---|---|
| ***C07C 233/65*** | (2006.01) |
| ***C07C 237/40*** | (2006.01) |
| ***C07C 255/50*** | (2006.01) |
| ***C07C 311/16*** | (2006.01) |
| ***C07D 205/04*** | (2006.01) |
| ***C07D 213/38*** | (2006.01) |
| ***C07D 213/74*** | (2006.01) |
| ***C07D 213/75*** | (2006.01) |
| ***C07D 213/81*** | (2006.01) |
| ***C07D 239/16*** | (2006.01) |
| ***C07D 239/22*** | (2006.01) |
| ***C07D 239/42*** | (2006.01) |
| ***C07D 241/12*** | (2006.01) |
| ***C07D 403/12*** | (2006.01) |
| ***C07D 405/12*** | (2006.01) |
| ***C07D 413/12*** | (2006.01) |
| ***C07F 7/18*** | (2006.01) |

(52) U.S. Cl.

CPC .......... *C07C 237/40* (2013.01); *C07C 255/50* (2013.01); *C07C 311/16* (2013.01); *C07D 205/04* (2013.01); *C07D 213/38* (2013.01); *C07D 213/74* (2013.01); *C07D 213/75* (2013.01); *C07D 213/81* (2013.01); *C07D 239/16* (2013.01); *C07D 239/22* (2013.01); *C07D 239/42* (2013.01); *C07D 241/12* (2013.01); *C07D 403/12* (2013.01); *C07D 405/12* (2013.01); *C07D 413/12* (2013.01); *C07F 7/1804* (2013.01)

(58) Field of Classification Search

CPC ................ C07D 213/81; C07D 239/16; C07D 239/22; C07D 239/42; C07D 241/12; C07D 403/12; C07D 405/12; C07D 413/12; A61P 31/12; C07C 233/65; C07C 237/40; C07C 255/50; C07C 311/16; C07F 7/1804

See application file for complete search history.

(56) References Cited

U.S. PATENT DOCUMENTS

| | | | |
|---|---|---|---|
| 2005/0154232 A1 * | 7/2005 | Lardy .................. | C07D 295/13 546/229 |
| 2007/0197625 A1 | 8/2007 | Casara et al. | |
| 2007/0244120 A1 | 10/2007 | Dumas et al. | |
| 2014/0187641 A1 | 7/2014 | Dalton et al. | |
| 2016/0031797 A1 | 2/2016 | Dalton et al. | |
| 2016/0143884 A1 | 5/2016 | Orlemans et al. | |

FOREIGN PATENT DOCUMENTS

| | | |
|---|---|---|
| RU | 2379302 C2 | 1/2010 |
| RU | 2008 129 807 A | 2/2010 |
| RU | 2 467 007 C2 | 11/2012 |
| RU | 2 628 800 C2 | 8/2017 |
| WO | 2003/033467 A1 | 4/2003 |
| WO | 2004/084901 A1 | 10/2004 |
| WO | 2005/021544 A2 | 3/2005 |
| WO | 2005/023255 A2 | 3/2005 |
| WO | 2005/058869 A1 | 6/2005 |
| WO | 2006/037117 A1 | 4/2006 |
| WO | 2006/097534 A1 | 9/2006 |
| WO | 2007/081517 A2 | 7/2007 |
| WO | 2007/135106 A1 | 11/2007 |
| WO | 2009/087238 A2 | 7/2009 |
| WO | 2010/143168 A2 | 12/2010 |
| WO | 2010/143169 A2 | 12/2010 |
| WO | 2011/163355 A1 | 12/2011 |
| WO | 2012/080953 A1 | 6/2012 |
| WO | 2012/131656 A2 | 10/2012 |
| WO | 2014/164667 A1 | 10/2014 |
| WO | 2015/001518 A1 | 1/2015 |
| WO | 2016/135053 A1 | 9/2016 |
| WO | 2016/135055 A1 | 9/2016 |
| WO | 2017/158201 A1 | 9/2017 |

OTHER PUBLICATIONS

Yin et al., "Pd-Catalyzed Intermolecular Amidation of Aryl Halides: The Discovery that Xantphos Can Be Trans-Chelating in a Palladium Complex," J. Am. Chem. Soc., vol. 124, pp. 6043-6048, 2002.

Nov. 6, 2023 Office Action issued in U.S. Appl. No. 17/259,451.

Apr. 11, 2023 Office Action issued in Chinese Patent Application No. 201980045913.6.

Oct. 7, 2019 Search Report Issued in International Patent Application No. PCT/EP2019/068465.

Schmidt et al.; "Transition metals in Organic Synthesis, Part 91: Palladium-catalyzed Approach to 2, 6-Dioxygenated Carbazole Alkaloids—First Total Synthesis of the Phytoalexin Carbalexin C"; Synlett; 2009; pp. 2,421-2,424.

Sep. 10, 2019 Search Report Issued in International Patent Application No. PCT/EP2019/068460.

Sep. 27, 2019 Search Report Issued in International Patent Application No. PCT/EP2019/068461.

Sep. 26, 2019 Search Report Issued in International Patent Application No. PCT/EP2019/068459.

U.S. Appl. No. 17/259,483, filed Jan. 11, 2021 in the name of Scherrer et al.

U.S. Appl. No. 17/259,364, filed Jan. 11, 2021 in the name of Scherrer et al.

U.S. Appl. No. 17/259,451, filed Jan. 11, 2021 in the name of Scherrer et al.

Berman Group IV viruses: Single-Stranded (+)Sense RNA; Chapter 42; pp. 237-246; 2012.

Berman Group V viruses: Single-Stranded (−)Sense RNA; Chapter 43; pp. 247-255; 2012.

Formulae of compounds having registry Nos. RN1875830-19-5, RN1216052-00-4, RN512834-81-0 and RN94631-91-1 found in "Registry database" and "entered STN before Feb. 29, 2016".

Mar. 24, 2023 Office Action issued in Chinese Patent Application No. 201980045893.2.

Apr. 12, 2023 Notice of Allowance issued in U.S. Appl. No. 17/259,483.

Apr. 26, 2023 Corrected Notice of Allowance issued in U.S. Appl. No. 17/259,483.

Aug. 16, 2022 Office Action issued in Russian Patent Application No. 2020142702/04.

(56) References Cited

OTHER PUBLICATIONS

Jul. 11, 2022 Office Action issued in Russian Patent Application No. 2020143617/04(081468).
Dec. 28, 2023 Office Action issued in U.S. Appl. No. 17/259,364.
Scherrer et al (2016) : STN International, CAPLUS database, Accession No. 2016 : 1435309.
Tazi et al (2015): STN International, CAPLUS database, Accession No. 2015 : 34989.
Jan. 3, 2023 Office Action Issued in U.S. Appl. No. 17/259,483.
Aug. 20, 2020 Search Report Issued in International Patent Application No. PCT/EP2020/070294.
U.S. Appl. No. 17/628,402, filed Jan. 19, 2022 in the name of Scherrer et al.
Registry(STN)[online ], date-of-search Jul. 11, 2023: Sep. 9, 2016 RN:1990473 -92- 1, Sep. 2, 2016 RN:1985111 -93-0, Sep. 2, 2016 RN:1985111 -90- 7, Sep. 2, 20162RN:1991597 -00- 2, May 13, 2016 RN:1909835 -58- 0, May 9, 2016 RN:1906298 -82-5.
R.I. Hernandez-Benitez et al., "Palladium-Catalyzed Synthesis of Diarylamines and 1- and 2-Oxy-genated Carbazoles: Total Syntheses of Natural Alkaloids Clauraila A, Clausenal, Clausine P, and 7-Methoxy-O-methylmukonal", Synthesis, Jul. 5, 2017, 49, A-O.
Suzuki et al., "Design, Synthesis, and Biological Activity of a Novel Series of Human Sirtuin-2-Selective Inhibitors", Journal of Medicinal Chemistry, 2012, 55(12), pp. 5760-5773.
Bianchi et al, "Compounds with antiulcer and antisecretory activity. I. 3-Aryl-benzimidazolin-2-ones and -thiones", Eur. J. Med. Chem. Chimica Therapeutica, Jul.-Aug. 1981-16, No. 4, pp. 321-326.
STN compounds having registry Nos. RN 1990430-84-6, entered Sep. 9, 2016; RN 1988220-74-1, entered Sep. 7, 2016; and RN 1923315-23-4, entered Jun. 2, 2016.
Registry (STN) Compounds (1)-(83), entered on or before Sep. 2016.
Dardonville et al, "Bisguanidine, bis(2-aminoimidazoline), and polyamine derivatives as potent and selective chemotherapeutic agents against Trypanosoma brucei rhodesiense. Synthesis and in vitro evaluation", J. Med. Chem. 2004, 47, 9, pp. 2296-2307.
STN database Compounds, 2016.
Database Registry [Online], CAS Registry No. 1110919-40-8, published Feb. 24, 2010.
Database Registry [Online], CAS Registry No. 924194-00-3, published Mar. 1, 2007.
Database Registry [Online], CAS Registry No. 600170-83-0, published Oct. 7, 2003.
Database Registry [Online], CAS Registry No. 1992203-70-9, published Sep. 13, 2006.
Database Registry [Online], CAS Registry No. 1992752-01-8, published Sep. 13, 2016.
Database Registry [Online], CAS Registry No. 2137046-09-2, published Oct. 30, 2017.
Database Registry [Online], CAS Registry No. 2109705-38-4, published Aug. 7, 2017.
Database Registry [Online], CAS Registry No. 2021522-02-9, published Oct. 31, 2016.
Database Registry [Online], CAS Registry No. 1882567-11-4, published Mar. 9, 2016.
Database Registry [Online], CAS Registry No. 1624283-58-4, published Sep. 22, 2014.
Database Registry [Online], CAS Registry No. 1382354-17-7, published Jul. 10, 2012.
Database Registry [Online], CAS Registry No. 1297213-68-3, published May 19, 2011.
Database Registry [Online], CAS Registry No. 97034-48-5, published Jul. 1, 1985.
Konstanze K. Julich-Gruner et al. "Synthesis of Carbalexin B, Clausine A, Clauszoline M, and 2,8-Dihydroxy-3-methylcarbazole," Chemistry-A European Journal, 2014, vol. 20, pp. 8493-8804.
Sep. 30, 2024 Office Action issued in U.S. Appl. No. 17/259,451.
Rao et al., "Hypervalent iodine(III) catalyzed oxidative C-N bond formation in water: synthesis of benzimidazole-fused heterocycles," RSC Advances, 2014, vol. 4, No. 49, pp. 25600-25604.
Peng et al., "Synthesis and antitumor activity evaluation of anilinoquinoline derivatives by the effect on the expression of polo-like kinase," Medicinal Chemistry Research, 2013, vol. 23, No. 3, pp. 1437-1446.
Venkatesh et al., "Palladium-Catalyzed Intramolecular N-Arylation of Heteroarenes: A Novel and Efficient Route to Benzimdazol[1,2-a]quinolines," The Journal of Organic Chemistry, 2006, vol. 71, No. 3, pp. 1280-1283.

* cited by examiner

ARYL-N-ARYL DERIVATIVES FOR TREATING A RNA VIRUS INFECTION

The present invention relates to compounds useful for preventing and/or treating a RNA virus infection, and most preferably a RNA virus infection caused by RNA viruses belonging to group IV or V of the Baltimore classification.

The present invention further relates to some new compounds, in particular useful for preventing and/or treating a RNA virus infection, and most preferably a RNA virus infection caused by a RNA virus belonging to group IV or V of the Baltimore classification.

It further relates to the pharmaceutical compositions containing said new compounds and to the chemical synthesis processes for obtaining them.

BACKGROUND

Viruses are one of the major causes of diseases around the world. Viruses are generally defined as small, non-living, infectious agents that replicate only within living cells, as they do not possess a completely autonomous replication mechanism. Although diverse in shape and size, they typically consist of a virus particle (known as a "virion"), made from a protein coat which comprises at least one nucleic acid molecule and optionally, depending on the type of virus, one or more proteins or nucleoproteins.

Because viruses do not possess a completely autonomous replication mechanism, they must necessarily rely on the machinery and metabolism of the infected cell or host, in order to replicate and produce multiple copies of themselves.

Even though their replication cycle varies greatly between species, it is generally recognized that the life cycle of viruses includes six basic steps: attachment, penetration, uncoating, replication, assembly and release.

Depending on the nature of the targeted virus, therapeutic molecules have been designed which may interfere with one or more of those mechanisms.

Among those, the replication step involves not only the multiplication of the viral genome, but also the synthesis of viral messenger RNA, of viral protein, and the modulation of the transcription or translation machinery of the host. However, it is also clear that the type of genome (single-stranded, double-stranded, RNA, DNA . . . ) characterizes dramatically this replication step. For instance, most DNA viruses assemble in the nucleus while most RNA viruses develop solely in the cytoplasm. Also, there is increasing evidence that single-stranded RNA viruses such as Influenza use the host RNA splicing and maturation machinery.

Accordingly, and considering the implications of a given type of genome in the replication step, the Baltimore classification of viruses was developed. This classification clusters viruses into families (or "groups") depending on their type of genome. The present virus classification, as in 2018, comprises seven different groups:

- Group I: double-stranded DNA viruses (dsDNA);
- Group II: single-stranded DNA viruses (ssDNA);
- Group III: double-stranded RNA viruses (dsRNA);
- Group IV: (+)strand or sense RNA viruses ((+)ssRNA);
- Group V: (−)strand or antisense RNA viruses ((−)ssRNA);
- Group VI: single-stranded RNA viruses having DNA intermediates (ssRNA-RT);
- Group VII: double-stranded DNA viruses having RNA intermediates (dsDNA-RT).

According to that classification, viruses belonging to the Group VI are not, stricto sensu, RNA viruses. For the same reasons, viruses belonging to the Group VII are not, stricto sensu, DNA viruses. One well-studied example of a virus family belonging to the Group VI is the family Retroviridae (retrovirus) which includes HIV. One well-studied example of a virus family belonging to the Group VII is the family Hepadnaviridae which includes the Hepatitis B virus (HBV).

As a representative of viruses pertaining to group IV one may cite the Picornaviruses (which is a family of viruses that includes well-known viruses like Hepatitis A virus, enteroviruses, rhinoviruses, poliovirus, and foot-and-mouth virus), SARS virus, Hepatitis C virus, yellow fever virus, and rubella virus. The Togaviridae family also pertains to the group IV and a known genus thereof is alphavirus, encompassing the Chikungunya virus. Flaviridae is also a family pertaining to group IV, encompassing a famous virus transmitted by mosquitoes, i.e. the Dengue virus.

As a representative of viruses pertaining to group V one may cite the Filoviridae virus family encompassing the Ebola virus, the Paramyxoviridae family encompassing the Respiratory Syncytial virus (RSV), the Rhabdoviridae family, the Orthomyxoviridae family encompassing the Influenzavirus A, Influenzavirus B and Influenzavirus C.

Groups within the virus families particularly focused in the framework of the present invention are the ones encompassing RNA viruses, especially single-stranded RNA viruses, and more specifically RNA viruses belonging to group IV and group V of the Baltimore classification.

There are few cures for diseases caused by RNA virus infections, in particular single-stranded RNA viruses, and more specifically RNA virus infections from viruses belonging to group IV and V of the Baltimore classification. Treatment is focused on relieving the symptoms. Therefore, there is still a need to identify new antiviral drugs to treat RNA virus infections, such as RNA virus infection from group IV and V, in particular small chemical molecules.

Definitions

As used herein, the term "patient" refers to either an animal, such as a valuable animal for breeding, company or preservation purposes, or preferably a human or a human child, which is afflicted with, or has the potential to be afflicted with, one or more diseases and conditions described herein.

In particular, as used in the present application, the term "patient" refers to a mammal such as a rodent, cat, dog, primate or human, preferably said subject is a human and also extends to birds.

The identification of those patients who are in need of treatment of herein-described diseases and conditions is well within the ability and knowledge of one skilled in the art. A veterinarian or a physician skilled in the art can readily identify, by the use of clinical tests, physical examination, medical/family history or biological and diagnostic tests, those patients who are in need of such treatment.

In the context of the invention, the term "treating" or "treatment", as used herein, means reversing, alleviating, inhibiting the progress of, or preventing the disease resulting from RNA virus infection, and more particularly RNA virus infection from group IV or V, or one or more symptoms of such disease.

As used herein, an "effective amount" refers to an amount of a compound of the present invention which is effective in preventing, reducing, eliminating, treating or controlling the symptoms of the herein-described diseases and conditions, i.e. RNA virus infection, and more particularly RNA virus infection from group IV or V. The term “controlling” is intended to refer to all processes wherein there may be a slowing, interrupting, arresting, or stopping of the progression of the diseases and conditions described herein, but does not necessarily indicate a total elimination of all disease and condition symptoms, and is intended to include prophylactic treatment.

The term “effective amount” includes “prophylaxis-effective amount” as well as “treatment-effective amount”.

The term “preventing”, as used herein, means reducing the risk of onset or slowing the occurrence of a given phenomenon, namely in the present invention, a disease resulting from a RNA virus infection, and more particularly a RNA virus infection from group IV or V.

As used herein, «preventing» also encompasses «reducing the likelihood of occurrence» or «reducing the likelihood of reoccurrence».

The term “prophylaxis-effective amount” refers to a concentration of compound of this invention that is effective in inhibiting, preventing, decreasing the likelihood of the disease by RNA viruses, and more particularly by a RNA virus from group IV or V of the Baltimore classification, or preventing the RNA virus infection and in particular a RNA virus infection from group IV or V or preventing the delayed onset of the disease by the RNA virus, and more particularly by a RNA virus from group IV or V, when administered before infection, i.e. before, during and/or slightly after the exposure period to the RNA virus, and in particular to the RNA virus from group IV or V.

Likewise, the term “treatment-effective amount” refers to a concentration of compound that is effective in treating the RNA virus infection, e.g. leads to a reduction in RNA viral infection, following examination when administered after infection has occurred.

As used herein, the term “pharmaceutically acceptable” refers to those compounds, materials, excipients, compositions or dosage forms which are, within the scope of sound medical judgment, suitable for contact with the tissues of human beings and animals without excessive toxicity, irritation, allergic response or other problem complications commensurate with a reasonable benefit/risk ratio.

As used herein, a “viral infection or related condition” refers to an infection of condition related to a virus, more particularly said virus having a RNA genome, and especially a RNA virus belonging to group IV or V according to the Baltimore classification. Viruses may be further classified in distinct families, orders and genus.

For reference, the content of the “Baltimore classification” which is reported herein further references to the virus taxonomy as set forth in the database of the 2017 International Committee of Taxonomy of Viruses (ICTV) as released online on Mar. 12, 2018 at ictvonline.org. This taxonomy is incorporated herein in its entirety.

Alphaviruses may in particular be considered by the invention and pertain to the Group IV RNA viruses and the Togaviridae family, which can be defined as positive-sense single-stranded RNA viruses or (+)ssRNA viruses. Their order is “Unassigned” according to the Virus Taxonomy of 2017. The Togaviridae family includes the Alphavirus and Rubivirus genus.

Examples of Alphaviruses which are considered by the invention include: Barmah Forest virus, Chikungunya virus, Mayaro virus, O’nyong’nyong virus, Ross River virus, Semliki Forest virus, Una virus, Eastern equine encephalitis virus, Tonate virus, Venezuelan equine encephalitis virus and Wester equine encephalitis virus.

Most preferably, an alphavirus infection or alphavirus related condition, according to the invention, is a Chikungunya virus infection or Chikungunya virus-related condition.

More particularly, Chikungunya virus (CHIKV) is a RNA virus which pertains to the alphavirus genus which in turn belongs to the Togaviridae family, i.e. Group IV from the Baltimore classification. Chikungunya is a mosquito-borne viral disease first described during an outbreak in southern Tanzania in 1952. CHIKV is an enveloped, positive sense, single-stranded RNA virus with a genome of approximately 12 kb nucleotides long. The genome of CHIKV is organized as follows: 5'-cap-nsP1-nsP2-nsP3-nsP4-(junction region)-C-E3-E2-6k-E1-poly(A)-3', in which the first four proteins (nsP1-4) are nonstructural proteins, and the structural proteins are the capsid (C) and the envelope proteins (E). There is no distinct serotypic difference among CHIKV isolated from Africa, Asia and the islands of the Indian Ocean. Phylogenetic analyses based on E1 gene sequences can group CHIKV into three genotypes (lineages): Asian, east/central/south African (ECSA), and West African. The Asian genotype differed from the ECSA and West African genotypes by nucleotide levels of −5% and −15%, respectively. The African genotypes (ECSA versus West African) were −15% divergent. The amino acid identities across the three genotypes varied from 95.2 to 99.8%.

Chikungunya virus may cause outbreaks associated with severe morbidity.

Chikungunya is a viral disease transmitted to humans by infected mosquitoes. Both *Ae. aegypti* and *Ae. albopictus* have been implicated in large outbreaks of Chikungunya. Whereas *Ae. aegypti* is confined within the tropics and sub-tropics, *Ae. albopictus* also occurs in temperate and even cold temperate regions. In recent decades, *Ae. albopictus* has spread from Asia to become established in areas of Africa, Europe and the Americas.

After infection with Chikungunya virus, there is an incubation period lasting 2-4 days on average, followed by disease symptoms. Among such symptoms, fever and severe joint pain may be cited. Other symptoms include muscle pain, headache, nausea, back pain, fatigue, myalgia and rash. Severe clinical manifestations of Chikungunya infection can also occur, for example, haemorrhagic fever, conjunctivitis, photophobia, hepatitis, stomatitis. Neurologic manifestations such as encephalitis, febrile seizures, meningeal syndrome and acute encephalopathy were also reported.

Joint pain is often debilitating and can vary in duration.

The proximity of mosquito breeding sites to human habitation is a significant risk factor for Chikungunya.

The distribution of Chikungunya virus mainly occurs in Africa, India and South Eastern Asia. In recent decades, mosquito vectors of Chikungunya have spread to Europe and the Americas. In 2007, disease transmission was reported for the first time in a localized outbreak in north-eastern Italy. Outbreaks have since been recorded in France and Croatia.

Dengue viruses which present various serotypes, may also be considered by the invention and pertain to the Group IV RNA viruses and the Flaviviridae family, which can be defined as a positive-sense single-stranded RNA or (+)ss RNA viruses. More particularly Dengue virus, is a (+)ssRNA virus belonging to group IV of the Baltimore classification. It is part of the Flavivirus genus, which belongs to the Flaviviridae family. Other viruses pertaining to the Flaviviridae family are hepatitis C virus and yellow fever virus.

Viruses of the Mononegavirales order are also particularly considered by the invention. The order Mononegavirales includes viruses belonging to Group V of the Baltimore classification. As of 2018, this order includes mainly the following virus families: Bornaviridae, Mymonaviridae, Filoviridae, Nyamiviridae, Paramyxoviridae, Pneumoviridae, Rhabdoviridae, and Sunviridae.

Human respiratory syncytial virus (HRSV) is a syncytial virus that causes respiratory tract infections. It is a major cause of lower respiratory tract infections and hospital visits during infancy and childhood. HRSV virus may in particular be considered by the invention and pertain to the Group V of RNA viruses. More particularly, RSV virus is a (−)ssRNA virus belonging to group V of the Baltimore classification. It is a pneumovirus which is part of the Paramyxoviridae family, which belongs to the Mononegavirales order. Among other viruses of the Mononegavirales order, those which are particularly considered by the invention include: measles virus, mumps virus, Nipah virus, rabies virus, and human parainfluenza virus (which includes HPIV-1, HPIV-2, HPIV-3 and HPIV-4). Of note, the Paramyxovirinae subfamily was conventionally merged into the Paramyxoviridae family, by reference to the taxonomy of the Mononegavirales order updated in 2016.

The virus genus which are particularly considered within the Paramyxoviridae family include: Aquaparamyxovirus, Avulavirus, Ferlavirus, Henipavirus, Morbillivirus, Respirovirus and Rubulavirus genus.

Viruses of the Orthomyxoviridae family are also particularly considered by the invention. The Orthomyxoviridae family belongs to an "Unassigned" order according to the 2017 Virus Taxonomy. The virus genus which are particularly considered within the Orthomyxoviridae family include: Alphainfluenzavirus, Betainfluenzavirus, Deltainfluenzavirus, Gammainfluenzavirus, Isavirus, Quaranjavirus, and Thogotovirus.

Influenzavirus A, Influenzavirus B, Influenzavirus C may in particular be considered by the invention and pertain to the Group V RNA viruses and the Orthomyxoviridae family, which can be defined as a negative-sense single-stranded RNA or (−)ss RNA viruses. Isavirus and Thogotovirus also belong to the Orthomyxoviridae order.

DETAILED DESCRIPTION OF THE INVENTION

The inventors have surprisingly found that aryl-N-aryl compounds are endowed with a broad-spectrum activity against RNA viruses, and more particularly single-stranded RNA viruses belonging to Group IV or V of the Baltimore classification. Groups IV and V include respectively (+)ssRNA viruses and (−)ssRNA viruses; which also refer to positive-sense single-stranded RNA viruses and negative-sense single-stranded RNA viruses.

For reference, the content of the «Baltimore classification» is considered in light of the Classification and Nomenclature of viruses as set forth in the 10th report on Virus Taxonomy dated 2017.

The present document discloses a compound of formula (I)

(I)

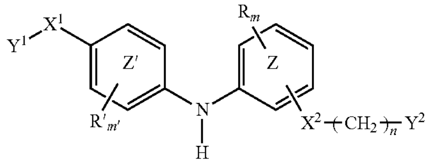

wherein:

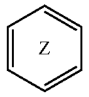

ring and

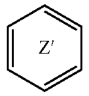

ring independently mean a phenylene or a pyridylene group, wherein the group $—X^2—(CH_2)_n—Y^2$ is in meta or para position on the

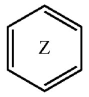

ring, in particular in meta position, with respect to the —NH— group, $X^1$ represents an alkenylene group, in particular an ethenylene group, a —NH—CO— group, a —CO—NH— group, a $—CR_aR_bO—$ group, $Y^1$ represents an aryl group selected from a 2-pyridyl group or a pyrimidinyl group, wherein one of the nitrogen atom of the pyrimidinyl group is in ortho position with respect to $X^1$, or alternatively $X^1—Y^1$ represents a group (A) of formula (A)

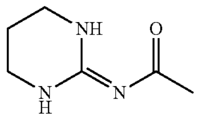

$X^2$ represents a —CO—NH— group, a —NH—CO—NH— group, a $—OCH_2—$ group, a —NH—CO— group or a $—SO_2—NH—$ group, n is 0, 1, 2 or 3, m and m' are independently 0, 1 or 2, $Y^2$ represents a hydrogen atom, a hydroxyl group or a —$CR^1R^2R^3$ group, wherein $R^1$, $R^2$ and $R^3$ independently represent a hydrogen atom, a fluorine atom or a $(C_1-C_4)$alkyl group, being understood that no more than one of $R^1$, $R^2$ and $R^3$ is a hydrogen atom, or $R^1$ and $R^2$ form together with the carbon atom bearing them a $(C_3-C_8)$cycloalkyl group, said $(C_3-C_8)$cycloalkyl group being optionally substituted by one or two $(C_1-C_4)$alkyl group, halogen atom or $(C_1-C_4)$alkoxy group and said $(C_3-C_8)$cycloalkyl group being optionally interrupted on said $R^1$ and/or $R^2$ by an oxygen atom, R and R' independently represent a halogen atom, a $(C_1-C_4)$alkyl group, a $(C_3-C_6)$cycloalkyl group, a $(C_1-C_5)$alkoxy group, a —$SO_2$—$NR_aR_b$ group, a —$SO_3H$ group, a —OH group, a —O—$SO_2$—$OR_c$ group or a —O—P(=O)—$(OR_c)(OR_d)$ group, $R_a$, $R_b$, $R_c$ and $R_d$ independently represent a hydrogen atom or a $(C_1-C_4)$ alkyl group, provided that when $X^1$ is a —$CR_aR_bO$— group, $Y^1$ may further be a 3-pyridyl, a 4-pyridyl or a phenyl group optionally substituted by one or two substituent(s) selected from a halogen atom, a $(C_1-C_4)$alkyl group, a cyano group, a $(C_1-C_5)$alkoxy group, a trifluoromethyl group, a trifluoromethoxy group, a —$SO_2$—$NR_aR_b$ group, a —$SO_3H$ group, a —OH group, a —O—$SO_2$—$OR_c$ group or a —O—P(=O)—$(OR_c)(OR_d)$ group, or any of its pharmaceutically acceptable salt, for use in the treatment and/or prevention of a RNA virus infection caused by a RNA virus belonging to group IV or V of the Baltimore classification and in particular a Chikungunya viral infection, a Dengue viral infection, an Influenza viral infection or a RSV viral infection or a virus-related condition.

According to a first aspect the present invention relates to a compound of formula (Ic)

(Ic)

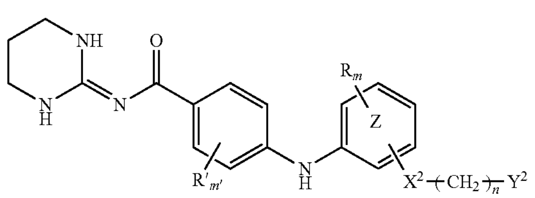

wherein $Y^1$, R, R', $R_a$, $R_b$, m, m',

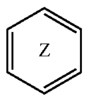

ring,

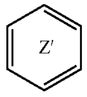

ring, $X^2$, n and $Y^2$ are as defined above for formula (I), or any of its pharmaceutically acceptable salt.

Still according to said first aspect, the present invention further relates to compounds of formula (Ic), wherein the group $—X^2—(CH_2)_n—Y^2$ is in meta or para position and preferably in meta position on the

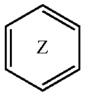

ring, with respect to the —NH— group, m is 0, n is 0, 1, 2 or 3, $Y^1$ represents a pyridyl or a phenyl group optionally substituted by one or two substituent(s) selected from a halogen atom, a $(C_1-C_4)$alkyl group and a cyano group, a $(C_1-C_5)$alkoxy group, a trifluoromethyl group, a trifluoromethoxy group, a —$SO_2$—$NR_aR_b$ group, a —$SO_3H$ group, a —OH group, a —O—$SO_2$—$OR_c$ group or a —O—P(=O)—$(OR_c)(OR_d)$ group, $Y^2$ represents a hydrogen atom, a hydroxyl group or a —$CR^1R^2R^3$ group, wherein $R^1$, $R^2$ and $R^3$ independently represent a hydrogen atom or a $(C_1-C_2)$alkyl group, being understood that no more than one of $R^1$, $R^2$ and $R^3$ is a hydrogen atom, or $R^1$ and $R^2$ form together with the carbon atom bearing them a $(C_3-C_6)$ cycloalkyl group, said $(C_3-C_6)$cycloalkyl group being optionally substituted by one or two halogen atom(s) and said $(C_3-C_6)$cycloalkyl group being optionally interrupted on said $R^1$ and/or $R^2$ by an oxygen atom, or any of its pharmaceutically acceptable salt.

According to a second aspect, the present invention relates to compounds of formula (Ic) as defined above for use in the treatment and/or prevention of a RNA virus infection caused by a RNA virus belonging to group IV or V of the Baltimore classification, and in particular a Chikungunya viral infection, a Dengue viral infection, an Influenza viral infection or a RSV viral infection or a virus-related condition.

According to a third aspect, the present invention relates to a compound of formula (Ic):

(Ic)

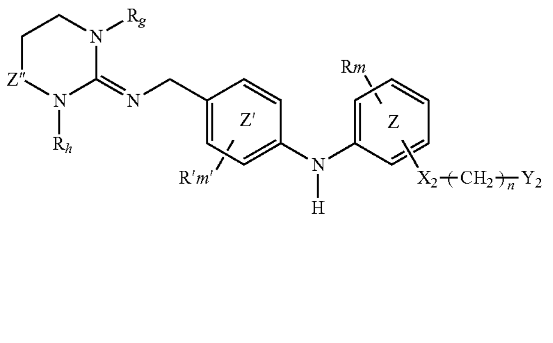

wherein:

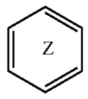

ring and

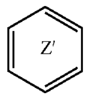

ring independently mean a phenylene or a pyridylene group,

Z" represents a —$CH_2$— group or a —CO— group, $R_g$ and $R_h$ independently represent a hydrogen atom or a ($C_1$-$C_4$)alkyl group, $X^2$ represents a —CO—$NR_k$— group, wherein $R_k$ represents a hydrogen atom or a methyl group, a —NH—CO—NH— group, a —$OCH_2$— group, a —CH(OH)— group, a —NH—CO— group a —O— group, a —O—$(CH_2)_s$—O—, wherein s is 2 or 3, a —CO— group, a —$SO_2$— group, a divalent 5-membered heteroaromatic ring comprising 1, 2, 3 or 4 heteroatoms, such as a triazole, an imidazole, a tetrazole or an oxadiazole, a NH—$SO_2$—, a —NH— group, or a —$SO_2$—NH— group, n is 0, 1, 2 or 3, m and m' are independently 0, 1 or 2, $Y^2$ represents a hydrogen atom, a halogen atom, a hydroxyl group, a ($C_1$-$C_4$)alkoxy group, a

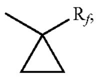

wherein $R_f$ represents a ($C_1$-$C_4$)alkyl group, a cyano group, a

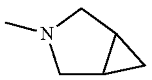

group, a

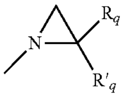

group, wherein $R_q$ and $R'_q$ independently represent a hydrogen atom or a methyl group, a morpholinyl group, optionally substituted by a ($C_1$-$C_4$)alkyl group, a piperazinyl group, a piperidinyl group, or a —$CR^1R^2R^3$ group, wherein $R^1$, $R^2$ and $R^3$ independently represent a hydrogen atom, a fluorine atom or a ($C_1$-$C_4$)alkyl group, said ($C_1$-$C_4$)alkyl group being optionally substituted by a trifluoromethyl group and/or optionally substituted by a hydroxyl group, being understood that no more than one of $R^1$, $R^2$ and $R^3$ is a hydrogen atom, or $R^1$ and $R^2$ form together with the carbon atom bearing them a ($C_3$-$C_8$)cycloalkyl group, said ($C_3$-$C_8$)cycloalkyl group being optionally substituted by one or two ($C_1$-$C_4$)alkyl group, halogen atom, hydroxy or ($C_1$-$C_4$)alkoxy group and said ($C_3$-$C_8$)cycloalkyl group being optionally interrupted on said $R^1$ and/or $R^2$ by one or two oxygen atom(s), R and R' independently represent a ($C_1$-$C_4$)alkyl group, optionally interrupted by a —$SO_2$— group or a —SO— group, a ($C_3$-$C_6$)cycloalkyl group, a trifluoromethyl group, a halogen atom, a ($C_1$-$C_5$)alkoxy group, a —$SO_2$—$NR_aR_b$ group, a —$SO_3H$ group, a —OH group, a —O—$SO_2$—$OR_c$ group, or a —O—P(═O)—$(OR_c)(OR_d)$ group, $R_a$, $R_b$, $R_c$ and $R_d$ independently represent a hydrogen atom or a ($C_1$-$C_4$)alkyl group, or any of its pharmaceutically acceptable salt.

In other words,

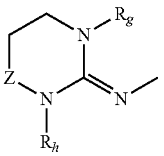

represents a group A of formula (A)

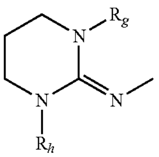

or a group B of formula (B)

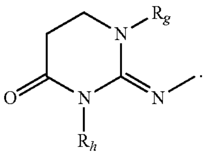

According to a fourth aspect, the present invention relates to a compound of formula (Ic) as defined above or any of its pharmaceutically acceptable salts, and any of compounds (19) to (31) and (91) to (181) as defined hereinafter for use as a medicament.

According to a fifth aspect, the present invention relates to a compound of formula (Ic) as defined above, for use in the treatment and/or prevention of a RNA virus infection caused by a RNA virus belonging to group IV or V of the Baltimore classification, and in particular a Chikungunya viral infection, a Dengue viral infection, an Influenza viral infection or a RSV viral infection or a virus-related condition.

The above-mentioned compounds (I) and (Ic) are particularly suitable for treating or preventing a virus infection or related condition, in particular a RNA virus infection caused by a RNA virus belonging to group IV or V of the Baltimore classification or related condition, and most preferably a Chikungunya viral infection, a Dengue viral infection, an Influenza viral infection or a RSV viral infection or a virus-related condition.

The above-mentioned compounds are even more particularly suitable for treating or preventing a Chikungunya viral infection or a RSV viral infection or a virus-related condition, most particularly a RSV viral infection.

Further aspects of the present invention will be described herein after such as the use of new compounds of formula (Ic) as a medicament, a pharmaceutical composition and a synthetic process.

According to a particular embodiment, a subject-matter of the present document describes a compound of formula (I) as defined above, wherein the alkenylene group is a (E)-alkenylene group, m and m' are independently 0 or 1, $Y^2$ represents a —$CR^1R^2R^3$ group, wherein $R^1$, $R^2$ and $R^3$ independently represent a hydrogen atom, a fluorine atom or a $(C_1\text{-}C_2)$alkyl group, being understood that no more than one of $R^1$, $R^2$ and $R^3$ is a hydrogen atom, or $R^1$ and $R^2$ form together with the carbon atom bearing them a $(C_3\text{-}C_6)$cycloalkyl group, said $(C_3\text{-}C_6)$cycloalkyl group being optionally substituted by one or two halogen atoms and said $(C_3\text{-}C_6)$cycloalkyl group being optionally interrupted on said $R^1$ and/or $R^2$ by an oxygen atom, R and R' independently represent a halogen atom, a $(C_1\text{-}C_2)$alkyl group, a $(C_3\text{-}C_6)$cycloalkyl group, or a $(C_1\text{-}C_2)$alkoxy group, or any of its pharmaceutically acceptable salt, for use in the treatment and/or prevention of a RNA virus infection caused by a RNA virus belonging to group IV or V of the Baltimore classification, and in particular a Chikungunya viral infection a Dengue viral infection, an Influenza viral infection or a RSV viral infection or a virus-related condition.

According to a further embodiment, the present document describes a compound of formula (I)

(I)

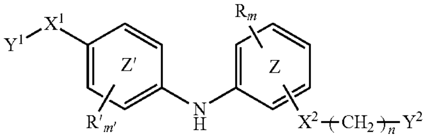

wherein:

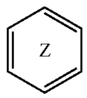

ring and

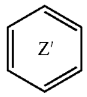

ring independently mean a phenylene or a pyridylene group, wherein the group $X^2\text{-}(CH_2)_n\text{-}Y^2$ is in meta or para position on the

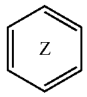

ring, with respect to the —NH— group, $X^1$ represents an alkenylene group, a —NH—CO— group, a —CO—NH— group, a —$CR_aR_bO$— group, $Y^1$ represents an aryl group selected from a 2-pyridyl group or a pyrimidinyl group, wherein one of the nitrogen atom of the pyrimidinyl group is in ortho position with respect to $X^1$, or alternatively $X^1$—$Y^1$ represents a group (A) of formula (A)

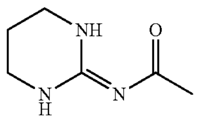

$X^2$ represents a —CO—NH— group, a —NH—CO—NH— group, a —$OCH_2$— group, a —NH—CO— group or a —$SO_2$—NH— group, n is 0, 1, 2 or 3, m and m' are independently 0, 1 or 2, $Y^2$ represents a hydrogen atom, a hydroxyl group or a —$CR^1R^2R^3$ group, wherein $R^1$, $R^2$ and $R^3$ independently represent a hydrogen atom, a fluorine atom or a $(C_1-C_4)$alkyl group, being understood that no more than one of $R^1$, $R^2$ and $R^3$ is a hydrogen atom, or $R^1$ and $R^2$ form together with the carbon atom bearing them a $(C_3-C_8)$cycloalkyl group, said $(C_3-C_8)$cycloalkyl group being optionally substituted by one or two $(C_1-C_4)$alkyl group, halogen atom or $(C_1-C_4)$alkoxy group and said $(C_3-C_8)$cycloalkyl group being optionally interrupted on said $R^1$ and/or $R^2$ by an oxygen atom, R and R' independently represent a halogen atom, a $(C_1-C_4)$alkyl group, a $(C_3-C_6)$cycloalkyl group, a $(C_1-C_5)$alkoxy group, a —$SO_2$—$NR_aR_b$ group, a —$SO_3H$ group, a —OH group, a —O—$SO_2$—$OR_c$ group or a —O—P(═O)—($OR_c$)($OR_d$) group, $R_a$, $R_b$, $R_c$ and $R_d$ independently represent a hydrogen atom or a $(C_1-C_4)$alkyl group, provided that when $X^1$ is a —$CR_aR_bO$— group, $Y^1$ may further be a 3-pyridyl, a 4-pyridyl or a phenyl group optionally substituted by one or two substituent(s) selected from a halogen atom, a $(C_1-C_4)$alkyl group, a cyano group, a $(C_1-C_5)$alkoxy group, a trifluoromethyl group, a trifluoromethoxy group, a —$SO_2$—$NR_aR_b$ group, a —$SO_3H$ group, a —OH group, a —O—$SO_2$—$OR_c$ group or a —O—P(═O)—($OR_c$)($OR_d$) group, and provided that when $Y^1$—$X^1$ represents a 2-pyridylethenylene group, $X^2$ represents a —CO—NH— group and $Y^2$ represents a —$CR^1R^2R^3$ group, wherein $R^1$, $R^2$ and $R^3$ independently represent a hydrogen atom or a $(C_1-C_4)$alkyl group, and m' is different from 0, or any of its pharmaceutically acceptable salt, for use in the treatment and/or prevention of a RNA virus infection caused by a RNA virus belonging to group IV or V of the Baltimore classification.

According to a particular embodiment, an additional subject-matter of the present invention is a compound of formula (Ic)

(Ic)

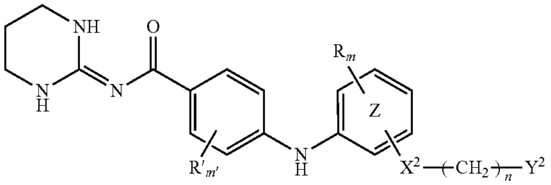

wherein

R, R', m, m',

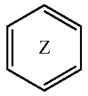

ring, $X^2$, n and $Y^2$ are as defined above, or any of its pharmaceutically acceptable salt, for use in the treatment and/or prevention of a RNA virus infection caused by a RNA virus belonging to group IV or V of the Baltimore classification, and in particular a Chikungunya viral infection, a Dengue viral infection, an Influenza viral infection or a RSV viral infection or a virus-related condition.

Still according to said particular embodiment, the present invention further relates to compounds of formula (Ic) as defined above, wherein m is 0, m' is 0 or 1, $X^2$ represents a —CO—NH— group or a —$SO_2$—NH— group, $Y^2$ represents a —$CR^1R^2R^3$ group, wherein $R^1$, $R^2$ and $R^3$ independently represent a hydrogen atom or a $(C_1-C_2)$alkyl group, being understood that no more than one of $R^1$, $R^2$ and $R^3$ is a hydrogen atom, or $R^1$ and $R^2$ form together with the carbon atom bearing them a $(C_3-C_6)$cycloalkyl group, or any of its pharmaceutically acceptable salt, for use in the treatment and/or prevention of a RNA virus infection caused by a RNA virus belonging to group IV or V of the Baltimore classification, and in particular a Chikungunya viral infection, a Dengue viral infection, an Influenza viral infection or a RSV viral infection or a virus-related condition.

According to a particular embodiment, the present invention relates to a compound of formula (Ic) as defined above, wherein

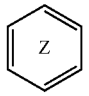

ring and

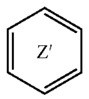

ring both represent a phenylene group or

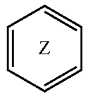

ring represents a pyridylene group and

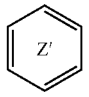

ring represents a phenylene group, or any of its pharmaceutically acceptable salt.

In another embodiment, the present invention relates to a compound of formula (Ic) as defined above, wherein m and m' are independently 0 or 1, $Y^2$ represents a —$CR^1R^2R^3$ group, wherein $R^1$, $R^2$ and $R^3$ independently represent a hydrogen atom, a fluorine atom or a $(C_1-C_2)$alkyl group, being understood that no more than one of $R^1$, $R^2$ and $R^3$ is a hydrogen atom, or $R^1$ and $R^2$ form together with the carbon atom bearing them a $(C_3-C_6)$cycloalkyl group, said $(C_3-C_6)$cycloalkyl group being optionally substituted by one or two halogen atom(s) and said $(C_3-C_6)$cycloalkyl group being optionally interrupted on said $R^1$ and/or $R^2$ by an oxygen atom, R and R' independently represent a halogen atom, a $(C_1-C_2)$alkyl group, a $(C_3-C_6)$cycloalkyl group, or a $(C_1-C_2)$alkoxy group, or any of its pharmaceutically acceptable salt.

In another embodiment, the present invention relates to a compound of formula (Ic), wherein $R_g$ is a hydrogen atom and $R_h$ represents a hydrogen atom or a $(C_1-C_4)$alkyl group, such as a methyl group, or any of its pharmaceutically acceptable salt.

In another embodiment, the present invention relates to a compound of formula (Ic), wherein $X^2$ represents a —CO—$NR_k$— group, wherein $R_k$ represents a hydrogen atom or a methyl group, a —NH—CO— group a —O— group, a —CO— group, a —CH(OH)— group, a —$SO_2$— group, a —NH— group, a divalent 5-membered heteroaromatic ring comprising 1, 2, 3 or 4 heteroatoms, such as a triazole, an imidazole, a tetrazole or an oxadiazole, a NH—$SO_2$—, or a —$SO_2$—NH— group, or any of its pharmaceutically acceptable salt.

In another embodiment, the present invention relates to a compound of formula (Ic), wherein $Y^2$ represents a hydrogen atom, a halogen atom, a

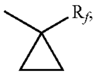

wherein $R_f$ represents a $(C_1-C_4)$alkyl group, a cyano group, a

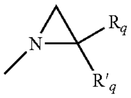

group, wherein $R_q$ and $R'_q$ independently represent a hydrogen atom or a methyl group, a morpholinyl group, optionally substituted by a $(C_1-C_4)$alkyl group, a

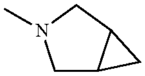

group, a $(C_1-C_4)$alkoxy group, or a —$CR^1R^2R^3$ group, wherein $R^1$, $R^2$ and $R^3$ independently represent a hydrogen atom, a fluorine atom or a $(C_1-C_4)$alkyl group, said $(C_1-C_4)$alkyl group being optionally substituted by a trifluoromethyl group, optionally substituted by a hydroxyl group, being understood that no more than one of $R^1$, $R^2$ and $R^3$ is a hydrogen atom, or $R^1$ and $R^2$ form together with the carbon atom bearing them a $(C_3-C_8)$cycloalkyl group, said $(C_3-C_8)$cycloalkyl group being optionally substituted by one or two $(C_1-C_4)$alkyl group, halogen atom, hydroxy or $(C_1-C_4)$alkoxy group and said $(C_3-C_8)$cycloalkyl group being optionally interrupted on said $R^1$ and/or $R^2$ by one or two oxygen atom(s), or any of its pharmaceutically acceptable salt.

In another embodiment, the present invention relates to a compound of formula (Ic), wherein R and R' independently represent a $(C_1-C_4)$alkyl group, optionally interrupted by a —$SO_2$— group or a —SO— group, a $(C_3-C_6)$cycloalkyl group, a trifluoromethyl group, or a halogen atom, or any of its pharmaceutically acceptable salt.

In another embodiment, the present invention relates to a compound of formula (Ic), wherein

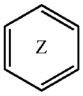

ring and

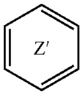

ring both represent a phenylene group or

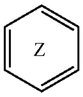

ring represents a pyridylene and

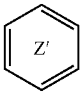

ring represents a phenylene group, m is 0 or 1, n is 0 or 1, $X^2$ represents a —CO—NH— group, a —CO—$N(CH_3)$— group, a —NH—CO— group, a —O— group or a a —CO— group, a —NH—$SO_2$— group, a —CH(OH)— group, a —$SO_2$— group, a divalent triazole, a divalent imidazole,
a divalent tetrazole,
a divalent oxadiazole,
a —NH— group, $Y^2$ represents
a hydrogen,
a morpholinyl group, optionally substituted by a $(C_1$-$C_4)$alkyl group,
a

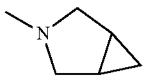

group,
a

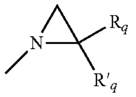

group, wherein $R_q$ and $R'_q$ independently represent a hydrogen atom or a methyl group,
a

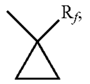

wherein $R_f$ represents a $(C_1$-$C_4)$alkyl group, a cyano group,
a $(C_1$-$C_4)$alkoxy group,
or
a —$CR^1R^2R^3$ group, wherein $R^1$, $R^2$ and $R^3$ independently represent a hydrogen atom, a fluorine atom or a $(C_1$-$C_4)$alkyl group, said $(C_1$-$C_4)$alkyl group being optionally substituted by a trifluoromethyl group, optionally substituted by a hydroxyl group, being understood that no more than one of $R^1$, $R^2$ and $R^3$ is a hydrogen atom, or $R^1$ and $R^2$ form together with the carbon atom bearing them a $(C_3$-$C_8)$cycloalkyl group, said $(C_3$-$C_8)$cycloalkyl group being optionally substituted by one or two $(C_1$-$C_4)$alkyl group, halogen atom, hydroxy or $(C_1$-$C_4)$alkoxy group and said $(C_3$-$C_8)$cycloalkyl group being optionally interrupted on said $R^1$ and/or $R^2$ by one or two oxygen atom(s), and R and R' independently represent
a $(C_1$-$C_4)$alkyl group,
a $(C_3$-$C_6)$cycloalkyl group, such as a cyclopropyl,
a trifluoromethyl group, or
a halogen atom, or any of its pharmaceutically acceptable salt.

In another embodiment, the present invention relates to a compound of formula (Ic), wherein

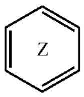

ring and

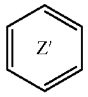

ring both represent a phenylene group,
m is 0, n is 1,
$X^2$ represents
a —CO—NH— group, or
a —O— group,
$Y^2$ represents
a —$CR^1R^2R^3$ group, wherein $R^1$, $R^2$ and $R^3$ independently represent a hydrogen atom, or a $(C_1$-$C_4)$alkyl group, being understood that no more than one of $R^1$, $R^2$ and $R^3$ is a hydrogen atom, such as an isopropyl group, or $R^1$ and $R^2$ form together with the carbon atom bearing them a $(C_3$-$C_8)$cycloalkyl group, such as a cyclopropyl,
and
R' represents
a $(C_1$-$C_4)$alkyl group, such as a tertiobutyl group, or
a $(C_3$-$C_6)$cycloalkyl group, such as a cyclopropyl,
or any of its pharmaceutically acceptable salt.

Any combination of the above-defined embodiments for R, R', m, m',

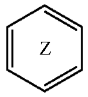

ring,

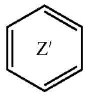

ring, $X^1$, $X^2$, n, $Y^1$, $Y^2$ with each others does form part of the instant invention.

According to a preferred embodiment of the present invention, the compound of formula (Ic) is chosen from:

(19) 4-((3-(N-(2-cyclopentylethyl)sulfamoyl)phenyl)amino)-N-(tetrahydropyrimidin-2(1H)-ylidene)benzamide
(20) N-(cyclopentylmethyl)-3-((4-((tetrahydropyrimidin-2(1H)-ylidene)carbamoyl)phenyl)amino)benzamide
(21) N-((3-methyloxetan-3-yl)methyl)-3-((4-((tetrahydropyrimidin-2(1H)-ylidene)carbamoyl)phenyl)amino)benzamide
(22) N-(2-cyclopentylethyl)-3-((4-((tetrahydropyrimidin-2(1H)-ylidene)carbamoyl)phenyl)amino)benzamide
(23) N-isopentyl-3-((4-((tetrahydropyrimidin-2(1H)-ylidene)carbamoyl)phenyl)amino)benzamide
(24) N-(2-cyclohexylethyl)-3-((4-((tetrahydropyrimidin-2(1H)-ylidene)carbamoyl)phenyl)amino)benzamide
(25) N-(2-cyclopropylethyl)-3-((4-((tetrahydropyrimidin-2(1H)-ylidene)carbamoyl)phenyl)amino)benzamide
(26) N-(2-cyclobutylethyl)-3-((4-((tetrahydropyrimidin-2(1H)-ylidene)carbamoyl)phenyl)amino)benzamide
(27) 4-((3-(isopentylcarbamoyl)phenyl)amino)-3-methyl-N-(tetrahydropyrimidin-2(1H)-ylidene)benzamide

(28) 4-((3-((2-cyclopentylethyl)carbamoyl)phenyl)amino)-3-methyl-N-(tetrahydropyrimidin-2(1H)-ylidene)benzamide

(29) 4-((3-(N-(3-methylbutyl)sulfamoyl)phenyl)amino)-N-(tetrahydropyrimidin-2(1H)-ylidene)benzamide

(30) 4-((3-(N-(1-methylbutyl)sulfamoyl)phenyl)amino)-N-(tetrahydropyrimidin-2(1H)-ylidene)benzamide

(31) 3-methyl-4-((3-(N-(2-cyclopentylethyl)sulfamoyl)phenyl)amino)-N-(tetrahydropyrimidin-2(1H)-ylidene)benzamide

(91) 4-{[2-chloro-3-(3-methylmorpholine-4-carbonyl)phenyl]amino}-3-cyclopropyl-N-[(2E)-4-oxo-1,3-diazinan-2-ylidene]benzamide

(92) 4-{[2-chloro-3-(2-methylmorpholine-4-carbonyl)phenyl]amino}-3-cyclopropyl-N-[(2E)-4-oxo-1,3-diazinan-2-ylidene]benzamide

(93) 4-({2-chloro-3-[(1,4-dioxan-2-yl)methoxy]phenyl}amino)-3-cyclopropyl-N-[(2E)-4-oxo-1,3-diazinan-2-ylidene]benzamide

(94) 3-tert-butyl-4-{[3-(3-methylbutanesulfonamido)phenyl]amino}-N-[(2E)-4-oxo-1,3-diazinan-2-ylidene]benzamide

(95) 4-{[2-chloro-3-(morpholine-4-carbonyl)phenyl]amino}-3-cyclopropyl-N-[(2E)-4-oxo-1,3-diazinan-2-ylidene]benzamide

(96) 3-cyclopropyl-N-(1,3-diazinan-2-ylidene)-4-({2-methyl-3-[(3-methylbutyl)carbamoyl]phenyl}amino)benzamide

(97) 4-{[3-(3-cyclohexylpropoxy)phenyl]amino}-3-cyclopropyl-N-[(2E)-4-oxo-1,3-diazinan-2-ylidene]benzamide

(98) 3-tert-butyl-N-[(2E)-4-oxo-1,3-diazinan-2-ylidene]-4-({3-[(propan-2-yl)carbamoyl]phenyl}amino)benzamide

(99) 3-cyclopropyl-N-(1,3-diazinan-2-ylidene)-4-({3-[(1-methylcyclopropyl)carbamoyl]phenyl}amino)benzamide (100) 3-tert-butyl-N-[(2E)-4-oxo-1,3-diazinan-2-ylidene]-4-({2-[(propan-2-yl)carbamoyl]phenyl}amino)benzamide (101) 4-({3-[(butan-2-yl)carbamoyl]phenyl}amino)-3-cyclopropyl-N-(1,3-diazinan-2-ylidene)benzamide (102) 3-cyclopropyl-N-(1,3-diazinan-2-ylidene)-4-({3-[(propan-2-yl)carbamoyl]phenyl}amino)benzamide (103) 4-{[3-(4-cyclohexyl-1-hydroxybutyl)phenyl]amino}-3-cyclopropyl-N-(1,3-diazinan-2-ylidene)benzamide (104) N-(1,3-diazinan-2-ylidene)-4-({3-[(3-methylbutyl)carbamoyl]phenyl}amino)-3-(trifluoromethyl)benzamide (105) 3-cyclopropyl-N-(1,3-diazinan-2-ylidene)-4-({3-[(4-methylpentyl)carbamoyl]phenyl}amino)benzamide (106) 4-{[2-(3-cyclohexylpropanesulfonyl)phenyl]amino}-3-cyclopropyl-N-(1,3-diazinan-2-ylidene)benzamide (107) 3-cyclopropyl-N-(1,3-diazinan-2-ylidene)-4-({3-[(5-methylhexyl)carbamoyl]phenyl}amino)benzamide (108) 3-cyclopropyl-N-[(2E)-1-methyl-1,3-diazinan-2-ylidene]-4-({3-[(propan-2-yl)carbamoyl]phenyl}amino)benzamide (109) 3-cyclopropyl-N-(1,3-diazinan-2-ylidene)-4-({3-[(1,1,1-trifluoropropan-2-yl)carbamoyl]phenyl}amino)benzamide (110) 3-cyclopropyl-N-(1,3-diazinan-2-ylidene)-4-({3-[(pentan-3-yl)carbamoyl]phenyl}amino)benzamide (111) N-(2-cyclohexylethyl)-2-({4-[(1,3-diazinan-2-ylidene)carbamoyl]-2-(trifluoromethyl)phenyl}amino)pyridine-4-carboxamide (112) 3-cyclopropyl-N-(1,3-diazinan-2-ylidene)-4-{[3-(difluoromethoxy)phenyl]amino}benzamide (113) 3-cyclopropyl-N-(1,3-diazinan-2-ylidene)-4-({3-[(3-methylbutyl)carbamoyl]phenyl}amino)benzamide (114) 3-cyclopropyl-4-{[3-(cyclopropylcarbamoyl)phenyl]amino}-N-(1,3-diazinan-2-ylidene)benzamide (115) 4-{[3-(3-cyclohexylpropoxy)phenyl]amino}-3-cyclopropyl-N-(1,3-diazinan-2-ylidene)benzamide (116) 3-cyclopropyl-4-{[3-(2-methylpropanamido)phenyl]amino}-N-[(2E)-4-oxo-1,3-diazinan-2-ylidene]benzamide (117) 4-{[3-(cyclohexylcarbamoyl)phenyl]amino}-3-cyclopropyl-N-(1,3-diazinan-2-ylidene)benzamide (118) 3-cyclopropyl-N-(1,3-diazinan-2-ylidene)-4-({3-[methyl(3-methylbutyl)carbamoyl]phenyl}amino)benzamide (119) 4-({3-[4-(cyclohexylmethyl)-1H-1,2,3-triazol-1-yl]phenyl}amino)-3-cyclopropyl-N-(1,3-diazinan-2-ylidene)benzamide (120) 3-cyclopropyl-N-[(2E)-4-oxo-1,3-diazinan-2-ylidene]-4-({3-[(propan-2-yl)carbamoyl]phenyl}amino)benzamide (121) 3-cyclopropyl-4-({3-[(1-methylcyclopropyl)carbamoyl]phenyl}amino)-N-[(2E)-4-oxo-1,3-diazinan-2-ylidene]benzamide (122) 3-cyclopropyl-4-{[2-cyclopropyl-3-(2-methylpropanamido)phenyl]amino}-N-[(2E)-4-oxo-1,3-diazinan-2-ylidene]benzamide (123) 4-{[3-(tert-butylcarbamoyl)phenyl]amino}-3-cyclopropyl-N-(1,3-diazinan-2-ylidene)benzamide (124) 3-cyclopropyl-N-(1,3-diazinan-2-ylidene)-4-{[3-(2,2,2-trifluoroethoxy)phenyl]amino}benzamide (125) 3-cyclopropyl-N-(1,3-diazinan-2-ylidene)-4-{[3-(2,2-difluoroethoxy)phenyl]amino}benzamide (126) 3-cyclopropyl-N-(1,3-diazinan-2-ylidene)-4-[(3-{[2-(oxan-4-yl)ethyl]carbamoyl}phenyl)amino]benzamide (127) 4-{[3-(cyclohexylmethoxy)phenyl]amino}-3-cyclopropyl-N-(1,3-diazinan-2-ylidene)benzamide (128) 3-cyclopropyl-N-(1,3-diazinan-2-ylidene)-4-{[2-methyl-3-(4-methylpentanamido)phenyl]amino}benzamide (129) 4-[(3-cyclobutoxyphenyl)amino]-3-cyclopropyl-N-(1,3-diazinan-2-ylidene)benzamide (130) 4-{[3-(2-cyclohexylethoxy)phenyl]amino}-3-cyclopropyl-N-(1,3-diazinan-2-ylidene)benzamide (131) 3-cyclopropyl-N-(1,3-diazinan-2-ylidene)-4-({3-[(2-methylpropyl)carbamoyl]phenyl}amino)benzamide (132) 3-cyclopropyl-N-(1,3-diazinan-2-ylidene)-4-({3-[(4-methylpentyl)oxy]phenyl}amino)benzamide (133) 3-cyclopropyl-N-(1,3-diazinan-2-ylidene)-4-({3-[(2,2,2-trifluoroethyl)carbamoyl]phenyl}amino)benzamide (134) 3-cyclopropyl-4-({3-[(oxan-3-yl)methoxy]phenyl}amino)-N-[(2E)-4-oxo-1,3-diazinan-2-ylidene]benzamide (135) 4-[(3-amino-2-methylphenyl)amino]-3-cyclopropyl-N-(1,3-diazinan-2-ylidene)benzamide (136) 4-[(3-{3-azabicyclo[3.1.0]hexane-3-carbonyl}phenyl)amino]-3-cyclopropyl-N-(1,3-diazinan-2-ylidene)benzamide (137) 3-cyclopropyl-N-(1,3-diazinan-2-ylidene)-4-{[3-(trifluoromethoxy)phenyl]amino}benzamide (138) N-(2-cyclohexylethyl)-4-({2-cyclopropyl-4-[(1,3-diazinan-2-ylidene)carbamoyl]phenyl}amino)pyridine-2-carboxamide (139) 3-cyclopropyl-N-(1,3-diazinan-2-ylidene)-4-({3-[2-(propan-2-yloxy)ethoxy]phenyl}amino)benzamide (140) 4-{[3-(4-cyclohexylbutoxy)phenyl]amino}-3-cyclopropyl-N-(1,3-diazinan-2-ylidene)benzamide (141) 4-{[3-(5-chloro-1H-imidazol-2-yl)-2-methylphenyl]amino}-3-cyclopropyl-N-(1,3-diazinan-2-ylidene)benzamide (142) 4-{[3-(5-chloro-1H-imidazol-2-yl)-2-methylphenyl]amino}-3-cyclopropyl-N-(1,3-diazinan-2-ylidene)benzamide (143) 4-{[3-(3-cyclohexylpropanesulfonyl)phenyl]amino}-3-cyclopropyl-N-(1,3-diazinan-2-ylidene)benzamide (144) 3-cyclopropyl-N-(1,3-diazinan-2-ylidene)-4-{[3-(oxetan-3-yloxy)phenyl]amino}benzamide (145) 3-cyclopropyl-4-{[3-(cyclopropylcarbamoyl)phenyl]amino}-N-[(2E)-4-oxo-1,3-diazinan-2-ylidene]benzamide (146) 3-cyclopropyl-4-({3-[(oxan-4-yl)methoxy]phenyl}amino)-N-[(2E)-4-oxo-1,3-diazinan-2-ylidene]benzamide (147) 3-cyclopropyl-N-(1,3-diazinan-2-ylidene)-4-({2-[(3-methylbutyl)carbamoyl]phenyl}amino)benzamide (148) 4-{[3-(3-cyclohexylpropanamido)-4-fluorophenyl]amino}-N-(1,3-diazinan-2-ylidene)-3-(trifluoromethyl)benzamide (149) 4-({3-[2-(3-cyclohexylpropyl)-2H-1,2,3,4-tetrazol-5-yl]phenyl}amino)-3-cyclopropyl-N-(1,3-diazinan-2-ylidene)benzamide (150) 3-cyclopropyl-4-({3-[2-(1,4-dioxan-2-yl)ethoxy]phenyl}amino)-N-[(2E)-4-oxo-1,3-diazinan-2-ylidene]benzamide (151) 3-cyclopropyl-4-({3-[(oxan-2-yl)methoxy]phenyl}amino)-N-[(2E)-4-oxo-1,3-diazinan-2-ylidene]benzamide (152) 3-cyclopropyl-N-(1,3-diazinan-2-ylidene)-4-({3-[(3,3-difluorocyclobutyl)carbamoyl]phenyl}amino)benzamide (153) 4-{[3-(3-cyclohexylpropanamido)phenyl]amino}-N-(1,3-diazinan-2-ylidene)-3-methylbenzamide (154) 3-cyclopropyl-N-(1,3-diazinan-2-ylidene)-4-{[3-(2,2-dimethylaziridine-1-carbonyl)phenyl]amino}benzamide (155) 3-cyclopropyl-N-(1,3-diazinan-2-ylidene)-4-({3-[(oxolan-3-yl)carbamoyl]phenyl}amino)benzamide (156) 4-{[3-(3-cyclohexylpropoxy)phenyl]amino}-N-(1,3-diazinan-2-ylidene)-3-methylbenzamide (157) 3-cyclopropyl-N-(1,3-diazinan-2-ylidene)-4-({3-[(oxan-4-yl)carbamoyl]phenyl}amino)benzamide (158) 3-cyclopropyl-N-(1,3-diazinan-2-ylidene)-4-{[3-(morpholine-4-carbonyl)phenyl]amino}benzamide (159) 3-cyclopropyl-N-(1,3-diazinan-2-ylidene)-4-({2-[(3,3,3-trifluoropropyl)carbamoyl]phenyl}amino)benzamide (160) 3-cyclopropyl-N-(1,3-diazinan-2-ylidene)-4-({3-[2-(2-methoxyethyl)-2H-1,2,3,4-tetrazol-5-yl]phenyl}amino)benzamide (161) 3-cyclopropyl-4-({3-[(1,4-dioxan-2-yl)methoxy]phenyl}amino)-N-[(2E)-4-oxo-1,3-diazinan-2-ylidene]benzamide (162) 3-cyclopropyl-N-(1,3-diazinan-2-ylidene)-4-{[3-(2-methylaziridine-1-carbonyl)phenyl]amino}benzamide (163) 3-cyclopropyl-N-(1,3-diazinan-2-ylidene)-4-{[3-(dimethylcarbamoyl)phenyl]amino}benzamide (164) 3-cyclopropyl-4-{[3-(morpholine-4-carbonyl)phenyl]amino}-N-[(2E)-4-oxo-1,3-diazinan-2-ylidene]benzamide (165) 4-({3-[(1-cyanocyclopropyl)carbamoyl]-2-methylphenyl}amino)-3-cyclopropyl-N-(1,3-diazinan-2-ylidene)benzamide (166) 3-cyclopropyl-N-(1,3-diazinan-2-ylidene)-4-({3-[(oxetan-3-yl)carbamoyl]phenyl}amino)benzamide (167) 3-cyclopropyl-N-(1,3-diazinan-2-ylidene)-4-{[3-(4-methylpiperazine-1-carbonyl)phenyl]amino}benzamide (168) 4-({3-[(1-methylcyclopropyl)carbamoyl]phenyl}amino)-N-[(2E)-4-oxo-1,3-diazinan-2-ylidene]-3-(propane-2-sulfonyl)benzamide (169) 3-cyclopropyl-N-(1,3-diazinan-2-ylidene)-4-{[4-methyl-3-(4-methylpentanamido)phenyl]amino}benzamide (170) 3-cyclopropyl-N-(1,3-diazinan-2-ylidene)-4-({4-methyl-3-[(3-methylbutyl)carbamoyl]phenyl}amino)benzamide (171) 3-cyclopropyl-N-(1,3-diazinan-2-ylidene)-4-({3-[1-(2-methoxyethyl)-1H-1,2,3,4-tetrazol-5-yl]phenyl}amino)benzamide (172) 4-({3-[(1-cyanocyclopropyl)carbamoyl]phenyl}amino)-3-cyclopropyl-N-(1,3-diazinan-2-ylidene)benzamide (173) 4-({3-[(1-methylcyclopropyl)carbamoyl]phenyl}amino)-3-(2-methylpropane-2-sulfonyl)-N-[(2E)-4-oxo-1,3-diazinan-2-ylidene]benzamide (174) 4-({3-[(1-methylcyclopropyl)carbamoyl]phenyl}amino)-N-[(2E)-4-oxo-1,3-diazinan-2-ylidene]-3-(propane-2-sulfinyl)benzamide (175) 3-methyl-4-{[3-(morpholine-4-carbonyl)phenyl]amino}-N-[(2E)-4-oxo-1,3-diazinan-2-ylidene]benzamide (176) 3-cyclopropyl-N-(1,3-diazinan-2-ylidene)-4-({3-[(1-hydroxypropan-2-yl)carbamoyl]phenyl}amino)benzamide (177) 3-cyclopropyl-N-(1,3-diazinan-2-ylidene)-4-({3-[(3-hydroxycyclobutyl)carbamoyl]phenyl}amino)benzamide (178) 3-cyclopropyl-N-(1,3-diazinan-2-ylidene)-4-{[3-(piperazine-1-carbonyl)phenyl]amino}benzamide (179) 3-cyclopropyl-N-(1,3-diazinan-2-ylidene)-4-({3-[(piperidin-4-yl)methoxy]phenyl}amino)benzamide (180) N-(1,3-diazinan-2-ylidene)-3-methyl-4-[(3-{[3-(morpholin-4-yl)propyl]carbamoyl}phenyl)amino]benzamide (181) 3-methanesulfonyl-4-({3-[(1-methylcyclopropyl)carbamoyl]phenyl}amino)-N-[(2E)-4-oxo-1,3-diazinan-2-ylidene]benzamide and their pharmaceutically acceptable salts.

The present invention therefore extends to compounds (19) to (31) and (91) to (181) and their pharmaceutically acceptable salts, such as hydrobromide, tartrate, citrate, trifluoroacetate, ascorbate, hydrochloride, tosylate, triflate, maleate, mesylate, formate, acetate and fumarate.

According to another aspect, a subject-matter of the present invention relates to compounds (19) to (31) and (91) to (181) or any of its pharmaceutically acceptable salts, for use as a medicament.

According to another aspect, a subject-matter of the present invention relates to a compound of formula (Ic) as defined above or any of its pharmaceutically acceptable salts, and any of compounds (19) to (31) and (91) to (181) or any of its pharmaceutically acceptable salts, for use as an agent for preventing, inhibiting or treating a RNA virus infection caused by a RNA virus belonging to group IV or V of the Baltimore classification.

Compounds (27), (28), (91)-(166) or any of their pharmaceutically acceptable salts may be particularly useful for preventing, inhibiting or treating RSV infection.

Compounds (22), (23), (24), (26), (27) and (28) or any of their pharmaceutically acceptable salts may be particularly useful for preventing, inhibiting or treating Chikungunya infection.

The compounds of the invention may exist in the form of free bases or of addition salts with pharmaceutically acceptable acids.

«Pharmaceutically acceptable salt thereof» refers to salts which are formed from acid addition salts formed with inorganic acids (e.g. hydrochloric acid, hydrobromic acid, sulfuric acid, phosphoric acid, nitric acid, and the like), as well as salts formed with organic acids such as acetic acid, oxalic acid, tartaric acid, succinic acid, malic acid, fumaric acid, maleic acid, ascorbic acid, benzoic acid, tannic acid, palmoic acid, alginic acid, polyglutamic acid, naphthalene sulfonic acid, naphthalene disulfonic acid, and poly-galacturonic acid.

Suitable physiologically acceptable acid addition salts of compounds of formula (Ic) include hydrobromide, tartrate, citrate, trifluoroacetate, ascorbate, hydrochloride, tosylate, triflate, maleate, mesylate, formate, acetate and fumarate.

The compounds of formula (Ic) and any of compounds (19) to (31) and (91) to (181) or any of their pharmaceutically acceptable salts may form solvates or hydrates and the invention includes all such solvates and hydrates.

The compounds of formula (Ic) may be present as well under tautomer forms and are part of the invention. The terms "hydrates" and "solvates" simply mean that the compounds (Ic) according to the invention can be in the form of a hydrate or solvate, i.e. combined or associated with one or more water or solvent molecules. This is only a chemical characteristic of such compounds, which can be applied for all organic compounds of this type.

In the context of the present invention, the term:

"halogen" is understood to mean chlorine, fluorine, bromine, or iodine, and in particular denotes chlorine, fluorine or bromine, "$(C_1\text{-}C_x)$alkyl", as used herein, respectively refers to a $C_1\text{-}C_x$ normal, secondary or tertiary saturated hydrocarbon, for example $(C_1\text{-}C_6)$alkyl. Examples are, but are not limited to, methyl, ethyl, 1-propyl, 2-propyl, butyl, pentyl, an "alkenylene" means a divalent $(C_1\text{-}C_x)$alkyl group comprising a double bond, and more particularly a ethenylene group, also known as vinylene or 1,2-ethenediyl, "$(C_3\text{-}C_6)$cycloalkyl", as used herein, refers to a cyclic saturated hydrocarbon. Examples are, but are not limited to, cyclopropyl, cyclobutyl, cyclopentyl, cyclohexyl, "$(C_1\text{-}C_x)$alkoxy", as used herein, refers to a O—$(C_1\text{-}C_x)$ alkyl moiety, wherein alkyl is as defined above, for example $(C_1\text{-}C_6)$alkoxy. Examples are, but are not limited to, methoxy, ethoxy, 1-propoxy, 2-propoxy, butoxy, pentoxy, "aryl", as used herein, refers to a monocyclic aromatic group containing 6 carbon atoms and containing between 0 and 2 heteroatoms, such as nitrogen, oxygen or sulphur, and in particular nitrogen. By way of examples of aryl groups, mention may be made of, but not limited to: phenyl, pyridine, pyrimidine, pyridazine, pyrazine and the like. In the framework of the present invention, the aryl is advantageously phenyl, pyridazine, pyrazine, pyridine, such as 2-pyridine or 3-pyridine and pyrimidine. The aryl is even more advantageously phenyl and pyridine, such as 2-pyridine or 3-pyridine.

a "divalent 5-membered heteroaromatic ring comprising 1, 2, 3 or 4 heteroatoms" as used herein, means a divalent ring consisting of an aromatic ring comprising 5 chains and 1, 2, 3 or 4 heteroatoms selected from nitrogen and oxygen atoms. In one embodiment, it comprises at least 1 heteroatom, and preferably at least one nitrogen atom. In another embodiment, it comprises at least 2 heteroatoms, with for example at least one nitrogen atom. According to a further embodiment, it comprises 2, 3 or 4 nitrogen atoms, preferably 3 nitrogen atoms. According to an even further embodiment, it comprises one nitrogen atom and one oxygen atom or two nitrogen atoms and one oxygen atom. Examples are, but not limited to, divalent triazole, such as 1,2,3- or 1,2,4-triazoles, oxadiazoles, such as 1,2,4-oxadiazole or 1,2,3-oxadiazole and divalent diazoles such as divalent diazole and divalent imidazole. According to a preferred embodiment, such divalent 5-membered heteroaromatic ring comprising 2 or 3 heteroatoms is a divalent triazole.

The compounds of formula (Ic) can comprise one or more asymmetric carbon atoms. They can thus exist in the form of enantiomers or of diastereoisomers. These enantiomers, diastereoisomers and their mixtures, including the racemic mixtures, are encompassed within the scope of the present invention.

The compounds of the present invention can be prepared by conventional methods of organic synthesis practiced by those skilled in the art. The general reaction sequences outlined below represent a general method useful for preparing the compounds of the present invention and are not meant to be limiting in scope or utility.

The compounds of general formula (I) and (Ic) can be prepared according to scheme 1 below.

Scheme 1

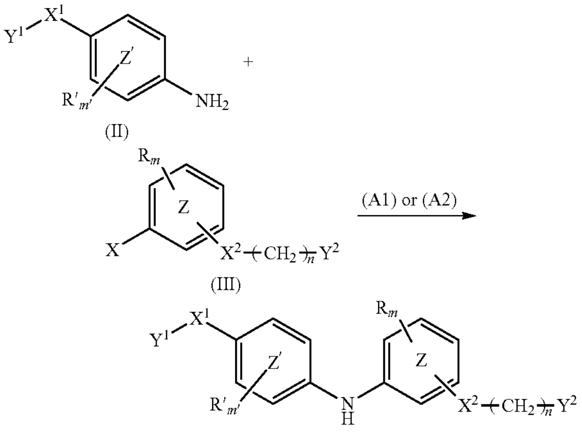

The synthesis is based on a coupling reaction starting from a halogeno aromatic compound of formula (III), wherein R, R', m, m',

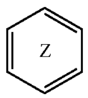

ring,

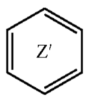

ring, $X^1$, $X^2$, n, $Y^1$, $Y^2$ are as defined above and X is a chlorine atom, an iodine atom or a bromine atom.

According to one embodiment, procedure (A1) may advantageously be used when the group

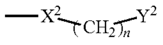

is in meta or para position on the

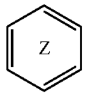

ring, with respect to the —NH— group.

According to route (A1), the compound of formula (III) may be placed in a protic solvent such as tert-butanol. The compound of formula (II) may then be added, for example in a molar ratio ranging from 1 to 1.5 with respect to the compound of formula (III) in presence of an inorganic base, such as $Cs_2CO_3$ or $K_2CO_3$, for example in a molar ratio ranging from 1 to 5 still with respect to the compound of formula (III), in the presence of a diphosphine, such as Xantphos (4,5-Bis(diphenylphosphino)-9,9-dimethylxanthene) or X-Phos (2-Dicyclohexylphosphino-2',4',6'-triisopropylbiphenyl) or rac-BINAP in particular in an amount ranging from 2 mol % to 15 mol % relative to the total amount of compound of formula (III), and in the presence of an organometallic catalyst, such as $Pd(OAc)_2$ or $Pd_2dba_3$, or BrettPhos Pd G3 in an amount ranging from 2 mol % to 25 mol % relative to the total amount of compound of formula (III). The reaction mixture can then be heated at a temperature ranging from 80 to 130° C., for example at 90° C., and stirred for a time ranging from 15 to 25 hours, for example during 20 hours, under inert gas and for example argon. The reaction mixture can be concentrated under reduced pressure and the residue can be diluted with an organic solvent such as ethyl acetate. The organic phase can be washed with water, decanted, dried over magnesium sulphate, filtered and then concentrated under reduced pressure to give a compound of formula (I) and (Ic).

According to one embodiment, procedure (A2) may advantageously be used when the group

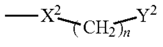

is in ortho position on the

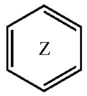

ring, with respect to the —NH— group.

According to procedure (A2), the compound of formula (II) may be placed in a polar aprotic solvent such as dimethylsulfoxide. The compound of formula (III) may then be added, for example in a molar ratio ranging from 1 to 1.5 with respect to the compound of formula (II) in presence of an inorganic base, such as $Cs_2CO_3$ or $K_2CO_3$, for example in a molar ratio ranging from 1 to 5 still with respect to the compound of formula (II), in the presence of a ligand, such as L-proline in particular in an amount ranging from 2 mol % to 25 mol % relative to the total amount of compound of formula (II), and in the presence of an organometallic catalyst, such as CuI, in an amount ranging from 2 mol % to 25 mol % relative to the total amount of compound of formula (II). The reaction mixture can then be heated at a temperature ranging from 80 to 130° C., for example at 90° C., and stirred for a time ranging from 15 to 25 hours, for example during 20 hours, under inert gas and for example argon. The reaction mixture can be diluted with an organic solvent such as ethyl acetate. The organic phase can be washed with water, decanted, dried over magnesium sulphate, filtered and then concentrated under reduced pressure to give a compound of formula (I) and (Ic).

The starting compounds of formula (II), (III) are available or can be prepared according to methods known to the person skilled in the art.

Accordingly, the present document further describes the synthesis process for manufacturing new compounds of formula (I) and (Ic) as defined above, comprising at least a step of coupling a compound of formula (II)

(II)

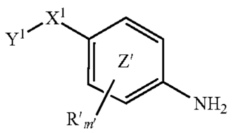

with a compound of formula (III)

(III)

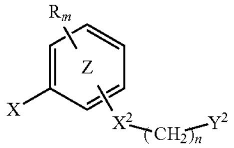

wherein $X^1$, $Y^1$, R, R', m, m',

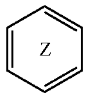

ring,

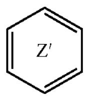

ring, $X^2$, $Y^2$ are as defined above and X is a chlorine atom, an iodine atom or a bromine atom, in presence of an inorganic base and a ligand and in the presence of an organometallic catalyst, to obtain a compound of formula (I) and (Ic).

The compounds of general formula (Ic) can be prepared according to scheme 1' below.

Scheme 1'

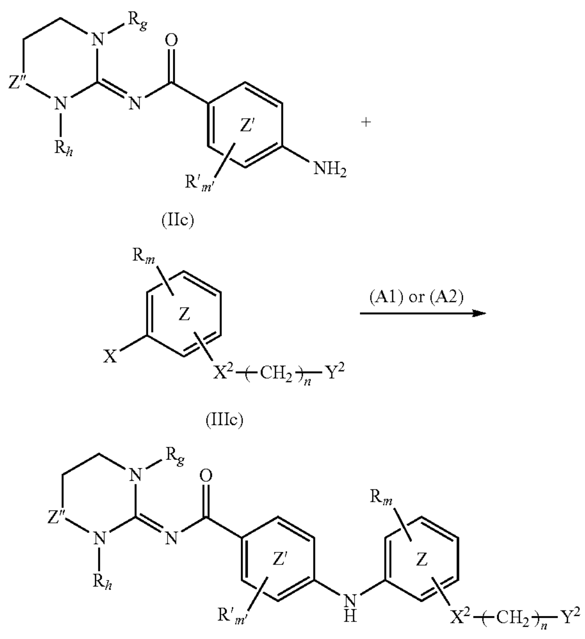

(IIc)

(IIIc)

(Ic)

More particularly, the present invention relates to the synthesis process for manufacturing the compounds of formula (Ic) as defined above, comprising at least a step of coupling a compound of formula (IIc)

(IIc)

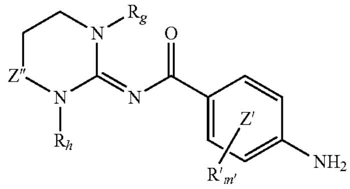

(IIc)

with a compound of formula (Mc)

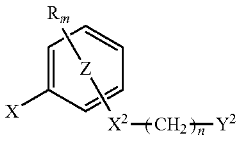

(IIIc)

wherein R, R', m, m',

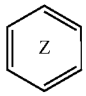

ring,

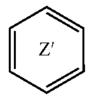

ring, $X^2$, $Y^2$, $R_h$, $R_g$ and Z" are as defined above, X is a chlorine atom, an iodine atom or a bromine atom, in presence of an inorganic base and a ligand and in the presence of an organometallic catalyst, to obtain a compound of formula (Ic).

More particularly, compounds of formula (IIc), when used to prepare compounds of formula (Ic) with Z"═$CH_2$, can be prepared according to scheme 4 below.

Preparation of (IIc) for (Ic)

Scheme 4

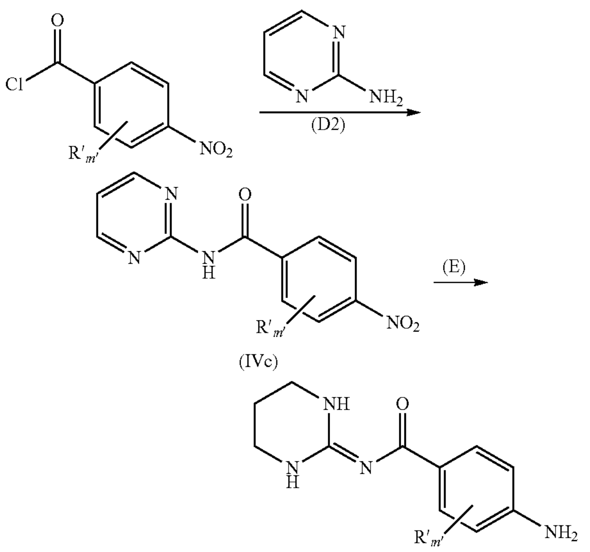

(IVc)

(IIc)

Intermediate compounds of formulae (IIc) and (IVc) are useful for preparing compounds of formula (Ic) according to the invention.

According to route (D2), the aminopyrimidine may be placed in a polar aprotic solvent such as dichloromethane. The nitrobenzoyl chloride derivative may then be added, for example in a molar ratio ranging from 1 to 1.5 with respect to the aminopyrimidine, in presence of an organic base such as N,N-diisopropylethylamine or triethylamine, for example in a molar ratio ranging from 1 to 2 still with respect to the aminopyrimidine, in the presence of a nucleophilic catalyst such as dimethylaminopyridine, for example in a molar ratio ranging from 0.1 to 1 still with respect to the aminopyrimidine. The reaction mixture can then be stirred at room temperature for a time ranging from 5 to 20 hours for example 18 hours, under inert gas and for example argon. The organic phase can be washed with water and the resulting precipitate can be filtered, washed with water and dichloromethane and dried under vacuum overnight to give a compound of formula (IVc).

According to route (E), the compound of formula (IVc) and 10% Pd/C in a ratio ranging from 2% to 10% relative to the amount of benzamide may be placed in a protic solvent such as ethanol. The reaction mixture can then be stirred at room temperature for a time ranging from 5 to 20 hours for example 16 hours under an atmosphere of $H_2$. The reaction mixture can then be filtered and the filtrate can be concentrated under reduced pressure to give a compound of formula (IIc).

According to one embodiment, in the case of Z" being a —CO— group, another route can be followed to prepare compounds of formula (Ic) and is displayed in scheme X below.

Scheme X

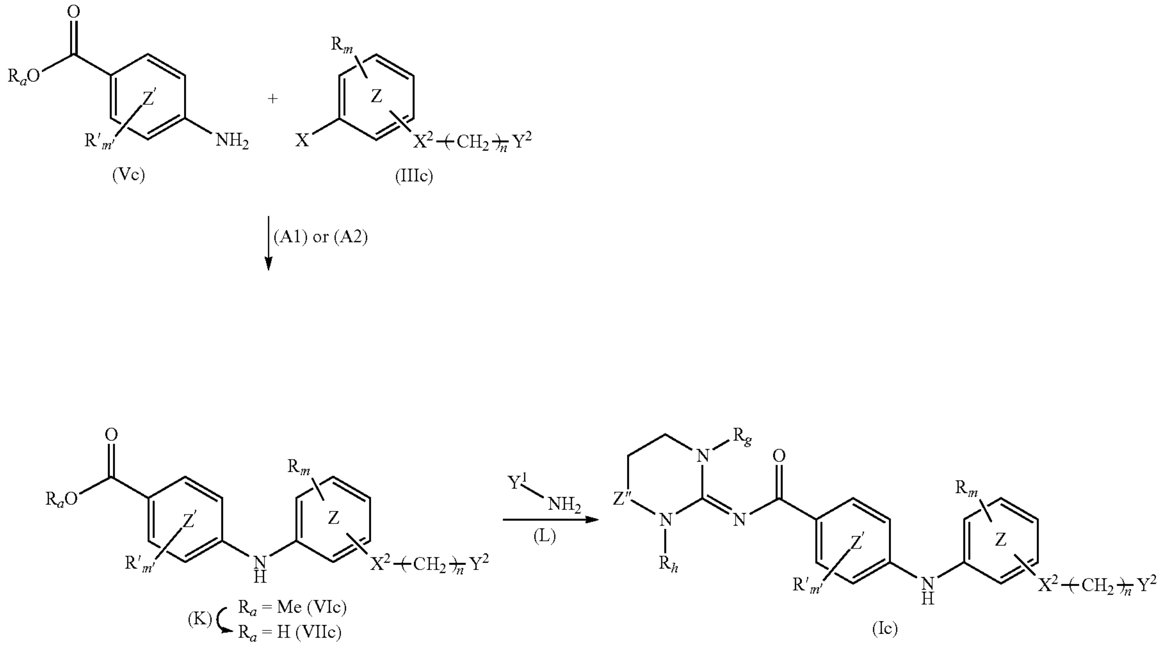

(Vc) (IIIc) (Ic)

The synthesis starts with a coupling reaction of a halogeno aromatic compound of formula (IIIc) with an aniline derivative (Vc), wherein R, R', $R_a$, m, m', $X^1$, $X^2$, n, $Y^1$, $Y^2$, Z, Z', Z" are as defined above and X is a chlorine atom, an iodine atom or a bromine atom, following procedure (A1) or (A2).

According to procedure (K), the compound of formula (VIc) may be placed in a protic solvent such as methanol and an aqueous solution of 2M NaOH may be added in a ratio ranging from 3 to 10 equivalents. The reaction mixture can then be heated at a temperature ranging from 50 to 90° C., for example at 80° C. and stirred for a time ranging from 1 to 24 hours, for example during 3 hours. The mixture can be concentrated under reduced pressure and, after addition of an aqueous solution of 2M HCl, extracted with an organic solvent such as dichloromethane. The combined organic phases can then be dried over magnesium sulphate, filtered and concentrated under reduced pressure to give a compound of formula (VIIc).

According to procedure (L), the compound of formula (VIIc) and carbonyldiimidazole (CDI), in a ratio ranging from 1.0 to 3 equivalents, for example 1.2 equivalent, may be placed in an anhydrous polar solvent such as N,N-dimethylformamide. The reaction mixture can then be stirred at room temperature for a time ranging from 1 to 3 hours, for example 1 hour. The amine derivative $Y^1$—$NH_2$ may then be added, for example in a molar ratio ranging from 1 to 2.5 with respect to compound (VIIc), in presence of an organic base such as triethylamine or N,N-diisopropylethylamine, for example in a molar ratio ranging from 2 to 5 still with respect to compound (VIIc). The reaction mixture can then be heated at a temperature ranging from 50 to 90° C., for example at 75° C. and stirred for a time ranging from 1 to 24 hours, for example during 16 hours. The reaction can be quenched upon addition of a saturated aqueous solution of sodium bicarbonate and the mixture extracted with an organic solvent such as ethyl acetate. The combined organic phases can then be dried over magnesium sulphate, filtered and concentrated under reduced pressure to afford a compound of formula (Ic).

The chemical structures and spectroscopic data of some compounds of formula (Ic) of the invention are illustrated respectively in the following Table I and Table II.

TABLE I
(Ic)
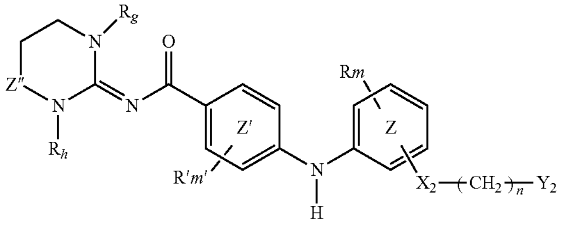
(Ic)
19
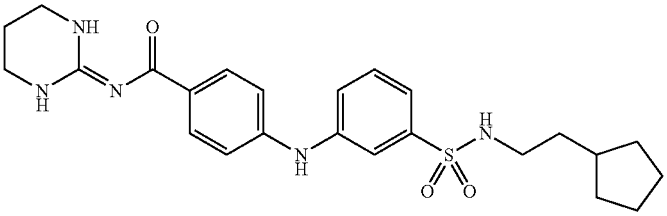 [SMILES: O=C(N=C1NCCCN1)c1ccc(Nc2cccc(S(=O)(=O)NCCC3CCCC3)c2)cc1]
20
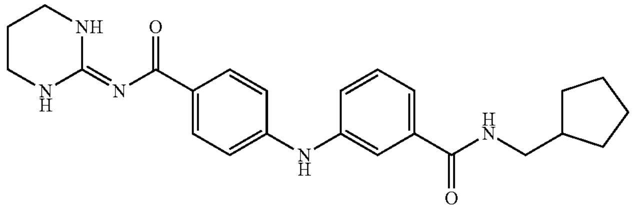 [SMILES: O=C(N=C1NCCCN1)c1ccc(Nc2cccc(C(=O)NCC3CCCC3)c2)cc1]
21
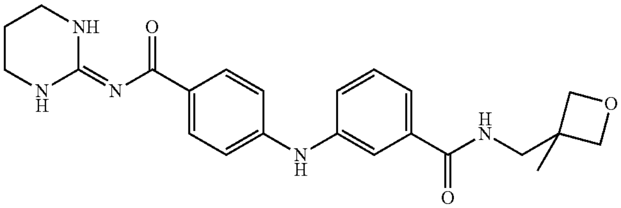 [SMILES: CC1(CNC(=O)c2cccc(Nc3ccc(C(=O)N=C4NCCCN4)cc3)c2)COC1]
22
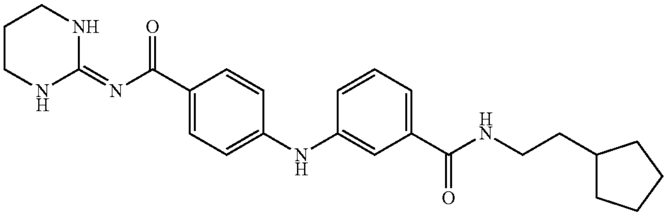 [SMILES: O=C(N=C1NCCCN1)c1ccc(Nc2cccc(C(=O)NCCC3CCCC3)c2)cc1]
23
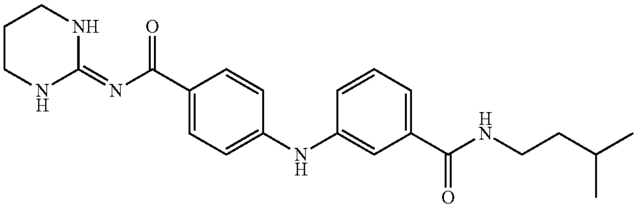 [SMILES: CC(C)CCNC(=O)c1cccc(Nc2ccc(C(=O)N=C3NCCCN3)cc2)c1]

TABLE I-continued
(Ic)
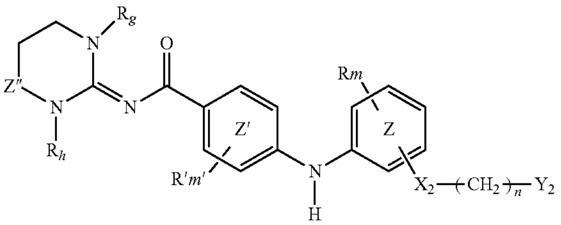
(Ic)
24
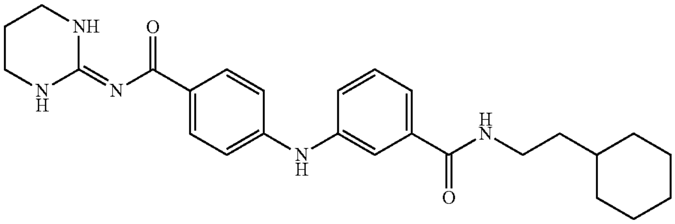 [SMILES: O=C(N=C1NCCCN1)c1ccc(Nc2cccc(C(=O)NCCC3CCCCC3)c2)cc1]
25
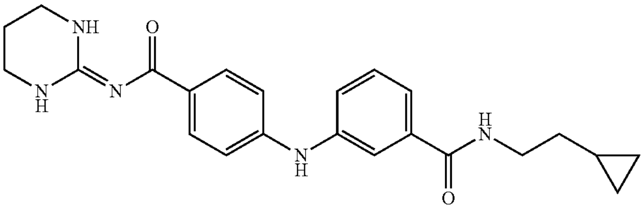 [SMILES: O=C(N=C1NCCCN1)c1ccc(Nc2cccc(C(=O)NCCC3CC3)c2)cc1]
26
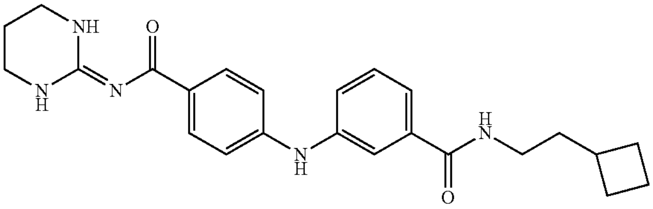 [SMILES: O=C(N=C1NCCCN1)c1ccc(Nc2cccc(C(=O)NCCC3CCC3)c2)cc1]
27
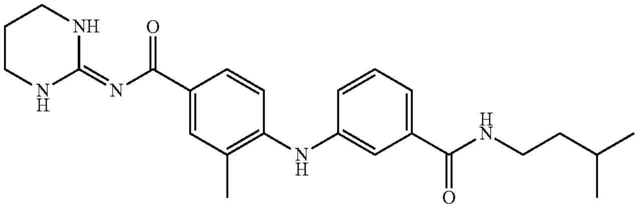 [SMILES: Cc1cc(C(=O)N=C2NCCCN2)ccc1Nc1cccc(C(=O)NCCC(C)C)c1]
28
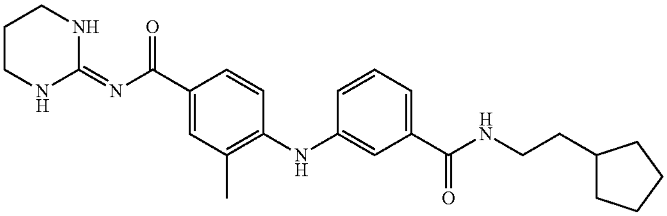 [SMILES: Cc1cc(C(=O)N=C2NCCCN2)ccc1Nc1cccc(C(=O)NCCC2CCCC2)c1]
29
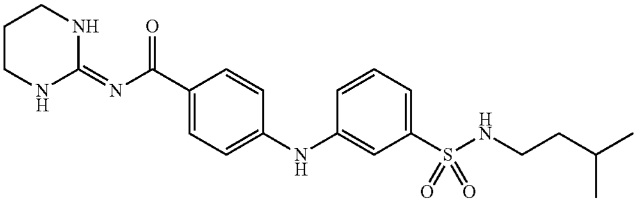 [SMILES: CC(C)CCNS(=O)(=O)c1cccc(Nc2ccc(C(=O)N=C3NCCCN3)cc2)c1]

TABLE I-continued
(Ic)
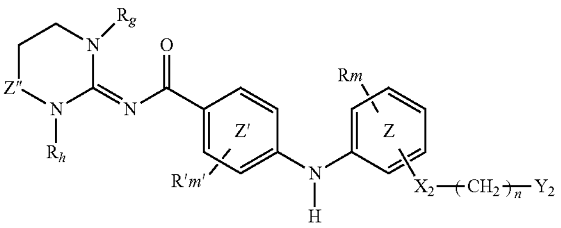
(Ic)
30
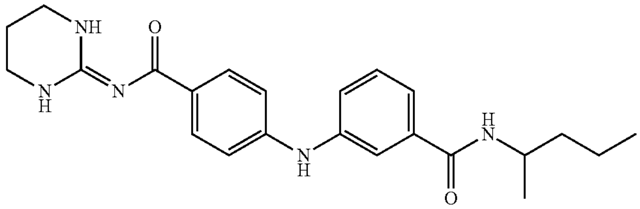 [SMILES: CCCC(C)NC(=O)c1cccc(Nc2ccc(C(=O)N=C3NCCCN3)cc2)c1]
31
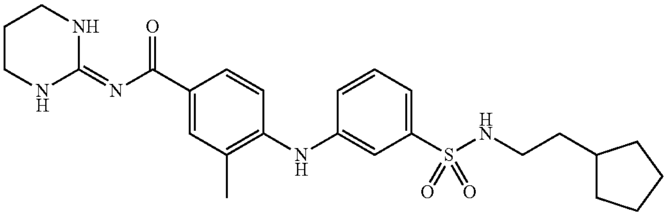 [SMILES: Cc1cc(C(=O)N=C2NCCCN2)ccc1Nc1cccc(S(=O)(=O)NCCC2CCCC2)c1]
91
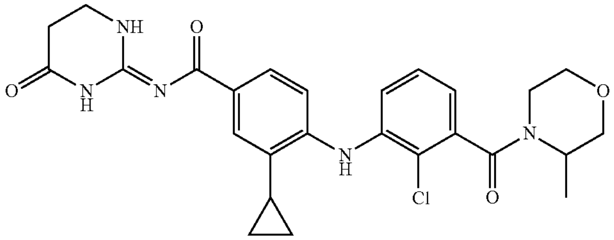 [SMILES: CC1COCCN1C(=O)c1cccc(Nc2ccc(C(=O)/N=C3\NCCC(=O)N3)cc2C2CC2)c1Cl]
92
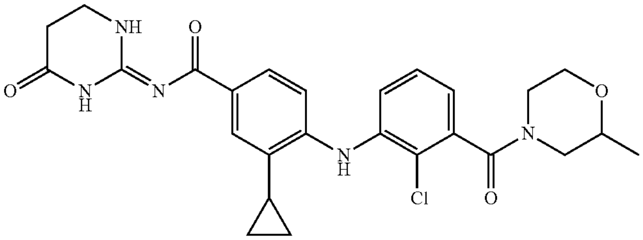 [SMILES: CC1CN(C(=O)c2cccc(Nc3ccc(C(=O)/N=C4\NCCC(=O)N4)cc3C3CC3)c2Cl)CCO1]
93
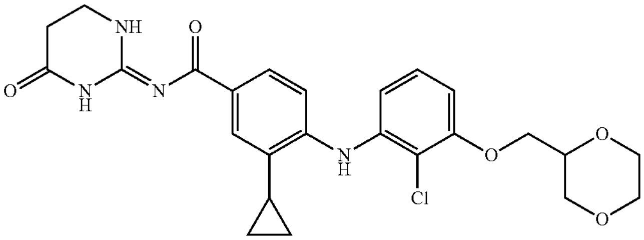 [SMILES: O=C1CCN/C(=N\C(=O)c2ccc(Nc3cccc(OCC4COCCO4)c3Cl)c(C3CC3)c2)N1]

TABLE I-continued
(Ic)
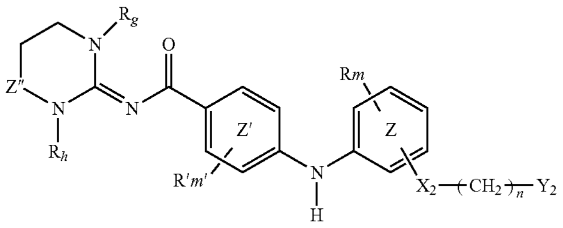
(Ic)
94
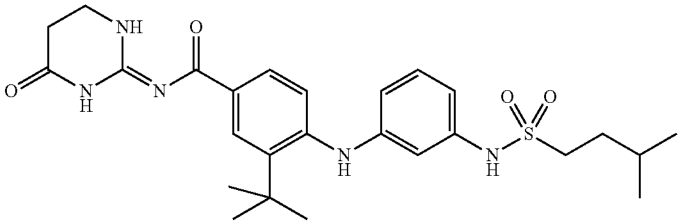 [SMILES: CC(C)CCS(=O)(=O)Nc1cccc(Nc2ccc(C(=O)/N=C3\NCCC(=O)N3)cc2C(C)(C)C)c1]
95
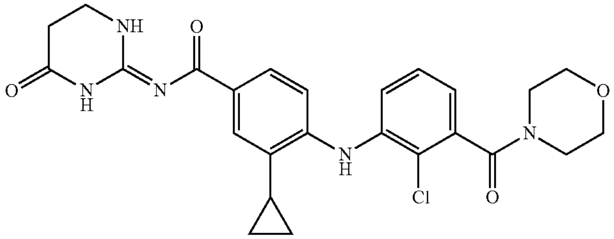 [SMILES: O=C1CCN/C(=N\C(=O)c2ccc(Nc3cccc(C(=O)N4CCOCC4)c3Cl)c(C3CC3)c2)N1]
96
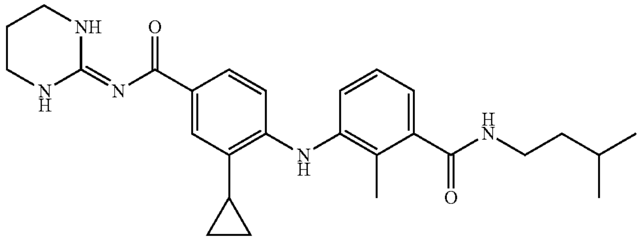 [SMILES: Cc1c(Nc2ccc(C(=O)N=C3NCCCN3)cc2C2CC2)cccc1C(=O)NCCC(C)C]
97
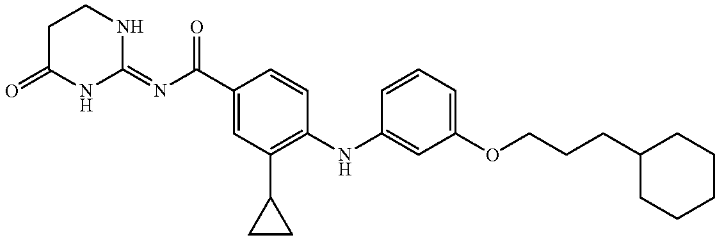 [SMILES: O=C1CCN/C(=N\C(=O)c2ccc(Nc3cccc(OCCCC4CCCCC4)c3)c(C3CC3)c2)N1]
98
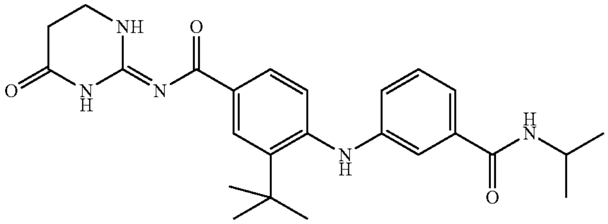 [SMILES: CC(C)NC(=O)c1cccc(Nc2ccc(C(=O)/N=C3\NCCC(=O)N3)cc2C(C)(C)C)c1]

TABLE I-continued
(Ic)
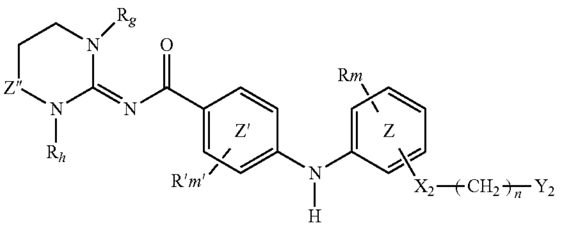
(Ic)
99
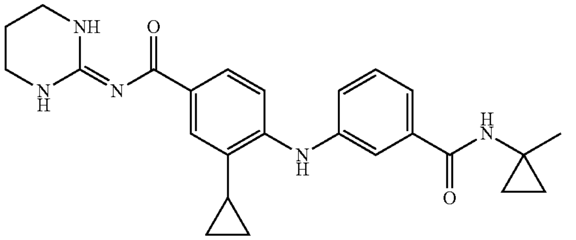 [SMILES: CC1(NC(=O)c2cccc(Nc3ccc(C(=O)N=C4NCCCN4)cc3C3CC3)c2)CC1]
100
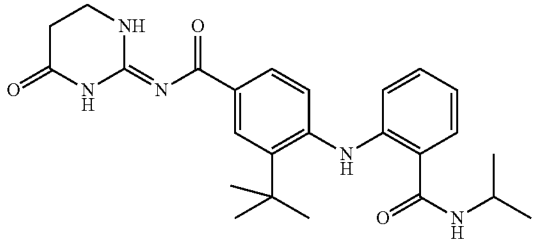 [SMILES: CC(C)NC(=O)c1ccccc1Nc1ccc(C(=O)/N=C2\NCCC(=O)N2)cc1C(C)(C)C]
101
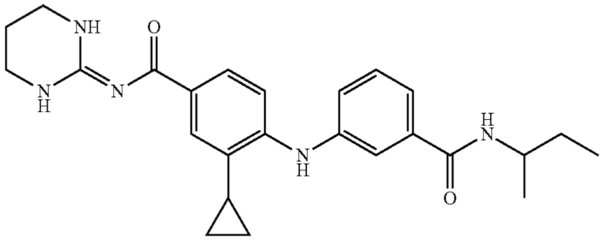 [SMILES: CCC(C)NC(=O)c1cccc(Nc2ccc(C(=O)N=C3NCCCN3)cc2C2CC2)c1]
102
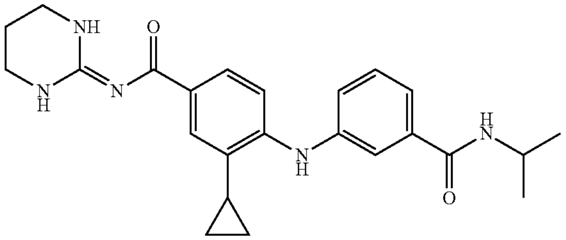 [SMILES: CC(C)NC(=O)c1cccc(Nc2ccc(C(=O)N=C3NCCCN3)cc2C2CC2)c1]
103
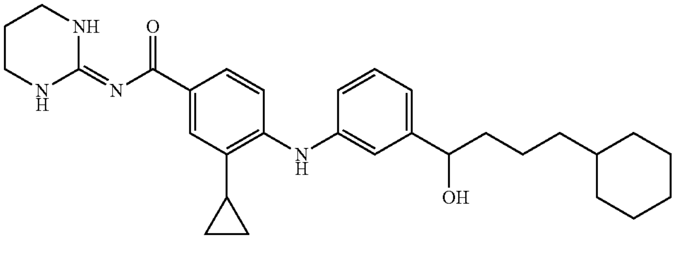 [SMILES: O=C(N=C1NCCCN1)c1ccc(Nc2cccc(C(O)CCCC3CCCCC3)c2)c(C2CC2)c1]

TABLE I-continued
(Ic)
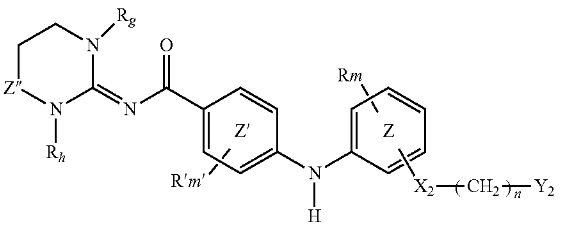
(Ic)
104
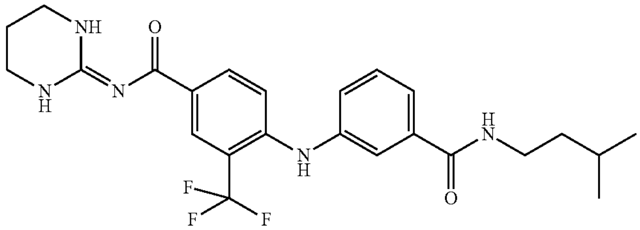 [SMILES: CC(C)CCNC(=O)c1cccc(Nc2ccc(C(=O)N=C3NCCCN3)cc2C(F)(F)F)c1]
105
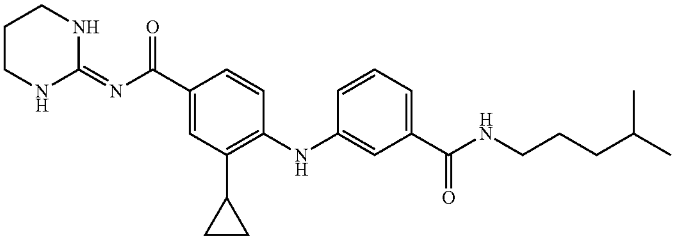 [SMILES: CC(C)CCCNC(=O)c1cccc(Nc2ccc(C(=O)N=C3NCCCN3)cc2C2CC2)c1]
106
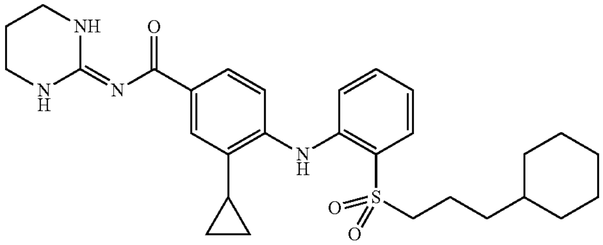 [SMILES: O=C(N=C1NCCCN1)c1ccc(Nc2ccccc2S(=O)(=O)CCCC2CCCCC2)c(C2CC2)c1]
107
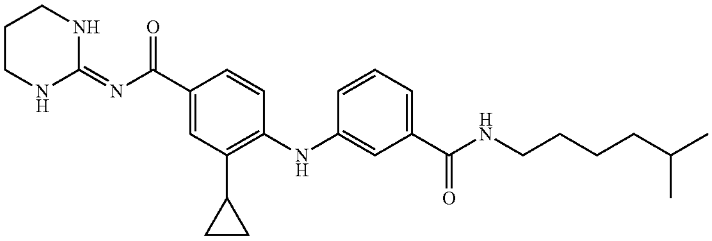 [SMILES: CC(C)CCCCNC(=O)c1cccc(Nc2ccc(C(=O)N=C3NCCCN3)cc2C2CC2)c1]
108
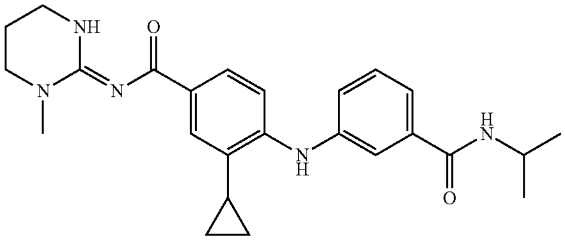 [SMILES: CC(C)NC(=O)c1cccc(Nc2ccc(C(=O)/N=C3\NCCCN3C)cc2C2CC2)c1]

TABLE I-continued
(Ic)
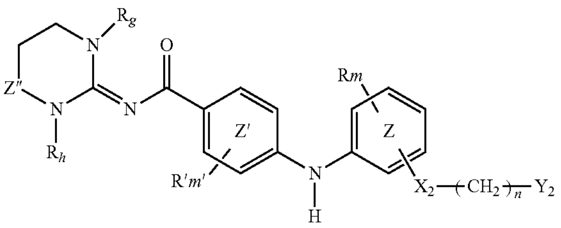
(Ic)
109
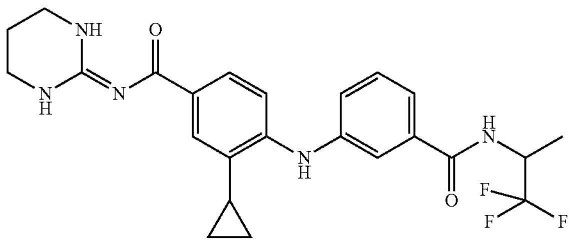 [SMILES: CC(NC(=O)c1cccc(Nc2ccc(C(=O)N=C3NCCCN3)cc2C2CC2)c1)C(F)(F)F]
110
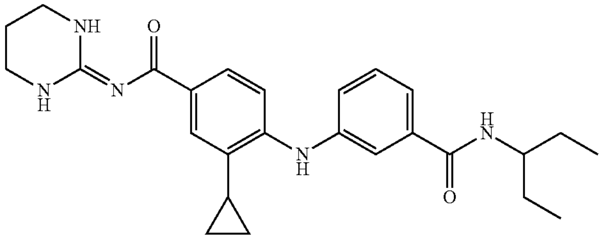 [SMILES: CCC(CC)NC(=O)c1cccc(Nc2ccc(C(=O)N=C3NCCCN3)cc2C2CC2)c1]
111
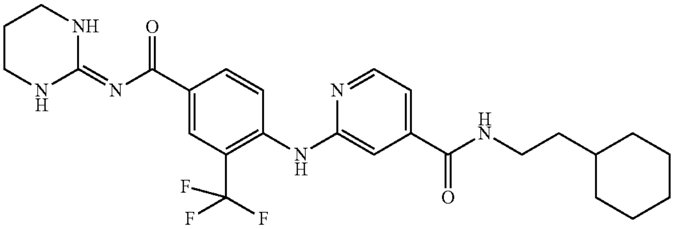 [SMILES: O=C(N=C1NCCCN1)c1ccc(Nc2cc(C(=O)NCCC3CCCCC3)ccn2)c(C(F)(F)F)c1]
112
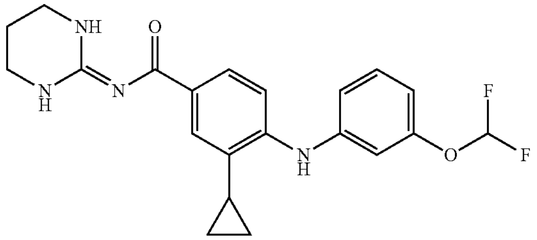 [SMILES: O=C(N=C1NCCCN1)c1ccc(Nc2cccc(OC(F)F)c2)c(C2CC2)c1]
113
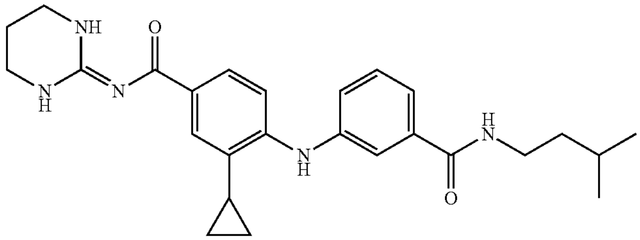 [SMILES: CC(C)CCNC(=O)c1cccc(Nc2ccc(C(=O)N=C3NCCCN3)cc2C2CC2)c1]

TABLE I-continued
(Ic)
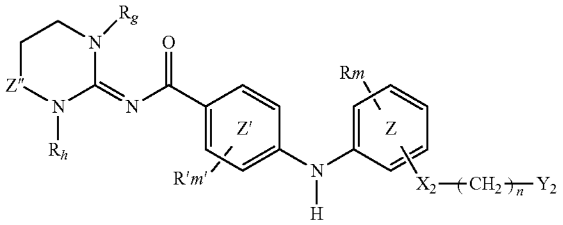
(Ic)
114
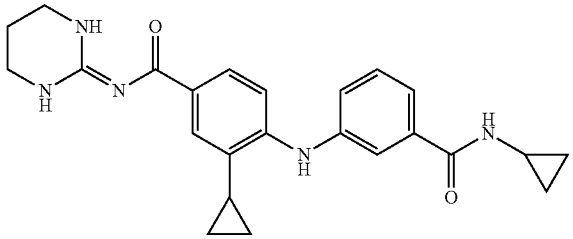 [SMILES: O=C(N=C1NCCCN1)c1ccc(Nc2cccc(C(=O)NC3CC3)c2)c(C2CC2)c1]
115
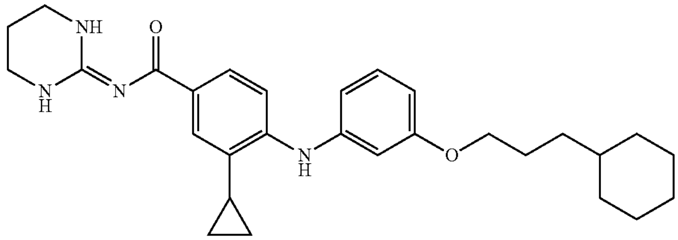 [SMILES: O=C(N=C1NCCCN1)c1ccc(Nc2cccc(OCCCC3CCCCC3)c2)c(C2CC2)c1]
116
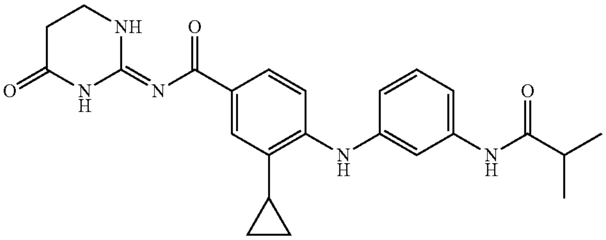 [SMILES: CC(C)C(=O)Nc1cccc(Nc2ccc(C(=O)/N=C3\NCCC(=O)N3)cc2C2CC2)c1]
117
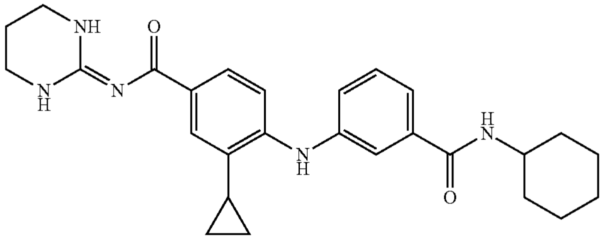 [SMILES: O=C(N=C1NCCCN1)c1ccc(Nc2cccc(C(=O)NC3CCCCC3)c2)c(C2CC2)c1]
118
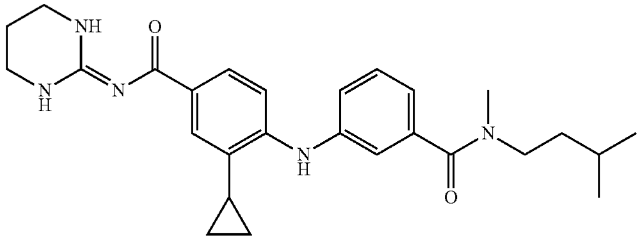 [SMILES: CC(C)CCN(C)C(=O)c1cccc(Nc2ccc(C(=O)N=C3NCCCN3)cc2C2CC2)c1]

TABLE I-continued
(Ic)
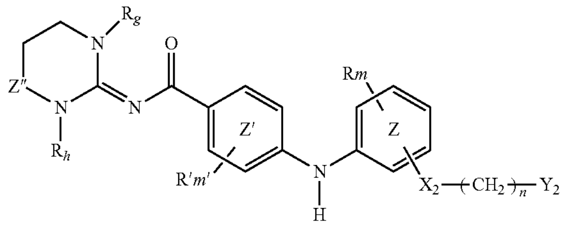
(Ic)
119
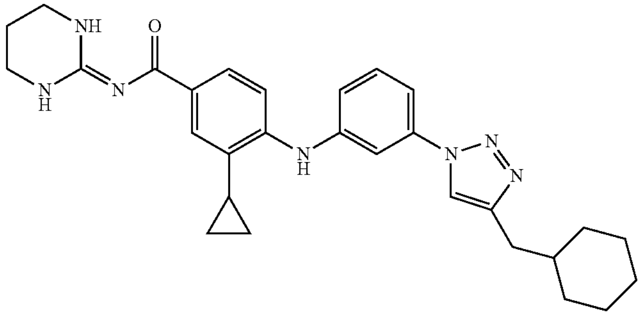 [SMILES: O=C(N=C1NCCCN1)c1ccc(Nc2cccc(-n3cc(CC4CCCCC4)nn3)c2)c(C2CC2)c1]
120
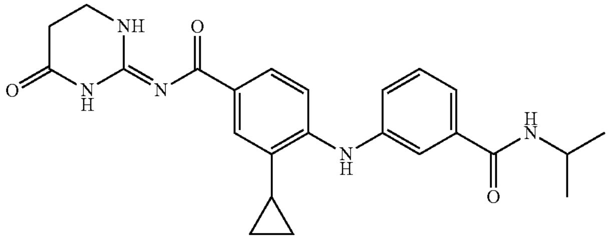 [SMILES: CC(C)NC(=O)c1cccc(Nc2ccc(C(=O)/N=C3\NCCC(=O)N3)cc2C2CC2)c1]
121
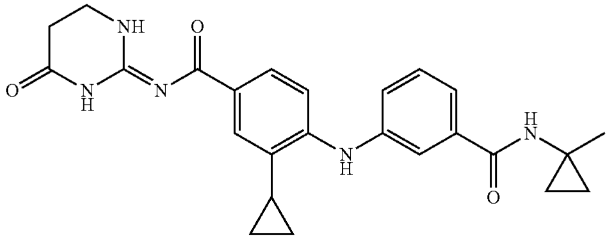 [SMILES: CC1(NC(=O)c2cccc(Nc3ccc(C(=O)/N=C4\NCCC(=O)N4)cc3C3CC3)c2)CC1]
122
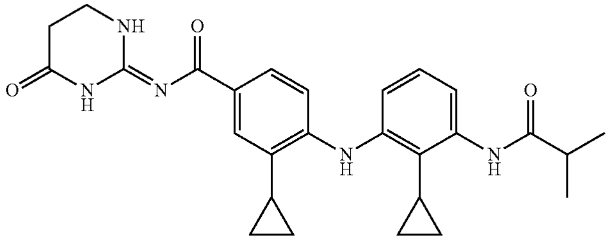 [SMILES: CC(C)C(=O)Nc1cccc(Nc2ccc(C(=O)/N=C3\NCCC(=O)N3)cc2C2CC2)c1C1CC1]
123
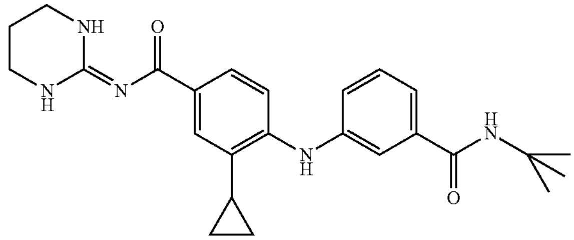 [SMILES: CC(C)(C)NC(=O)c1cccc(Nc2ccc(C(=O)N=C3NCCCN3)cc2C2CC2)c1]

TABLE I-continued
(Ic)
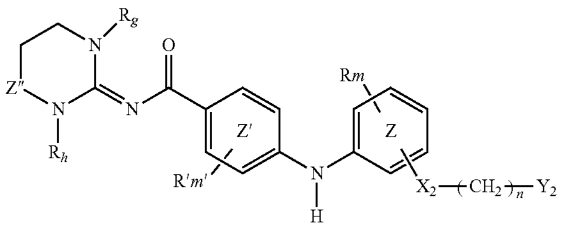
(Ic)
124
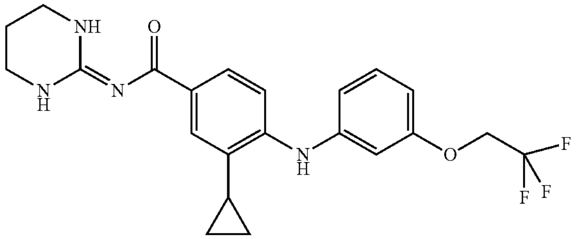 [SMILES: O=C(N=C1NCCCN1)c1ccc(Nc2cccc(OCC(F)(F)F)c2)c(C2CC2)c1]
125
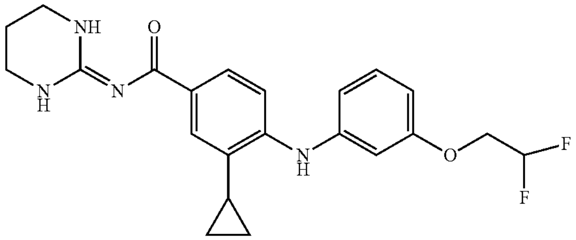 [SMILES: O=C(N=C1NCCCN1)c1ccc(Nc2cccc(OCC(F)F)c2)c(C2CC2)c1]
126
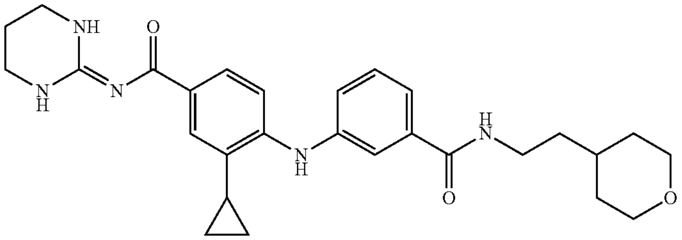 [SMILES: O=C(N=C1NCCCN1)c1ccc(Nc2cccc(C(=O)NCCC3CCOCC3)c2)c(C2CC2)c1]
127
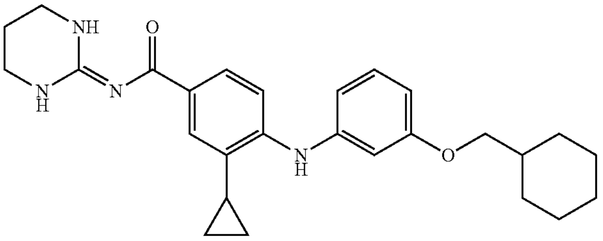 [SMILES: O=C(N=C1NCCCN1)c1ccc(Nc2cccc(OCC3CCCCC3)c2)c(C2CC2)c1]
128
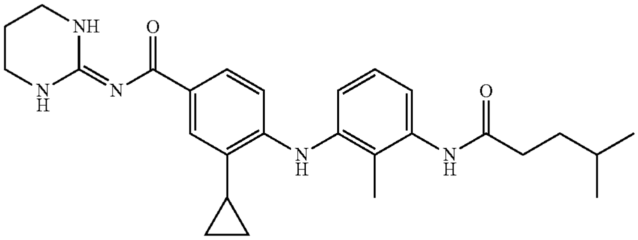 [SMILES: Cc1c(NC(=O)CCC(C)C)cccc1Nc1ccc(C(=O)N=C2NCCCN2)cc1C1CC1]

TABLE I-continued
(Ic)
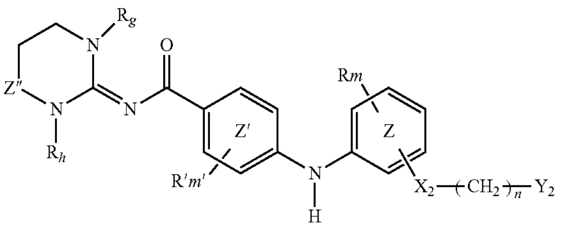
(Ic)
129
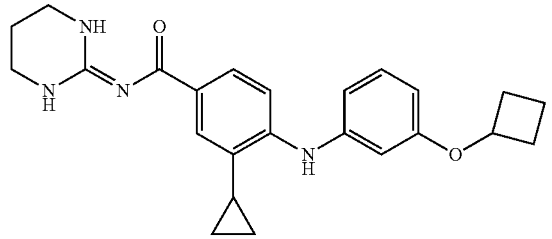 [SMILES: O=C(N=C1NCCCN1)c1ccc(Nc2cccc(OC3CCC3)c2)c(C2CC2)c1]
130
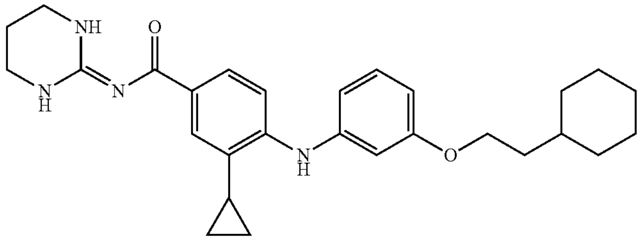 [SMILES: O=C(N=C1NCCCN1)c1ccc(Nc2cccc(OCCC3CCCCC3)c2)c(C2CC2)c1]
131
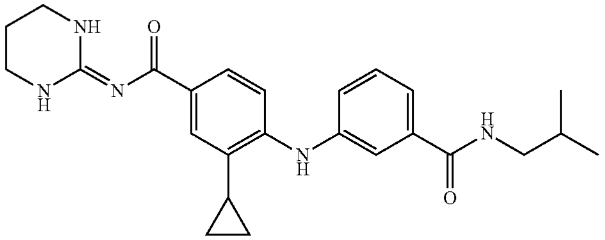 [SMILES: CC(C)CNC(=O)c1cccc(Nc2ccc(C(=O)N=C3NCCCN3)cc2C2CC2)c1]
132
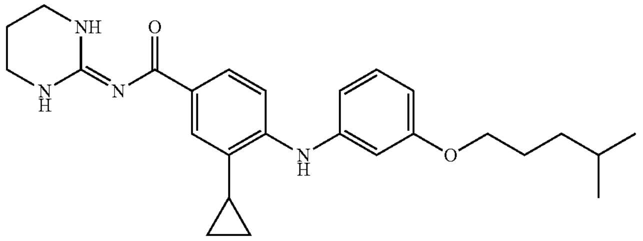 [SMILES: CC(C)CCCOc1cccc(Nc2ccc(C(=O)N=C3NCCCN3)cc2C2CC2)c1]
133
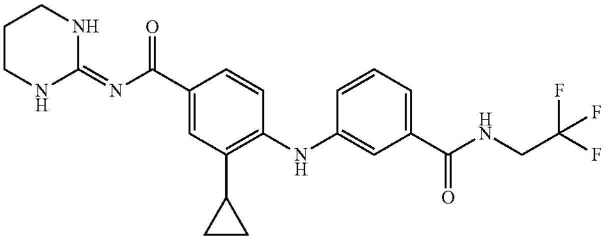 [SMILES: O=C(N=C1NCCCN1)c1ccc(Nc2cccc(C(=O)NCC(F)(F)F)c2)c(C2CC2)c1]

TABLE I-continued
(Ic)
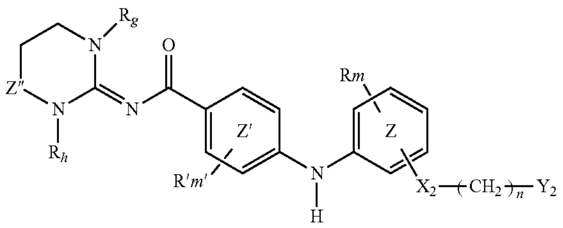
(Ic)
134
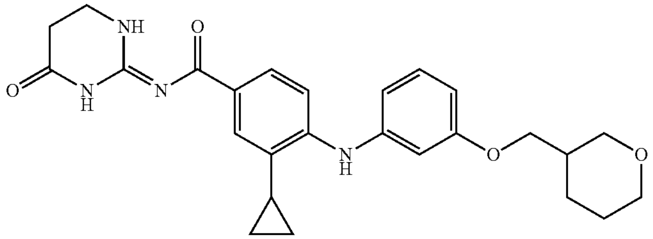
135
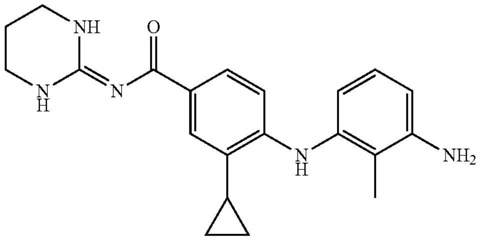 [SMILES: Cc1c(N)cccc1Nc1ccc(C(=O)N=C2NCCCN2)cc1C1CC1]
136
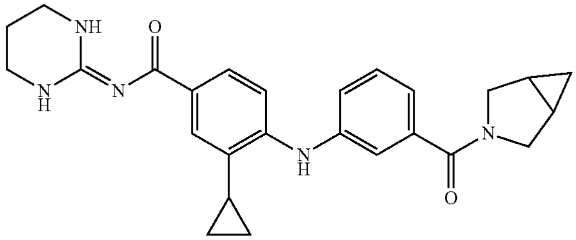 [SMILES: O=C(N=C1NCCCN1)c1ccc(Nc2cccc(C(=O)N3CC4CC4C3)c2)c(C2CC2)c1]
137
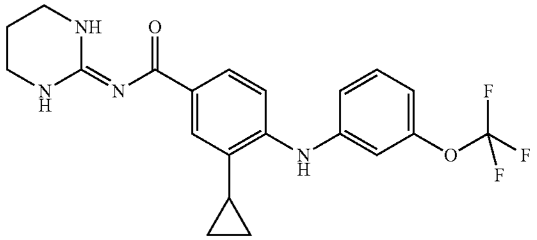 [SMILES: O=C(N=C1NCCCN1)c1ccc(Nc2cccc(OC(F)(F)F)c2)c(C2CC2)c1]
138
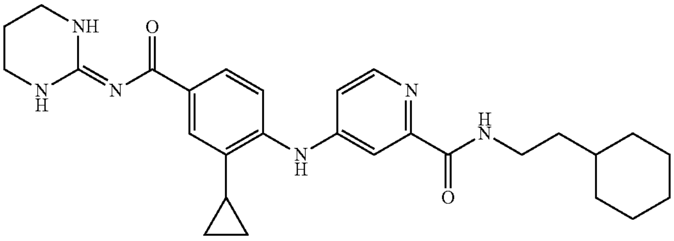 [SMILES: O=C(N=C1NCCCN1)c1ccc(Nc2ccnc(C(=O)NCCC3CCCCC3)c2)c(C2CC2)c1]

TABLE I-continued
(Ic)
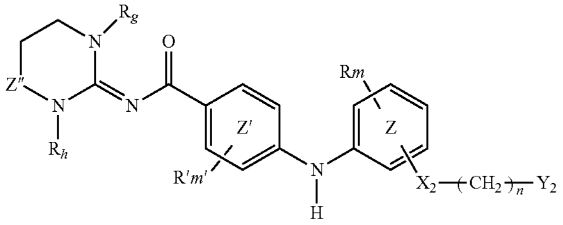
(Ic)
139
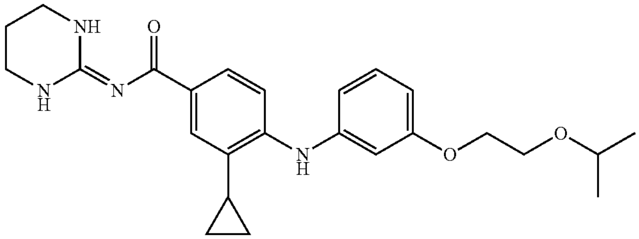 [SMILES: CC(C)OCCOc1cccc(Nc2ccc(C(=O)N=C3NCCCN3)cc2C2CC2)c1]
140
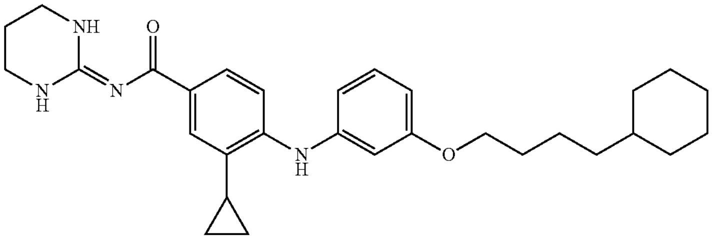 [SMILES: O=C(N=C1NCCCN1)c1ccc(Nc2cccc(OCCCCC3CCCCC3)c2)c(C2CC2)c1]
141
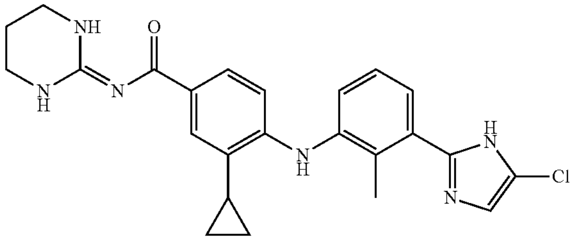 [SMILES: Cc1c(Nc2ccc(C(=O)N=C3NCCCN3)cc2C2CC2)cccc1-c1ncc(Cl)[nH]1]
142
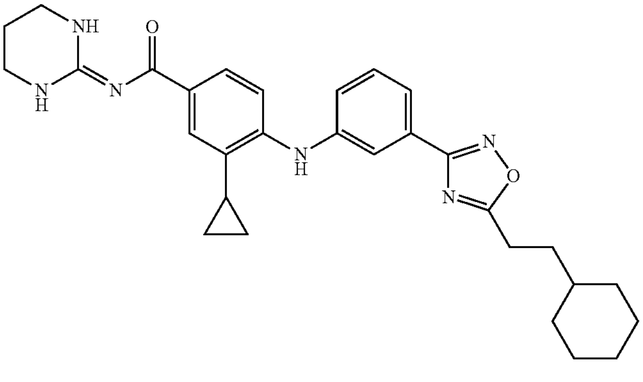 [SMILES: O=C(N=C1NCCCN1)c1ccc(Nc2cccc(-c3noc(CCC4CCCCC4)n3)c2)c(C2CC2)c1]

TABLE I-continued
(Ic)
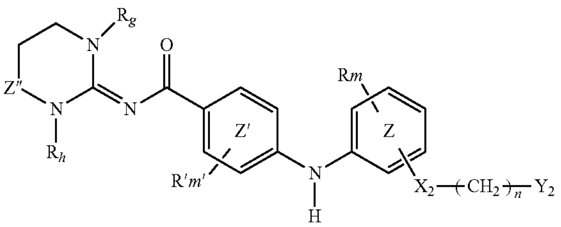
(Ic)
143
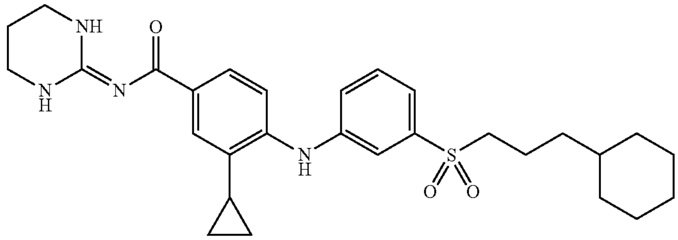 [SMILES: O=C(N=C1NCCCN1)c1ccc(Nc2cccc(S(=O)(=O)CCCC3CCCCC3)c2)c(C2CC2)c1]
144
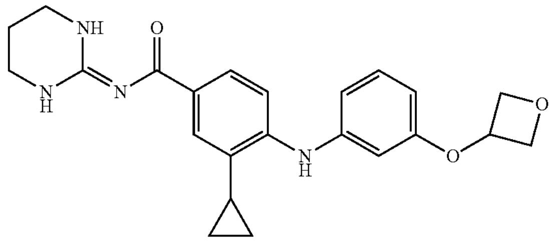 [SMILES: O=C(N=C1NCCCN1)c1ccc(Nc2cccc(OC3COC3)c2)c(C2CC2)c1]
145
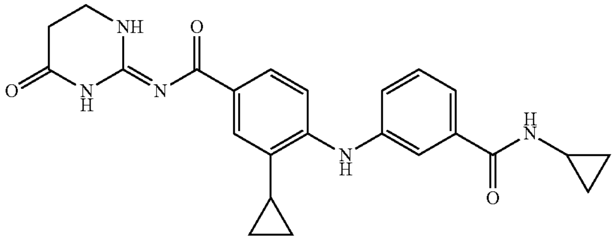 [SMILES: O=C1CCN/C(=N\C(=O)c2ccc(Nc3cccc(C(=O)NC4CC4)c3)c(C3CC3)c2)N1]
146
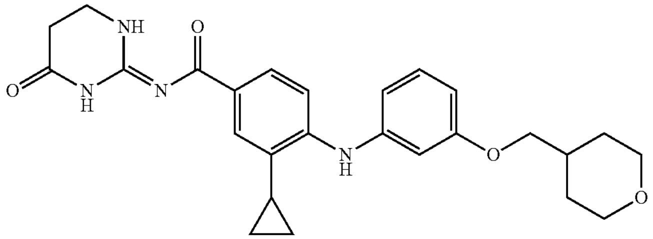 [SMILES: O=C1CCN/C(=N\C(=O)c2ccc(Nc3cccc(OCC4CCOCC4)c3)c(C3CC3)c2)N1]
147
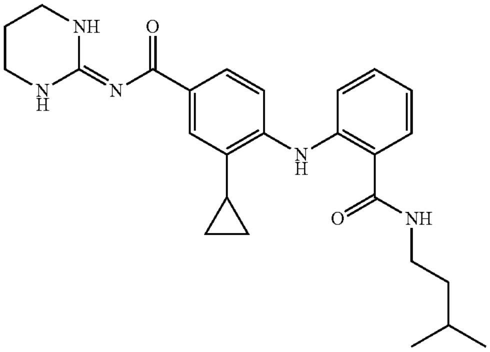 [SMILES: CC(C)CCNC(=O)c1ccccc1Nc1ccc(C(=O)N=C2NCCCN2)cc1C1CC1]

TABLE I-continued
(Ic)
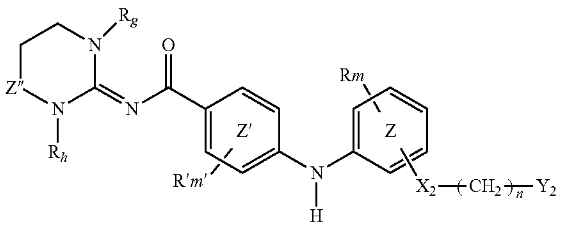
(Ic)
148
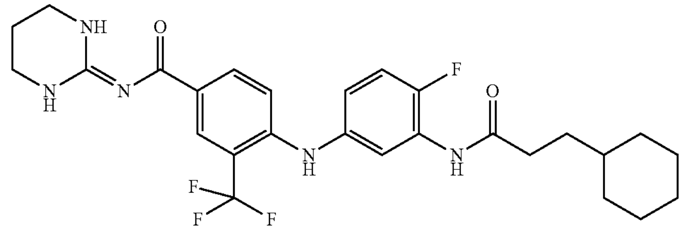 [SMILES: O=C(CCC1CCCCC1)Nc1cc(Nc2ccc(C(=O)N=C3NCCCN3)cc2C(F)(F)F)ccc1F]
149
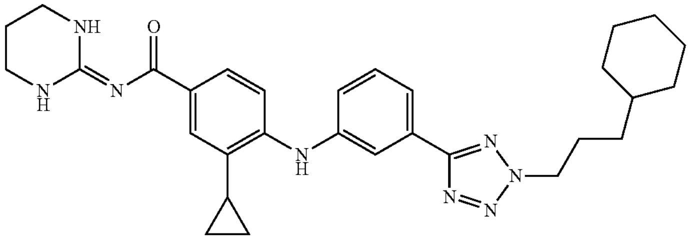 [SMILES: O=C(N=C1NCCCN1)c1ccc(Nc2cccc(-c3nnn(CCCC4CCCCC4)n3)c2)c(C2CC2)c1]
150
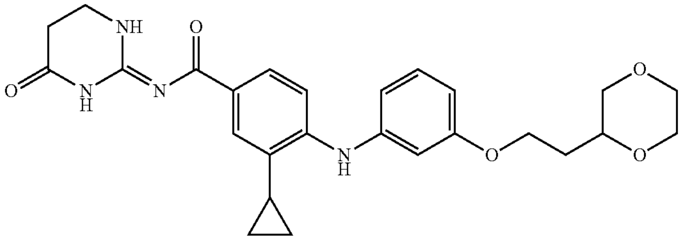 [SMILES: O=C1CCN/C(=N\C(=O)c2ccc(Nc3cccc(OCCC4COCCO4)c3)c(C3CC3)c2)N1]
151
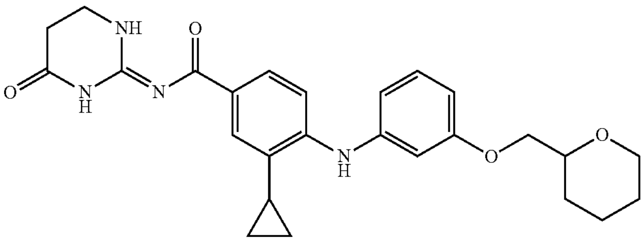 [SMILES: O=C1CCN/C(=N\C(=O)c2ccc(Nc3cccc(OCC4CCCCO4)c3)c(C3CC3)c2)N1]
152
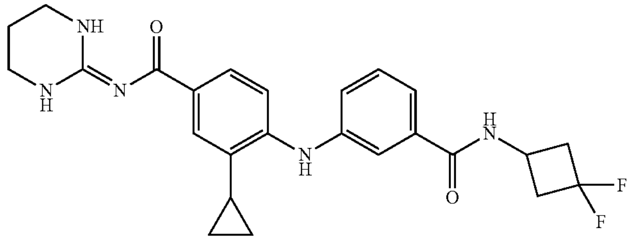 [SMILES: O=C(N=C1NCCCN1)c1ccc(Nc2cccc(C(=O)NC3CC(F)(F)C3)c2)c(C2CC2)c1]

TABLE I-continued
(Ic)
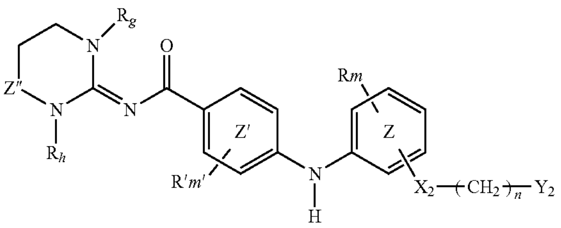
(Ic)
153
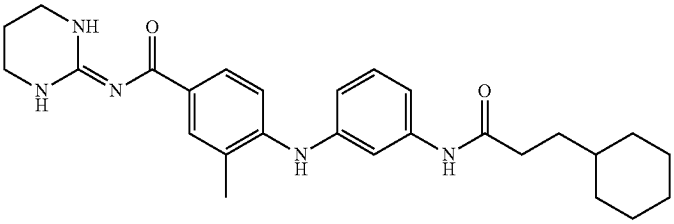 [SMILES: Cc1cc(C(=O)N=C2NCCCN2)ccc1Nc1cccc(NC(=O)CCC2CCCCC2)c1]
154
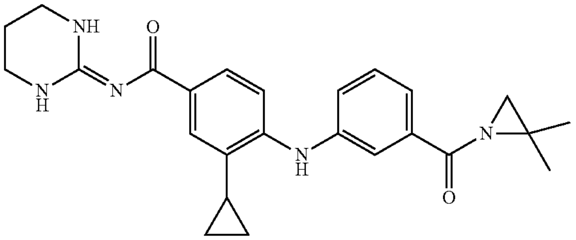 [SMILES: CC1(C)CN1C(=O)c1cccc(Nc2ccc(C(=O)N=C3NCCCN3)cc2C2CC2)c1]
155
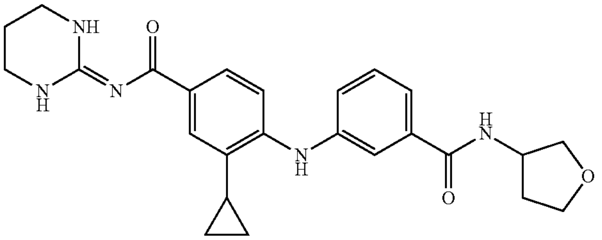 [SMILES: O=C(N=C1NCCCN1)c1ccc(Nc2cccc(C(=O)NC3CCOC3)c2)c(C2CC2)c1]
156
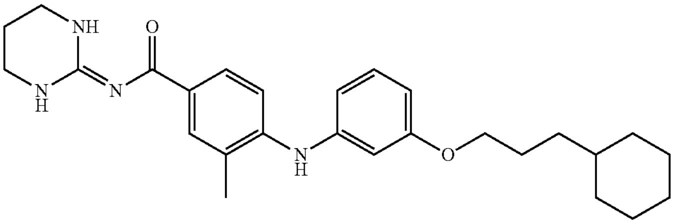 [SMILES: Cc1cc(C(=O)N=C2NCCCN2)ccc1Nc1cccc(OCCCC2CCCCC2)c1]
157
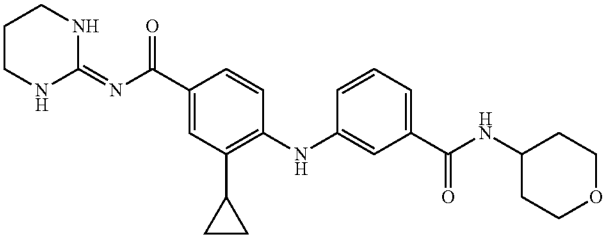 [SMILES: O=C(N=C1NCCCN1)c1ccc(Nc2cccc(C(=O)NC3CCOCC3)c2)c(C2CC2)c1]

TABLE I-continued
(Ic)
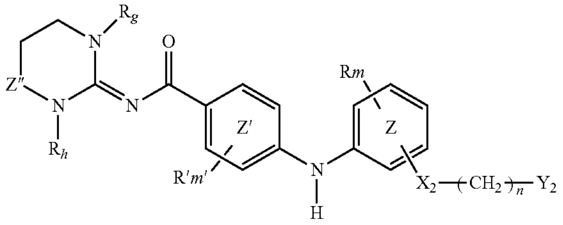
(Ic)
158
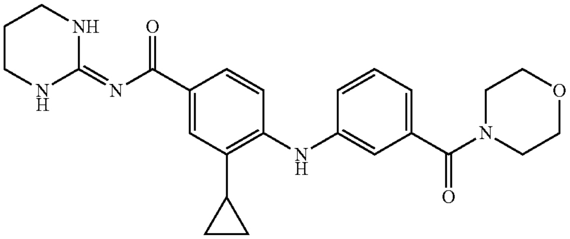 [SMILES: O=C(N=C1NCCCN1)c1ccc(Nc2cccc(C(=O)N3CCOCC3)c2)c(C2CC2)c1]
159
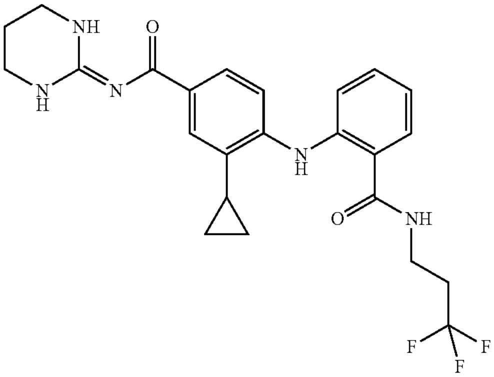 [SMILES: O=C(N=C1NCCCN1)c1ccc(Nc2ccccc2C(=O)NCCC(F)(F)F)c(C2CC2)c1]
160
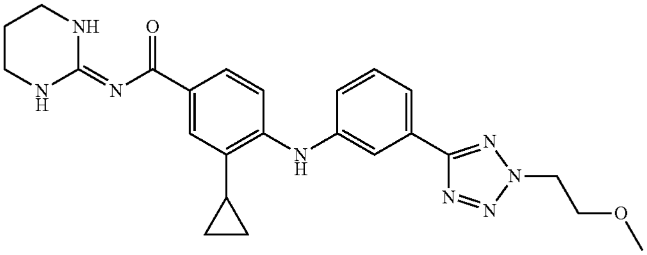 [SMILES: COCCn1nnc(-c2cccc(Nc3ccc(C(=O)N=C4NCCCN4)cc3C3CC3)c2)n1]
161
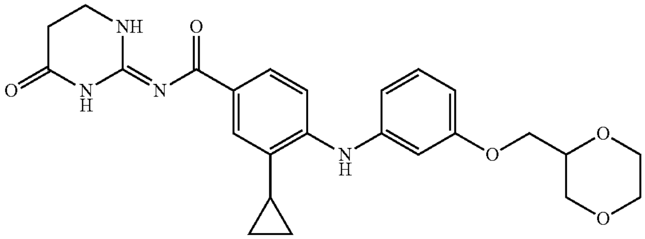

TABLE I-continued
(Ic)
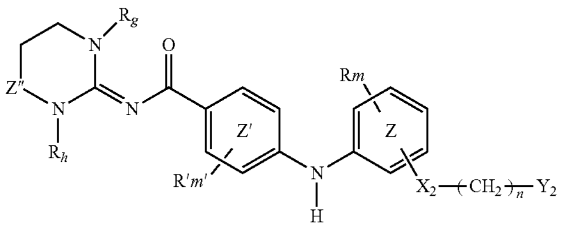
(Ic)
162
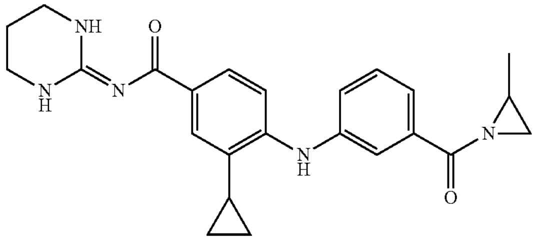 [SMILES: CC1CN1C(=O)c1cccc(Nc2ccc(C(=O)N=C3NCCCN3)cc2C2CC2)c1]
163
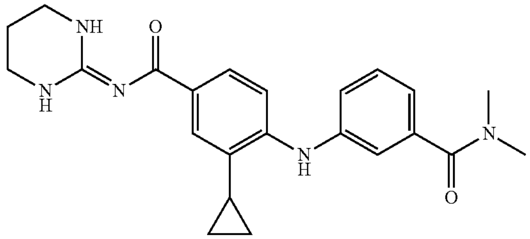 [SMILES: CN(C)C(=O)c1cccc(Nc2ccc(C(=O)N=C3NCCCN3)cc2C2CC2)c1]
164
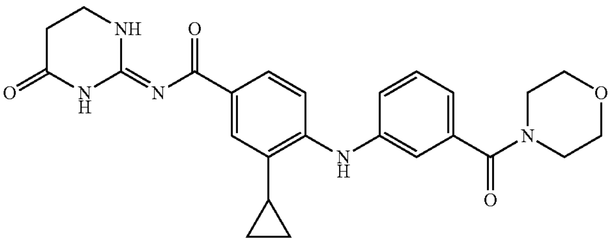 [SMILES: O=C1CCN/C(=N\C(=O)c2ccc(Nc3cccc(C(=O)N4CCOCC4)c3)c(C3CC3)c2)N1]
165
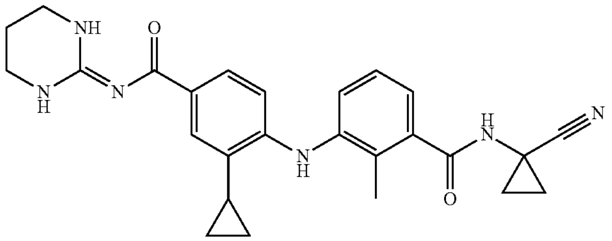 [SMILES: Cc1c(Nc2ccc(C(=O)N=C3NCCCN3)cc2C2CC2)cccc1C(=O)NC1(C#N)CC1]
166
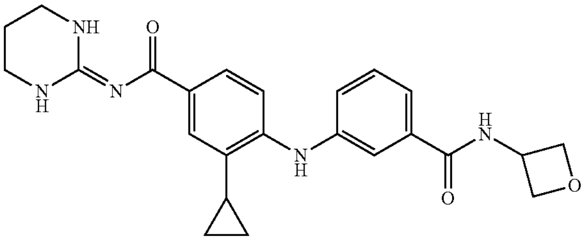 [SMILES: O=C(N=C1NCCCN1)c1ccc(Nc2cccc(C(=O)NC3COC3)c2)c(C2CC2)c1]

TABLE I-continued
(Ic)
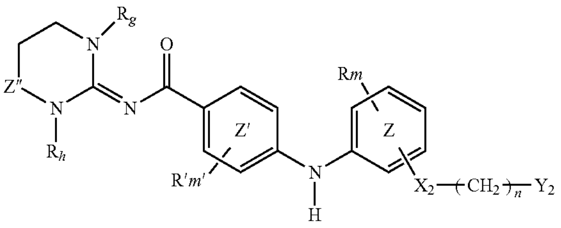
(Ic)
167
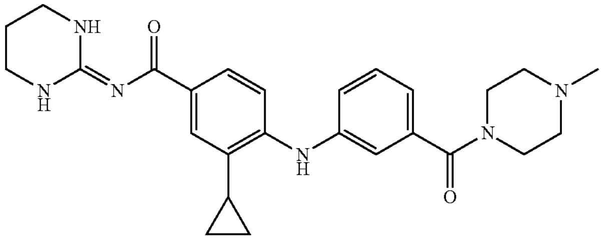 [SMILES: CN1CCN(C(=O)c2cccc(Nc3ccc(C(=O)N=C4NCCCN4)cc3C3CC3)c2)CC1]
168
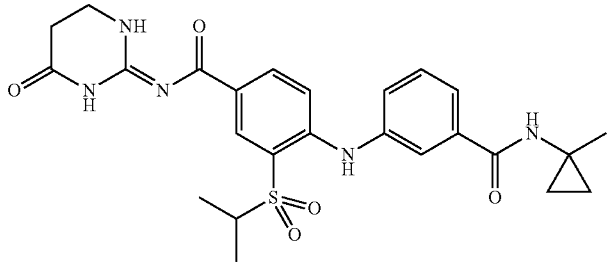 [SMILES: CC(C)S(=O)(=O)c1cc(C(=O)/N=C2\NCCC(=O)N2)ccc1Nc1cccc(C(=O)NC2(C)CC2)c1]
169
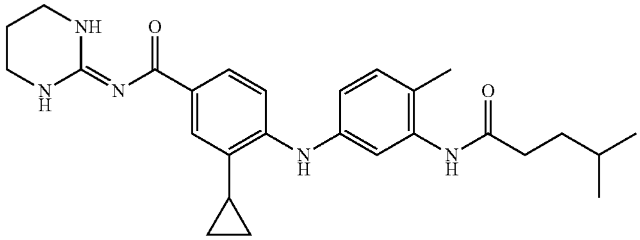 [SMILES: Cc1ccc(Nc2ccc(C(=O)N=C3NCCCN3)cc2C2CC2)cc1NC(=O)CCC(C)C]
170
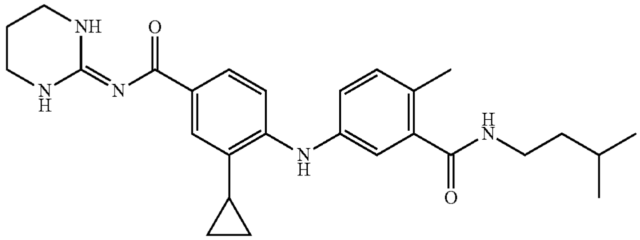 [SMILES: Cc1ccc(Nc2ccc(C(=O)N=C3NCCCN3)cc2C2CC2)cc1C(=O)NCCC(C)C]
171
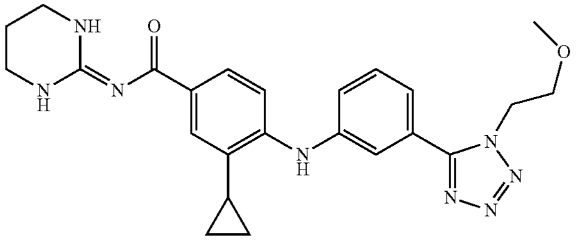 [SMILES: COCCn1nnnc1-c1cccc(Nc2ccc(C(=O)N=C3NCCCN3)cc2C2CC2)c1]

TABLE I-continued
(Ic)
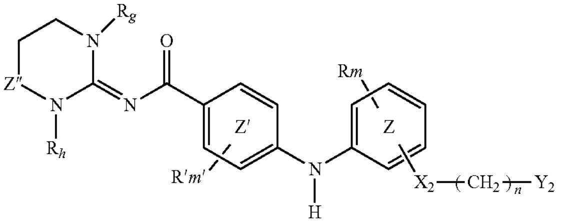
(Ic)
172
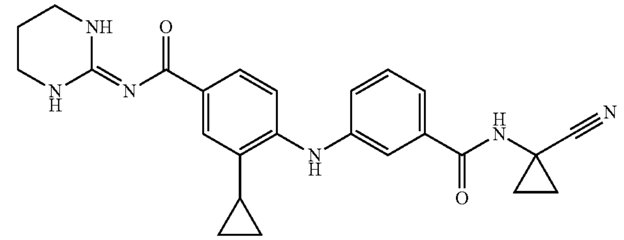 [SMILES: N#CC1(NC(=O)c2cccc(Nc3ccc(C(=O)N=C4NCCCN4)cc3C3CC3)c2)CC1]
173
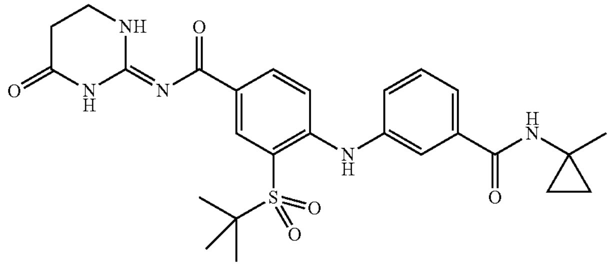 [SMILES: CC1(NC(=O)c2cccc(Nc3ccc(C(=O)/N=C4\NCCC(=O)N4)cc3S(=O)(=O)C(C)(C)C)c2)CC1]
174
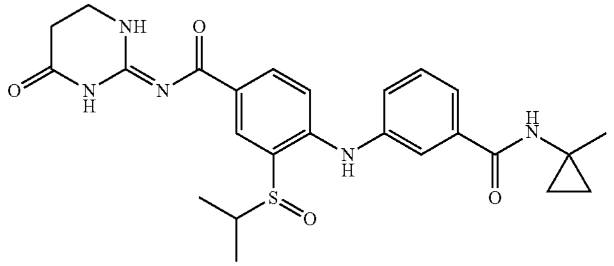 [SMILES: CC(C)S(=O)c1cc(C(=O)/N=C2\NCCC(=O)N2)ccc1Nc1cccc(C(=O)NC2(C)CC2)c1]
175
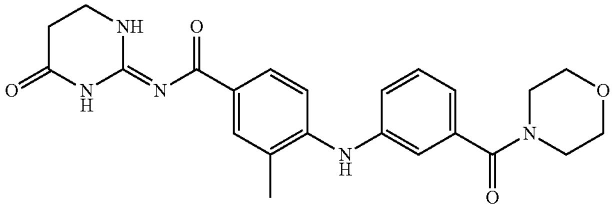 [SMILES: Cc1cc(C(=O)/N=C2\NCCC(=O)N2)ccc1Nc1cccc(C(=O)N2CCOCC2)c1]
176
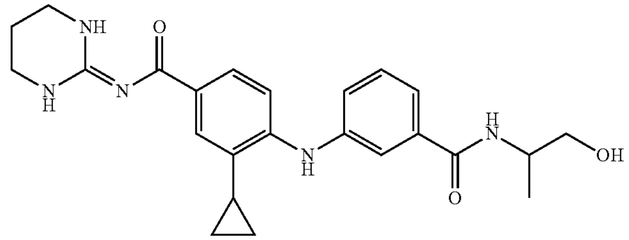 [SMILES: CC(CO)NC(=O)c1cccc(Nc2ccc(C(=O)N=C3NCCCN3)cc2C2CC2)c1]

TABLE I-continued
(Ic)
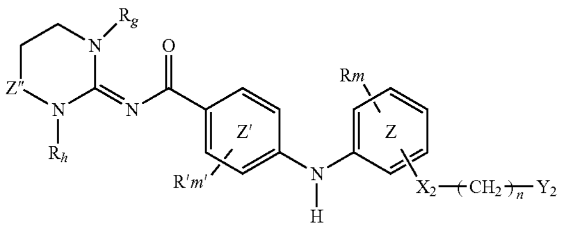
(Ic)
177
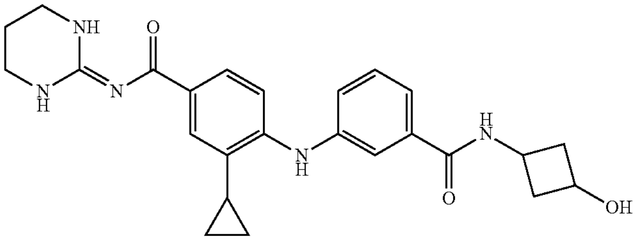 [SMILES: O=C(N=C1NCCCN1)c1ccc(Nc2cccc(C(=O)NC3CC(O)C3)c2)c(C2CC2)c1]
178
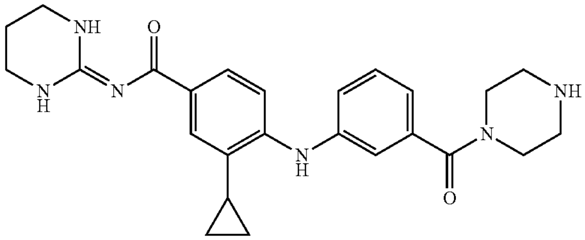 [SMILES: O=C(N=C1NCCCN1)c1ccc(Nc2cccc(C(=O)N3CCNCC3)c2)c(C2CC2)c1]
179
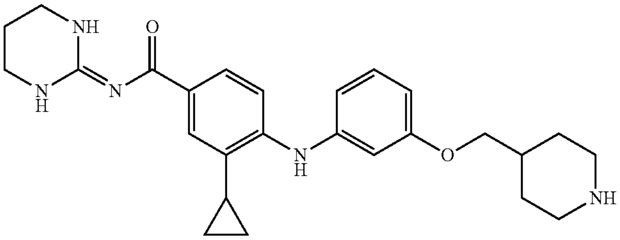 [SMILES: O=C(N=C1NCCCN1)c1ccc(Nc2cccc(OCC3CCNCC3)c2)c(C2CC2)c1]
180
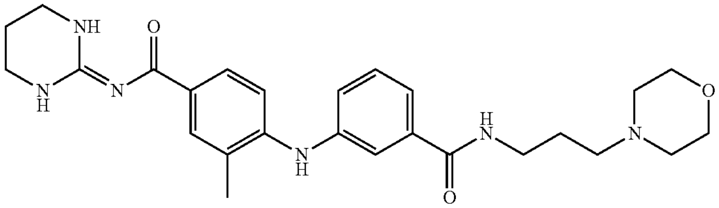 [SMILES: Cc1cc(C(=O)N=C2NCCCN2)ccc1Nc1cccc(C(=O)NCCCN2CCOCC2)c1]
181
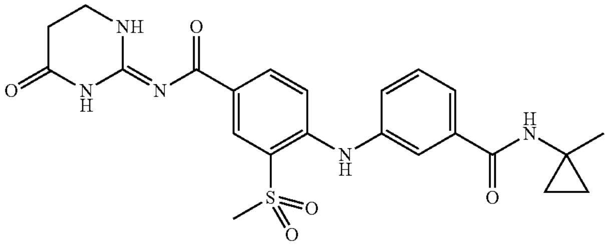 [SMILES: CC1(NC(=O)c2cccc(Nc3ccc(C(=O)/N=C4\NCCC(=O)N4)cc3S(C)(=O)=O)c2)CC1]

TABLE II

| Ex | Characterizations |
|---|---|
| 19 | $^{1}$H NMR (300 MHz, $CDCl_3$) δ 8.02 (d, J = 8.6 Hz, 2H), 7.52 (s, 1H), 7.44-7.37 (m, 2H), 7.30-7.26 (m, 2H), 6.97 (d, J = 8.7 Hz, 2H), 6.07 (s, 1H), 3.42 (t, J = 5.8 Hz, 4H), 2.95-2.90 (m, 2H), 2.06-1.94 (m, 2H), 2.03-1.95 (m, 4H), 1.58-1.39 (m, 5H), 1.03-0.94 (m, 2H). $[M + H]^+$ = 470.3 |
| 20 | $^{1}$H NMR (300 MHz, $d_6$-DMSO) δ 8.78 (s, 2H), 8.57 (s, 1H), 8.42 (t, J = 5.7 Hz, 1H), 7.93 (d, J = 8.6 Hz, 2H), 7.58 (s, 1H), 7.37-7.32 (m, 2H), 7.28-7.23 (m, 1H), 7.02 (d, J = 8.7 Hz, 2H), 3.35-3.25 (m, 4H), 3.17 (d, J = 6.3 Hz, 2H), 2.15 (dt, J = 14.7, 7.2 Hz, 1H), 1.86-1.78 (m, 2H), 1.72-1.45 (m, 6H), 1.32-1.19 (m, 2H). $[M + H]^+$ = 420.4 |
| 21 | $^{1}$H NMR (300 MHz, $d_6$-DMSO) δ 8.78 (s, 2H), 8.60 (s, 2H), 7.93 (d, J = 8.5 Hz, 2H), 7.60 (s, 1H), 7.40-7.33 (m, 2H), 7.30-7.23 (m, 1H), 7.03 (d, J = 8.6 Hz, 2H), 4.48 (d, J = 5.7 Hz, 2H), 4.20 (d, J = 5.7 Hz, 2H), 3.44 (d, J = 5.9 Hz, 2H), 3.35-3.27 (m, 4H), 1.84-1.78 (m, 2H), 1.26 (s, 2H). $[M + H]^+$ = 422.3 |
| 22 | $^{1}$H NMR (300 MHz, $d_6$-DMSO) δ 8.77 (s, 2H), 8.55 (s, 1H), 8.37 (t, J = 5.6 Hz, 1H), 7.93 (d, J = 8.7 Hz, 2H), 7.59 (s, 1H), 7.37-7.29 (m, 2H), 7.27-7.21 (m, 1H), 7.02 (d, J = 8.7 Hz, 2H), 3.51-3.39 (m, 1H), 3.29-3.22 (m, 6H), 1.84-1.75 (m, 5H), 1.58-1.47 (m, 7H). $^{13}$C NMR (75 MHz, $d_6$-DMSO) δ 175.0, 166.6, 159.1, 145.8, 143.1, 136.5, 131.1, 130.4, 129.6, 120.5, 119.7, 119.4, 116.9, 115.1, 38.6, 37.9, 35.9, 32.7, 25.2, 20.5 $[M + H]^+$ = 434.0 |
| 23 | $^{1}$H NMR (300 MHz, $d_6$-DMSO) δ 8.78 (s, 2H), 8.56 (s, 1H), 8.36 (t, J = 5.5 Hz, 1H), 7.93 (d, J = 8.7 Hz, 2H), 7.58 (s, 1H), 7.35-7.30 (m, 2H), 7.28-7.21 (m, 1H), 7.02 (d, J = 8.7 Hz, 2H), 3.30-3.23 (m, 6H), 1.88-1.76 (m, 2H), 1.61 (dq, J = 13.3, 6.7 Hz, 1H), 1.41 (dd, J = 14.4, 6.9 Hz, 2H), 0.91 (d, J = 6.6 Hz, 6H). |
| 24 | $^{1}$H NMR (300 MHz, $d_6$-DMSO) δ 8.77 (s, 2H), 8.55 (s, 1H), 8.34 (t, J = 5.4 Hz, 1H), 7.92 (d, J = 8.7 Hz, 2H), 7.57 (s, 1H), 7.33-7.28 (m, 2H), 7.28-7.20 (m, 1H), 7.01 (d, J = 8.7 Hz, 2H), 3.30-3.22 (m, 6H), 1.83-1.80 (m, 2H), 1.76-1.59 (m, 5H), 1.41 (dd, J = 14.3, 6.8 Hz, 2H), 1.32-1.12 (m, 4H), 0.94-0.84 (m, 2H). $[M + H]^+$ = 448.4 |
| 25 | $^{1}$H NMR (300 MHz, $CDCl_3$) δ 8.06 (d, J = 8.5 Hz, 2H), 7.52 (s, 1H), 7.33-7.24 (m, 2H), 7.03 (d, J = 8.6 Hz, 2H), 6.27 (s, 1H), 6.07 (s, 1H), 3.54 (dd, J = 12.9, 6.7 Hz, 2H), 3.33 (t, J = 5.7 Hz, 4H), 1.99-1.89 (m, 2H), 1.52 (q, J = 6.9 Hz, 2H), 0.79-0.64 (m, 1H), 0.49 (q, J = 5.4 Hz, 2H), 0.11 (q, J = 4.9 Hz, 2H). $[M + H]^+$ = 406.4 |
| 26 | $^{1}$H NMR (300 MHz, $d_6$-DMSO) δ 8.78 (s, 2H), 8.56 (s, 1H), 8.33 (t, J = 5.5 Hz, 1H), 7.93 (d, J = 8.6 Hz, 2H), 7.58 (s, 1H), 7.37-7.28 (m, 2H), 7.27-7.21 (m, 1H), 7.02 (d, J = 8.7 Hz, 2H), 3.29-3.27 (m, 4H), 3.16 (dd, J = 13.2, 6.5 Hz, 2H), 2.37-2.22 (m, 1H), 2.10-1.97 (m, 2H), 1.88-1.76 (m,4H), 1.65-1.58 (m, 4H). $[M + H]^+$ = 420.4 |
| 27 | $^{1}$H NMR (300 MHz, $d_6$-DMSO) δ 8.83 (s, 2H), 8.32 (t, J = 5.5 Hz, 1H), 7.88 (d, J = 1.3 Hz, 1H), 7.77 (dd, J = 8.3, 1.7 Hz, 1H), 7.70 (s, 1H), 7.50 (s, 1H), 7.34-7.27 (m, 2H), 7.16-7.10 (m, 2H), 3.32-3.20 (m, 6H), 2.24 (s, 3H), 1.88-1.79 (m, 2H), 1.61 (dt, J = 13.3, 6.7 Hz, 1H), 1.40 (dd, J = 14.4, 7.0 Hz, 2H), 0.90 (d, J = 6.6 Hz, 6H). $[M + H]^+$ = 422.4 |
| 28 | $^{1}$H NMR (300 MHz, $d_6$-DMSO) δ 8.80 (s, 1H), 8.33 (t, J = 5.6 Hz, 1H), 7.88 (d, J = 1.2 Hz, 1H), 7.77 (dd, J = 8.4, 1.7 Hz, 1H), 7.68 (s, 1H), 7.49 (s, 1H), 7.32-7.28 (m, 2H), 7.15-7.10 (m, 2H), 3.32-3.19 (m, 6H), 2.23 (s, 3H), 1.84-1.77 (m, 5H), 1.64-1.45 (m, 6H), 1.09-1.04 (m, 2H). $[M + H]^+$ = 448.4 |
| 29 | $^{1}$H NMR (300 MHz, $CDCl_3$) δ 8.00 (d, J = 7.9 Hz, 2H), 7.53 (s, 1H), 7.46-7.19 (m, 2H), 6.94 (d, J = 8.1 Hz, 2H), 6.18 (s, 1H), 3.41 (s, 4H), 2.91 (t, J = 7.0 Hz, 2H), 1.98 (s, 2H), 1.61-1.47 (m, 1H), 1.34-1.24 (m, 2H), 0.81 (d, J = 6.4 Hz, 6H). $[M + H]^+$ = 444.3 |
| 30 | $^{1}$H NMR (300 MHz, $d_6$-DMSO) δ 8.78 (s, 2H), 8.57 (s, 1H), 8.10 (d, J = 8.3 Hz, 1H), 7.93 (d, J = 8.6 Hz, 2H), 7.57 (s, 1H), 7.33 (d, J = 5.0 Hz, 2H), 7.30-7.25 (m, 1H), 7.02 (d, J = 8.7 Hz, 2H), 4.06-3.94 (m, 1H), 3.31-3.27 (d, J = 4.9 Hz, 4H), 1.88-1.78 (m, 1H), 1.59-1.51 (m, 1H), 1.50-1.40 (m, 1H), 1.37-1.28 (m, 2H), 1.12 (d, J = 6.6 Hz, 3H), 0.88 (t, J = 7.2 Hz, 3H). $[M + H]^+$ = 408.4 |
| 31 | $^{1}$H NMR (300 MHz, $d_6$-DMSO) δ 8.81 (s, 1H), 7.99 (s, 1H), 7.91 (s, 1H), 7.81 (d, J = 9.9 Hz, 1H), 7.50 (t, J = 5.4 Hz, 1H), 7.40 (t, J = 7.9 Hz, 1H), 7.35 (s, 1H), 7.18-7.14 (m, 3H), 3.51-3.39 (m, 1H), 3.32-3.28 (m, 4H), 2.78-2.72 (m, 2H), 2.23 (s, 3H), 1.88-1.78 (m, 2H), 1.70-1.60 (m, 2H), 1.57-1.33 (m, 6H). $[M + H]^+$ = 484.4 |
| 91 | $^{1}$H NMR (400 MHz, DMSO-d6) δ 10.80 (s, 1H), 10.18 (s, 1H), 7.87 (d, J = 5.3 Hz, 2H), 7.47 (s, 1H), 7.32 (td, J = 7.9, 3.6 Hz, 1H), 7.19 (t, J = 8.1 Hz, 1H), 7.03 (t, J = 8.6 Hz, 1H), 6.94 (d, J = 7.4 Hz, 1H), 4.63-4.18(m, 1H), 3.92 (s, 2H), 3.57-3.51 (m, 3H), 3.36 (dd, J = 16.4, 9.8 Hz, 2H), 3.22-2.94 (m, 1H), 2.62 (t, J = 7.0 Hz, 2H), 1.90 (s, 1H), 1.31-1.19 (m, 3H), 0.96 (d, J = 8.2 Hz, 2H), 0.64 (d, J = 4.0 Hz, 2H) $[M + H]^+$ = 510.0 |
| 92 | $^{1}$H NMR (400 MHz, DMSO-d6) δ 10.80 (s, 1H), 10.18 (s, 1H), 7.87 (d, J = 5.8 Hz, 2H), 7.48 (s, 1H), 7.32 (td, J = 7.7, 2.9 Hz, 1H), 7.22-7.15 (m, 1H), 7.01 (dd, J = 9.0, 2.5 Hz, 1H), 6.90 (d, J = 6.1 Hz, 1H), 4.46-4.27 (m, 1H), 3.96-3.69 (m, 1H), 3.55 (t, J = 6.9 Hz, 4H), 3.15 (s, 1.5H), 2.99-2.80 (m, 1H), 2.62 (t, J = 7.0 Hz, 2.5H), 1.89 (ddd, J = 13.8, 8.6, 5.5 Hz, 1H), 1.18-0.98 (m, 3H), 0.95 (d, J = 8.1 Hz, 2H), 0.64 (d, J = 4.7 Hz, 2H) $[M + H]^+$ = 510.0 |
| 93 | $^{1}$H NMR (400 MHz, DMSO-d6) δ 10.80 (s, 1H), 10.18 (s, 1H), 7.86 (d, J = 10.6 Hz, 2H), 7.31 (s, 1H), 7.20 (t, J = 8.2 Hz, 1H), 7.01 (d, J = 8.3 Hz, 1H), 6.85 (d, J = 8.1 Hz, 1H), 6.78 (d, J = 8.3 Hz, 1H), 4.07 (qd, J = 10.6, 4.9 Hz, 2H), 3.95-3.83 (m, 2H), 3.78 (d, J = 2.7 Hz, 1H), 3.72-3.60 (m, 2H), 3.59-3.43 (m, 4H), 2.62 (t, J = 7.0 Hz, 2H), 1.88 (ddd, J = 13.7, 8.3, 5.4 Hz, 1H), 1.01-0.92 |

TABLE II-continued

| Ex | Characterizations |
|---|---|
| | (m, 2H), 0.63 (q, J = 5.5 Hz, 2H)<br>$[M + H]^+$ = 498.9 |
| 94 | $^1$H NMR (400 MHz, DMSO-d6) δ 10.83 (s, 1H), 10.21 (s, 1H), 9.48 (s, 1H), 8.27 (d, J = 1.9 Hz, 1H), 7.90 (dd, J = 8.2, 1.9 Hz, 1H), 7.18-7.10 (m, 2H), 7.06 (t, J = 8.0 Hz, 1H), 6.62 (t, J = 2.1 Hz, 1H), 6.59-6.54 (m, 1H), 6.53-6.48 (m, 1H), 3.56 (t, J = 7.1 Hz, 2H), 3.06-2.97 (m, 2H), 2.63 (t, J = 7.1 Hz, 2H), 1.62-1.47 (m, 3H), 1.39 (s, 9H), 0.80 (d, J = 6.4 Hz, 6H)<br>$[M + H]^+$ = 514.0 |
| 95 | $^1$H NMR (400 MHz, DMSO-d6) δ 10.80 (s, 1H), 10.18 (s, 1H), 7.87 (d, J = 5.9 Hz, 2H), 7.48 (s, 1H), 7.32 (t, J = 7.8 Hz, 1H), 7.18 (d, J = 7.9 Hz, 1H), 7.02 (d, J = 8.9 Hz, 1H), 6.94 (d, J = 7.4 Hz, 1H), 3.67 (s, 4H), 3.56 (d, J = 5.7 Hz, 4H), 3.20 (d, J = 5.1 Hz, 2H), 2.62 (t, J = 7.0 Hz, 2H), 1.89 (t, J = 5.2 Hz, 1H), 0.95 (d, J = 8.4 Hz, 2H), 0.64 (d, J = 4.5 Hz, 2H)<br>$[M + H]^+$ = 495.9 |
| 96 | $^1$H NMR (500 MHz, DMSO-d6) δ 8.75 (s, 2H), 8.20 (t, J = 5.7 Hz, 1H), 7.75-7.67 (m, 2H), 7.17 (t, J = 7.7 Hz, 1H), 7.09 (d, J = 7.8 Hz, 1H), 7.04 (s, 1H), 6.96 (d, J = 7.4 Hz, 1H), 6.57 (d, J = 8.4 Hz, 1H), 3.29-3.21 (m, 6H), 2.15 (s, 3H), 1.87 (ddd, J = 13.8, 8.4, 5.5 Hz, 1H), 1.81 (q, J = 5.8 Hz, 2H), 1.65 (dp, J = 13.4, 6.6 Hz, 1H), 1.41 (q, J = 7.0 Hz, 2H), 0.96-0.92 (m, 2H), 0.91 (d, J = 6.6 Hz, 6H), 0.59-0.55 (m, 2H)<br>$[M + H]^+$ = 462.4 |
| 97 | $^1$H NMR (400 MHz, DMSO-d6) δ 10.78 (s, 1H), 10.15 (s, 1H), 7.85-7.77 (m, 2H), 7.67 (s, 1H), 7.15 (t, J = 8.4 Hz, 2H), 6.70 (d, J = 7.9 Hz, 1H), 6.67 (t, J = 2.1 Hz, 1H), 6.47 (dd, J = 8.1, 2.1 Hz, 1H), 3.90 (t, J = 6.5 Hz, 2H), 3.54 (t, J = 7.0 Hz, 2H), 2.61 (t, J = 7.0 Hz, 2H), 1.94 (ddd, J = 13.7, 8.4, 5.5 Hz, 1H), 1.69 (t, J = 14.5 Hz, 7H), 1.34-1.08 (m, 6H), 1.02-0.81 (m, 4H), 0.61 (q, J = 5.8 Hz, 2H)<br>$^{13}$C NMR (151 MHz, DMSO) δ 160.0, 157.6, 146.3, 144.8, 131.0, 130.2, 128.0, 115.7, 111.4, 107.5, 105.4, 68.0, 37.2, 36.8, 33.7, 33.3, 30.5, 26.6, 26.5, 26.3, 11.5, 7.6<br>$[M + H]^+$ = 489.1 |
| 98 | $^1$H NMR (400 MHz, DMSO-d6) δ 10.83 (s, 1H), 10.21 (s, 1H), 8.27 (d, J = 1.8 Hz, 1H), 8.04 (d, J = 7.8 Hz, 1H), 7.90 (dd, J = 8.2, 1.8 Hz, 1H), 7.29 (s, 1H), 7.18 (s, 3H), 7.13 (d, J = 8.2 Hz, 1H), 6.90-6.82 (m, 1H), 4.06 (dq, J = 13.3, 6.6 Hz, 1H), 3.56 (t, J = 7.0 Hz, 2H), 2.63 (t, J = 7.0 Hz, 2H), 1.41 (s, 9H), 1.14 (d, J = 6.6 Hz, 6H)<br>$^{13}$C NMR (151 MHz, DMSO) δ 177.4, 170.2, 166.1, 157.8, 147.1, 145.0, 144.0, 136.5, 133.5, 129.1, 128.7, 128.1, 126.6, 118.5, 117.3, 115.5, 41.3, 36.8, 35.2, 30.9, 30.5, 22.8<br>$[M + H]^+$ = 450.1 |
| 99 | $^1$H NMR (400 MHz, DMSO-d6) δ 8.77 (s, 2H), 8.52 (s, 1H), 7.78-7.66 (m, 3H), 7.49-7.45 (m, 1H), 7.28-7.22 (m, 2H), 7.17-7.11 (m, 1H), 7.08 (d, J = 8.4 Hz, 1H), 3.30-3.24 (m, 4H), 1.97-1.88 (m, 1H), 1.81 (d, J = 5.1 Hz, 2H), 1.34 (s, 3H), 0.95-0.88 (m, 2H), 0.73-0.67 (m, 2H), 0.60-0.53 (m, 4H)<br>$[M + H]^+$ = 432.2 |
| 100 | $^1$H NMR (400 MHz, DMSO-d6) δ 10.83 (s, 1H), 10.20 (s, 1H), 9.70 (s, 1H), 8.35 (d, J = 7.8 Hz, 1H), 8.27 (d, J = 1.7 Hz, 1H), 7.91 (dd, J = 8.3, 1.9 Hz, 1H), 7.66 (dd, J = 7.9, 1.5 Hz, 1H), 7.27 (t, J = 8.3 Hz, 2H), 6.98 (d, J = 7.7 Hz, 1H), 6.81-6.75 (m, 1H), 4.18-4.05 (m, 1H), 3.56 (t, J = 6.9 Hz, 2H), 2.63 (t, J = 7.0 Hz, 2H), 1.42 (s, 9H), 1.18 (d, J = 6.6 Hz, 6H)<br>$[M + H]^+$ = 450.3 |
| 101 | $^1$H NMR (400 MHz, DMSO-d6) δ 8.76 (s, 2H), 8.02 (d, J = 8.4 Hz, 1H), 7.77-7.72 (m, 2H), 7.68 (d, J = 1.8 Hz, 1H), 7.52-7.49 (m, 1H), 7.31-7.25 (m, 2H), 7.17-7.12 (m, 1H), 7.09 (d, J = 8.4 Hz, 1H), 3.94-3.85 (m, 1H), 3.29-3.24 (m, 4H), 1.97-1.89 (m, 1H), 1.85-1.76 (m, 2H), 1.57-1.41 (m, 2H), 1.11 (d, J = 6.8 Hz, 3H), 0.96-0.89 (m, 2H), 0.85 (t, J = 7.5 Hz, 3H), 0.60-0.53 (m, 2H)<br>$[M + H]^+$ = 434.3 |
| 102 | $^1$H NMR (400 MHz, DMSO-d6) δ 8.78 (s, 2H), 8.11 (d, J = 7.8 Hz, 1H), 7.80-7.67 (m, 3H), 7.54-7.49 (m, 1H), 7.32-7.26 (m, 2H), 7.16 (dt, J = 6.3, 2.5 Hz, 1H), 7.10 (d, J = 8.4 Hz, 1H), 4.08 (dq, J = 13.2, 6.6 Hz, 1H), 3.28 (t, J = 4.6 Hz, 4H), 1.95 (tt, J = 8.4, 5.4 Hz, 1H), 1.82 (t, J = 5.6 Hz, 2H), 1.15 (d, J = 6.6 Hz, 6H), 0.98-0.89 (m, 2H), 0.62-0.54 (m, 2H)<br>$^{13}$C NMR (151 MHz, DMSO) δ 175.1, 166.1, 159.2, 144.6, 144.5, 136.5, 132.6, 131.8, 129.2, 127.3, 127.0, 120.4, 119.0, 117.3, 116.7, 41.3, 38.5, 22.8, 20.4, 11.6, 7.8<br>$[M + H]^+$ = 450.1 |
| 103 | $^1$H NMR (500 MHz, DMSO-d6) δ ppm 9.75-8.45 (m, 2 H), 7.71 (dd, J = 8.51, 2.20 Hz, 1 H), 7.67 (d, J = 1.92 Hz, 1 H), 7.31-7.18 (m, 1 H), 7.17-7.12 (m, 1 H), 7.09 (d, J = 8.51 Hz, 1 H), 7.04-6.95 (m, 1 H), 6.93-6.74 (m, 1 H), 5.21-4.88 (m, 1 H), 4.62-4.32 (m, 1 H), 3.49-3.33 (m, 4H), 1.95 (tt, J = 8.27, 5.32 Hz, 1 H), 1.90-1.77 (m, 2 H), 1.58-1.42 (m, 2 H), 1.02-0.90 (m, 2 H), 0.73-1.71 (m, 15 H), 0.64 (br s, 2 H)<br>$[M + H]^+$ = 489.4 |
| 104 | $^1$H NMR (400 MHz, DMSO-d6) δ 8.80 (s, 2H), 8.33 (d, J = 5.1 Hz, 2H), 8.08 (d, J = 8.6 Hz, 1H), 7.79 (s, 1H), 7.59 (s, 1 H), 7.43 (d, J = 7.6 Hz, 1H), 7.35 (t, J = 7.8 Hz, 1H), 7.29-7.20 (m, 2H), 3.30-3.27 (m, 4H), 3.27-3.20 (m, 2H), 1.87-1.78 (m, 2H), 1.60 (dt, J = 13.3, 6.7 Hz, 1H), 1.40 (q, J = 7.0 Hz, 2H), 0.90 (d, J = 6.6 Hz, 6H)<br>$[M + H]^+$ = 476.2 |
| 105 | $^1$H NMR (400 MHz, DMSO-d6) δ 8.81-8.74 (m, 2H), 8.32 (t, J = 5.6 Hz, 1H), 7.79-7.67 (m, 3H), 7.52-7.49 (m, 1H), 7.32-7.25 (m, 2H), 7.18-7.13 (m, 1H), 7.10 (d, J = 8.4 Hz, 1H), 3.29-3.25 (m, 4H), 3.24 3.16 (m, 2H), 1.99-1.90 (m, 1H), 1.86-1.77 (m, 2H), 1.59-1.44 (m, 3H), 1.22-1.13 (m, 2H), 0.96-0.89 (m, 2H), 0.86 (d, J = 6.6 Hz, 6H), 0.60-0.54 (m, 2H)<br>$[M + H]^+$ = 462.4 |
| 106 | $^1$H NMR (500 MHz, DMSO-d6) δ 8.79 (s, 2H), 8.23 (s, 1H), 7.88-7.83 (m, 2H), 7.77 (dd, J = 8.0, 1.5 Hz, 1H), 7.60 7.55 (m, 1H), 7.36 (d, J = 8.3 Hz, 1H), 7.27-7.24 (m, 1H), 7.08 (t, J = 7.6 Hz, 1H), 3.27 (d, J = 8.0 Hz, 6H), 1.82 (p, J = 5.7 Hz, 2H), 1.77 (td, J = 8.4, 4.3 Hz, 1H), 1.62-1.50 (m, 5H), 1.46 (d, J = 13.4 Hz, 2H), 1.18-1.11 (m, 2H), 1.09-0.99 (m, 4H), 0.98-0.92 (m, 2H), 0.75-0.66 (m, 2H), 0.61-0.57 (m, 2H)<br>$[M + H]^+$ = 523.3 |

TABLE II-continued

| Ex | Characterizations |
|---|---|
| 107 | $^1$H NMR (400 MHz, DMSO-d6) δ 8.78 (s, 2H), 8.32 (t, J = 5.6 Hz, 1H), 7.79-7.73 (m, 2H), 7.70 (d, J = 1.9 Hz, 1H), 7.51 (d, J = 1.9 Hz, 1H), 7.32-7.25 (m, 2H), 7.16 (dt, J = 5.9, 2.7 Hz, 1H), 7.10 (d, J = 8.4 Hz, 1H), 3.29 (s, 4H), 3.26-3.16 (m, 2H), 1.99-1.90 (m, 1H), 1.88-1.76 (m, 2H), 1.59-1.43 (m, 3H), 1.35-1.22 (m, 2H), 1.22-1.13 (m, 2H), 0.98-0.90 (m, 2H), 0.86 (d, J = 6.6 Hz, 6H), 0.62 0.55 (m, 2H)<br>$[M + H]^+$ = 476.4 |
| 108 | $^1$H NMR (400 MHz, DMSO-d6) δ 10.32 (s, 1H), 8.12 (d, J = 7.7 Hz, 1H), 7.82 (dd, J = 8.3, 1.6 Hz, 1H), 7.78 (s, 1H), 7.71 (d, J = 1.3 Hz, 1H), 7.53 (s, 1H), 7.29 (d, J = 6.6 Hz, 2H), 7.17 (dt, J = 6.4, 2.1 Hz, 1H), 7.11 (d, J = 8.4 Hz, 1H), 4.08 (dq, J = 13.5, 6.7 Hz, 1H), 3.39-3.33 (m, 4H), 3.14 (s, 3H), 1.94 (dh, J = 23.7, 5.5 Hz, 3H), 1.15 (d, J = 6.6 Hz, 6H), 0.99-0.90 (m, 2H), 0.58 (q, J = 5.5 Hz, 2H)<br>$[M + H]^+$ = 434.1 |
| 109 | $^1$H NMR (400 MHz, DMSO-d6) δ 8.81-8.71 (m, 3H), 7.82 (s, 1H), 7.77 (dd, J = 1.8, 8.5 Hz, 1H), 7.70 (d, J = 1.8 Hz, 1H), 7.57-7.50 (m, 1H), 7.37-7.28 (m, 2H), 7.23-7.17 (m, 1H), 7.11 (d, J = 8.4 Hz, 1H), 4.91-4.76 (m, 1H), 3.30-3.26 (m, 4H), 1.99-1.91 (m, 1H), 1.87-1.78 (m, 2H), 1.35 (d, J = 7.0 Hz, 3H), 0.97-0.90 (m, 2H), 0.62-0.55 (m, 2H)<br>$[M + H]^+$ = 474.2 |
| 110 | $^1$H NMR (400 MHz, DMSO-d6) δ 8.78 (s, 2H), 7.93 (d, J = 8.6 Hz, 1H), 7.78-7.73 (m, 2H), 7.69 (d, J = 2.0 Hz, 1H), 7.53-7.50 (m, 1H), 7.33-7.25 (m, 2H), 7.16 (td, J = 2.4, 6.5 Hz, 1H), 7.10 (d, J = 8.6 Hz, 1H), 3.80-3.70 (m, 1H), 3.31-3.24 (m, 4H), 1.99-1.90 (m, 1H), 1.86-1.77 (m, 2H), 1.57-1.40 (m, 4H), 0.97-0.90 (m, 2H), 0.85 (t, J = 7.4 Hz, 6H), 0.61-0.54 (m, 2H)<br>$[M + H]^+$ = 448.2 |
| 111 | $^1$H NMR (400 MHz, DMSO-d6) δ 8.82 (s, 2H), 8.54 (t, J = 5.6 Hz, 1H), 8.46 (s, 1H), 8.37 (d, J = 1.9 Hz, 1H), 8.22-8.13 (m, 2H), 7.77 (d, J = 8.5 Hz, 1H), 7.32 (s, 1H), 7.12 (dd, J = 5.3, 1.3 Hz, 1H), 4.03 (q, J = 7.1 Hz, 0H), 3.31-3.22 (m, 6H), 1.83 (t, J = 5.5 Hz, 2H), 1.77-1.58 (m, 5H), 1.42 (q, J = 6.9 Hz, 2H), 1.35-1.26 (m, 1H), 1.23-1.10 (m, 3H), 0.90 (q, J = 10.5, 9.3 Hz, 2H)<br>$[M + H]^+$ = 517.2 |
| 112 | $^1$H NMR (500 MHz, DMSO-d6) d ppm 8.79 (br. s, 2 H), 7.87 (s, 1 H), 7.77 (dd, J = 8.23, 1.65 Hz, 1 H), 7.67 (d, J = 1.92 Hz, 1 H), 7.22 (t, J = 8.10 Hz, 1 H), 7.18-7.12 (m, 1 H), 7.16 (t, J = 74.60 Hz, 1 H), 6.85 (dd, J = 8.23, 1.92 Hz, 1 H), 6.74 (t, J = 2.20 Hz, 1 H), 6.57 (dd, J = 7.96, 2.20 Hz, 1 H), 3.30-3.25 (m, 4 H), 1.98-1.90 (m, 1 H), 1.81 (quin, J = 5.76 Hz, 2 H), 0.97-0.90 (m, 2 H), 0.64-0.53 (m, 2 H)<br>$[M + H]^+$ = 401.3 |
| 113 | $^1$H NMR (500 MHz, DMSO-d6) δ 8.77 (s, 2H), 8.28 (t, J = 5.6 Hz, 1H), 7.76 (dd, J = 8.4, 1.8 Hz, 1H), 7.73 (s, 1H), 7.69 (d, J = 1.7 Hz, 1H), 7.50 (s, 1H), 7.31-7.26 (m, 2H), 7.17-7.13 (m, 1H), 7.09 (d, J = 8.4 Hz, 1H), 3.26 (dd, J = 12.7, 6.3 Hz, 6H), 1.94 (ddd, J = 13.7, 8.4, 5.4 Hz, 1H), 1.81 (p, J = 5.8 Hz, 2H), 1.60 (dp, J = 13.4, 6.6 Hz, 1H), 1.40 (q, J = 7.0 Hz, 2H), 0.95-0.91 (m, 2H), 0.89 (d, J = 6.6 Hz, 6H), 0.60-0.54 (m, 2H)<br>$[M + H]^+$ = 448.4 |
| 114 | $^1$H NMR (400 MHz, DMSO-d6) δ 8.78 (s, 2H), 8.33 (d, J = 4.2 Hz, 1H), 7.84-7.64 (m, 3H), 7.56-7.46 (m, 1H), 7.34-7.23 (m, 2H), 7.16 (td, J = 2.3, 6.7 Hz, 1H), 7.10 (d, J = 8.4 Hz, 1H), 3.31-3.25 (m, 4H), 2.88-2.78 (m, 1H), 2.00-1.89 (m, 1H), 1.82 (quin, J = 5.7 Hz, 2H), 0.98-0.90 (m, 2H), 0.73-0.63 (m, 2H), 0.61-0.51 (m, 4H)<br>$[M + H]^+$ = 418.2 |
| 115 | $^1$H NMR (300 MHz, DMSO) δ 8.85 (bs, 1H), 7.75 (dd, J = 8.4, 1.8 Hz, 1H), 7.67 (d, J = 1.6 Hz, 1H), 7.63 (bs, 1H), 7.16-7.10 (m, 2H), 6.66 (d, J = 8.0 Hz, 1H), 6.62 (bs, 1H), 6.44 (d, J = 7.9 Hz, 1H), 3.89 (t, J = 6.4 Hz, 2H), 3.33-3.29 (m, 4H), 1.99-1.90 (m, 1H), 1.87-1.80 (m, 2H), 1.72-1.61 (m, 7H), 1.32-1.14 (m, 6H), 0.99-0.92 (m, 2H), 0.62-0.57 (m, 2H)<br>$[M + H]^+$ = 475.5 |
| 116 | $^1$H NMR (400 MHz, DMSO-d6) δ 10.79 (s, 1H), 10.17 (s, 1H), 9.73 (s, 1H), 7.82 (d, J = 8.4 Hz, 1H), 7.79 (s, 1H), 7.71 (s, 1H), 7.53 (s, 1H), 7.20-7.08 (m, 3H), 6.80 (d, J = 7.9 Hz, 1H), 3.54 (t, J = 7.0 Hz, 2H), 2.61 (t, J = 7.0 Hz, 2H), 2.59 (s, 1H), 1.95 (td, J = 8.4, 4.2 Hz, 1H), 1.08 (d, J = 6.8 Hz, 6H), 0.99-0.88 (m, 2H), 0.60 (q, J = 5.5 Hz, 2H)<br>$[M + H]^+$ = 434.0 |
| 117 | $^1$H NMR (400 MHz, DMSO-d6) δ 8.77 (s, 2H), 8.08 (d, J = 7.9 Hz, 1H), 7.78-7.67 (m, 3H), 7.52-7.49 (m, 1H), 7.31-7.24 (m, 2H), 7.15 (td, J = 2.4, 6.4 Hz, 1H), 7.09 (d, J = 8.4 Hz, 1H), 3.80-3.66 (m, 1H), 3.30-3.24 (m, 4H), 1.98-1.89 (m, 1H), 1.86-1.76 (m, 4H), 1.76-1.68 (m, 2H), 1.65-1.55 (m, 1H), 1.37-1.22 (m, 4H), 1.18-1.05 (m, 1H), 0.97-0.89 (m, 2H), 0.61-0.53 (m, 2H)<br>$[M + H]^+$ = 460.2 |
| 118 | $^1$H NMR (500 MHz, DMSO-d6) δ 8.76 (s, 2H), 7.76 (dd, J = 7.2, 2.7 Hz, 2H), 7.68 (s, 1H), 7.25 (d, J = 7.8 Hz, 1H), 7.08 (dd, J = 20.6, 7.7 Hz, 2H), 6.93 (s, 1H), 6.77 (s, 1H), 3.43 (s, 1H), 3.28 (d, J = 4.9 Hz, 4H), 3.21 (s, 1H), 2.89 (s, 3H), 1.94 (s, 1H), 1.85-1.78 (m, 2H), 1.57 (s, 1H), 1.41 (d, J = 35.6 Hz, 3H), 0.92 (d, J = 7.1 Hz, 4H), 0.71 (s, 3H), 0.57 (q, J = 5.6 Hz, 2H)<br>$[M + H]^+$ = 462.2 |
| 119 | $^1$H NMR (300 MHz, $CDCl_3$) δ 8.04 (d, J = 6.8 Hz, 1H), 8.02 (s, 1H), 7.70 (s, 1H), 7.57 (t, J = 2.0 Hz, 1H), 7.43 (t, J = 8.0 Hz, 1H), 7.34-7.28 (m, 2H), 7.23 (dd, J = 8.0, 1.2 Hz, 1H), 6.61 (s, 1H), 3.44 (t, J = 5.8 Hz, 4H), 2.67 (d, J = 6.8 Hz, 2H), 2.00 (q, J = 5.7 Hz, 2H), 1.82-1.61 (m, 6H), 1.29-1.16 (m, 4H), 1.05-0.98 (m, 4H), 0.85-0.78 (m, 2H)<br>$[M + H]^+$ = 498.5 |
| 120 | $^1$H NMR (400 MHz, DMSO-d6) δ 10.79 (s, 1H), 10.16 (s, 1H), 8.14 (d, J = 7.8 Hz, 1H), 7.87 (s, 1H), 7.82 (d, J = 8.1 Hz, 2H), 7.60 (t, J = 1.8 Hz, 1H), 7.38 (dt, J = 7.6, 1.4 Hz, 1H), 7.33 (t, J = 7.7 Hz, 1H), 7.28-7.21 (m, 1H), 7.12 (d, J = 8.3 Hz, 1H), 4.08 (dp, J = 13.7, 6.9 Hz, 1H), 3.54 (t, J = 7.0 Hz, 2H), 2.62 (t, J = 7.0 Hz, 2H), 1.96 (tt, J = 8.4, 5.6 Hz, 1H), 1.16 (d, J = 6.6 Hz, 6H), 1.02-0.92 (m, 2H), 0.67-0.58 (m, 2H)<br>$^{13}$C NMR (151 MHz, DMSO) δ 170.2, 165.9, 157.6, 146.3, 143.6, 136.5, 131.0, 129.2, 128.0, 128.0, 121.6, 119.9, 118.4, 115.4, 41.4,36.8, 30.5, 22.8, 11.6, 7.6<br>$[M + H]^+$ = 434.2 |

TABLE II-continued

| Ex | Characterizations |
|---|---|
| 121 | $^1$H NMR (400 MHz, DMSO-d6) δ 10.79 (s, 1H), 10.16 (s, 1H), 8.55 (s, 1H), 7.87-7.78 (m, 3H), 7.59-7.53 (m, 1H), 7.31 (q, J = 7.4 Hz, 2H), 7.23 (dt, J = 7.0, 2.1 Hz, 1H), 7.12 (d, J = 8.2 Hz, 1H), 3.54 (t, J = 7.1 Hz, 2H), 2.62 (t, J = 7.0 Hz, 2H), 1.95 (ddd, J = 13.7, 8.3, 5.4 Hz, 1H), 1.36 (s, 3H), 1.01-0.91 (m, 2H), 0.77-0.66 (m, 2H), 0.60 (dd, J = 6.2, 1.7 Hz, 4H)<br>$[M + H]^1$ = 446.3 |
| 122 | $^1$H NMR (400 MHz, DMSO-d6) δ 10.79 (s, 1H), 10.15 (s, 1H), 9.29 (s, 1H), 7.87 (s, 1H), 7.81 (d, J = 8.3 Hz, 1H), 7.34 (s, 1H), 7.21-7.12 (m, 2H), 7.08 (d, J = 7.4 Hz, 1H), 6.87 (d, J = 8.7 Hz, 1H), 3.53 (s, 2H), 2.71-2.67 (m, 1H), 2.62 (d, J = 6.9 Hz, 2H), 1.93 (s, 1H), 1.59 (s, 1H), 1.15 (d, J = 6.8 Hz, 6H), 1.01 (d, J = 8.3 Hz, 2H), 0.85 (d, J = 7.9 Hz, 2H), 0.65 (d, J = 5.0 Hz, 2H), 0.35 (d, J = 3.9 Hz, 2H)<br>$[M + H]^+$ = 474.1 |
| 123 | $^1$H NMR (400 MHz, DMSO-d6) δ 8.83-8.74 (m, 2H), 7.76 (dd, J = 1.8, 8.4 Hz, 1H), 7.72-7.67 (m, 2H), 7.62 (s, 1H), 7.45-7.42 (m, 1H), 7.29-7.21 (m, 2H), 7.14 (td, J = 2.0, 7.2 Hz, 1H), 7.10 (d, J = 8.4 Hz, 1H), 3.30-3.24 (m, 4H), 1.98-1.89 (m, 1H), 1.86-1.77 (m, 2H), 1.36 (s, 9H), 0.97-0.90 (m, 2H), 0.61-0.54 (m, 2H)<br>$[M + H]^+$ = 434.3 |
| 124 | $^1$H NMR (400 MHz, DMSO-d6) δ 8.82-8.73 (m, 2H), 7.76 (dd, J = 1.9, 8.3 Hz, 1H), 7.70-7.62 (m, 2H), 7.20-7.11 (m, 2H), 6.71 (dd, J = 1.7, 7.8 Hz, 1H), 6.66 (t, J = 2.2 Hz, 1H), 6.51 (dd, J = 2.3, 7.8 Hz, 1H), 4.67 (q, J = 8.9 Hz, 2H), 3.29-3.23 (m, 4H), 1.98-1.88 (m, 1H), 1.85-1.77 (m, 2H), 0.97-0.89 (m, 2H), 0.60-0.53 (m, 2H)<br>$[M + H]^+$ = 433.2 |
| 125 | $^1$H NMR (400 MHz, DMSO-d6) δ 8.77 (m, 2H), 7.76 (dd, J = 1.9, 8.4 Hz, 1H), 7.68 (d, J = 1.8 Hz, 1H), 7.62 (s, 1H), 7.18-7.10 (m, 2H), 6.69 (dd, J = 1.3, 8.0 Hz, 1H), 6.64 (t, J = 2.3 Hz, 1H), 6.51-6.19 (m, 2H), 4.24 (dt, J = 3.6, 14.7 Hz, 2H), 3.30-3.24 (m, 4H), 1.98-1.89 (m, 1H), 1.81 (quin, J = 5.6 Hz, 2H), 0.97-0.90 (m, 2H), 0.60-0.53 (m, 2H)<br>$[M + H]^+$ = 415.2 |
| 126 | $^1$H NMR (500 MHz, DMSO-d6) δ 8.77 (s, 2H), 8.31 (t, J = 5.6 Hz, 1H), 7.79-7.72 (m, 2H), 7.69 (d, J = 1.9 Hz, 1H), 7.53-7.48 (m, 1H), 7.28 (s, 2H), 7.16 (dt, J = 6.6, 2.4 Hz, 1H), 7.10 (d, J = 8.4 Hz, 1H), 3.82 (dd, J = 11.2, 3.0 Hz, 2H), 3.30-3.21 (m, 8H), 1.94 (tt, J = 8.4, 5.4 Hz, 1H), 1.82 (p, J = 5.7 Hz, 2H), 1.64 1.57 (m, 2H), 1.53 (ddt, J = 10.5, 7.2, 3.8 Hz, 1H), 1.45 (q, J = 6.9 Hz, 2H), 1.15 (qd, J = 12.1, 4.4 Hz, 2H), 0.97-0.89 (m, 2H), 0.63-0.54 (m, 2H)<br>$[M + H]^+$ = 490.2 |
| 127 | $^1$H NMR (400 MHz, DMSO-d6) δ 8.82-8.71 (m, 2H), 7.75 (dd, J = 2.0, 8.4 Hz, 1H), 7.68 (d, J = 1.8 Hz, 1H), 7.54 (s, 1H), 7.16-7.05 (m, 2H), 6.65-6.57 (m, 2H), 6.40 (dd, J = 1.7, 8.3 Hz, 1H), 3.72 (d, J = 6.4 Hz, 2H), 3.30-3.25 (m, 4H), 1.98-1.89 (m, 1H), 1.86-1.60 (m, 8H), 1.32-1.12 (m, 3H), 1.09-0.90 (m, 4H), 0.60-0.53 (m, 2H)<br>$[M + H]^+$ = 447.3 |
| 128 | $^1$H NMR (500 MHz, DMSO-d6) δ 9.33 (s, 1H), 8.75 (s, 2H), 7.72 (s, 1H), 7.67 (dd, J = 8.4, 1.7 Hz, 1H), 7.13 (t, J = 7.8 Hz, 1H), 7.08 (d, J = 7.0 Hz, 2H), 6.96 (d, J = 7.5 Hz, 1H), 6.45 (d, J = 8.4 Hz, 1H), 3.29-3.22 (m, 4H), 2.33 (t, J = 7.6 Hz, 2H), 2.01 (s, 3H), 1.87 (ddd, J = 13.6, 8.3, 5.4 Hz, 1H), 1.80 (p, J = 5.6 Hz, 2H), 1.59 (dt, J = 13.1, 6.8 Hz, 1H), 1.51 (q, J = 7.1 Hz, 2H), 0.96-0.93 (m, 2H), 0.91 (d, J = 6.5 Hz, 6H), 0.59-0.54 (m, 2H)<br>$[M + H]^+$ = 462.4 |
| 129 | $^1$H NMR (400 MHz, DMSO-d6) δ 8.77 (s, 2H), 7.76 (dd, J = 8.4, 2.0 Hz, 1H), 7.68 (d, J = 1.9 Hz, 1H), 7.56 (s, 1H), 7.16-7.03 (m, 2H), 6.67-6.58 (m, 1H), 6.51 (t, J = 2.2 Hz, 1H), 6.32 (dd, J = 8.1, 2.4 Hz, 1H), 4.61 (p, J = 7.3 Hz, 1H), 3.28 (d, J = 8.7 Hz, 4H), 2.43-2.30 (m, 3H), 2.09-1.89 (m, 2H), 1.87-1.70 (m, 3H), 1.63 (q, J = 9.2, 8.3 Hz, 1H), 1.00-0.88 (m, 2H), 0.64-0.50 (m, 2H)<br>$[M + H]^+$ = 405.3 |
| 130 | $^1$H NMR (400 MHz, DMSO-d6) δ 8.77 (s, 2H), 7.76 (dd, J = 8.4, 2.0 Hz, 1H), 7.68 (d, J = 2.0 Hz, 1H), 7.54 (s, 1H), 7.17-7.05 (m, 2H), 6.67-6.54 (m, 2H), 6.41 (dd, J = 7.9, 2.3 Hz, 1H), 3.94 (t, J = 6.6 Hz, 2H), 3.29 (d, J = 4.5 Hz, 4H), 1.99-1.88 (m, 1H), 1.88-1.77 (m, 2H), 1.77-1.55 (m, 7H), 1.51-1.39 (m, 1H), 1.27-1.09 (m, 3H), 0.99-0.84 (m, 4H), 0.61-0.52 (m, 2H)<br>$[M + H]^+$ = 461.3 |
| 131 | $^1$H NMR (400 MHz, DMSO-d6) δ 7.71 (d, J = 1.9 Hz, 1H), 7.54 (d, J = 2.2 Hz, 1H), 7.33-7.29 (m, 2H), 8.79 (s, 2H), 8.36 (t, J = 5.8 Hz, 1H), 7.82-7.74 (m, 2H), 7.22-7.15 (m, 1H), 7.12 (d, J = 8.4 Hz, 1H), 3.34-3.24 (m, 4H), 3.07 (t, J = 7.0, 5.8 Hz, 2H), 2.01-1.91 (m, 1H), 1.89-1.79 (m, 3H), 1.00-0.92 (m, 2H), 0.90 (d, J = 6.7 Hz, 6H), 0.62-0.57 (m, 2H)<br>$[M + H]^+$ = 434.4 |
| 132 | $^1$H NMR (300 MHz, DMSO) δ 8.79 (s, 2H), 7.76 (dd, J = 8.3, 1.7 Hz, 1H), 7.69 (s, 1H), 7.56 (s, 1H), 7.17-7.05 (m, 2H), 6.63 (d, J = 8.1 Hz, 1H), 6.60 (s, 1H), 6.41 (dd, J = 8.2, 1.7 Hz, 1H), 3.90 (t, J = 6.4 Hz, 2H), 3.29 (t, J = 4.9 Hz, 4H), 2.00-1.89 (m, 1H), 1.84-1.79 (m, 2H), 1.75-1.64 (m, 2H), 1.62-1.53 (m, 1H), 1.29 (dd, J = 15.4, 7.3 Hz, 2H), 0.95 (q, J = 5.6 Hz, 2H), 0.90 (d, J = 5.2 Hz, 6H), 0.57 (q, J = 5.6 Hz, 2H)<br>$^{13}$C NMR (151 MHz, DMSO) δ 160.0, 145.7, 144.7, 131.7, 130.1, 127.2, 126.9, 116.9, 110.5, 106.7, 104.3, 67.9, 38.5, 35.2, 27.7, 27.1, 22.9, 20.4, 11.5, 7.8<br>$[M + H]^+$ = 435.5 |
| 133 | $^1$H NMR (400 MHz, DMSO-d6) δ 8.97 (t, J = 5.8 Hz, 1H), 8.77 (br. s., 2H), 7.82 (s, 1H), 7.77 (dd, J = 1.8, 8.4 Hz, 1H), 7.69 (d, J = 1.5 Hz, 1H), 7.54 (s, 1H), 7.32 (d, J = 4.8 Hz, 2H), 7.24-7.16 (m, 1H), 7.11 (d, J = 8.4 Hz, 1H), 4.11-3.98 (m, 2H), 3.30-3.24 (m, 4H), 1.99-1.89 (m, 1H), 1.86-1.77 (m, 2H), 0.96-0.89 (m, 2H), 0.61-0.54 (m, 2H)<br>$[M + H]^+$ = 460.2 |
| 134 | $^1$H NMR (400 MHz, DMSO-d6) δ 10.79 (s, 1H), 10.15 (s, 1H), 7.85 7.76 (m, 2H), 7.68 (s, 1H), 7.15 (t, J = 8.0 Hz, 2H), 6.75-6.70 (m, 1H), 6.68 (t, J = 2.2 Hz, 1H), 6.49 (dd, J = 7.9, 2.2 Hz, 1H), 3.92-3.69 (m, 4H), 3.54 (t, J = 7.0 Hz, 2H), 3.41-3.32 (m, 1H), 3.26 (dd, J = 11.1, 9.1 Hz, 1H), 2.61 (t, J = 7.0 Hz, 2H), 2.02-1.88 (m, 2H), 1.83 (d, J = 8.3 Hz, 1H), 1.65-1.44 (m, 2H), 1.44-1.27 (m, 1H), 1.02-0.92 (m, 2H), 0.66-0.57 (m, 2H)<br>$[M + H]^+$ = 463.3 |

TABLE II-continued

| Ex | Characterizations |
|---|---|
| 135 | $^1H$ NMR (300 MHz, $CDCl_3$) δ 8.04 (s, 1H), 7.97 (d, J = 8.8 Hz, 1H), 7.03 (t, J = 7.9 Hz, 1H), 6.71 (d, J = 8.0 Hz, 1H), 6.64 (d, J = 8.7 Hz, 1H), 6.59 (d, J = 7.8 Hz, 1H), 6.41 (s, 1H), 3.48 (t, J = 5.8 Hz, 4H), 2.08-1.99 (m, 5H), 1.78-1.68 (m, 1H), 1.01 (q, J = 5.7 Hz, 2H), 0.85 (q, J = 5.7 Hz, 2H) $[M + H]^+$ = 364.3 |
| 136 | $^1H$ NMR (400 MHz, DMSO-d6) δ 8.77 (s, 2H), 7.79-7.74 (m, 2H), 7.67 (d, J = 1.8 Hz, 1H), 7.28-7.22 (m, 1H), 7.13-7.05 (m, 2H), 7.03-6.99 (m, 1H), 6.85 (d, J = 7.9 Hz, 1H), 3.90 (d, J = 11.9 Hz, 1H), 3.59 (d, J = 8.1 Hz, 1H), 3.42-3.32 (m, 2H), 3.30-3.24 (m, 4H), 1.98-1.89 (m, 1H), 1.85-1.76 (m, 2H), 1.58-1.48 (m, 2H), 0.97-0.88 (m, 2H), 0.68 0.61 (m, 1H), 0.60-0.54 (m, 2H), 0.05 (q, J = 3.9 Hz, 1H) $[M + H]^+$ = 444.2 |
| 137 | $^1H$ NMR (300 MHz, $CDCl_3$) δ 7.99-7.94 (m, 2H), 7.31 (t, J = 8.1 Hz, 1H), 7.23 (s, 1H), 7.06 (dd, J = 7.9, 1.9 Hz, 1H), 6.99 (s, 1H), 6.82 (d, J = 8.3 Hz, 1H), 6.39 (s, 1H), 3.42 (t, J = 5.6 Hz, 4H), 1.99 (q, J = 5.6 Hz, 2H), 1.82-1.72 (m, 1H), 0.98 (q, J = 5.9 Hz, 2H), 0.76 (q, J = 5.9 Hz, 2H) $[M + H]^+$ = 419.3 |
| 138 | $^1H$ NMR (300 MHz, $CDCl_3$) δ 8.28 (d, J = 5.6 Hz, 1H), 8.08 (dd, J = 8.4, 2.0 Hz, 1H), 8.04-7.99 (m, 2H), 7.78 (d, J = 2.3 Hz, 1H), 7.43 (d, J = 8.4 Hz, 1H), 7.09 (dd, J = 5.6, 2.5 Hz, 1H), 6.73 (s, 1H), 3.53-3.43 (m, 6H), 2.09-1.99 (m, 2H), 1.74 (ddd, J = 30.4, 16.7, 7.1 Hz, 8H), 1.54 (dd, J = 14.5, 6.9 Hz, 2H), 1.27-1.20 (m, 4H), 1.03-1.00 (m, 2H), 0.86-0.78 (m, 2H) $[M + H]^+$ = 489.6 |
| 139 | $^1H$ NMR (400 MHz, DMSO-d6) δ 8.77 (s, 2H), 7.76 (dd, J = 8.4, 2.0 Hz, 1H), 7.68 (d, J = 2.0 Hz, 1H), 7.56 (s, 1H), 7.17-7.07 (m, 2H), 6.70-6.57 (m, 2H), 6.42 (dd, J = 8.0, 2.3 Hz, 1H), 4.05-3.97 (m, 2H), 3.72-3.57 (m, 3H), 3.31-3.23 (m, 4H), 1.99-1.89 (m, 1H), 1.82 (t, J = 5.9 Hz, 2H), 1.11 (d, J = 6.1 Hz, 6H), 0.98-0.89 (m, 2H), 0.60-0.53 (m, 2H) $[M + H]^+$ = 437.3 |
| 140 | $^1H$ NMR (400 MHz, DMSO-d6) δ 8.77 (s, 2H), 7.76 (dd, J = 8.4, 2.0 Hz, 1H), 7.68 (d, J = 2.0 Hz, 1H), 7.55 (s, 1H), 7.17-6.95 (m, 2H), 6.70-6.51 (m, 2H), 6.41 (dd, J = 8.0, 2.4 Hz, 1H), 3.90 (t, J = 6.5 Hz, 2H), 3.31-3.25 (m, 4H), 2.03-1.87 (m, 1H), 1.87-1.76 (m, 2H), 1.74-1.55 (m, 7H), 1.39 (q, J = 7.3 Hz, 2H), 1.28 1.03 (m, 6H), 0.98-0.77 (m, 4H), 0.60-0.52 (m, 2H) $[M + H]^+$ = 489.4 |
| 141 | $^1H$ NMR (300 MHz, $CDCl_3$) δ 8.00 (s, 1H), 7.98 (d, J = 8.8 Hz, 1H), 7.30 (d, J = 8.3 Hz, 1H), 7.19 (d, J = 7.7 Hz, 1H), 7.03 (s, 1H), 6.63 (d, J = 8.4 Hz, 1H), 6.45 (s, 1H), 3.50 (t, J = 5.7 Hz, 4H), 2.30 (s, 3H), 2.10-1.99 (m, 2H), 1.79-1.68 (m, 1H), 1.01 (q, J = 5.5 Hz, 2H), 0.80 (q, J = 5.5 Hz, 2H) $[M + H]^+$ = 449.3 |
| 142 | $^1H$ NMR (300 MHz, $CDCl_3$) δ 8.02 (s, 1H), 8.00 (d, J = 8.7 Hz, 1H), 7.84 (s, 1H), 7.73 (d, J = 7.5 Hz, 1H), 7.43 (t, J = 7.8 Hz, 1H), 7.36 (d, J = 6.8 Hz, 1H), 6.54 (s, 1H), 3.46 (t, J = 5.8 Hz, 4H), 3.00-2.92 (m, 2H), 2.08-1.98 (m, 2H), 1.81-1.64 (m, 6H), 1.34-1.20 (m, 6H), 1.04-0.96 (m, 4H), 0.80 (q, J = 5.6 Hz, 2H) $[M + H]^+$ = 360.3 |
| 143 | $^1H$ NMR (500 MHz, DMSO-d6) δ 8.77 (s, 2H), 8.17 (s, 1H), 7.79 (dd, J = 8.3, 1.8 Hz, 1H), 7.69 (d, J = 1.7 Hz, 1H), 7.44 (t, J = 7.9 Hz, 1H), 7.38 (s, 1H), 7.25 (dd, J = 8.1, 2.1 Hz, 1H), 7.22 (d, J = 7.8 Hz, 1H), 7.15 (d, J = 8.3 Hz, 1H), 3.30-3.26 (m, 4H), 3.21-3.17 (m, 2H), 1.93 (ddd, J = 13.6, 8.4, 5.2 Hz, 1H), 1.82 (q, J = 5.8 Hz, 2H), 1.65-1.50 (m, 7H), 1.21-1.05 (m, 6H), 0.94-0.89 (m, 2H), 0.84-0.73 (m, 2H), 0.63-0.56 (m, 2H) $[M + H]^+$ = 523.3 |
| 144 | $^1H$ NMR (400 MHz, DMSO-d6) δ 8.77 (s, 2H), 7.77 (dd, J = 8.4, 2.0 Hz, 1H), 7.67 (s, 1H), 7.62 (s, 1H), 7.12 (t, J = 8.1 Hz, 2H), 6.66 (dd, J = 7.6, 2.0 Hz, 1H), 6.43 (t, J = 2.3 Hz, 1H), 6.23 (dd, J = 8.1, 2.4 Hz, 1H), 5.28-5.14 (m, 1H), 4.87 (dd, J = 7.2, 6.1 Hz, 2H), 4.54 (dd, J = 7.3, 5.0 Hz, 2H), 3.30-3.26 (m, 4H), 1.98-1.89 (m, 1H), 1.86-1.77 (m, 2H), 0.98-0.90 (m, 2H), 0.61-0.53 (m, 2H) $[M + H]^+$ = 407.2 |
| 145 | $^1H$ NMR (400 MHz, DMSO-d6) δ 10.78 (s, 1H), 10.16 (s, 1H), 8.36 (d, J = 4.2 Hz, 1H), 7.87 (s, 1H), 7.82 (d, J = 8.2 Hz, 2H), 7.58 (d, J = 1.1 Hz, 1H), 7.37-7.29 (m, 2H), 7.24 (dt, J = 6.2, 2.5 Hz, 1H), 7.12 (d, J = 8.3 Hz, 1H), 3.54 (t, J = 7.0 Hz, 2H), 2.83 (tt, J = 8.1, 4.0 Hz, 1H), 2.62 (t, J = 7.0 Hz, 2H), 1.96 (tt, J = 8.4, 5.4 Hz, 1H), 1.01-0.90 (m, 2H), 0.68 (td, J = 7.1, 4.7 Hz, 2H), 0.62 (dd, J = 5.4, 1.9 Hz, 2H), 0.56 (dd, J = 3.6, 2.6 Hz, 2H) $[M + H]^+$ = 432.3 |
| 146 | $^1H$ NMR (400 MHz, DMSO-d6) δ 10.79 (s, 1H), 10.16 (s, 1H), 7.86-7.75 (m, 2H), 7.69 (s, 1H), 7.15 (t, J = 8.5 Hz, 2H), 6.75-6.66 (m, 2H), 6.49 (dd, J = 8.2, 1.9 Hz, 1H), 3.88 (dd, J = 11.1, 3.5 Hz, 2H), 3.79 (d, J = 6.4 Hz, 2H), 3.54 (t, J = 7.0 Hz, 2H), 3.32 (t, 2H), 2.61 (t, J = 7.0 Hz, 2H), 2.04-1.89 (m, 2H), 1.67 (d, J = 11.5 Hz, 2H), 1.32 (qd, J = 12.3, 4.4 Hz, 2H), 1.02-0.92 (m, 2H), 0.61 (q, J = 5.4 Hz, 2H) $[M + H]^+$ = 463.0 |
| 147 | $^1H$ NMR (300 MHz, $CDCl_3$) δ 9.62 (s, 1H), 8.03 (dd, J = 8.5, 1.9 Hz, 1H), 7.94 (d, J = 1.7 Hz, 1H), 7.49 (d, J = 8.1 Hz, 1H), 7.44 (dd, J = 7.8, 1.2 Hz, 1H), 7.39 (d, J = 8.5 Hz, 1H), 7.33 (t, J = 7.2 Hz, 1H), 6.88 (t, J = 7.2 Hz, 1H), 6.09 (t, J = 5.3 Hz, 1H), 3.48-3.41 (m, 6H), 2.04-1.96 (m, 2H), 1.93-1.82 (m, 1H), 1.76-1.61 (m, 1H), 1.50 (dd, J = 14.7, 7.1 Hz, 2H), 1.07 (q, J = 5.8 Hz, 2H), 0.95 (d, J = 6.6 Hz, 6H), 0.76 (q, J = 5.8 Hz, 2H) $[M + H]^+$ = 448.4 |
| 148 | $^1H$ NMR (400 MHz, DMSO-d6) δ 9.62 (s, 1H), 8.79 (s, 2H), 8.28 (d, J = 1.8 Hz, 1H), 8.04 (d, J = 10.2 Hz, 1H), 7.75 (d, J = 4.6 Hz, 1H), 7.67 (s, 1H), 7.22-7.15 (m, 1H), 7.15-7.11 (m, 1H), 6.92-6.86 (m, 1H), 3.29 (s, 4H), 2.37 (t, J = 7.7 Hz, 2H), 2.04-1.98 (m, 1H), 1.85-1.78 (m, 2H), 1.72-1.59 (m, 5H), 1.49-1.43 (m, 2H), 1.20-1.11 (m, 3H), 0.92-0.85 (m, 2H) $[M + H]^+$ = 534.2 |
| 149 | $^1H$ NMR (300 MHz, $CDCl_3$) δ 9.75 (s, 1H), 8.09 (s, 1H), 8.07 (d, J = 9.4 Hz, 1H), 7.96 (s, 1H), 7.86 (d, J = 7.6 Hz, 1H), 7.47 (t, J = 7.9 Hz, 1H), 7.36 (d, J = 9.4 Hz, 1H), 7.29 (d, J = 8.5 Hz, 1H), 6.69 (s, 1H), 4.63 (t, J = 7.3 Hz, 2H), 3.51 (t, J = 5.8 Hz, 4H), 2.12-2.01 (m, 4H), 1.80-1.60 (m, 7H), 1.31-1.17 (m, 6H), 1.08-1.01 (m, 2H), 0.94-0.84 (dd, J = 9.7, 5.9 Hz, 4H) $[M + H]^+$ = 527.5 |

TABLE II-continued

| Ex | Characterizations |
|---|---|
| 150 | $^{1}$H NMR (400 MHz, DMSO-d6) δ 10.79 (s, 1H), 10.16 (s, 1H), 7.81 (d, J = 8.4 Hz, 1H), 7.79 (s, 1H), 7.70 (s, 1H), 7.17 (d, J = 8.8 Hz, 2H), 6.72 (d, J = 8.2 Hz, 1H), 6.68 (s, 1H), 6.48 (d, J = 8.0 Hz, 1H), 4.00 (t, J = 6.5 Hz, 2H), 3.72 (t, J = 11.0 Hz, 2H), 3.63 (d, J = 11.0 Hz, 2H), 3.57-3.51 (m, 3H), 3.49-3.42 (m, 1H), 3.27-3.18 (m, 1H), 2.61 (t, J = 7.1 Hz, 2H), 1.95 (s, 1H), 1.76 (s, 2H), 0.97 (d, J = 8.2 Hz, 2H), 0.61 (d, J = 4.3 Hz, 2H)<br>$[M + H]^+$ = 479.0 |
| 151 | $^{1}$H NMR (400 MHz, DMSO-d6) δ 10.79 (s, 1H), 10.16 (s, 1H), 7.81 (d, J = 8.5 Hz, 1H), 7.79 (s, 1H), 7.69 (s, 1H), 7.18-7.12 (m, 2H), 6.71 (d, J = 7.8 Hz, 1H), 6.68 (s, 1H), 6.48 (d, J = 10.4 Hz, 1H), 3.87 (d, J = 6.2 Hz, 3H), 3.59 (s, 1H), 3.54 (t, J = 7.1 Hz, 2H), 3.39 (s, 1H), 2.61 (t, J = 7.0 Hz, 2H), 1.95 (s, 1H), 1.81 (s, 1H), 1.64 (d, J = 11.9 Hz, 1H), 1.49 (s, 3H), 1.37-1.24 (m, 1H), 1.00-0.94 (m, 2H), 0.61 (d, J = 3.8 Hz, 2H)<br>$[M + H]^+$ = 463.1 |
| 152 | $^{1}$H NMR (400 MHz, DMSO-d6) δ 8.80 (s, 2H), 8.75 (d, J = 6.7 Hz, 1H), 7.84-7.74 (m, 2H), 7.71 (d, J = 1.9 Hz, 1H), 7.57-7.51 (m, 1H), 7.35-7.31 (m, 2H), 7.24-7.18 (m, 1H), 7.12 (d, J = 8.4 Hz, 1H), 4.32-4.20 (m, 1H), 3.30 (s, 4H), 3.02-2.88 (m, 2H), 2.84-2.70 (m, 2H), 2.01-1.90 (m, 1H), 1.88-1.77 (m, 2H), 1.00-0.90 (m, 2H), 0.64-0.54 (m, 2H)<br>$[M + H]^+$ = 468.2 |
| 153 | $^{1}$H NMR (300 MHz, $CDCl_3$) δ 7.98 (s, 1H), 7.94 (d, J = 8.9 Hz, 1H), 7.36 (s, 1H), 7.22 (d, J = 8.6 Hz, 1H), 7.20 (t, J = 8.3 Hz, 1H), 7.05 (d, J = 7.9 Hz, 1H), 6.83 (d, J = 8.0 Hz, 1H), 5.65 (s, 1H), 3.42-3.39 (m, 4H), 2.42-2.30 (m, 2H), 2.27 (s, 3H), 2.02-1.94 (m, 2H), 1.75-1.57 (m, 8H), 1.30-1.14 (m, 5H)<br>$[M + H]^+$ = 462.5 |
| 154 | $^{1}$H NMR (400 MHz, DMSO-d6) δ 8.83-8.74 (m, 2H), 7.91 (s, 1H), 7.78 (dd, J = 1.9, 8.4 Hz, 1H), 7.68 (d, J = 1.8 Hz, 1H), 7.51-7.44 (m, 1H), 7.40-7.28 (m, 2H), 7.26-7.19 (m, 1H), 7.14 (d, J = 8.3 Hz, 1H), 3.30-3.24 (m, 4H), 2.24 (s, 2H), 2.01-1.90 (m, 1H), 1.86-1.76 (m, 2H), 1.16 (s, 6H), 0.97-0.83 (m, 2H), 0.62-0.52 (m, 2H)<br>$[M + H]^+$ = 432.0 |
| 155 | $^{1}$H NMR (400 MHz, DMSO-d6) δ 8.77 (s, 2H), 8.42 (d, J = 6.6 Hz, 1H), 7.78-7.73 (m, 2H), 7.69 (d, J = 1.8 Hz, 1H), 7.54-7.51 (m, 1H), 7.34-7.26 (m, 2H), 7.19-7.14 (m, 1H), 7.09 (d, J = 8.4 Hz, 1H), 4.47-4.39 (m, 1H), 3.88-3.79 (m, 2H), 3.74-3.66 (m, 1H), 3.56 (dd, J = 4.5, 8.9 Hz, 1H), 3.30-3.25 (m, 4H), 2.16-2.08 (m, 1H), 1.97-1.87 (m, 2H), 1.86-1.77 (m, 2H), 0.96-0.90 (m, 2H), 0.61-0.54 (m, 2H)<br>$[M + H]^+$ = 448.2 |
| 156 | $^{1}$H NMR (300 MHz, $CDCl_3$) δ 7.97 (s, 1H), 7.91 (dd, J = 8.5, 1.9 Hz, 1H), 7.24 (d, J = 8.5 Hz, 1H), 7.17 (t, J = 8.2 Hz, 1H), 6.68-6.60 (m, 2H), 6.55-6.47 (m, 1H), 5.59 (s, 1H), 3.89 (t, J = 6.6 Hz, 2H), 3.40-3.34 (m, 4H), 2.28 (s, 3H), 1.96 (dt, J = 11.6, 6.6 Hz, 2H), 1.83-1.61 (m, 8H), 1.38-1.13 (m, 7H) |
| 157 | $^{1}$H NMR (400 MHz, DMSO-d6) δ 8.77 (s, 2H), 8.21 (d, J = 7.9 Hz, 1H), 7.79-7.73 (m, 2H), 7.69 (d, J = 1.8 Hz, 1H), 7.54-7.50 (m, 1H), 7.33-7.25 (m, 2H), 7.16 (td, J = 2.8, 5.8 Hz, 1H), 7.09 (d, J = 8.4 Hz, 1H), 4.04-3.93 (m, 1H), 3.90-3.83 (m, 2H), 3.41-3.33 (m, 2H), 3.30-3.24 (m, 4H), 1.98-1.89 (m, 1H), 1.85-1.77 (m, 2H), 1.77-1.68 (m, 2H), 1.56 (dq, J = 4.4, 12.0 Hz, 2H), 0.96-0.89 (m, 2H), 0.60-0.54 (m, 2H)<br>$[M + H]^+$ = 462.2 |
| 158 | $^{1}$H NMR (400 MHz, DMSO-d6) δ 8.83-8.73 (m, 2H), 7.81-7.76 (m, 2H), 7.69 (d, J = 1.9 Hz, 1H), 7.28 (t, J = 7.8 Hz, 1H), 7.13 (d, J = 8.3 Hz, 1H), 7.09 (ddd, J = 8.2, 2.4, 1.0 Hz, 1H), 6.99 (t, J = 1.9 Hz, 1H), 6.82 (dt, J = 7.5, 1.3 Hz, 1H), 3.72-3.35 (m, 8H), 3.30-3.24 (m, 4H), 2.00-1.90 (m, 1H), 1.87-1.77 (m, 2H), 0.98-0.89 (m, 2H), 0.64-0.54 (m, 2H)<br>$[M + H]^+$ = 448.3 |
| 159 | $^{1}$H NMR (300 MHz, $CDCl_3$) δ 9.52 (s, 1H), 7.96 (d, J = 8.5 Hz, 1H), 7.93 (s, 1H), 7.44 (t, J = 7.3 Hz, 2H), 7.36 (d, J = 8.4 Hz, 1H), 7.33 (t, J = 7.9 Hz, 1H), 6.86 (t, J = 7.4 Hz, 1H), 6.45 (t, J = 6.1 Hz, 1H), 3.73-3.64 (m, 2H), 3.40 (t, J = 5.7 Hz, 4H), 2.56-2.37 (m, 2H), 2.05-1.93 (m, 2H), 1.92-1.83 (m, 1H), 1.05 (q, J = 5.8 Hz, 2H), 0.74 (q, J = 5.8 Hz, 2H)<br>$[M + H]^+$ = 474.3 |
| 160 | $^{1}$H NMR (300 MHz, $CDCl_3$) δ 10.22 (s, 2H), 8.14 (s, 1H), 8.11 (dd, J = 8.4, 1.6 Hz, 1H), 7.98 (bs, 1H), 7.90 (d, J = 7.6 Hz, 1H), 7.49 (t, J = 7.8 Hz, 1H), 7.38 (dd, J = 8.4, 1.6 Hz, 1H), 7.30 (d, J = 8.4 Hz, 1H), 6.77 (s, 1H), 4.84 (t, J = 5.5 Hz, 2H), 3.99 (t, J = 5.5 Hz, 2H), 3.54 (t, J = 5.7 Hz, 4H), 3.38 (s, 3H), 2.11-2.05 (m, 2H), 1.80-1.70 (m, 1H), 1.11-1.02 (m, 2H), 0.93-0.88 (dt, J = 10.0, 5.0 Hz, 2H)<br>$[M + H]^+$ = 461.4 |
| 161 | $^{1}$H NMR (400 MHz, DMSO-d6) δ 10.79 (s, 1H), 10.16 (s, 1H), 7.82 (d, J = 8.4 Hz, 1H), 7.79 (s, 1H), 7.70 (s, 1H), 7.16 (t, J = 7.9 Hz, 2H), 6.73 (d, J = 8.1 Hz, 1H), 6.68 (s, 1H), 6.49 (d, J = 10.4 Hz, 1H), 3.92 (d, J = 6.0 Hz, 2H), 3.88-3.73 (m, 3H), 3.70-3.58 (m, 2H), 3.57-3.45 (m, 3H), 3.39 (t, J = 10.4 Hz, 1H), 2.61 (t, J = 7.0 Hz, 2H), 1.98-1.90 (m, 1H), 1.00-0.92 (m, 2H), 0.61 (q, J = 5.5 Hz, 2H)<br>$[M + H]^+$ = 465.0 |
| 162 | $^{1}$H NMR (400 MHz, DMSO-d6) δ 8.78 (s, 2H), 7.90 (s, 1H), 7.79 (dd, J = 8.3, 2.0 Hz, 1H), 7.69 (d, J = 2.0 Hz, 1H), 7.57 (t, J = 1.9 Hz, 1H), 7.43-7.31 (m, 2H), 7.24 (ddd, J = 7.6, 2.4, 1.5 Hz, 1H), 7.15 (d, J = 8.3 Hz, 1H), 3.29 (s, 4H), 2.62 (td, J = 5.7, 3.6 Hz, 1H), 2.46 (d, J = 6.0 Hz, 1H), 2.09 (d, J = 3.6 Hz, 1H), 2.01-1.91 (m, 1H), 1.82 (p, J = 5.8 Hz, 2H), 1.26 (d, J = 5.5 Hz, 3H), 0.97-0.89 (m, 2H), 0.63-0.55 (m, 2H)<br>$[M + H]^+$ = 417.8 |
| 163 | $^{1}$H NMR (400 MHz, DMSO-d6) δ 8.77 (m, 2H), 7.79-7.73 (m, 2H), 7.68 (d, J = 1.8 Hz, 1H), 7.26 (t, J = 7.8 Hz, 1H), 7.11 (d, J = 8.4 Hz, 1H), 7.10-7.04 (m, 1H), 6.98 (m, 1H), 6.81 (d, J = 7.7 Hz, 1H), 3.30-3.24 (m, 4H), 2.94 (br. s., 6H), 1.94 (m, 1H), 1.81 (m, 2H), 0.97-0.90 (m, 2H), 0.60-0.53 (m, 2H)<br>$[M + H]^+$ = 406.3 |
| 164 | $^{1}$H NMR (400 MHz, DMSO-d6) δ 10.79 (s, 1H), 10.17 (s, 1H), 7.91 (s, 1H), 7.86-7.77 (m, 2H), 7.32 (t, J = 7.8 Hz, 1H), 7.21-7.13 (m, 2H), 7.08 (s, 1H), 6.89 (d, J = 7.4 Hz, 1H), 3.75-3.34 (m, |

TABLE II-continued

| Ex | Characterizations |
|---|---|
| | 10H), 2.62 (t, J = 7.0 Hz, 2H), 2.02-1.90 (m, 1H), 1.02-0.92 (m, 2H), 0.63 (q, J = 5.1 Hz, 2H)<br>$[M + H]^+$ = 462.0 |
| 165 | $^1$H NMR (300 MHz, $CDCl_3$) δ 8.08 (d, J = 8.1 Hz, 1H), 8.04 (s, 1H), 7.39 (d, J = 7.6 Hz, 1H), 7.22 (d, J = 7.7 Hz, 1H), 7.14 (d, J = 8.2 Hz, 1H), 6.76 (d, J = 8.9 Hz, 1H), 6.45 (s, 1H), 3.50 (t, J = 5.7 Hz, 4H), 2.30 (s, 3H), 2.10-2.01 (m, 2H), 1.80-1.72 (m, 1H), 1.66 (dd, J = 8.2, 5.7 Hz, 2H), 1.40 (dd, J = 8.3, 5.7 Hz, 2H), 1.03 (q, J = 6.0 Hz, 2H), 0.83 (q, J = 6.0 Hz, 2H)<br>$[M + H]^+$ = 457.3 |
| 166 | $^1$H NMR (300 MHz, $CDCl_3$) δ 7.94 (d, J = 7.0 Hz, 2H), 7.55 (s, 1H), 7.40-7.30 (m, 3H), 7.21 (d, J = 9.1 Hz, 1H), 6.79 (s, 1H), 6.42 (s, 1H), 5.23 (dt, J = 13.1, 6.4 Hz, 1H), 5.01 (t, J = 6.4 Hz, 2H), 4.62 (t, J = 6.5 Hz, 2H), 3.39 (t, J = 5.7 Hz, 4H), 2.03-1.91 (m, 2H), 1.75 (ddd, J = 13.7, 8.2, 5.4 Hz, 1H), 0.97 (q, J = 5.6 Hz, 2H), 0.73 (q, J = 5.6 Hz, 2H)<br>$[M + H]^+$ = 434.3 |
| 167 | $^1$H NMR (400 MHz, DMSO-d6) δ 8.82-8.74 (m, 2H), 7.80-7.74 (m, 2H), 7.68 (d, J = 1.8 Hz, 1H), 7.29-7.23 (m, 1H), 7.12 (d, J = 8.1 Hz, 1H), 7.08 (dd, J = 1.3, 8.1 Hz, 1H), 6.96 (t, J = 1.9 Hz, 1H), 6.78 (d, J = 7.7 Hz, 1H), 3.65-3.33 (m, 4H), 3.30-3.24 (m, 4H), 2.36-2.22 (m, 4H), 2.18 (s, 3H), 1.98-1.89 (m, 1H), 1.86-1.77 (m, 2H), 0.96-0.89 (m, 2H), 0.61-0.54 (m, 2H)<br>$[M + H]^+$ = 461.3 |
| 168 | $^1$H NMR (400 MHz, DMSO-d6) δ 10.94 (s, 1H), 10.21 (s, 1H), 8.67 (s, 1H), 8.51 (d, J = 2.0 Hz, 1H), 8.40 (s, 1H), 8.18 (dd, J = 8.8, 2.0 Hz, 1H), 7.70 (s, 1H), 7.60 (dt, J = 6.9, 1.8 Hz, 1H), 7.48-7.41 (m, 2H), 7.24 (d, J = 8.8 Hz, 1H), 3.56 (td, J = 7.1, 2.7 Hz, 2H), 3.53-3.49 (m, 1H), 2.63 (t, J = 7.0 Hz, 2H), 1.37 (s, 3H), 1.24 (d, J = 6.8 Hz, 6H), 0.76-0.71 (m, 2H), 0.64-0.58 (m, 2H)<br>$[M + H]^+$ = 512.2 |
| 169 | $^1$H NMR (500 MHz, DMSO-d6) δ 9.13 (s, 1H), 8.76 (s, 2H), 7.72 (dd, J = 8.4, 1.8 Hz, 1H), 7.67 (d, J = 1.7 Hz, 1H), 7.45 (s, 1H), 7.20 (s, 1H), 7.05 (dd, J = 8.3, 4.1 Hz, 2H), 6.82 (dd, J = 8.2, 2.0 Hz, 1H), 3.29-3.24 (m, 4H), 2.31 (t, J = 7.6 Hz, 2H), 2.12 (s, 3H), 1.92 (ddd, J = 13.7, 8.4, 5.4 Hz, 1H), 1.81 (p, J = 5.5 Hz, 2H), 1.57 (dt, J = 13.0, 6.5 Hz, 1H), 1.49 (q, J = 7.1 Hz, 2H), 0.95-0.91 (m, 2H), 0.90 (d, J = 6.5 Hz, 6H), 0.58-0.51 (m, 2H)<br>$[M + H]^+$ = 462.4 |
| 170 | $^1$H NMR (500 MHz, DMSO-d6) δ 8.75 (s, 2H), 8.12 (t, J = 5.6 Hz, 1H), 7.73 (dd, J = 8.4, 1.8 Hz, 1H), 7.68 (d, J = 1.7 Hz, 1H), 7.55 (s, 1H), 7.08 (dd, J = 8.6, 2.8 Hz, 2H), 7.04-6.99 (m, 2H), 3.29-3.25 (m, 4H), 3.21 (q, J = 6.5 Hz, 2H), 2.23 (s, 3H), 1.91 (ddd, J = 13.6, 8.3, 5.4 Hz, 1H), 1.81 (p, J = 5.8 Hz, 2H), 1.62 (dp, J = 13.3, 6.7 Hz, 1H), 1.38 (q, J = 7.0 Hz, 2H), 0.96-0.91 (m, 2H), 0.89 (d, J = 6.6 Hz, 6H), 0.59-0.52 (m, 2H)<br>$[M + H]^+$ = 462.4 |
| 171 | $^1$H NMR (300 MHz, $CDCl_3$) δ 10.18 (s, 2H), 8.15 (dd, J = 8.7, 2.0 Hz, 1H), 8.09 (d, J = 1.6 Hz, 1H), 7.70 (bs, 1H), 7.54-7.49 (m, 2H), 7.47-7.41 (m, 1H), 7.29 (d, J = 62 Hz, 1H), 6.84 (s, 1H), 4.59 (t, J = 5.1 Hz, 2H), 3.97 (t, J = 5.1 Hz, 2H), 3.54 (t, J = 5.7 Hz, 4H), 3.28 (s, 3H), 2.13-2.02 (m, 2H), 1.84-1.72 (m, 1H), 1.09-1.02 (m, 2H), 0.89-0.84 (m, 2H)<br>$[M + H]^+$ = 461.4 |
| 172 | $^1$H NMR (300 MHz, $CDCl_3$) δ 9.93 (s, 1H), 8.05 (d, J = 8.5 Hz, 1H), 8.01 (s, 1H),7.65 (s, 1H), 7.51-7.46 (m, 1H), 7.37 (d, J = 4.3 Hz, 2H), 7.14 (d, J = 8.4 Hz, 1H), 6.69 (s, 1H), 3.50 (t, J = 5.7 Hz, 4H), 2.10-2.02 (m, 2H), 1.70-1.67 (m, 1H), 1.63 (dd, J = 8.4, 5.9 Hz, 2H), 1.41 (dd, J = 8.4, 5.9 Hz, 2H), 1.02 (q, J = 5.3 Hz, 2H), 0.81 (q, J = 5.3 Hz, 2H)<br>$[M + H]^+$ = 443.3 |
| 173 | $^1$H NMR (400 MHz, DMSO-d6) δ 10.94 (s, 1H), 10.22 (s, 1H), 8.73 (s, 1H), 8.67 (s, 1H), 8.49 (d, J = 2.1 Hz, 1H), 8.18 (dd, J = 8.8, 2.1 Hz, 1H), 7.68 (s, 1H), 7.61-7.57 (m, 1H), 7.47-7.41 (m, 2H), 7.27 (d, J = 8.9 Hz, 1H), 3.56 (td, J = 7.0, 2.8 Hz, 2H), 2.63 (t, J = 7.1 Hz, 2H), 1.37 (s, 3H), 1.32 (s, 9H), 0.76-0.72 (m, 2H), 0.63-0.59 (m, 2H)<br>$[M + H]^+$ = 526.3 |
| 174 | $^1$H NMR (400 MHz, DMSO-d6) δ 10.90 (s, 1H), 10.22 (s, 1H), 8.63 (s, 1H), 8.61 (s, 1H), 8.30 (d, J = 2.0 Hz, 1H), 8.09 (dd, J = 8.5, 2.0 Hz, 1H), 7.57 (t, J = 1.8 Hz, 1H), 7.45 (d, J = 7.5 Hz, 1H), 7.37 (t, J = 7.8 Hz, 1H), 7.30-7.20 (m, 2H), 3.59-3.53 (m, 2H), 3.19 (p, J = 6.7 Hz, 1H), 2.63 (t, J = 7.1 Hz, 2H), 1.36 (s,3H), 1.17 (d, J = 6.9 Hz, 3H), 1.10 (d, J = 6.8 Hz, 3H), 0.75-0.70 (m, 2H), 0.62-0.57 (m, 2H)<br>$[M + H]^+$ = 496.2 |
| 175 | $^1$H NMR (400 MHz, DMSO-d6) δ 10.79 (s, 1H), 10.21 (s, 1H), 7.95 (s, 1H), 7.87 (d, J = 8.5 Hz, 1H), 7.79 (s, 1H), 7.32 (t, J = 7.8 Hz, 1H), 7.16 (t, J = 9.2 Hz, 2H), 7.06 (s, 1H), 6.88 (d, J = 7.6 Hz, 1H), 5.76 (s, 1H), 3.67-3.35 (m, 10H), 2.62 (t, J = 7.0 Hz, 2H), 2.26 (s, 3H)<br>$[M + H]^+$ = 436.0 |
| 176 | $^1$H NMR (400 MHz, DMSO-d6) δ 8.77 (s, 2H), 7.96 (d, J = 7.9 Hz, 1H), 7.78-7.72 (m, 2H), 7.69 (d, J = 1.8 Hz, 1H), 7.54-7.50 (m, 1H), 7.33 7.25 (m, 2H), 7.16 (td, J = 2.2, 7.1 Hz, 1H), 7.09 (d, J = 8.4 Hz, 1H), 4.68 (t, J = 5.8 Hz, 1H), 3.99 (td, J = 6.8, 13.8 Hz, 1H), 3.44 (td, J = 5.6, 10.8 Hz, 1H), 3.35-3.32 (m, 1H), 3.30-3.25 (m, 4H), 1.98-1.89 (m, 1H), 1.86-1.77 (m, 2H), 1.11 (d, J = 6.6 Hz, 3H), 0.96-0.89 (m, 2H), 0.60-0.54 (m, 2H)<br>$[M + H]^+$ = 436.2 |
| 177 | Mixture of cis and trans isomers<br>trans isomer : 1H NMR (500 MHz, DMSO-d6) δ ppm 0.50-0.65 (m, 2 H), 0.88-0.97 (m, 2 H), 1.81 (quin, J = 5.7 Hz, 2 H), 1.90-2.01 (m, 1 H), 2.13 (ddd, J = 12.6, 8.0, 4.7 Hz, 2 H), 2.20-2.30 (m, 2 H), 3.24-3.29 (m, 4 H), 4.23-4.34 (m, 1 H), 4.36-4.46 (m, 1 H), 4.99 (d, J = 5.2 Hz, 1 H), 7.09 (d, J = 8.2 Hz, 1 H), 7.13-7.20 (m, 1 H), 7.25-7.34 (m, 2 H), 7.48-7.55 (m, 1 H), 7.69 (d, J = 1.6 Hz, 1 H), 7.71-7.80 (m, 2 H), 8.48 (d, J = 7.1 Hz, 1 H), 8.77 (s, 2 H).<br>cis isomer: 1H NMR (500 MHz, DMSO-d6) δ ppm 0.50-0.65 (m, 2 H), 0.88-0.97 (m, 2 H), 1.81 (quin, J = 5.7 Hz, 2 H), 1.84-1.92 (m, 2 H), 1.90-2.01 (m, 1 H), 2.51-2.56 (m, 2 H), 3.24-3.29 (m, 4 H), 3.79-3.92 (m, 2 H), 5.07 (d, J = 5.5 Hz, 1 H), 7.09 (d, J = 8.2 Hz, 1 H), 7.13-7.20 (m, 1 H), 7.25-7.34 (m, 2 H), 7.48-7.55 (m, 1 H), 7.69 (d, J = 1.6 Hz, 1 H), 7.71-7.80 (m, 2 H), 8.46 (d, J = 7.4 Hz, 1 H), 8.77 (s, 2 H)<br>$[M + H]^+$ = 448.2 |

TABLE II-continued

| Ex | Characterizations |
|---|---|
| 178 | $^1$H NMR (500 MHz, DMSO-d6) δ ppm 0.51-0.64 (m, 2 H), 0.87-0.99 (m, 2 H), 1.81 (br t, J = 5.6 Hz, 2 H), 1.94 (tt, J = 8.4, 5.2 Hz, 1 H), 2.57-2.77 (m, 4 H), 3.19-3.61 (m, 4 H), 3.23-3.30 (m, 4 H), 6.78 (d, J = 7.7 Hz, 1 H), 6.95 (t, J = 1.8 Hz, 1 H), 7.07 (dt, J = 8.2, 1.1 Hz, 1 H), 7.12 (d, J = 8.2 Hz, 1 H), 7.26 (t, J = 7.8 Hz, 1 H), 7.67 (d, J = 1.9 Hz, 1 H), 7.73-7.80 (m, 2 H), 8.73-8.81 (m, 2 H) [M + H]$^+$ = 447.3 |
| 179 | $^1$H NMR (400 MHz, DMSO-d6) δ ppm 0.50-0.62 (m, 2 H), 0.86-0.98 (m, 2 H), 1.07-1.38 (m, 3 H), 1.60-2.86 (m, 8 H), 2.88-3.07 (m, 2 H), 3.24-3.30 (m, 4 H), 3.74 (br dd, J = 11.4, 5.9 Hz, 2 H), 6.40 (br d, J = 7.9 Hz, 1 H), 6.59 (br d, J = 2.0 Hz, 1 H), 6.62 (br d, J = 7.9 Hz, 1 H), 7.04-7.19 (m, 2 H), 7.55 (s, 1 H), 7.67 (d, J = 1.5 Hz, 1 H), 7.75 (dd, J = 8.3, 1.5 Hz, 1 H), 8.77 (br s, 2 H) [M + H]$^+$ = 448.3 |
| 180 | $^1$H NMR (300 MHz, $CDCl_3$) δ 7.98 (bs, 1H), 7.94-7.87 (m, 2H), 7.51 (bs, 1H), 7.32-7.27 (m, 2H), 7.23-7.15 (m, 2H), 3.67-3.61 (m, 4H), 3.54 (q, J = 5.7 Hz, 2H), 3.31 (t, J = 5.6 Hz, 4H), 2.52 (t, J = 6.0 Hz, 2H), 2.46 (bs, 4H), 2.28 (s, 3H), 1.98-1.88 (m, 2H), 1.77 (quint, J = 6.0 Hz, 2H) [M + H]$^+$ = 479.4 |
| 181 | $^1$H NMR (400 MHz, DMSO-d6) δ 10.94 (s, 1H), 10.23 (s, 1H), 8.67 (s, 1H), 8.59 (d, J = 2.0 Hz, 1H), 8.22 (s, 1H), 8.17 (dd, J = 8.8, 2.1 Hz, 1H), 7.96 (s, 0H), 7.72 (s, 1H), 7.64-7.56 (m, 1H), 7.45 (dd, J = 4.9, 1.8 Hz, 2H), 7.25-7.22 (m, 1H), 3.56 (td, J = 7.1, 2.8 Hz, 2H), 3.29 (s, 3H), 2.63 (t, J = 7.1 Hz, 2H), 1.36 (s, 3H), 0.75-0.71 (m, 2H), 0.63-0.58 (m, 2H) [M + H]$^+$ = 484.2 |

The following examples are provided as illustrations and in no way limit the scope of this invention.

The following examples illustrate in detail the preparation of some compounds according to the invention. The structures of the products obtained have been confirmed by NMR spectra.

EXAMPLES

Example 1: Compound (22) in Table I

According to route (D2), a reaction mixture of 2-aminopyrimidine (2.0 g, 21.0 mmoles, 1.0 eq.), 4-nitrobenzoyl chloride (4.68 g, 25.2 mmoles, 1.2 eq.), N,N-diisopropylethylamine (5.21 mL, 31.5 mmoles, 1.5 eq.) and dimethylaminopyridine (2.6 g, 21.0 mmole, 1 eq.) in dichloromethane (45 mL) was stirred at room temperature for 18 hours under an inert atmosphere of argon. After washing the organic phase with water, the resulting precipitate formed was filtered, washed with diethyl ether and dried under reduced pressure to give 4-nitro-N-(pyrimidin-2-yl)benzamide (2.0 g, 39%).

$^1$H NMR (300 MHz, $d_6$-DMSO) δ 11.39 (s, 1H), 8.76 (d, J=4.8 Hz, 2H), 8.34 (d, J=8.8 Hz, 2H), 8.16 (d, J=8.8 Hz, 2H), 7.30 (t, J=4.8 Hz, 1H).

According to route (E), 4-nitro-N-(pyrimidin-2-yl)benzamide (1 g, 4.1 mmoles, 1 eq.) and 10% Pd/C (2.2 g) were placed in EtOH (20.5 mL). The reaction mixture was stirred at room temperature for 16 hours under an atmosphere of $H_2$. The reaction mixture was then filtered on celite, washed with EtOH and the filtrate was concentrated under reduced pressure. The resulting residue was purified by column chromatography on silica gel to afford 4-amino-N-(tetrahydropyrimidin-2(1H)-ylidene)benzamide (580 mg, 65%).

$^1$H NMR (300 MHz, $d_6$-DMSO) δ 8.77 (s, 2H), 7.75 (d, J=8.5 Hz, 2H), 6.48 (d, J=8.5 Hz, 2H), 5.50 (s, 2H), 3.28 (t, J=5.7 Hz, 4H), 1.86-1.76 (m, 2H).

2-Cyclopentylethan-1-amine hydrochloride (3.0 g, 19.1 mmoles, 1.1 eq.) was placed in a 3N NaOH aqueous solution (13 mL) and dichloromethane (3.2 mL) was added to the solution. The reaction mixture was cooled down to 0° C. with an ice bath and a solution of 3-bromobenzoyl chloride (2.3 mL, 17.4 mmoles, 1 eq.) in dichloromethane (5.5 mL) was added dropwise. The reaction mixture was then stirred at room temperature for 18 hours under an inert atmosphere of argon. Upon decantation, the organic phase was washed with a saturated aqueous solution of brine, dried over $MgSO_4$, filtered and concentrated under reduced pressure to afford 3-bromo-N-(2-cyclopentylethyl)benzamide (4.6 g, 89%).

$^1$H NMR (300 MHz, $CDCl_3$) δ 7.89 (t, J=1.7 Hz, 1H), 7.67 (d, J=7.9 Hz, 1H), 7.62 (d, J=7.9 Hz, 1H), 7.30 (t, J=7.9 Hz, 1H), 6.07 (s, 1H), 3.46 (dd, J=7.4, 5.9 Hz, 2H), 1.90-1.76 (m, 3H), 1.67-1.52 (m, 6H), 1.20-1.09 (m, 2H).

According to route (A1), a reaction mixture of 3-bromo-N-(2-cyclopentylethyl)benzamide (296 mg, 1.0 mmole, 1 eq.), 4-amino-N-(tetrahydropyrimidin-2(1H)-ylidene)benzamide (218 mg, 1.0 mmole, 1 eq.), $Pd_2(dba)_3$ (92 mg, 0.1 mmole, 10 mol %), XPhos (95 mg, 0.2 mmole, 20 mol %) and $K_2CO_3$ (553 mg, 4.0 mmoles, 4 eq.) in t-BuOH (4 mL) was heated in a microwave reactor at 120° C. for 60 minutes. The reaction mixture was then concentrated under reduced pressure and the resulting residue was diluted with ethyl acetate. The organic phase was washed with water, dried over $MgSO_4$, filtered and concentrated under reduced pressure. The resulting residue was purified by column chromatography on silica gel to give N-(2-cyclopentylethyl)-3-({4-[(tetrahydropyrimidin-2(1H)-ylidene)carbamoyl]phenyl}amino)benzamide (22) (240 mg, 55%).

$^1$H NMR (300 MHz, $d_6$-DMSO) δ 8.77 (s, 2H), 8.55 (s, 1H), 8.37 (t, J=5.6 Hz, 1H), 7.93 (d, J=8.7 Hz, 2H), 7.59 (s, 1H), 7.37-7.29 (m, 2H), 7.27-7.21 (m, 1H), 7.02 (d, J=8.7 Hz, 2H), 3.51-3.39 (m, 1H), 3.29-3.22 (m, 6H), 1.84-1.75 (m, 5H), 1.58-1.47 (m, 7H).

$^{13}$C NMR (75 MHz, $d_6$-DMSO) δ 175.0, 166.6, 159.1, 145.8, 143.1, 136.5, 131.1, 130.4, 129.6, 120.5, 119.7, 119.4, 116.9, 115.1, 38.6, 37.9, 35.9, 32.7, 25.2, 20.5 [M+H]$^+$=434.0

Example 2: Compound (97) in Table I

3-Bromophenol (701 mg, 3.97 mmoles, 1.2 eq.) was placed in N,N-dimethylformamide (4 mL) with $Cs_2CO_3$ (1.3 g, 3.97 mmoles, 1.2 eq.). Upon addition of (3-bromopropyl)cyclohexane (715 mg, 3.31 mmoles, 1 eq.), the reaction mixture was stirred at room temperature for 16 hours under an inert atmosphere of argon. To the reaction mixture was added a saturated aqueous solution of $NaHCO_3$ and it was extracted with ethyl acetate. The combined organic phases were dried over magnesium sulphate, filtered and concentrated under reduced pressure. The resulting residue was purified by column chromatography on silica gel to give 1-bromo-3-(3-cyclohexylpropoxy)benzene (882 mg, 90%).

$^1$H NMR (500 MHz, $d_6$-DMSO) δ 7.22 (t, J=8.1 Hz, 1H), 7.14-7.08 (m, 2H), 6.93 (dd, J=8.3, 2.3 Hz, 1H), 3.95 (t, J=6.5 Hz, 2H), 1.68 (tt, J=15.1, 9.2 Hz, 7H), 1.32-1.06 (m, 6H), 0.92-0.82 (m, 2H).

According to procedure (A1), a reaction mixture of 1-bromo-3-(3-cyclohexylpropoxy)benzene (547 mg, 1.84 mmole, 1.1 eq.), methyl 4-amino-3-cyclopropyl-benzoate (320 mg, 1.67 mmole, 1 eq.), BrettPhos Pd G3 (31.9 mg, 33.5 μmoles, 2 mol %) and $Cs_2CO_3$ (818 mg, 2.51 mmoles, 1.5 eq.) in anhydrous DMF (8 mL) was degassed with $N_2$ and heated at 80° C. for 75 minutes under inert atmosphere. The reaction mixture was cooled down to room temperature, filtered over a pad of celite and the pad was washed with EtOAc. A saturated aqueous solution of brine was then added to the filtrate and the mixture was extracted with EtOAc. The combined organic phases were dried over $MgSO_4$, filtered and concentrated under reduced pressure. The resulting residue was purified by column chromatography on silica gel to give methyl 4-{[3-(3-cyclohexylpropoxy)phenyl]amino}-3-cyclopropylbenzoate (1.35 g, 80%).

$^1$H NMR (400 MHz, $d_6$-DMSO) δ 7.82 (s, 1H), 7.66 (dd, J=8.5, 2.0 Hz, 1H), 7.54 (d, J=2.0 Hz, 1H), 7.24-7.14 (m, 2H), 6.76 (d, J=7.9 Hz, 1H), 6.73 (t, J=2.1 Hz, 1H), 6.56 (dd, J=8.1, 2.2 Hz, 1H), 3.92 (t, J=6.5 Hz, 2H), 3.78 (s, 3H), 1.94 (ddd, J=13.8, 8.3, 5.4 Hz, 1H), 1.75-1.58 (m, 7H), 1.35-1.08 (m, 6H), 1.04-0.94 (m, 2H), 0.88 (q, J=10.0, 9.3 Hz, 2H), 0.65-0.56 (m, 2H).

According to procedure (K), methyl 4-{[3-(3-cyclohexylpropoxy)phenyl]amino}-3-cyclopropylbenzoate (575 mg, 1.34 mmole, 1 eq.) was placed in methanol (10 mL) and an aqueous solution of 2M NaOH (4.7 mL, 9.4 mmoles, 7 eq.) was added. The reaction mixture was heated at 80° C. and stirred for 3 hours. It was then concentrated under reduced pressure and, after addition of an aqueous solution of 2M HCl (7 mL, 14 mmoles, 10.5 eq.), extracted with dichloromethane. The combined organic phases were dried over magnesium sulphate, filtered and concentrated under reduced pressure to give 4-{[3-(3-cyclohexylpropoxy)phenyl]amino}-3-cyclopropylbenzoic acid (540 mg, 97%).

$^1$H NMR (400 MHz, $d_6$-DMSO) δ 12.37 (s, 1H), 7.76 (s, 1H), 7.64 (dd, J=8.5, 2.0 Hz, 1H), 7.52 (d, J=1.9 Hz, 1H), 7.18 (t, J=8.6 Hz, 2H), 6.74 (d, J=7.9 Hz, 1H), 6.71 (d, J=2.1 Hz, 1H), 6.53 (dd, J=8.1, 2.1 Hz, 1H), 3.91 (t, J=6.5 Hz, 2H), 1.94 (ddd, J=13.6, 8.4, 5.4 Hz, 1H), 1.75-1.58 (m, 7H), 1.35-1.09 (m, 6H), 0.98 (dd, J=4.0, 2.0 Hz, 2H), 0.88 (q, J=10.1, 9.3 Hz, 2H), 0.65-0.56 (m, 2H).

According to procedure (L), a reaction mixture of 4-{[3-(3-cyclohexylpropoxy)phenyl]amino}-3-cyclopropylbenzoic acid (100 mg, 241 μmoles, 1 eq.) and CDI (47.0 mg, 290 μmoles, 1.2 eq.) in anhydrous DMF (1.0 mL) was stirred at room temperature for 1 hour. The mixture was then added to a solution of beta-alacleatinine hydrochloride (72.2 mg, 483 μmoles, 2 eq.) and DIPEA (126 μL, 724 μmoles, 3 eq.) in anhydrous DMF (1.0 mL) and the resulting mixture was heated at 75° C. and stirred for 16 hours. The reaction mixture was then cooled down to room temperature, quenched with a saturated aqueous solution of sodium bicarbonate and extracted with EtOAc. The combined organic layers were then washed with a saturated aqueous solution of brine, dried over $MgSO_4$, filtered and concentrated under reduced pressure. The resulting residue was purified by column chromatography on silica gel to give 4-{[3-(3-cyclohexylpropoxy)phenyl]amino}-3-cyclopropyl-N-[(2E)-4-oxo-1,3-diazinan-2-ylidene]benzamide (97) (75.0 mg, 62%).

$^1$H NMR (400 MHz, $d_6$-DMSO) δ 10.78 (s, 1H), 10.15 (s, 1H), 7.85-7.77 (m, 2H), 7.67 (s, 1H), 7.15 (t, J=8.4 Hz, 2H), 6.70 (d, J=7.9 Hz, 1H), 6.67 (t, J=2.1 Hz, 1H), 6.47 (dd, J=8.1, 2.1 Hz, 1H), 3.90 (t, J=6.5 Hz, 2H), 3.54 (t, J=7.0 Hz, 2H), 2.61 (t, J=7.0 Hz, 2H), 1.94 (ddd, J=13.7, 8.4, 5.5 Hz, 1H), 1.69 (t, J=14.5 Hz, 7H), 1.34-1.08 (m, 6H), 1.02-0.81 (m, 4H), 0.61 (q, J=5.8 Hz, 2H).

$^{13}$C NMR (151 MHz, $d_6$-DMSO) δ 160.0, 157.6, 146.3, 144.8, 131.0, 130.2, 128.0, 115.7, 111.4, 107.5, 105.4, 68.0, 37.2, 36.8, 33.7, 33.3, 30.5, 26.6, 26.5, 26.3, 11.5, 7.6

$[M+H]^+$=489.1

Example 3: Compound (98) in Table I

To a solution of 3-bromobenzoic acid (2.00 g, 9.95 mmoles, 1 eq.) and isopropylamine (940 μL, 10.9 mmoles, 1.1 eq.) in anhydrous DMF (10 mL) was added HATU (3.78 g, 9.95 mmoles, 1 eq.) and DIPEA (2.60 mL, 114.9 mmoles, 1.5 eq.) and the reaction mixture then stirred at room temperature overnight. The reaction was quenched with 1M aqueous hydrochloric acid and extracted with EtOAc. The combined organic layers were then dried over $MgSO_4$, filtered and concentrated under reduced pressure. The resulting residue was purified by column chromatography on silica gel to afford 3-bromo-N-isopropylbenzamide (1.88 g, 76%).

$^1$H NMR (400 MHz, $d_6$-DMSO) δ 8.34 (d, J=7.4 Hz, 1H), 8.03 (s, 1H), 7.85 (d, J=7.8 Hz, 1H), 7.75-7.68 (m, 1H), 7.43 (t, J=7.9 Hz, 1H), 4.17-4.00 (m, J=6.7 Hz, 1H), 1.17 (d, J=6.6 Hz, 6H).

According to route (A1), a reaction mixture of 3-bromo-N-isopropylbenzamide (197 mg, 0.796 mmole, 1.1 eq.), methyl 4-amino-3-tert-butyl-benzoate (150 mg, 0.724 mmole, 1 eq.), $Pd(OAc)_2$ (4.9 mg, 0.022 mmole, 3 mol %), rac-BINAP (9.0 mg, 0.015 mmole, 2 mol %) and $K_2CO_3$ (300 mg, 2.17 mmoles, 3 eq.) in anhydrous toluene (3 mL) was degassed with $N_2$ and heated at 110° C. for 75 minutes under inert atmosphere. The reaction mixture was cooled down to room temperature, filtered over a pad of celite and the pad was washed with EtOAc. A saturated aqueous solution of brine was then added to the filtrate and the mixture was extracted with EtOAc. The combined organic phases were dried over $MgSO_4$, filtered and concentrated under reduced pressure. The resulting residue was purified by column chromatography on silica gel to give methyl 3-tert-butyl-4-{[3-(isopropylcarbamoyl)phenyl]amino}benzoate (163 mg, 60%).

$^1$H NMR (400 MHz, $d_6$-DMSO) δ 8.09 (d, J=7.8 Hz, 1H), 8.01 (d, J=2.0 Hz, 1H), 7.74 (dd, J=8.3, 1.9 Hz, 1H), 7.39 (s, 1H), 7.33-7.22 (m, 3H), 7.17 (d, J=8.4 Hz, 1H), 6.98 (d, J=7.6 Hz, 1H), 4.07 (dq, J=13.4, 6.6 Hz, 1H), 3.83 (s, 3H), 1.42 (s, 9H), 1.15 (d, J=6.6 Hz, 6H).

According to procedure (K), methyl 3-tert-butyl-4-{[3-(isopropylcarbamoyl)phenyl]amino}benzoate (160 mg, 0.434 mmole, 1 eq.) was placed in methanol (2 mL) and an aqueous solution of 2M NaOH (1.3 mL, 2.61 mmoles, 6 eq.) was added. The reaction mixture was heated at 80° C. and stirred for 3 hours. It was then concentrated under reduced pressure and, after addition of an aqueous solution of 2M HCl (10 eq.), extracted with dichloromethane. The combined organic phases were dried over magnesium sulphate, filtered and concentrated under reduced pressure to give 3-tert-butyl-4-{[3-(isopropylcarbamoyl)phenyl]amino}benzoic acid (142 mg, 90%).

$^1$H NMR (400 MHz, $d_6$-DMSO) δ 12.64 (s, 1H), 8.07 (d, J=7.7 Hz, 1H), 8.02 (s, 1H), 7.73 (d, J=8.4 Hz, 1H), 7.35 (s, 1H), 7.27-7.19 (m, 3H), 7.16 (d, J=8.2 Hz, 1H), 6.94 (d, J=6.5 Hz, 1H), 4.14-3.99 (m, 1H), 1.42 (s, 9H), 1.15 (d, J=6.6 Hz, 6H).

According to procedure (L), a reaction mixture of 3-tert-butyl-4-{[3-(isopropylcarbamoyl)phenyl]amino}benzoic acid (65.0 mg, 180 μmoles, 1 eq.) and CDI (35.0 mg, 216 μmoles, 1.2 eq.) in anhydrous DMF (1.0 mL) was stirred at room temperature for 1 hour. The mixture was then added to a solution of beta-alacleatinine hydrochloride (53.8 mg, 359 μmoles, 2 eq.) and DIPEA (93.9 μL, 539 μmoles, 3 eq.) in anhydrous DMF (1.0 mL) and the resulting mixture was heated at 75° C. and stirred for 16 hours. The reaction mixture was then cooled down to room temperature, quenched with a saturated aqueous solution of sodium bicarbonate and extracted with EtOAc. The combined organic layers were then washed with a saturated aqueous solution of brine, dried over $MgSO_4$, filtered and concentrated under reduced pressure. The resulting residue was purified by column chromatography on silica gel to give 3-tert-butyl-4-{[3-(isopropylcarbamoyl)phenyl]amino}-N-[(2E)-4-oxo-1,3-diazinan-2-ylidene]benzamide (98) (37.0 mg, 45%).

$^1$H NMR (400 MHz, $d_6$-DMSO) δ 10.83 (s, 1H), 10.21 (s, 1H), 8.27 (d, J=1.8 Hz, 1H), 8.04 (d, J=7.8 Hz, 1H), 7.90 (dd, J=8.2, 1.8 Hz, 1H), 7.29 (s, 1H), 7.18 (s, 3H), 7.13 (d, J=8.2 Hz, 1H), 6.90-6.82 (m, 1H), 4.06 (dq, J=13.3, 6.6 Hz, 1H), 3.56 (t, J=7.0 Hz, 2H), 2.63 (t, J=7.0 Hz, 2H), 1.41 (s, 9H), 1.14 (d, J=6.6 Hz, 6H).

$^{13}$C NMR (151 MHz, $d_6$-DMSO) δ 177.4, 170.2, 166.1, 157.8, 147.1, 145.0, 144.0, 136.5, 133.5, 129.1, 128.7, 128.1, 126.6, 118.5, 117.3, 115.5, 41.3, 36.8, 35.2, 30.9, 30.5, 22.8 $[M+H]^+$=450.1

Example 4: Compound (102) in Table I

According to route (A1), a reaction mixture of 3-bromo-N-isopropylbenzamide (135 mg, 0.547 mmole, 1.1 eq.), methyl 4-amino-3-cyclopropyl-benzoate (100 mg, 0.497 mmole, 1 eq.), BrettPhos Pd G3 (23.7 mg, 24.8 μmoles, 5 mol %) and $Cs_2CO_3$ (243 mg, 0.745 mmole, 1.5 eq.) in anhydrous DMF (2 mL) was degassed with $N_2$ and heated at 80° C. for 75 minutes under inert atmosphere. The reaction mixture was cooled down to room temperature, filtered over a pad of celite and the pad was washed with EtOAc. A saturated aqueous solution of brine was then added to the filtrate and the mixture was extracted with EtOAc. The combined organic phases were dried over $MgSO_4$, filtered and concentrated under reduced pressure. The resulting residue was purified by column chromatography on silica gel to give methyl 3-cyclopropyl-4-{[3-(isopropylcarbamoyl)phenyl]amino}benzoate (131 mg, 71%).

$^1$H NMR (400 MHz, $d_6$-DMSO) δ 8.17 (d, J=7.8 Hz, 1H), 8.01 (s, 1H), 7.67 (dd, J=8.8, 1.9 Hz, 2H), 7.55 (d, J=2.0 Hz, 1H), 7.47 (dt, J=7.6, 1.3 Hz, 1H), 7.38 (t, J=7.8 Hz, 1H), 7.31 (ddd, J=7.9, 2.1, 1.1 Hz, 1H), 7.12 (d, J=8.5 Hz, 1H), 4.09 (dq, J=13.3, 6.6 Hz, 1H), 3.79 (s, 3H), 1.96 (tt, J=8.3, 5.6 Hz, 1H), 1.16 (d, J=6.6 Hz, 6H), 1.04-0.95 (m, 2H), 0.65-0.57 (m, 2H).

According to procedure (K), methyl 3-cyclopropyl-4-{[3-(isopropylcarbamoyl)phenyl]amino}benzoate (130 mg, 0.350 mmole, 1 eq.) was placed in methanol (2 mL) and an aqueous solution of 2M NaOH (0.88 mL, 1.75 mmole, 5 eq.) was added. The reaction mixture was heated at 80° C. and stirred for 3 hours. It was then concentrated under reduced pressure and, after addition of an aqueous solution of 2M HCl (10 eq.), extracted with dichloromethane. The combined organic phases were dried over magnesium sulphate, filtered and concentrated under reduced pressure to give 3-cyclopropyl-4-{[3-(isopropylcarbamoyl)phenyl]amino}benzoic acid (115 mg, 92%).

$^1$H NMR (400 MHz, $d_6$-DMSO) δ 12.38 (s, 1H), 8.16 (d, J=7.8 Hz, 1H), 7.96 (s, 1H), 7.69-7.61 (m, 2H), 7.54 (d, J=2.0 Hz, 1H), 7.44 (dt, J=7.6, 1.3 Hz, 1H), 7.37 (t, J=7.7 Hz, 1H), 7.29 (ddd, J=7.9, 2.1, 1.1 Hz, 1H), 7.12 (d, J=8.5 Hz, 1H), 4.09 (dq, J=13.2, 6.6 Hz, 1H), 1.96 (tt, J=8.3, 5.4 Hz, 1H), 1.16 (d, J=6.6 Hz, 6H), 1.03-0.92 (m, 2H), 0.68-0.57 (m, 2H).

According to procedure (L), a reaction mixture of 3-cyclopropyl-4-{[3-(isopropylcarbamoyl)phenyl]amino}benzoic acid (82.0 mg, 230 μmoles, 1 eq.) and CDI (44.8 mg, 276 μmoles, 1.2 eq.) in anhydrous DMF (1.0 mL) was stirred at room temperature for 1 hour. The mixture was then added to a solution of 1,4,5,6-tetrahydropyrimidin-2-amine hydrochloride (65.7 mg, 460 μmoles, 2 eq.) and DIPEA (120 μL, 691 μmoles, 3 eq.) in anhydrous DMF (1.0 mL) and the resulting mixture was heated at 75° C. and stirred for 16 hours. The reaction mixture was then cooled down to room temperature, quenched with a saturated aqueous solution of sodium bicarbonate and extracted with EtOAc. The combined organic layers were then washed with a saturated aqueous solution of brine, dried over $MgSO_4$, filtered and concentrated under reduced pressure. The resulting residue was purified by column chromatography on silica gel followed by preparative HPLC to give 3-cyclopropyl-N-(1,3-diazinan-2-ylidene)-4-{[3-(isopropylcarbamoyl)phenyl]amino}benzamide (102) (17.8 mg, 18%).

$^1$H NMR (400 MHz, $d_6$-DMSO) δ 10.79 (s, 1H), 10.16 (s, 1H), 8.14 (d, J=7.8 Hz, 1H), 7.87 (s, 1H), 7.82 (d, J=8.1 Hz, 2H), 7.60 (t, J=1.8 Hz, 1H), 7.38 (dt, J=7.6, 1.4 Hz, 1H), 7.33 (t, J=7.7 Hz, 1H), 7.28-7.21 (m, 1H), 7.12 (d, J=8.3 Hz, 1H), 4.08 (dp, J=13.7, 6.9 Hz, 1H), 3.54 (t, J=7.0 Hz, 2H), 2.62 (t, J=7.0 Hz, 2H), 1.96 (tt, J=8.4, 5.6 Hz, 1H), 1.16 (d, J=6.6 Hz, 6H), 1.02-0.92 (m, 2H), 0.67-0.58 (m, 2H).

$^{13}$C NMR (151 MHz, $d_6$-DMSO) δ 170.2, 165.9, 157.6, 146.3, 143.6, 136.5, 131.0, 129.2, 128.0, 128.0, 121.6, 119.9, 118.4, 115.4, 41.4, 36.8, 30.5, 22.8, 11.6, 7.6 $[M+H]^+$=434.2

Example 5: Compound (120) in Table I

According to procedure (L), a reaction mixture of 3-cyclopropyl-4-{[3-(isopropylcarbamoyl)phenyl]amino}benzoic acid (50.0 mg, 148 μmoles, 1 eq.) and CDI (28.8 mg, 177 μmoles, 1.2 eq.) in anhydrous DMF (1.0 mL) was stirred at room temperature for 1 hour. The mixture was then added to a solution of beta-alacleatinine hydrochloride (44.2 mg, 296 μmoles, 2 eq.) and DIPEA (77.2 μL, 443 μmoles, 3 eq.) in anhydrous DMF (1.0 mL) and the resulting mixture was heated at 75° C. and stirred for 16 hours. The reaction mixture was then cooled down to room temperature, quenched with a saturated aqueous solution of sodium bicarbonate and extracted with EtOAc. The combined organic layers were then washed with a saturated aqueous solution of brine, dried over $MgSO_4$, filtered and concentrated under reduced pressure. The resulting residue was purified by column chromatography on silica gel to give 3-cyclopropyl-4-{[3-(isopropylcarbamoyl)phenyl]amino}-N-[(2E)-4-oxo-1,3-diazinan-2-ylidene]benzamide (120) (30.0 mg, 45%).

$^1H$ NMR (400 MHz, $d_6$-DMSO) δ 8.79 (s, 2H), 8.12 (d, J=7.6 Hz, 1H), 7.75 (d, J=7.6 Hz, 2H), 7.68 (s, 1H), 7.54 (s, 1H), 7.31 (s, 2H), 7.18 (s, 1H), 7.10 (d, J=8.3 Hz, 1H), 4.14-4.02 (m, 1H), 3.29 (s, 4H), 2.00-1.91 (m, 1H), 1.83 (s, 2H), 1.15 (d, J=6.6 Hz, 6H), 0.95 (d, J=7.4 Hz, 2H), 0.59 (d, J=4.2 Hz, 2H).

$^{13}C$ NMR (151 MHz, $d_6$-DMSO) δ 175.1, 166.1, 159.2, 144.6, 144.5, 136.5, 132.6, 131.8, 129.2, 127.3, 127.0, 120.4, 119.0, 117.3, 116.7, 41.3, 38.5, 22.8, 20.4, 11.6, 7.8

$[M+H]^+$=420.3

Pharmacological Data

Example 6: Chikungunya Virus

The compounds of the invention have been the subject of pharmacological tests which have demonstrated their relevance as active substances in therapy and in particular for preventing, inhibiting or treating Chikungunya virus infection.

Material and Methods

Inhibition of Chikungunya Virus (CHIKV) Production in Infected HEK293T Cell Line.

The ability of the compounds to inhibit viral replication was assessed with an experiment in which infected cells were treated by compounds of formula (Ic) at 1 μM. As a positive control for inhibition of Chikungunya, Ribavirin was used. Toxicity of the compounds was assessed in parallel.

Amplification of Cells

Human embryonic kidney cells 293T (HEK293T, CRL-11268) were maintained in Dulbecco's modified Eagle's Medium (DMEM, 31966-021, Thermo Fisher Scientific) supplemented with 10% of fetal bovine serum (FBS), penicillin and streptomycin. After removal of the medium, cells were washed with $Ca^{2+}$ and $Mg^{2+}$-free salt solution to remove all traces of serum. After aspiration of wash solution, cells were dissociated with 0.25% Trypsin-EDTA solution and incubated 30 s at least in 37° C. incubator. Concentration of cell suspension was determined by an automatic cell counter (EVE, NanoEntek) and, if needed, adjusted to $0.33\times10^6$ cells/mL with DMEM medium supplemented with 10% FBS.

Preparation of the Compounds

100 μL of the cell suspension were dispatched in a ViewPlate-96 Black (6005182, PerkinElmer) and in a transparent 96-well cell culture plate (655180, Greiner bio-one). After an incubation for 24 h at 37° C. under 5% of $CO_2$, compounds were added at the proper concentration.

Screen at 1 μM

An intermediate dilution was prepared with DMSO (D8418, Sigma) at 2 mM in a 96-well V-bottom microplate from the stock solution:

Mix 1 μL of the 50 mM stock library in 25 μL of DMSO.

Mix 2 μL of the 25 mM stock library in 25 μL of DMSO.

Determination of $IC_{50}$ Values

An intermediate dilution was prepared with DMSO (D8418, Sigma) at 25 mM in a 96-well V-bottom microplate from the stock solution:

Mix 2 μL of the 50 mM stock library in 2 μL of DMSO.

Perform serial dilution in 2 μL of DMSO 13 times to reach 0.0015 mM. Proceed as follows in table III:

TABLE III

| | Concentration (mM) | Volume of DMSO 100% (μL) | Volume of solution |
|---|---|---|---|
| A | 12.5 | 2 | 2 μL of 50 mM solution |
| B | 6.25 | 2 | 2 μL of solution A |
| C | 3.125 | 2 | 2 μL of solution B |
| D | 1.56 | 2 | 2 μL of solution C |
| E | 0.78 | 2 | 2 μL of solution D |
| F | 0.39 | 2 | 2 μL of solution E |
| G | 0.195 | 2 | 2 μL of solution F |
| H | 0.0976 | 2 | 2 μL of solution G |
| I | 0.0488 | 2 | 2 μL of solution H |
| J | 0.0244 | 2 | 2 μL of solution I |
| K | 0.0122 | 2 | 2 μL of solution J |
| L | 0.0061 | 2 | 2 μL of solution K |
| M | 0.0030 | 2 | 2 μL of solution L |
| N | 0.0015 | 2 | 2 μL of solution M |

For both screen and determination of $IC_{50}$, 1 μL of each solution was added in a 1 mL Masterblock 96 wells (Greiner bio-one, 780261) containing 1 mL of DMEM medium. As a positive control, 5 μL of a 80 mM Ribavirin solution (R9644, Sigma) is added to 1 mL of DMEM. On the other hand, DMSO is used as a negative control.

Infection

Cells were infected with 30 μL of CHIKV strain of La Réunion outbreak (LR2006-OPY1) with GFP modification in 5' (CHIK 5'LR) (Tsetsarkin K, Higgs S, McGee C E, De Lamballerie X, Charrel R N, Vanlandingham D L. Infectious Clones of Chikungunya Virus (La Réunion-Isolate-Ref-SKU: 001N-EVA249 (PMID: 17187566) available at european-virus-archive.com) for Vector Competence Studies. Vector Borne Zoonotic Dis. 2006; 6 (4)). This modified virus was used to infect cells at MOI 0.1. The LR2006-OPY1 strain of CHIKV (CHIKV-LR) was obtained from the World Reference Center for Arboviruses at the University of Texas Medical Branch, Galveston, TX. This strain was originally isolated from the serum of a febrile French patient returning from La Réunion Island.

Cell Lysis

Medium was removed after 22 h at 37° C. under 5% of $CO_2$ and cells were washed as described above. 60 μL of RIPA buffer (50 mM Tris-HCl pH8, 100 mM NaCl, 1 mM $MgCl_2$, 1% Triton X-100) was added to cells and incubated for at least 20 min before reading fluorescence signal. Pierce 660 nm Protein Assay Reagent (22660, Thermo scientific) was used to normalize fluorescence signal by protein quantity.

CellTiter 96® AQueous One Solution Cell Proliferation Assay (MTS) (G3581, Promega) was used to check the toxicity of the compounds. We added 20 μL of MTS solution and read absorbance at 492 nm one hour later.

Results

A first round of experiments has been performed wherein the results are expressed as inhibition percentage, which is calculated as follows, through the following steps:

1. Fluorescence intensity (FI)/Absorbance 660 nm (A660)=A

This ratio allows considering the infection (GFP virus) to the protein amount.

2. A'=A−background noise of non-infected plate,
3. B=Fluorescence intensity (FI)/Absorbance 660 nm (A660) of infected but non treated plates, 4. C=A'/B, which is then converted as the percentage of infection after treatment, compared to non-treated sample, and subsequently as the infection percentage. For instance, a value of 100 in Table IV here below means that, after treatment, the signal attributed to GFP fluorescence is abolished, which is correlated to the absence of infection.
5. C'=100-C This value corresponds to the inhibition's percentage.

The following Table IV encompasses said C' value for some compounds, as calculated above with a mean of 2 experiments, and corresponding standard deviation.

Some values were originally above 100. In these cases, the value has been lowered to 100. This means that some molecules also have an impact on the viability of the cells. In other words, the A value may be lower than the background noise.

Moreover, for each measure, the test was performed with Ribavirin as control. The value of the inhibition percentage was checked, giving 100%.

TABLE IV

| | % CHIKV Inhibition | |
|---|---|---|
| Ex | Mean (n = 2) | Standard deviation (n = 2) |
| 22 | 94 | 5 |
| 23 | 98 | 0 |
| 24 | 100 | 0 |
| 26 | 97 | 0 |
| 27 | 96 | 1 |
| 28 | 97 | 0 |

A second round of experiments has been performed, giving the results as $IC_{50}$ values.

The $IC_{50}$ values range between 0.1 nM and 1 μM, in particular between 0.5 and 500 nM and even more particularly between 1 and 400 nM, for example between 1 and 200 nM. For example compounds 22, 23 and 24 have $IC_{50}$ values ranging between 100 et 400 nM.

Conclusion

Based on the previous results, it can be concluded that the compounds of formula (Ic) are suitable chemical compounds for treating and/or preventing RNA virus infections caused by RNA viruses of group IV, more particularly, alphavirus infections, and most particularly Chikungunya virus infections.

Example 7: RSV Virus

The compounds of the invention have been the subject of pharmacological tests which have demonstrated their relevance as active substances in therapy and in particular for preventing, inhibiting or treating RSV virus infection.

Material and Methods

Protocol for Screening Antiviral Compounds for RSV Inhibition and Cytotoxicity Using Viral ToxGlo Assay HEp-2 cells were maintained in Eagle's minimum essential medium (EMEM) with Earle's BSS adjusted to contain 2 mM L-glutamine, 10% fetal bovine serum, 100 U/ml penicillin and 100 μg/ml streptomycin. For the purposes of the screening assay they were grown to 90% confluency, trypsinized and recovered. The trypsin was neutralised with cell culture media and cells were centrifuged at 150×g for 5 minutes before discarding the supernatant and resuspending cell pellet in assay media (EMEM with Earle's BSS adjusted to contain 2 mM L-glutamine, 2% fetal bovine serum and 100 U/ml penicillin and 100 μg/ml streptomycin). The cells were seeded into white clear-bottomed cell culture plates at a density of $1.5\times10^4$ cells/well in 50 μl and $4\times10^3$ cells/well in 25 μl for 96 well plates and 384 well plates respectively. For the media/background control column assay media only was added. Cell plates were placed in a humid chamber and incubated overnight at 37° C./5% $CO_2$. After overnight incubation cells were checked for confluency and healthy appearance.

Test articles were made up at 10× test concentration in a maximum DMSO concentration of 10% (final assay concentration maximal 1% DMSO) and added to the cell plates in volumes of 10 μl for 96 well plates and 5 μl for 384 well plates. For cell control and virus control wells the test article solvent only was added. Virus or assay media for cytotoxicity test wells and media/cell control wells was added immediately after test articles at an MOI of 0.5, 40 or 20 μl for 96 and 384 well plates respectively. Virus suspension was prepared by thawing RSV A2 frozen stocks and diluting to the required concentration of plaque forming units in assay media on ice.

Cell plates were further incubated inside a humid chamber for 72 h p.i at 37° C./5% $CO_2$. After the incubation period cells were observed under the microscope to check for characteristic cytopathic effect in virus control wells and healthy cells in the cell control wells. After plates were adjusted to room temperature 20/40 μl Viral ToxGlo (Promega) was added to each well of the 384/96 well cell plates. Plates were incubated at room temperature, protected from light on a plate rocker for 20 minutes before measuring the luminescence on a spectrophotometer (Biotek Synergy HTX).

RSV inhibition was calculated as percentage of cytopathic effect inhibition relative to the virus control and cytotoxicity as percentage of cell survival relative to cell control wells. This allowed $EC_{50}$ values to be calculated for each test article where a virus inhibition or cytotoxic dose response was identified. $EC_{50}$ values ranging between 0.001 μM and 2.5 μM were found, and more particularly for compounds 27, 28, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 161, 162, 163, 164, 165 and 166.

TABLE V

| Ex | $EC_{50}$ (nM) |
|---|---|
| 27 | 365 |
| 28 | 308 |
| 91 | 2 |
| 92 | 2 |
| 93 | 13 |
| 94 | 17 |
| 95 | 19 |
| 96 | 20 |
| 97 | 25 |
| 98 | 33 |
| 99 | 34 |
| 100 | 37 |
| 101 | 40 |
| 102 | 41 |
| 103 | 44 |
| 104 | 50 |
| 105 | 62 |
| 106 | 67 |

TABLE V-continued

| Ex | $EC_{50}$ (nM) |
|---|---|
| 107 | 68 |
| 108 | 77 |
| 109 | 79 |
| 110 | 80 |
| 111 | 86 |
| 112 | 97 |
| 113 | 102 |
| 114 | 110 |
| 115 | 110 |
| 116 | 122 |
| 117 | 125 |
| 118 | 126 |
| 119 | 130 |
| 120 | 136 |
| 121 | 139 |
| 122 | 141 |
| 123 | 147 |
| 124 | 150 |
| 125 | 151 |
| 126 | 165 |
| 127 | 172 |
| 128 | 209 |
| 129 | 223 |
| 130 | 234 |
| 131 | 246 |
| 132 | 259 |
| 133 | 261 |
| 134 | 265 |
| 135 | 286 |
| 136 | 298 |
| 137 | 304 |
| 138 | 310 |
| 139 | 340 |
| 140 | 368 |
| 141 | 370 |
| 142 | 387 |
| 143 | 398 |
| 144 | 413 |
| 145 | 421 |
| 146 | 439 |
| 147 | 460 |
| 148 | 463 |
| 149 | 494 |
| 150 | 512 |
| 151 | 525 |
| 152 | 593 |
| 153 | 704 |
| 154 | 917 |
| 155 | 949 |
| 156 | 966 |
| 157 | 1030 |
| 158 | 1032 |
| 159 | 1103 |
| 161 | 1308 |
| 162 | 1374 |
| 163 | 1472 |
| 164 | 1504 |
| 165 | 1756 |
| 166 | 2739 |

Conclusion

Based on the previous results, it can be concluded that the compounds of formula (Ic) are suitable chemical compounds for treating and/or preventing RNA virus infections caused by RNA viruses of group V, more particularly, pneumovirus infections, and most particularly RSV virus infections.

The present invention further relates to a pharmaceutical composition comprising at least one new compound as defined above or any of its pharmaceutically acceptable salts, or at least any of compounds (19) to (31) and (91) to (181) as defined above or any of its pharmaceutically acceptable salts and also at least one pharmaceutically acceptable excipient.

Pharmaceutical compositions of the invention can contain one or more compound(s) of the invention in any form described herein.

Still a further object of the present invention consists of the use of at least one compound of formula (Ic), as defined above, and compounds (19) to (31) and (91) to (181) as defined above, or one of their pharmaceutically acceptable salts according to the present invention for preparing a drug to prevent or treat, in a subject, a RNA virus infection caused by a RNA virus from group IV or Group V according to the Baltimore classification, and for example a Chikungunya infection, a Dengue infection, an Influenza infection or a RSV infection.

Therefore, the present invention relates to one compound of formula (Ic), as defined above, and compounds (19) to (31) and (91) to (181) or one of their acceptable salts as an agent for inhibiting, preventing or treating a RNA virus infection, and most preferably a RNA virus infection from group IV or V, and for example a Chikungunya infection, a Dengue infection, an Influenza infection or a RSV infection.

According to a particular embodiment, the treatment is continuous or non-continuous.

A "continuous treatment" means a long-term treatment which can be implemented with various administration frequencies, such as once every day, every three days, once a week, or once every two weeks or once every month.

According to one embodiment, the compound of formula (Ic), or anyone of its pharmaceutically acceptable salts, is administered at a dose varying from 0.1 to 1000 mg, in particular varying from 0.1 to 10 mg, or for example varying from 10 to 200 mg, or for example varying from 200 to 1000 mg.

Another object of the invention relates to a therapeutic method for treating and/or preventing a subject from a RNA virus infection, and most preferably a RNA virus infection caused by a virus belonging to group IV or V of the Baltimore classification comprising the administration of a therapeutically effective quantity of a compound of formula (Ic), compounds (19) to (31) and (91) to (181), as defined above, or one of their acceptable salts.

In a specific embodiment, the invention provides a use of a compound of formula (Ic) according to the invention or a pharmaceutically acceptable salt thereof or a pharmaceutically active derivative thereof or a method according to the invention wherein the compound of formula (Ic) is to be administered in combination with a co-agent useful in the treatment of said RNA virus infection, and most preferably said RNA virus infection from group IV or V, and for example Chikungunya infection, Dengue infection, Influenza infection or RSV infection.

The compounds can be administered through any mode of administration such as, for example, intramuscular, intravenous, intranasal or oral route, etc.

Compounds of the present invention may, in appropriate cases, be administered as prodrugs, such as esters, of compounds with which the invention is concerned. "Prodrug" means a compound which is convertible in vivo by metabolic means (e.g. by hydrolysis, reduction or oxidation) to a compound of the present invention. For example, an ester prodrug of a compound of the present invention may be convertible by hydrolysis in vivo to the parent molecule. Suitable esters of compounds of the present invention are for example acetates, citrates, lactates, tartrates, malonates, oxalates, salicylates, propionates, succinates, fumarates, maleates, methylene-bis-β-hydroxynaphthoates, gentisates, isethionates, di-p-toluoyltartrates, methanesulphonates, ethanesulphonates, benzenesulphonates, p-toluenesulphonates, cyclohexylsulfamates and quinates. Examples of ester prodrugs are those described by F. J. Leinweber, Drug Metab. Res., 1987, 18, 379. As used herein, references to the compounds of the present invention are meant to also include any prodrug or metabolite forms.

The inventive composition can further include one or more additives such as diluents, excipients, stabilizers and preservatives. Such additives are well known to those skilled in the art and are described notably in' "*Ullmann's Encyclopedia of Industrial Chemistry, 6th Ed.*" (various editors, 1989-1998, Marcel Dekker) and in "*Pharmaceutical Dosage Forms and Drug Delivery Systems*" (ANSEL et al., 1994, WILLIAMS & WILKINS).

The aforementioned excipients are selected according to the dosage form and the desired mode of administration.

According to another embodiment, pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

Compositions of this invention may be administered in any manner, including, but not limited to, orally, parenterally, sublingually, transdermally, vaginally, rectally, transmucosally, topically, intranasally via inhalation, via buccal or intranasal administration, or combinations thereof. Parenteral administration includes, but is not limited to, intravenous, intra-arterial, intra-peritoneal, subcutaneous, intramuscular, intra-thecal, and intra-articular. The compositions of this invention may also be administered in the form of an implant, which allows slow release of the compositions as well as a slow controlled i.v. infusion.

For example, a compound of formula (Ic) can be present in any pharmaceutical form which is suitable for enteral or parenteral administration, in association with appropriate excipients, for example in the form of plain or coated tablets, hard gelatine, soft shell capsules and other capsules, suppositories, or drinkable, such as suspensions, syrups, or injectable solutions or suspensions, in doses which enable the daily administration of from 0.1 to 1000 mg of active substance.

In a particular embodiment, a compound of formula (Ic) according to the invention is administered orally.

Oral route of administration is in particular preferred in the prophylaxis or treatment aspect of the invention.

The invention claimed is:

1. A compound of formula (Ic) or a pharmaceutically acceptable salt thereof:

(Ic)

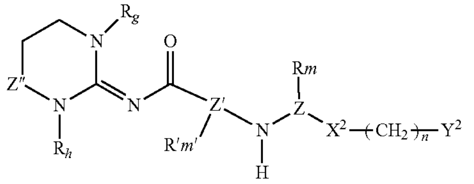

Z is phenylene or pyridylene,

Z' is phenylene or pyridylene, where the ring is connected to the adjacent —C(O)— and —N(H)— in the para-orientation, Z" is $—CH_2—$ or —CO—, $R_g$ and $R_h$ are each independently H or $(C_1-C_4)$alkyl, $X^2$ is $—CO—NR_k—$, —NH—CO—NH—, $—OCH_2—$, —CH(OH)—, —NH—CO—, —O—, $—O—(CH_2)_s—O—$, —CO—, $—SO_2—$, $—NH—SO_2—$, —NH—, $—SO_2—NH—$, or a divalent 5-membered heteroaromatic ring comprising 1, 2, 3 or 4 heteroatoms, wherein $R_k$ is H or methyl, n is 0, 1, 2, or 3, s is 2 or 3, R and R' are each independently (C1-C4)alkyl optionally interrupted by —SO2- or —SO—, $(C_3-C_6)$cycloalkyl, trifluoromethyl, halogen, $(C_1-C_5)$alkoxy, $—SO_2—NR_aR_b$, $—SO_3H$, —OH, $—O—SO_2—OR_c$, or $—O—P(═O)—(OR_c)(OR_d)$, wherein m and m' are independently 0, 1, or 2 and $R_a$, $R_b$, $R_c$ and $R_d$ are independently H or $(C_1-C_4)$alkyl; and $Y^2$ is H, halogen, hydroxyl, $(C_i-C_4)$alkoxy, piperazinyl, piperidinyl, $—CR^1R^2R^3$,

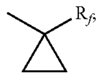

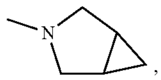
,

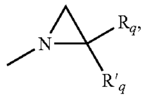

or morpholinyl optionally substituted by $(C_1-C_4)$alkyl, wherein $R_f$ is $(C_1-C_4)$alkyl or cyano, $R_q$ and $R'_q$ are each independently H or methyl, and $R^1$, $R^2$, and $R^3$ are each independently H, F, or $(C_1-C_4)$ alkyl, said $(C_1-C_4)$alkyl optionally substituted by trifluoromethyl and/or hydroxyl, with the proviso that no more than one of $R^1$, $R^2$, and $R^3$ is a hydrogen atom, or $R^1$ and $R^2$ are taken together with the carbon atom bearing them form a $(C_3-C_8)$cycloalkyl optionally interrupted by 1 or 2 oxygen ring atom(s) and optionally substituted by one or two ($C_1$-$C_4$)alkyl, halogen, hydroxy, or ($C_1$-$C_4$)alkoxy.

2. A compound of formula (Ic) or a pharmaceutically acceptable salt thereof according to claim 1, wherein the divalent 5-membered heteroaromatic ring comprising 1, 2, 3 or 4 heteroatoms is selected from a triazole, an imidazole, a tetrazole and an oxadiazole.

3. The compound of formula (Ic) or a pharmaceutically acceptable salt thereof according to claim 1, wherein Z and Z' both are phenylene or Z is pyridylene and Z' is phenylene.

4. The compound of formula (Ic) or a pharmaceutically acceptable salt thereof according to claim 1, wherein $R_g$ is H and $R_h$ is H or ($C_1$-$C_4$)alkyl.

5. The compound of formula (Ic) or a pharmaceutically acceptable salt thereof according to claim 1, wherein $X^2$ is —CO—$NR_k$—, —NH—CO—, —O—, —CO—, —CH(OH)—, —$SO_2$—, —NH—, —NH—$SO_2$—, —$SO_2$—NH—, or a divalent 5-membered heteroaromatic ring comprising 1, 2, 3 or 4 heteroatoms.

6. The compound of formula (Ic) or a pharmaceutically acceptable salt thereof according to claim 5, wherein the divalent 5-membered heteroaromatic ring comprising 1, 2, 3 or 4 heteroatoms is selected from triazole, imidazole, tetrazole, and oxadiazole.

7. The compound of formula (Ic) or a pharmaceutically acceptable salt thereof according to claim 1, wherein $Y^2$ is H, halogen, ($C_1$-$C_4$)alkoxy, —$CR^1R^2R^3$,

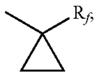

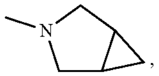

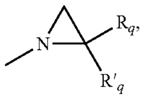

or morpholinyl optionally substituted by ($C_1$-$C_4$)alkyl.

8. The compound of formula (Ic) or a pharmaceutically acceptable salt thereof according to claim 1, wherein R and R' are each independently (C1-C4)alkyl optionally interrupted by —SO2- or —SO—, ($C_3$-$C_6$)cycloalkyl, trifluoromethyl, or halogen.

9. The compound of formula (Ic) or a pharmaceutically acceptable salt thereof according to claim 1, wherein Z and Z' both are phenylene or Z is pyridylene and Z' is phenylene, m and n are each independently 0 or 1, $X^2$ is —CO—NH—, —CO—N($CH_3$)—, —NH—, —NH—CO—, —O—, —CO—, —CH(OH)—, —$SO_2$—, divalent triazole, divalent imidazole, divalent tetrazole, or divalent oxadiazole;

$Y^2$ is H, —$CR^1R^2R^3$,

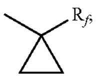

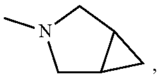

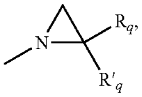

or morpholinyl optionally substituted by ($C_1$-$C_4$)alkyl; and

R and R' are each independently (C1-C4)alkyl, ($C_3$-$C_6$)cycloalkyl, trifluoromethyl, or halogen.

10. The compound of formula (Ic) or a pharmaceutically acceptable salt thereof according to claim 1, wherein Z and Z' both are phenylene, m is 0 and n is 1, $X^2$ is —CO—NH—, —O—;

$Y^2$ is —$CR^1R^2R^3$, wherein $R^1$, $R^2$, and $R^3$ are each independently H or ($C_1$-$C_4$)alkyl with the proviso that no more than one of $R^1$, $R^2$, and $R^3$ is a hydrogen atom, or $R^1$ and $R^2$ are taken together with the carbon atom bearing them form a ($C_3$-$C_8$)cycloalkyl; and R' is ($C_1$-$C_4$)alkyl or ($C_3$-$C_6$)cycloalkyl.

11. A compound of formula (Ic) according to claim 1 selected from

| | (Ic) |
|---|---|
| 19 | 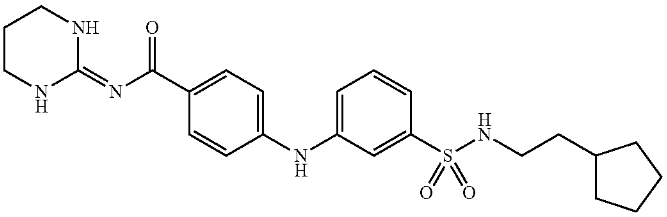 [SMILES: O=C(N=C1NCCCN1)c1ccc(Nc2cccc(S(=O)(=O)NCCC3CCCC3)c2)cc1] |

-continued
(Ic)
20
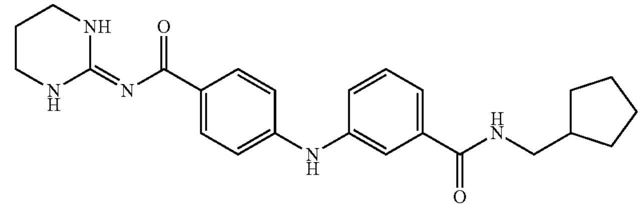 [SMILES: O=C(N=C1NCCCN1)c1ccc(Nc2cccc(C(=O)NCC3CCCC3)c2)cc1]
21
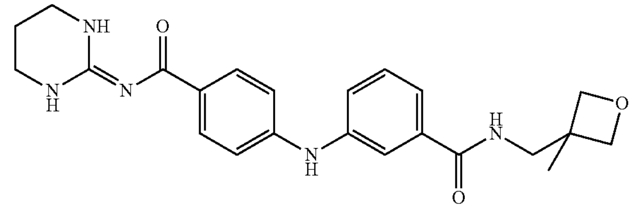 [SMILES: CC1(CNC(=O)c2cccc(Nc3ccc(C(=O)N=C4NCCCN4)cc3)c2)COC1]
22
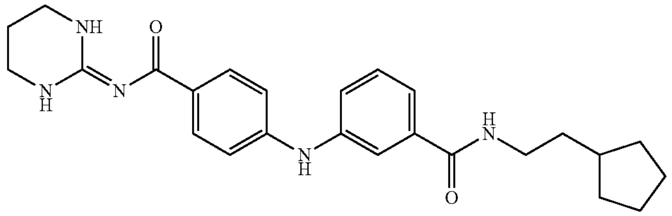 [SMILES: O=C(N=C1NCCCN1)c1ccc(Nc2cccc(C(=O)NCCC3CCCC3)c2)cc1]
23
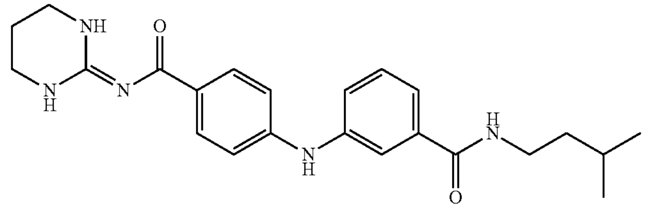 [SMILES: CC(C)CCNC(=O)c1cccc(Nc2ccc(C(=O)N=C3NCCCN3)cc2)c1]
24
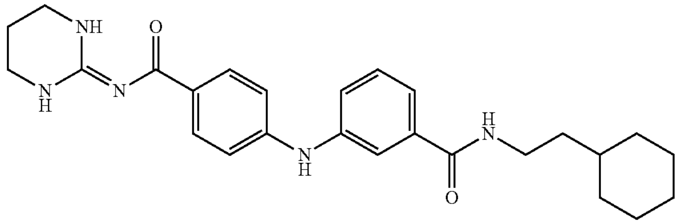 [SMILES: O=C(N=C1NCCCN1)c1ccc(Nc2cccc(C(=O)NCCC3CCCCC3)c2)cc1]
25
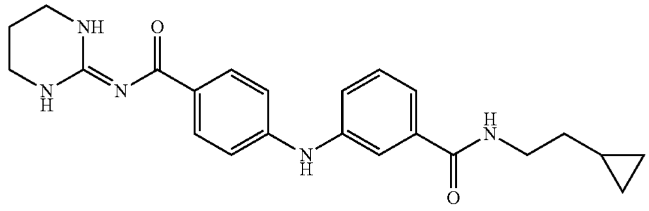 [SMILES: O=C(N=C1NCCCN1)c1ccc(Nc2cccc(C(=O)NCCC3CC3)c2)cc1]
26
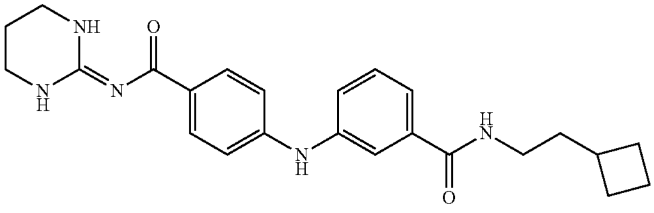 [SMILES: O=C(N=C1NCCCN1)c1ccc(Nc2cccc(C(=O)NCCC3CCC3)c2)cc1]

-continued
| (Ic) | |
|---|---|
| 27 | 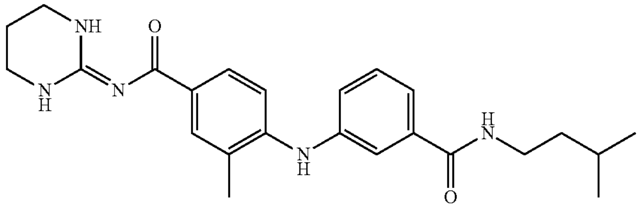 [SMILES: Cc1cc(C(=O)N=C2NCCCN2)ccc1Nc1cccc(C(=O)NCCC(C)C)c1] |
| 28 | 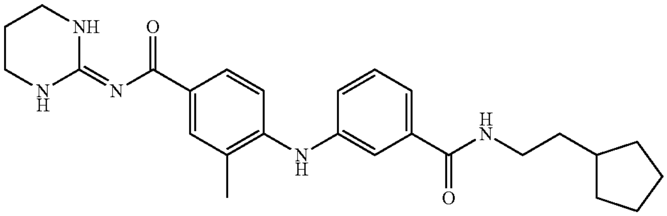 [SMILES: Cc1cc(C(=O)N=C2NCCCN2)ccc1Nc1cccc(C(=O)NCCC2CCCC2)c1] |
| 29 | 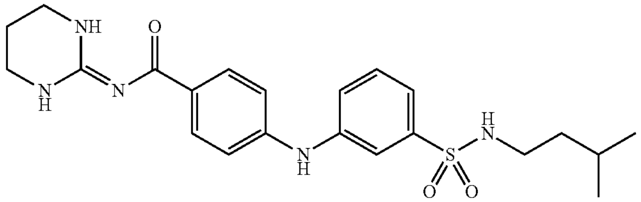 [SMILES: CC(C)CCNS(=O)(=O)c1cccc(Nc2ccc(C(=O)N=C3NCCCN3)cc2)c1] |
| 30 | 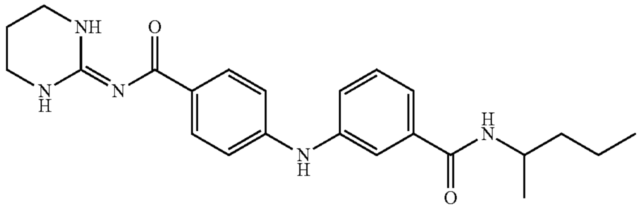 [SMILES: CCCC(C)NC(=O)c1cccc(Nc2ccc(C(=O)N=C3NCCCN3)cc2)c1] |
| 31 | 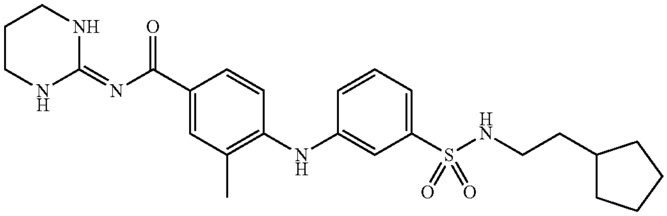 [SMILES: Cc1cc(C(=O)N=C2NCCCN2)ccc1Nc1cccc(S(=O)(=O)NCCC2CCCC2)c1] |
| 91 | 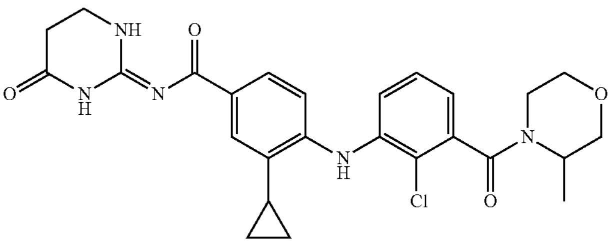 [SMILES: CC1COCCN1C(=O)c1cccc(Nc2ccc(C(=O)/N=C3\NCCC(=O)N3)cc2C2CC2)c1Cl] |
| 92 | 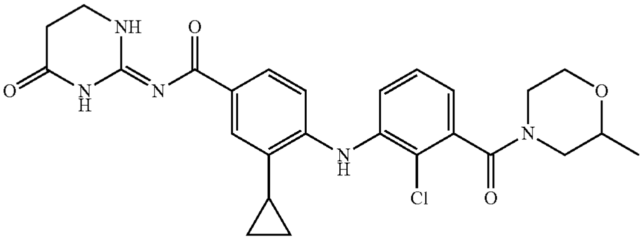 [SMILES: CC1CN(C(=O)c2cccc(Nc3ccc(C(=O)/N=C4\NCCC(=O)N4)cc3C3CC3)c2Cl)CCO1] |

-continued
| (Ic) |
|---|
93
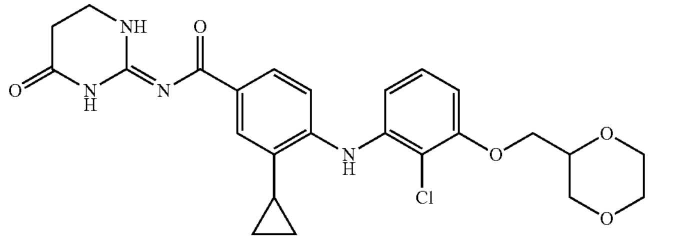 [SMILES: O=C1CCN/C(=N\C(=O)c2ccc(Nc3cccc(OCC4COCCO4)c3Cl)c(C3CC3)c2)N1]
94
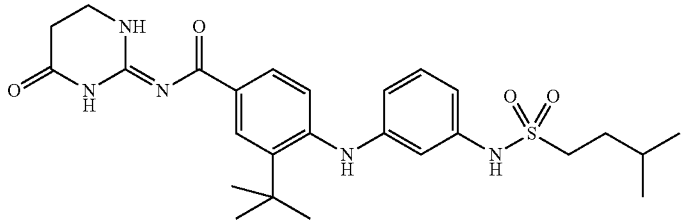 [SMILES: CC(C)CCS(=O)(=O)Nc1cccc(Nc2ccc(C(=O)/N=C3\NCCC(=O)N3)cc2C(C)(C)C)c1]
95
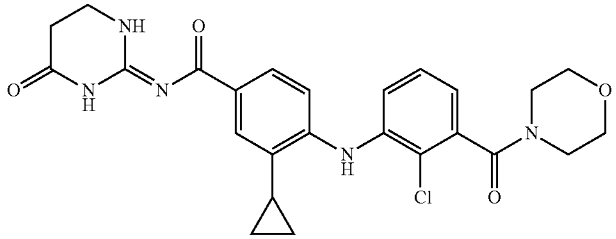 [SMILES: O=C1CCN/C(=N\C(=O)c2ccc(Nc3cccc(C(=O)N4CCOCC4)c3Cl)c(C3CC3)c2)N1]
96
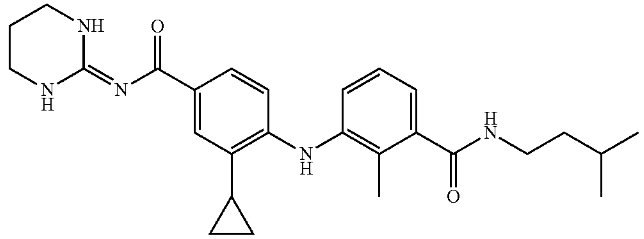 [SMILES: Cc1c(Nc2ccc(C(=O)N=C3NCCCN3)cc2C2CC2)cccc1C(=O)NCCC(C)C]
97
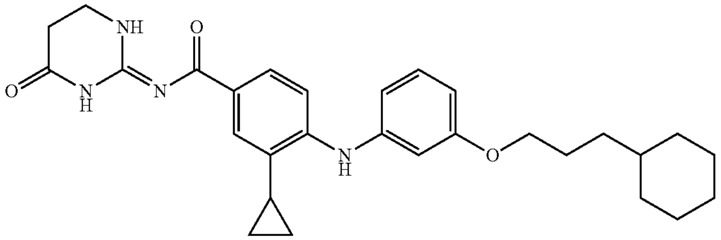 [SMILES: O=C1CCN/C(=N\C(=O)c2ccc(Nc3cccc(OCCCC4CCCCC4)c3)c(C3CC3)c2)N1]
98
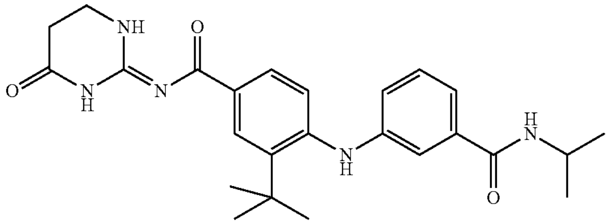 [SMILES: CC(C)NC(=O)c1cccc(Nc2ccc(C(=O)/N=C3\NCCC(=O)N3)cc2C(C)(C)C)c1]

-continued
(Ic)
99 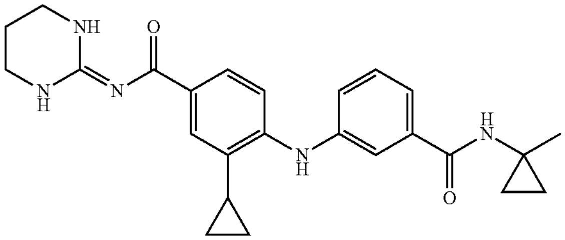 [SMILES: CC1(NC(=O)c2cccc(Nc3ccc(C(=O)N=C4NCCCN4)cc3C3CC3)c2)CC1]
100 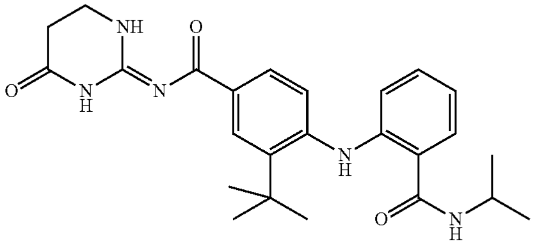 [SMILES: CC(C)NC(=O)c1ccccc1Nc1ccc(C(=O)/N=C2\NCCC(=O)N2)cc1C(C)(C)C]
101 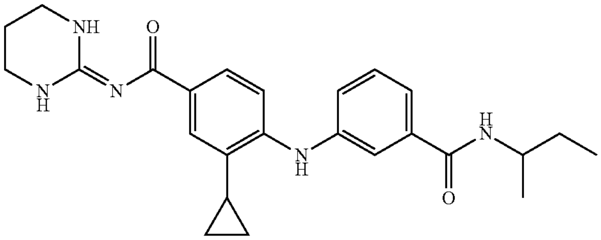 [SMILES: CCC(C)NC(=O)c1cccc(Nc2ccc(C(=O)N=C3NCCCN3)cc2C2CC2)c1]
102 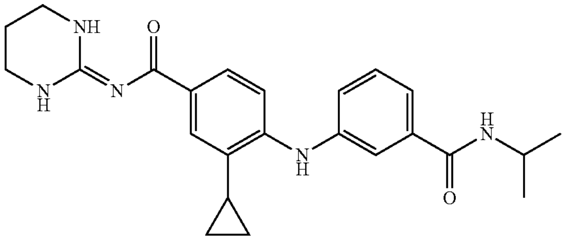 [SMILES: CC(C)NC(=O)c1cccc(Nc2ccc(C(=O)N=C3NCCCN3)cc2C2CC2)c1]
103 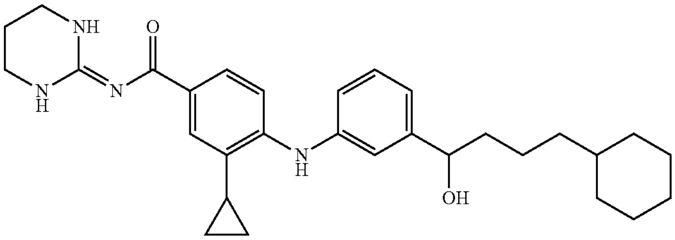 [SMILES: O=C(N=C1NCCCN1)c1ccc(Nc2cccc(C(O)CCCC3CCCCC3)c2)c(C2CC2)c1]
104 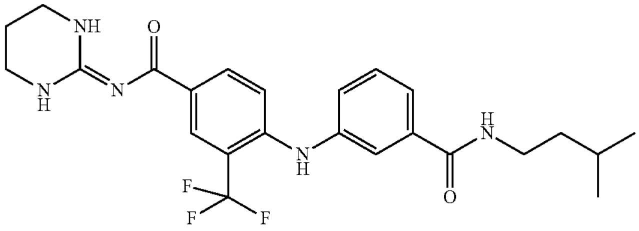 [SMILES: CC(C)CCNC(=O)c1cccc(Nc2ccc(C(=O)N=C3NCCCN3)cc2C(F)(F)F)c1]

-continued
| (Ic) |
| --- |
| 105 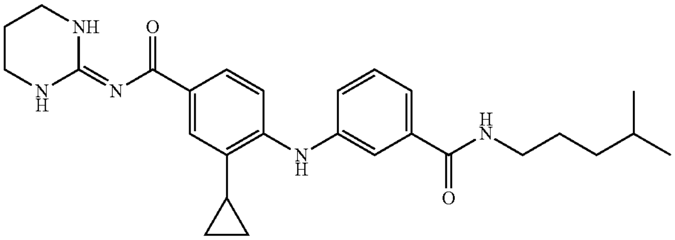 [SMILES: CC(C)CCCNC(=O)c1cccc(Nc2ccc(C(=O)N=C3NCCCN3)cc2C2CC2)c1] |
| 106 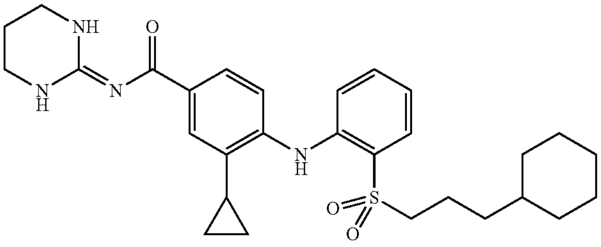 [SMILES: O=C(N=C1NCCCN1)c1ccc(Nc2ccccc2S(=O)(=O)CCCC2CCCCC2)c(C2CC2)c1] |
| 107 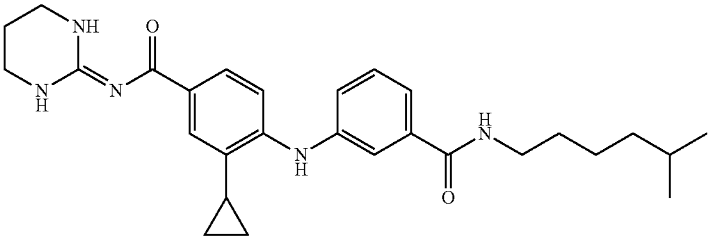 [SMILES: CC(C)CCCCNC(=O)c1cccc(Nc2ccc(C(=O)N=C3NCCCN3)cc2C2CC2)c1] |
| 108 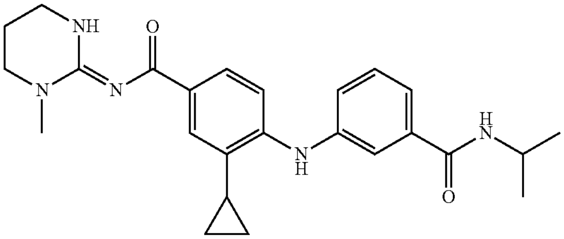 [SMILES: CC(C)NC(=O)c1cccc(Nc2ccc(C(=O)/N=C3\NCCCN3C)cc2C2CC2)c1] |
| 109 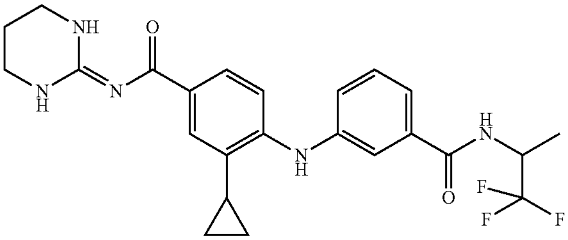 [SMILES: CC(NC(=O)c1cccc(Nc2ccc(C(=O)N=C3NCCCN3)cc2C2CC2)c1)C(F)(F)F] |
| 110 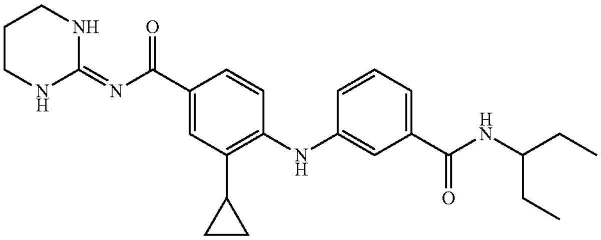 [SMILES: CCC(CC)NC(=O)c1cccc(Nc2ccc(C(=O)N=C3NCCCN3)cc2C2CC2)c1] |

-continued
| (Ic) | |
|---|---|
| 111 | 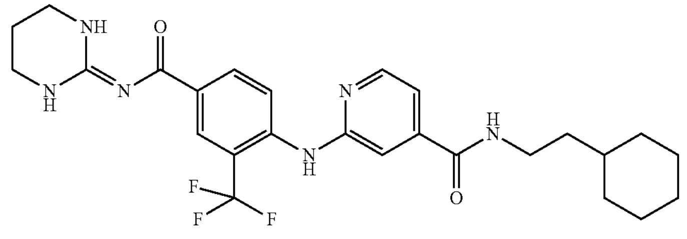 [SMILES: O=C(N=C1NCCCN1)c1ccc(Nc2cc(C(=O)NCCC3CCCCC3)ccn2)c(C(F)(F)F)c1] |
| 112 | 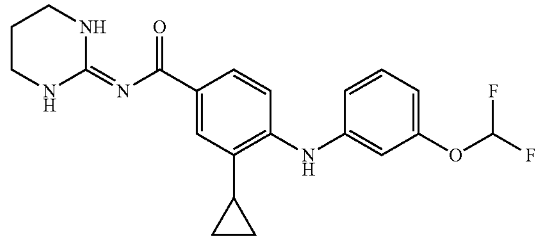 [SMILES: O=C(N=C1NCCCN1)c1ccc(Nc2cccc(OC(F)F)c2)c(C2CC2)c1] |
| 113 | 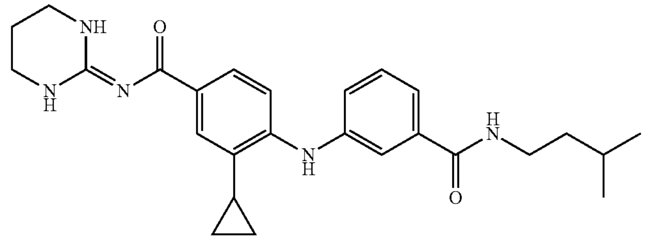 [SMILES: CC(C)CCNC(=O)c1cccc(Nc2ccc(C(=O)N=C3NCCCN3)cc2C2CC2)c1] |
| 114 | 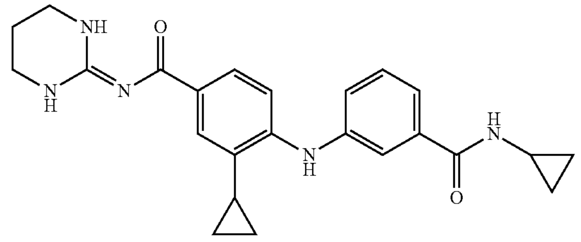 [SMILES: O=C(N=C1NCCCN1)c1ccc(Nc2cccc(C(=O)NC3CC3)c2)c(C2CC2)c1] |
| 115 | 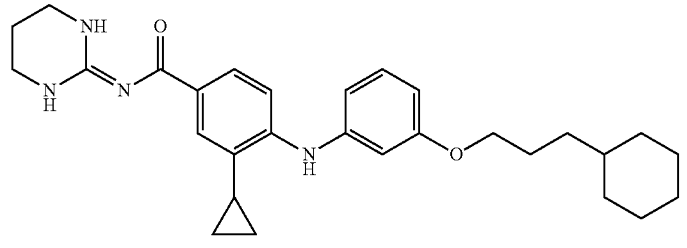 [SMILES: O=C(N=C1NCCCN1)c1ccc(Nc2cccc(OCCCC3CCCCC3)c2)c(C2CC2)c1] |
| 116 | 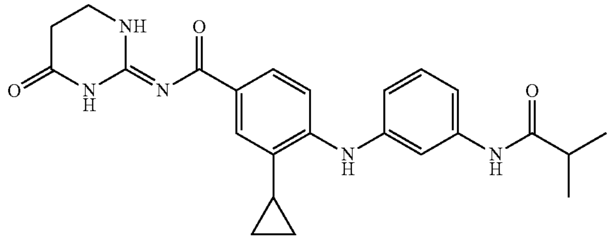 [SMILES: CC(C)C(=O)Nc1cccc(Nc2ccc(C(=O)/N=C3\NCCC(=O)N3)cc2C2CC2)c1] |

-continued
| (Ic) | |
|---|---|
| 117 | 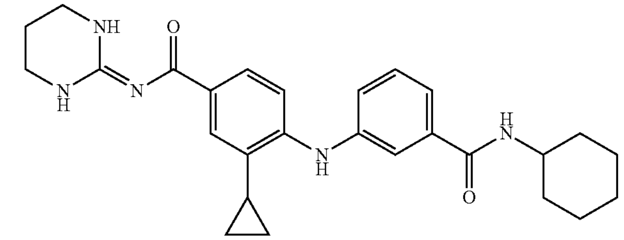 [SMILES: O=C(N=C1NCCCN1)c1ccc(Nc2cccc(C(=O)NC3CCCCC3)c2)c(C2CC2)c1] |
| 118 | 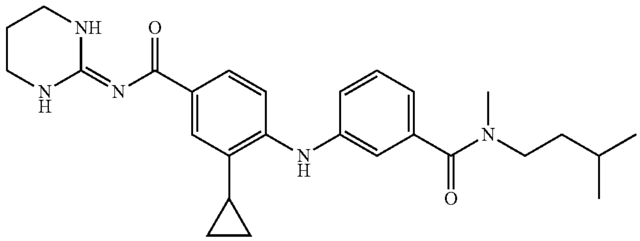 [SMILES: CC(C)CCN(C)C(=O)c1cccc(Nc2ccc(C(=O)N=C3NCCCN3)cc2C2CC2)c1] |
| 119 | 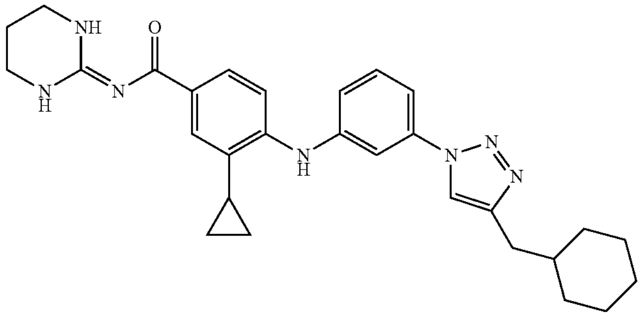 [SMILES: O=C(N=C1NCCCN1)c1ccc(Nc2cccc(-n3cc(CC4CCCCC4)nn3)c2)c(C2CC2)c1] |
| 120 | 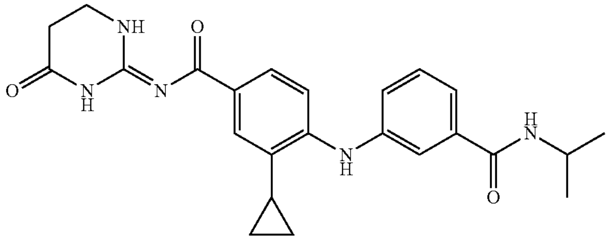 [SMILES: CC(C)NC(=O)c1cccc(Nc2ccc(C(=O)/N=C3\NCCC(=O)N3)cc2C2CC2)c1] |
| 121 | 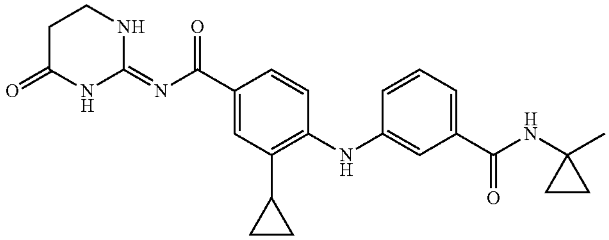 [SMILES: CC1(NC(=O)c2cccc(Nc3ccc(C(=O)/N=C4\NCCC(=O)N4)cc3C3CC3)c2)CC1] |
| 122 | 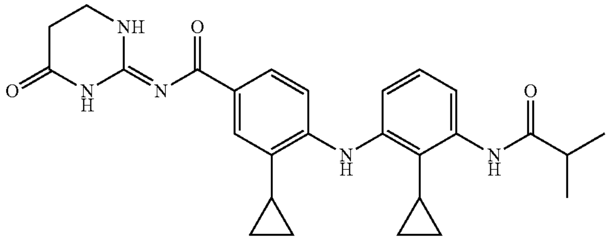 [SMILES: CC(C)C(=O)Nc1cccc(Nc2ccc(C(=O)/N=C3\NCCC(=O)N3)cc2C2CC2)c1C1CC1] |

-continued
| (Ic) |
| --- |
123
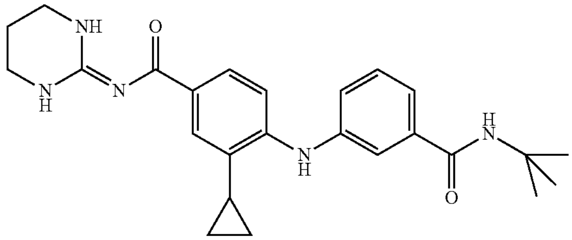
124
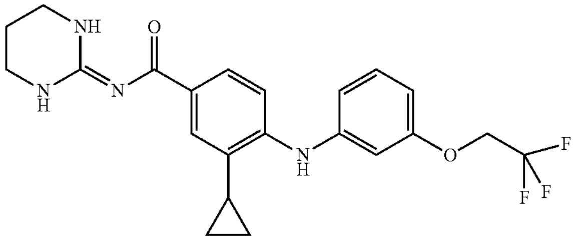 [SMILES: O=C(N=C1NCCCN1)c1ccc(Nc2cccc(OCC(F)(F)F)c2)c(C2CC2)c1]
125
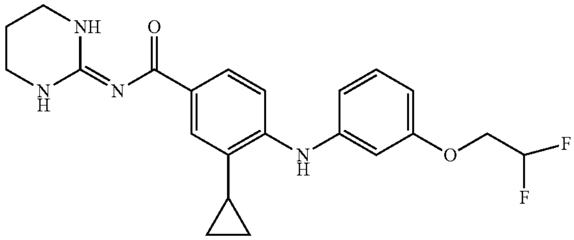 [SMILES: O=C(N=C1NCCCN1)c1ccc(Nc2cccc(OCC(F)F)c2)c(C2CC2)c1]
126
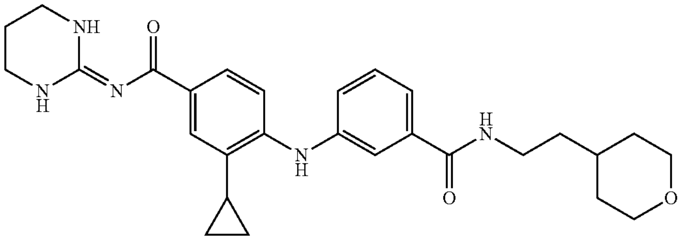 [SMILES: O=C(N=C1NCCCN1)c1ccc(Nc2cccc(C(=O)NCCC3CCOCC3)c2)c(C2CC2)c1]
127
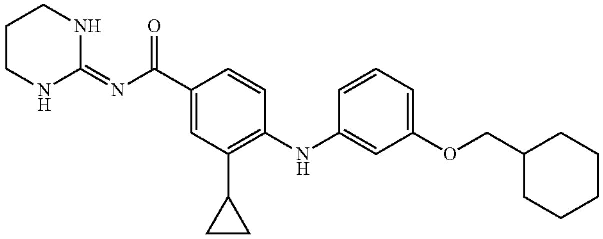 [SMILES: O=C(N=C1NCCCN1)c1ccc(Nc2cccc(OCC3CCCCC3)c2)c(C2CC2)c1]
128
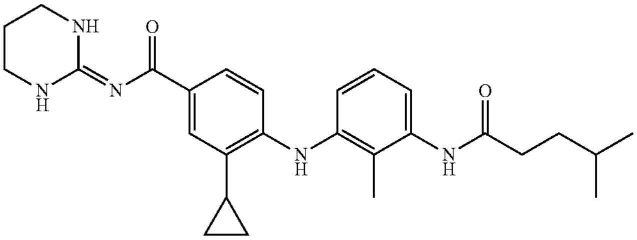 [SMILES: Cc1c(NC(=O)CCC(C)C)cccc1Nc1ccc(C(=O)N=C2NCCCN2)cc1C1CC1]

-continued
| (Ic) |
| --- |
129
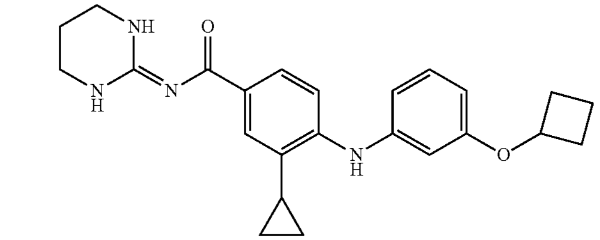 [SMILES: O=C(N=C1NCCCN1)c1ccc(Nc2cccc(OC3CCC3)c2)c(C2CC2)c1]
130
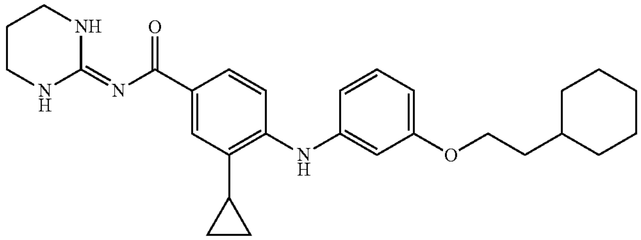 [SMILES: O=C(N=C1NCCCN1)c1ccc(Nc2cccc(OCCC3CCCCC3)c2)c(C2CC2)c1]
131
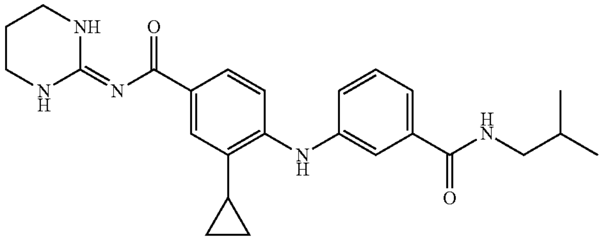 [SMILES: CC(C)CNC(=O)c1cccc(Nc2ccc(C(=O)N=C3NCCCN3)cc2C2CC2)c1]
132
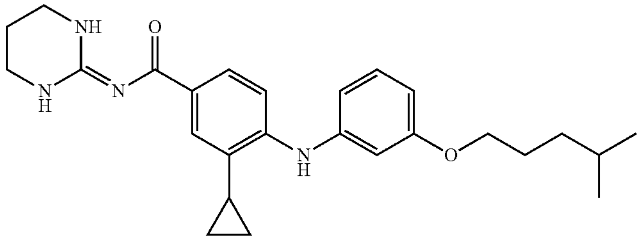 [SMILES: CC(C)CCCOc1cccc(Nc2ccc(C(=O)N=C3NCCCN3)cc2C2CC2)c1]
133
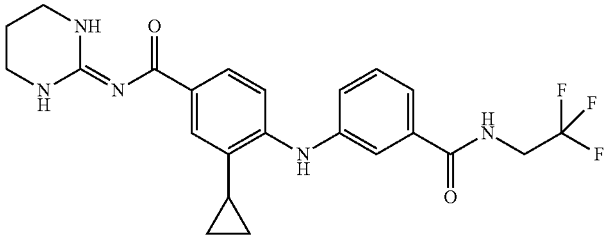 [SMILES: O=C(N=C1NCCCN1)c1ccc(Nc2cccc(C(=O)NCC(F)(F)F)c2)c(C2CC2)c1]
134
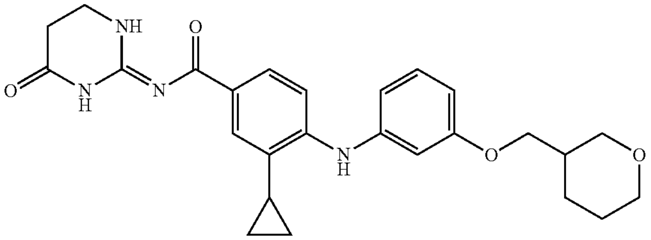 [SMILES: O=C1CCN/C(=N\C(=O)c2ccc(Nc3cccc(OCC4CCCOC4)c3)c(C3CC3)c2)N1]

-continued
| (Ic) |
|---|
135
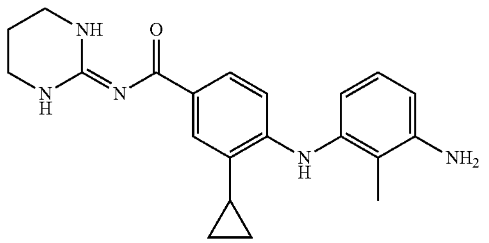 [SMILES: Cc1c(N)cccc1Nc1ccc(C(=O)N=C2NCCCN2)cc1C1CC1]
136
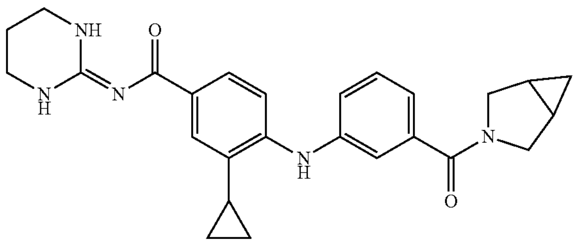 [SMILES: O=C(N=C1NCCCN1)c1ccc(Nc2cccc(C(=O)N3CC4CC4C3)c2)c(C2CC2)c1]
137
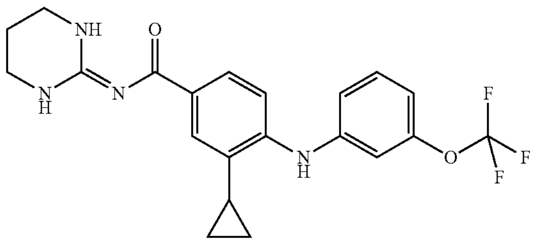 [SMILES: O=C(N=C1NCCCN1)c1ccc(Nc2cccc(OC(F)(F)F)c2)c(C2CC2)c1]
138
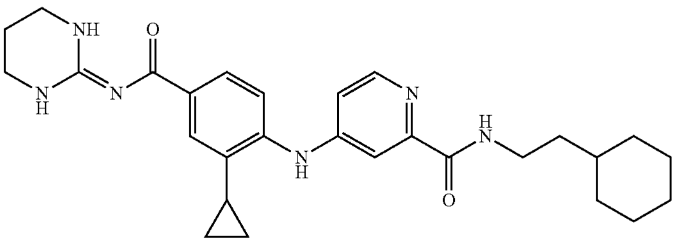 [SMILES: O=C(N=C1NCCCN1)c1ccc(Nc2ccnc(C(=O)NCCC3CCCCC3)c2)c(C2CC2)c1]
139
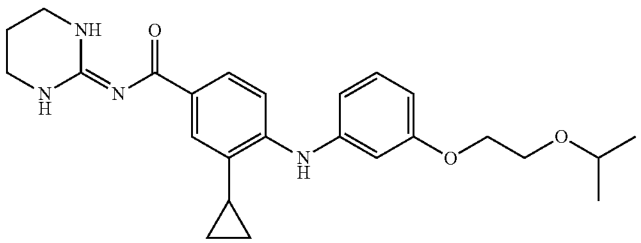 [SMILES: CC(C)OCCOc1cccc(Nc2ccc(C(=O)N=C3NCCCN3)cc2C2CC2)c1]
140
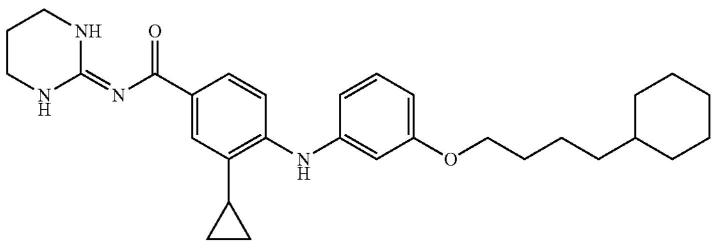 [SMILES: O=C(N=C1NCCCN1)c1ccc(Nc2cccc(OCCCCC3CCCCC3)c2)c(C2CC2)c1]

-continued
| (Ic) |
|---|
| 141 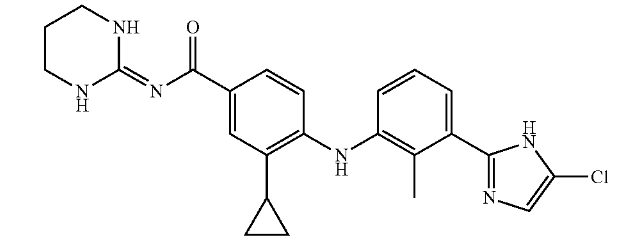 [SMILES: Cc1c(Nc2ccc(C(=O)N=C3NCCCN3)cc2C2CC2)cccc1-c1ncc(Cl)[nH]1] |
| 142 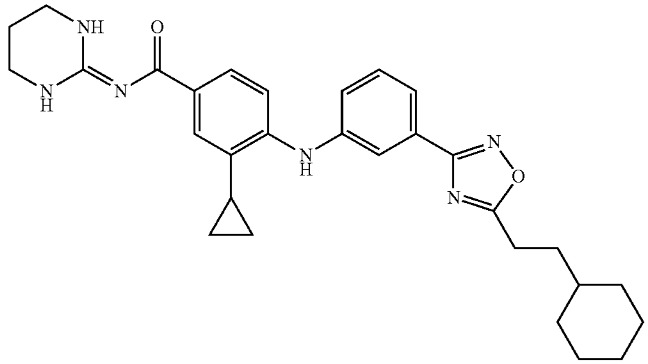 [SMILES: O=C(N=C1NCCCN1)c1ccc(Nc2cccc(-c3noc(CCC4CCCCC4)n3)c2)c(C2CC2)c1] |
| 143 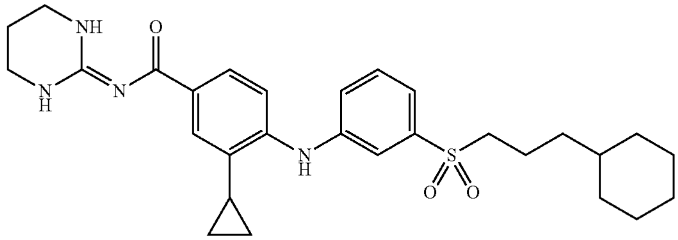 [SMILES: O=C(N=C1NCCCN1)c1ccc(Nc2cccc(S(=O)(=O)CCCC3CCCCC3)c2)c(C2CC2)c1] |
| 144 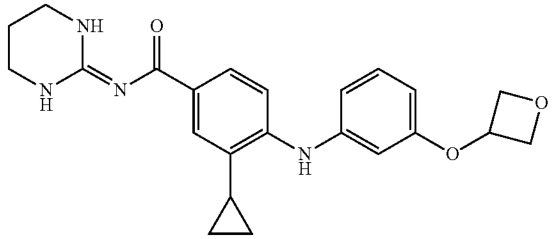 [SMILES: O=C(N=C1NCCCN1)c1ccc(Nc2cccc(OC3COC3)c2)c(C2CC2)c1] |
| 145 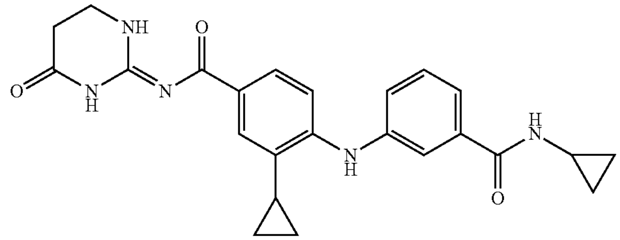 [SMILES: O=C1CCN/C(=N\C(=O)c2ccc(Nc3cccc(C(=O)NC4CC4)c3)c(C3CC3)c2)N1] |

-continued
(Ic)
146
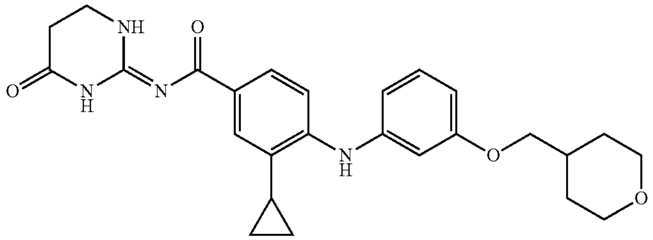 [SMILES: O=C1CCN/C(=N\C(=O)c2ccc(Nc3cccc(OCC4CCOCC4)c3)c(C3CC3)c2)N1]
147
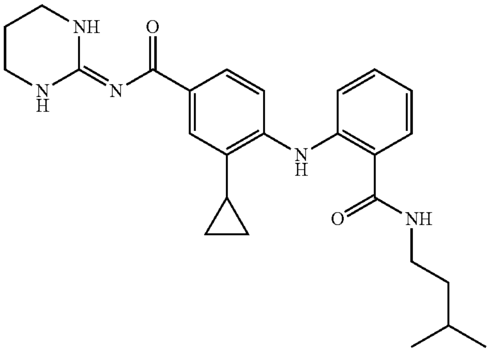 [SMILES: CC(C)CCNC(=O)c1ccccc1Nc1ccc(C(=O)N=C2NCCCN2)cc1C1CC1]
148
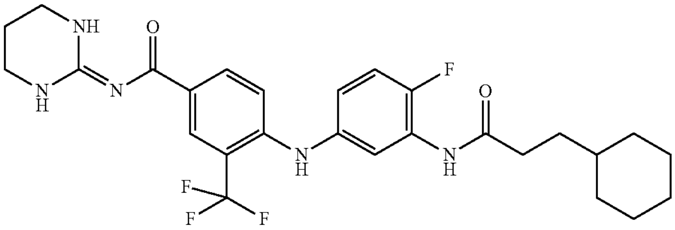 [SMILES: O=C(CCC1CCCCC1)Nc1cc(Nc2ccc(C(=O)N=C3NCCCN3)cc2C(F)(F)F)ccc1F]
149
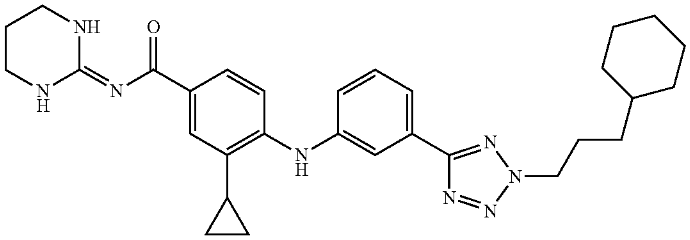 [SMILES: O=C(N=C1NCCCN1)c1ccc(Nc2cccc(-c3nnn(CCCC4CCCCC4)n3)c2)c(C2CC2)c1]
150
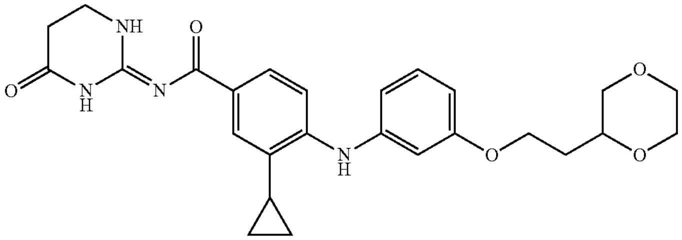 [SMILES: O=C1CCN/C(=N\C(=O)c2ccc(Nc3cccc(OCCC4COCCO4)c3)c(C3CC3)c2)N1]
151
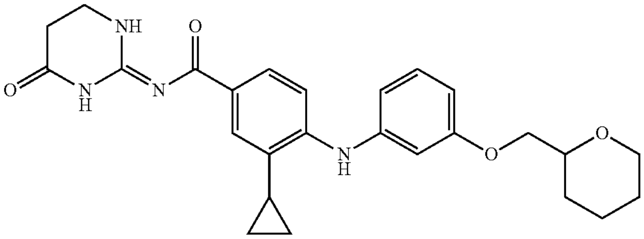

-continued
| (Ic) |
|---|
152
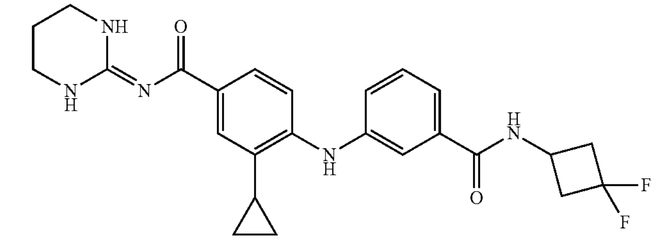 [SMILES: O=C(N=C1NCCCN1)c1ccc(Nc2cccc(C(=O)NC3CC(F)(F)C3)c2)c(C2CC2)c1]
153
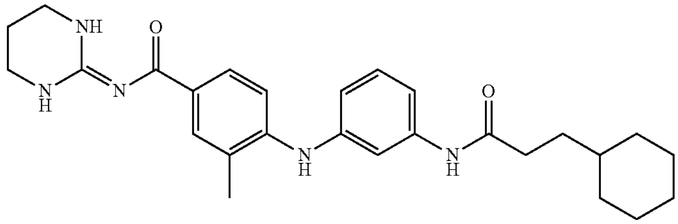 [SMILES: Cc1cc(C(=O)N=C2NCCCN2)ccc1Nc1cccc(NC(=O)CCC2CCCCC2)c1]
154
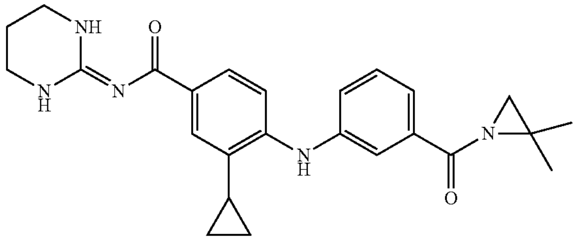 [SMILES: CC1(C)CN1C(=O)c1cccc(Nc2ccc(C(=O)N=C3NCCCN3)cc2C2CC2)c1]
155
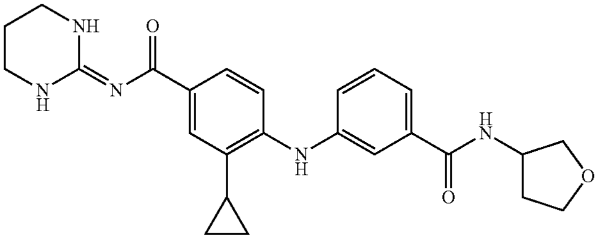 [SMILES: O=C(N=C1NCCCN1)c1ccc(Nc2cccc(C(=O)NC3CCOC3)c2)c(C2CC2)c1]
156
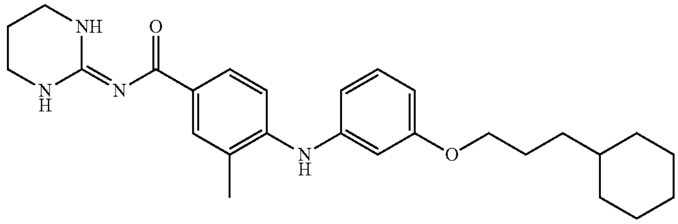 [SMILES: Cc1cc(C(=O)N=C2NCCCN2)ccc1Nc1cccc(OCCCC2CCCCC2)c1]
157
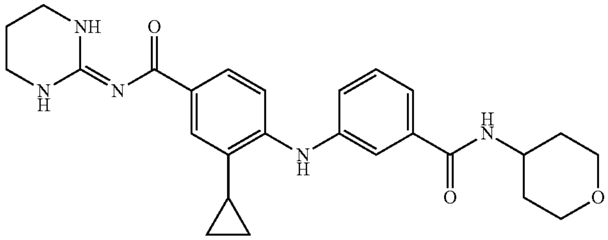 [SMILES: O=C(N=C1NCCCN1)c1ccc(Nc2cccc(C(=O)NC3CCOCC3)c2)c(C2CC2)c1]

-continued
| (Ic) | |
|---|---|
| 158 | 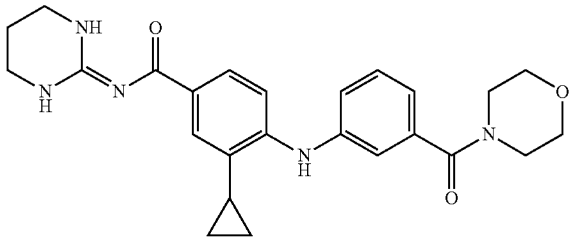 [SMILES: O=C(N=C1NCCCN1)c1ccc(Nc2cccc(C(=O)N3CCOCC3)c2)c(C2CC2)c1] |
| 159 | 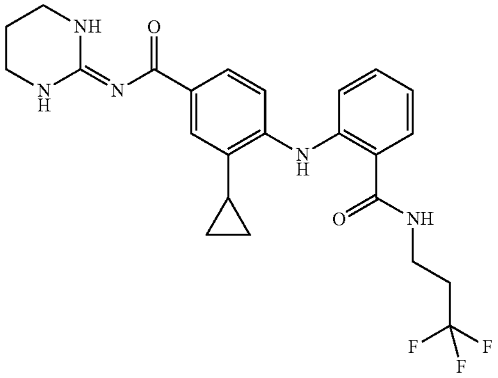 [SMILES: O=C(N=C1NCCCN1)c1ccc(Nc2ccccc2C(=O)NCCC(F)(F)F)c(C2CC2)c1] |
| 160 | 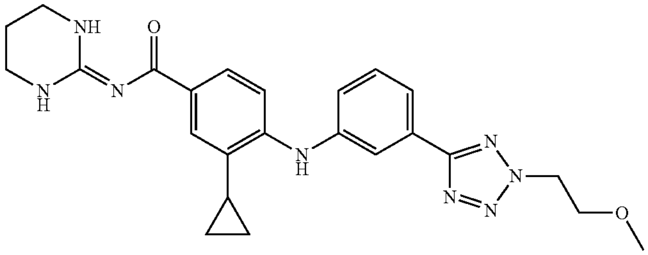 [SMILES: COCCn1nnc(-c2cccc(Nc3ccc(C(=O)N=C4NCCCN4)cc3C3CC3)c2)n1] |
| 161 | 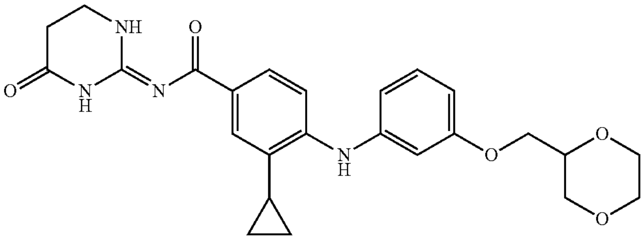 |
| 162 | 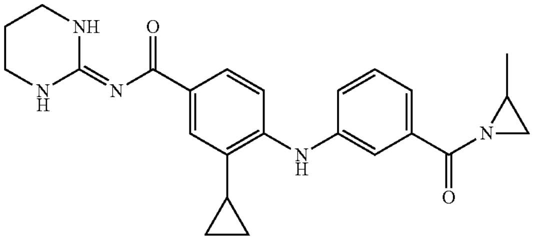 [SMILES: CC1CN1C(=O)c1cccc(Nc2ccc(C(=O)N=C3NCCCN3)cc2C2CC2)c1] |

-continued
| (Ic) | |
|---|---|
| 163 | 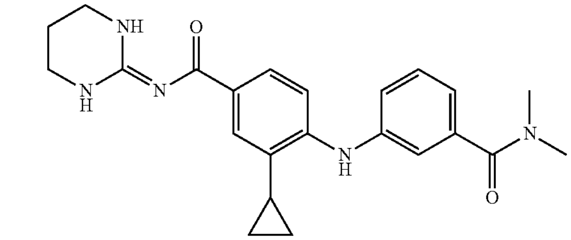 [SMILES: CN(C)C(=O)c1cccc(Nc2ccc(C(=O)N=C3NCCCN3)cc2C2CC2)c1] |
| 164 | 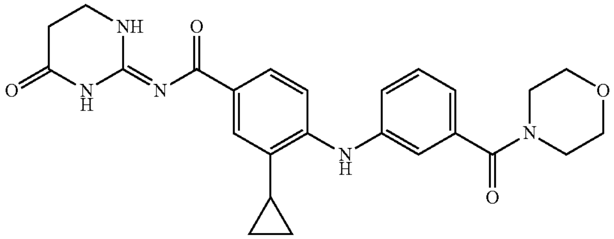 [SMILES: O=C1CCN/C(=N\C(=O)c2ccc(Nc3cccc(C(=O)N4CCOCC4)c3)c(C3CC3)c2)N1] |
| 165 | 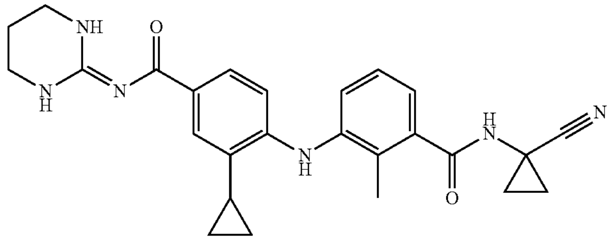 [SMILES: Cc1c(Nc2ccc(C(=O)N=C3NCCCN3)cc2C2CC2)cccc1C(=O)NC1(C#N)CC1] |
| 166 | 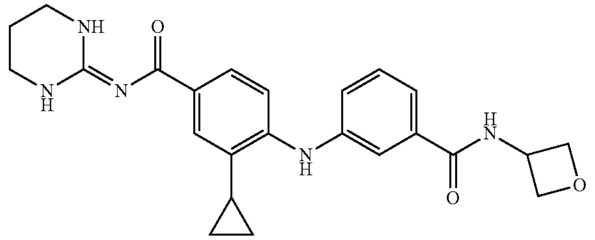 [SMILES: O=C(N=C1NCCCN1)c1ccc(Nc2cccc(C(=O)NC3COC3)c2)c(C2CC2)c1] |
| 167 | 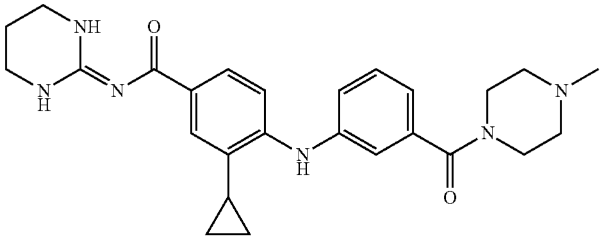 [SMILES: CN1CCN(C(=O)c2cccc(Nc3ccc(C(=O)N=C4NCCCN4)cc3C3CC3)c2)CC1] |
| 168 | 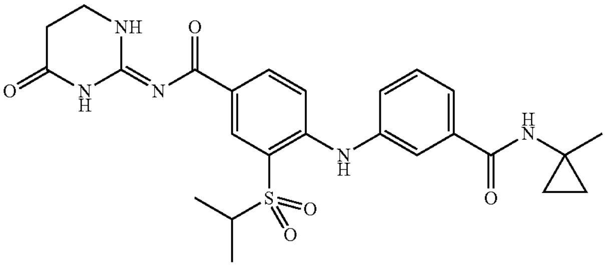 [SMILES: CC(C)S(=O)(=O)c1cc(C(=O)/N=C2\NCCC(=O)N2)ccc1Nc1cccc(C(=O)NC2(C)CC2)c1] |

-continued
| (Ic) |
| --- |
| 169 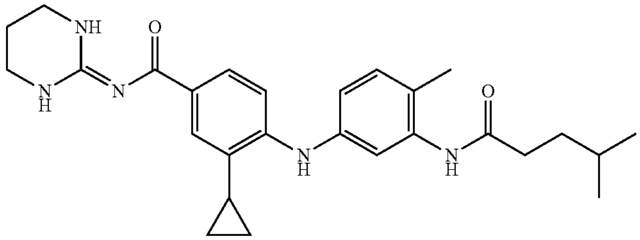 [SMILES: Cc1ccc(Nc2ccc(C(=O)N=C3NCCCN3)cc2C2CC2)cc1NC(=O)CCC(C)C] |
| 170 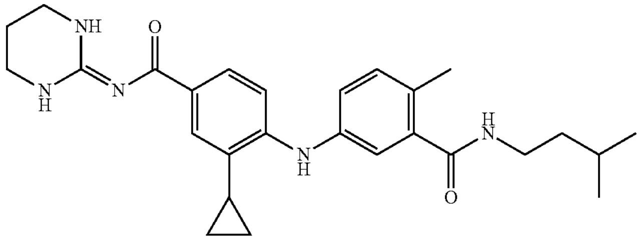 [SMILES: Cc1ccc(Nc2ccc(C(=O)N=C3NCCCN3)cc2C2CC2)cc1C(=O)NCCC(C)C] |
| 171 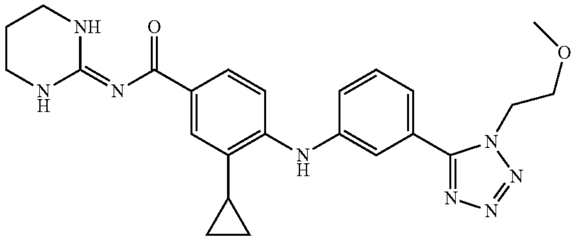 [SMILES: COCCn1nnnc1-c1cccc(Nc2ccc(C(=O)N=C3NCCCN3)cc2C2CC2)c1] |
| 172 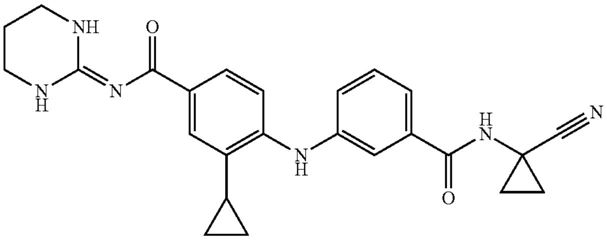 [SMILES: N#CC1(NC(=O)c2cccc(Nc3ccc(C(=O)N=C4NCCCN4)cc3C3CC3)c2)CC1] |
| 173 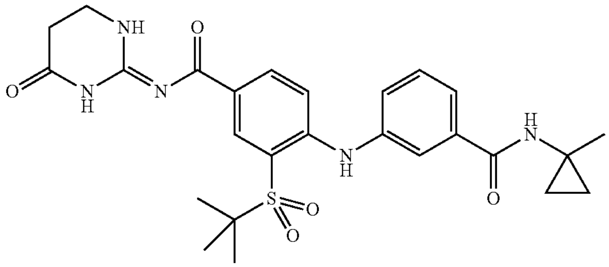 [SMILES: CC1(NC(=O)c2cccc(Nc3ccc(C(=O)/N=C4\NCCC(=O)N4)cc3S(=O)(=O)C(C)(C)C)c2)CC1] |
| 174 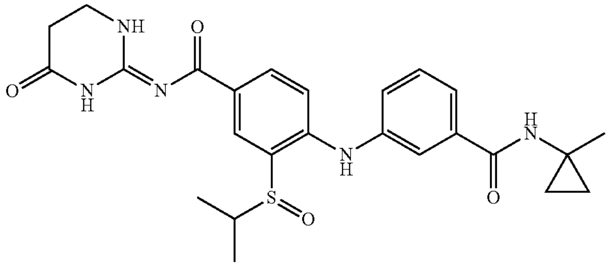 [SMILES: CC(C)S(=O)c1cc(C(=O)/N=C2\NCCC(=O)N2)ccc1Nc1cccc(C(=O)NC2(C)CC2)c1] |

-continued
| (Ic) | |
|---|---|
| 175 | 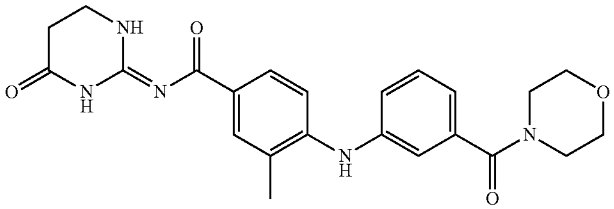 [SMILES: Cc1cc(C(=O)/N=C2\NCCC(=O)N2)ccc1Nc1cccc(C(=O)N2CCOCC2)c1] |
| 176 | 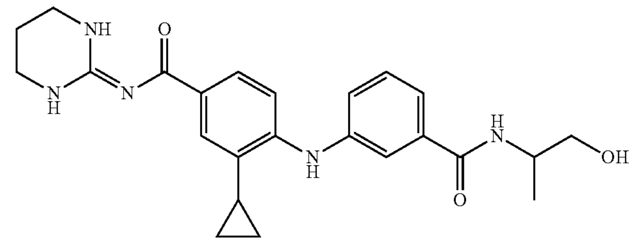 [SMILES: CC(CO)NC(=O)c1cccc(Nc2ccc(C(=O)N=C3NCCCN3)cc2C2CC2)c1] |
| 177 | 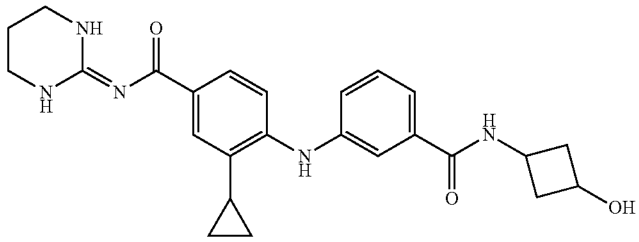 [SMILES: O=C(N=C1NCCCN1)c1ccc(Nc2cccc(C(=O)NC3CC(O)C3)c2)c(C2CC2)c1] |
| 178 | 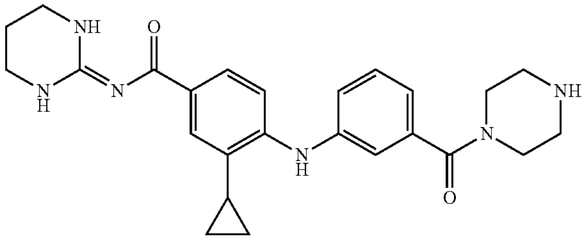 [SMILES: O=C(N=C1NCCCN1)c1ccc(Nc2cccc(C(=O)N3CCNCC3)c2)c(C2CC2)c1] |
| 179 | 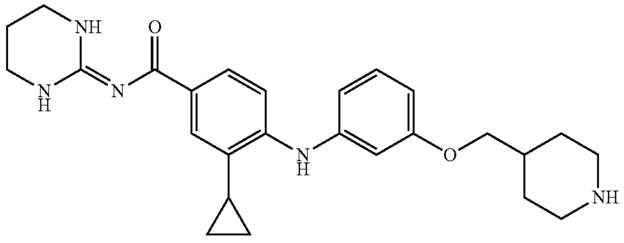 [SMILES: O=C(N=C1NCCCN1)c1ccc(Nc2cccc(OCC3CCNCC3)c2)c(C2CC2)c1] |
| 180 | 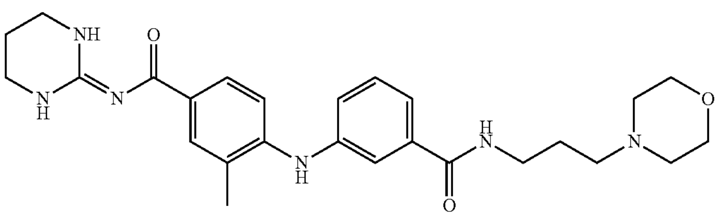 [SMILES: Cc1cc(C(=O)N=C2NCCCN2)ccc1Nc1cccc(C(=O)NCCCN2CCOCC2)c1] |

-continued

| (Ic) |
| --- |

and

181
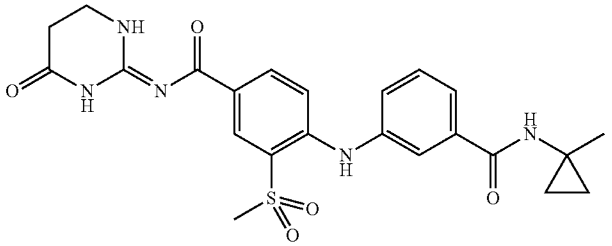 [SMILES: CC1(NC(=O)c2cccc(Nc3ccc(C(=O)/N=C4\NCCC(=O)N4)cc3S(C)(=O)=O)c2)CC1]

or a pharmaceutically acceptable salt thereof.

12. A method of treating a RNA virus infection or a disease caused by a RNA virus belonging to group IV or V of the Baltimore classification, comprising administering a therapeutically effective amount of a compound of formula (Ic) according to claim 11, or a pharmaceutically acceptable salt thereof, to a patient in need thereof, wherein the compound is selected from compounds 19-31 and 91-181.

13. The method according to claim 12, wherein the RNA virus infection caused by a RNA virus belonging to group IV or V of the Baltimore classification is selected from RSV infection, Chikungunya, influenza and Dengue.

14. A method of treating a RNA virus infection or a disease caused by a RNA virus belonging to group IV or V of the Baltimore classification, comprising administering a therapeutically effective amount of a compound of formula (Ic) according to claim 1, or a pharmaceutically acceptable salt thereof, to a patient in need thereof.

15. The method according to claim 14, wherein the RNA virus infection caused by a RNA virus belonging to group IV or V of the Baltimore classification is selected from RSV infection, Chikungunya, influenza and Dengue.

16. A pharmaceutical composition comprising:

a) a compound of formula (Ic) or a pharmaceutically acceptable salt thereof according to claim 1; or b) one or more compounds selected from compounds 19-31 and 91-181

| (Ic) |
| --- |

19
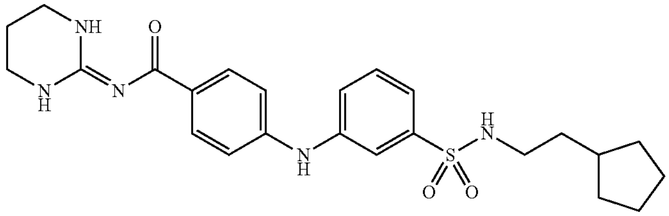 [SMILES: O=C(N=C1NCCCN1)c1ccc(Nc2cccc(S(=O)(=O)NCCC3CCCC3)c2)cc1]

20
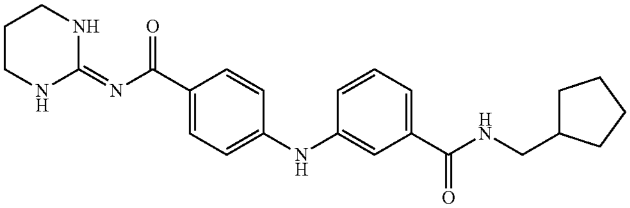 [SMILES: O=C(N=C1NCCCN1)c1ccc(Nc2cccc(C(=O)NCC3CCCC3)c2)cc1]

21
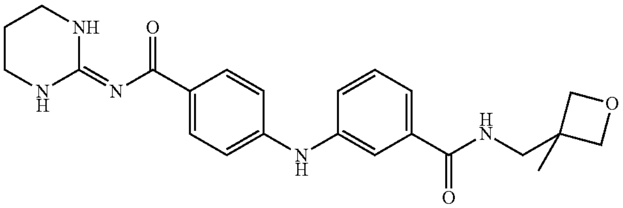 [SMILES: CC1(CNC(=O)c2cccc(Nc3ccc(C(=O)N=C4NCCCN4)cc3)c2)COC1]

-continued
| (Ic) |
|---|
| 22 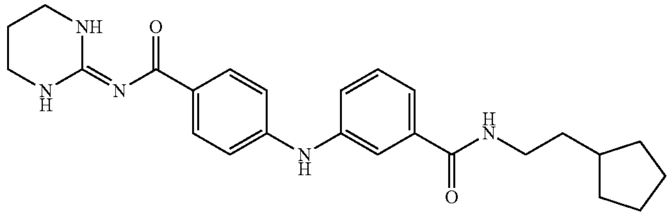 [SMILES: O=C(N=C1NCCCN1)c1ccc(Nc2cccc(C(=O)NCCC3CCCC3)c2)cc1] |
| 23 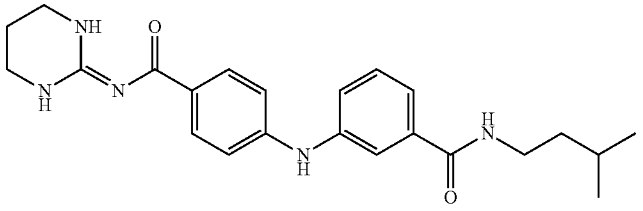 [SMILES: CC(C)CCNC(=O)c1cccc(Nc2ccc(C(=O)N=C3NCCCN3)cc2)c1] |
| 24 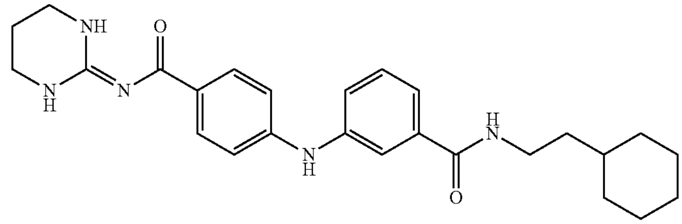 [SMILES: O=C(N=C1NCCCN1)c1ccc(Nc2cccc(C(=O)NCCC3CCCCC3)c2)cc1] |
| 25 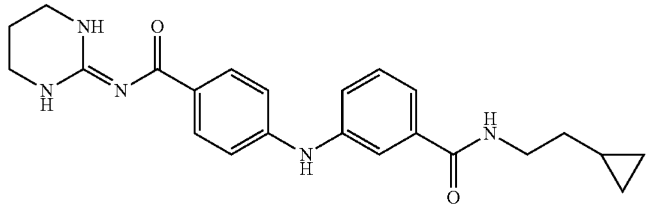 [SMILES: O=C(N=C1NCCCN1)c1ccc(Nc2cccc(C(=O)NCCC3CC3)c2)cc1] |
| 26 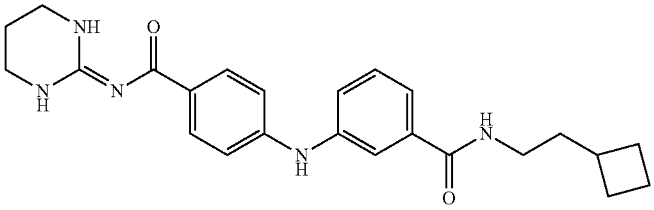 [SMILES: O=C(N=C1NCCCN1)c1ccc(Nc2cccc(C(=O)NCCC3CCC3)c2)cc1] |
| 27 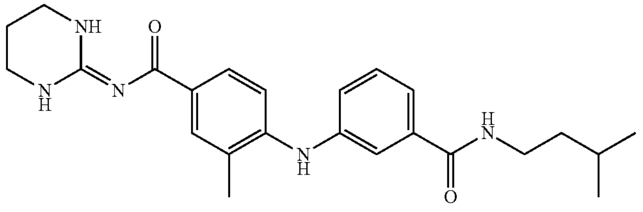 [SMILES: Cc1cc(C(=O)N=C2NCCCN2)ccc1Nc1cccc(C(=O)NCCC(C)C)c1] |
| 28 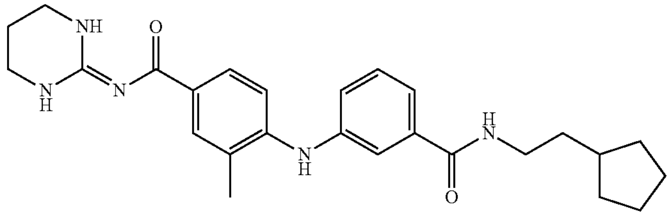 [SMILES: Cc1cc(C(=O)N=C2NCCCN2)ccc1Nc1cccc(C(=O)NCCC2CCCC2)c1] |

-continued
(Ic)
29
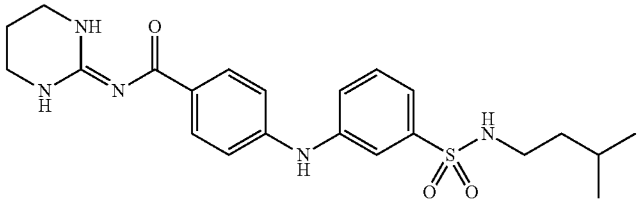 [SMILES: CC(C)CCNS(=O)(=O)c1cccc(Nc2ccc(C(=O)N=C3NCCCN3)cc2)c1]
30
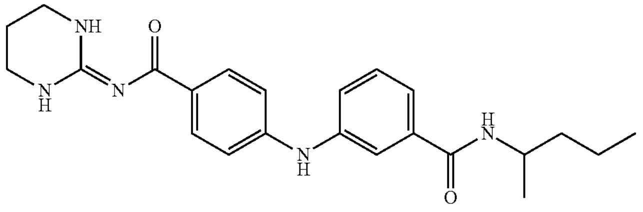 [SMILES: CCCC(C)NC(=O)c1cccc(Nc2ccc(C(=O)N=C3NCCCN3)cc2)c1]
31
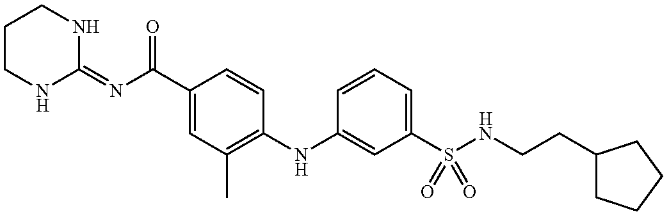 [SMILES: Cc1cc(C(=O)N=C2NCCCN2)ccc1Nc1cccc(S(=O)(=O)NCCC2CCCC2)c1]
91
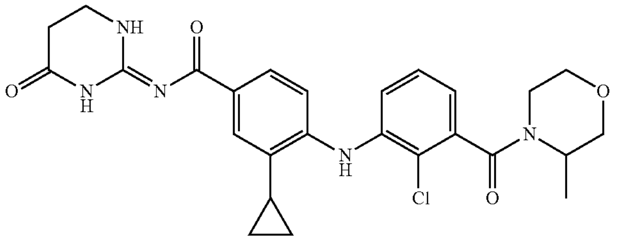
92
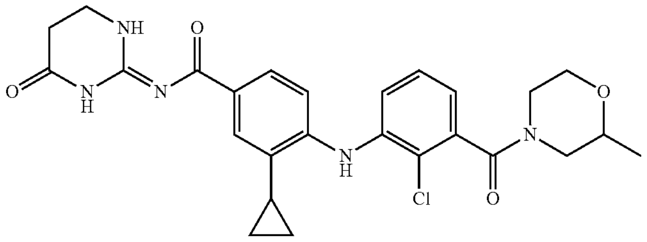 [SMILES: CC1CN(C(=O)c2cccc(Nc3ccc(C(=O)/N=C4\NCCC(=O)N4)cc3C3CC3)c2Cl)CCO1]
93
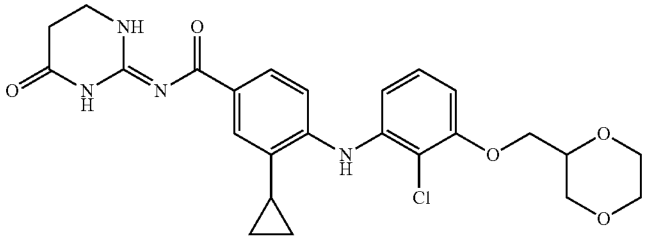 [SMILES: O=C1CCN/C(=N\C(=O)c2ccc(Nc3cccc(OCC4COCCO4)c3Cl)c(C3CC3)c2)N1]

-continued
| (Ic) |
|---|
94 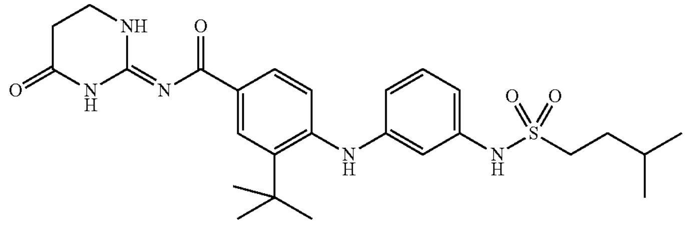 [SMILES: CC(C)CCS(=O)(=O)Nc1cccc(Nc2ccc(C(=O)/N=C3\NCCC(=O)N3)cc2C(C)(C)C)c1]
95 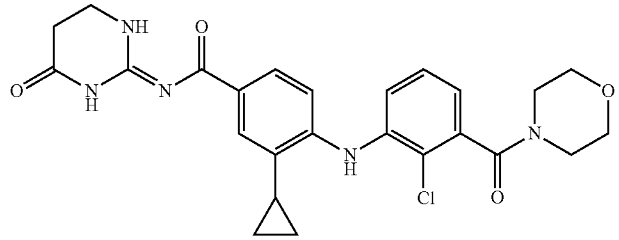 [SMILES: O=C1CCN/C(=N\C(=O)c2ccc(Nc3cccc(C(=O)N4CCOCC4)c3Cl)c(C3CC3)c2)N1]
96 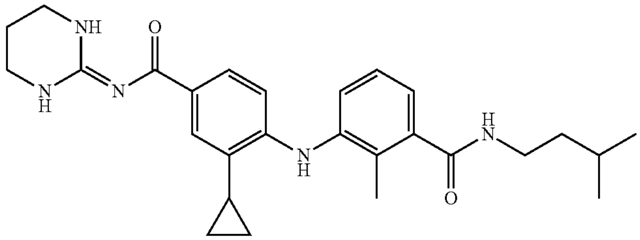 [SMILES: Cc1c(Nc2ccc(C(=O)N=C3NCCCN3)cc2C2CC2)cccc1C(=O)NCCC(C)C]
97 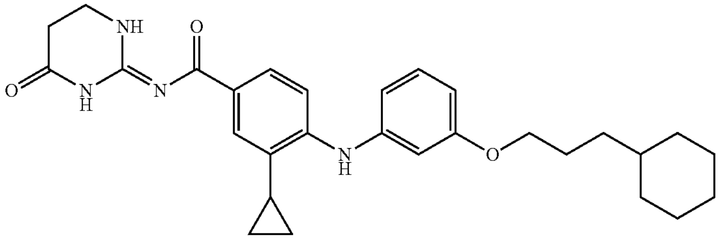 [SMILES: O=C1CCN/C(=N\C(=O)c2ccc(Nc3cccc(OCCCC4CCCCC4)c3)c(C3CC3)c2)N1]
98 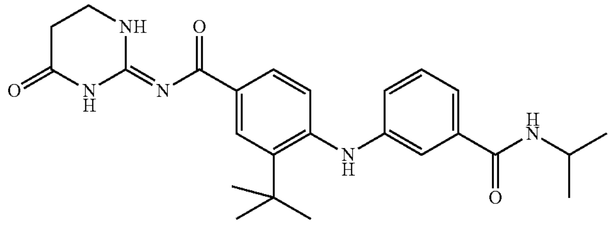 [SMILES: CC(C)NC(=O)c1cccc(Nc2ccc(C(=O)/N=C3\NCCC(=O)N3)cc2C(C)(C)C)c1]
99 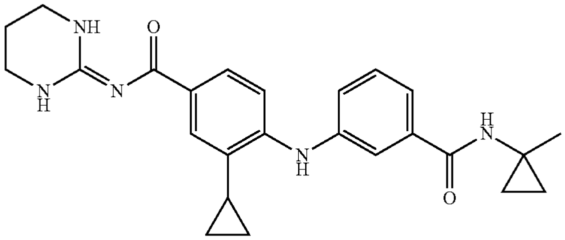 [SMILES: CC1(NC(=O)c2cccc(Nc3ccc(C(=O)N=C4NCCCN4)cc3C3CC3)c2)CC1]

-continued
| (Ic) | |
|---|---|
| 100 | 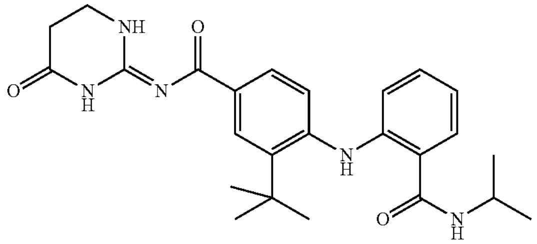 [SMILES: CC(C)NC(=O)c1ccccc1Nc1ccc(C(=O)/N=C2\NCCC(=O)N2)cc1C(C)(C)C] |
| 101 | 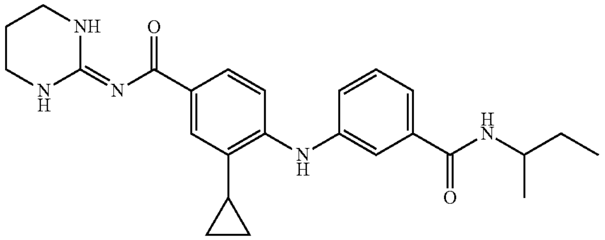 [SMILES: CCC(C)NC(=O)c1cccc(Nc2ccc(C(=O)N=C3NCCCN3)cc2C2CC2)c1] |
| 102 | 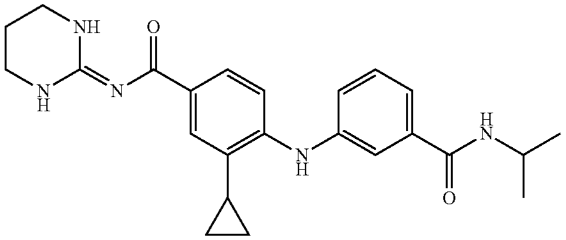 [SMILES: CC(C)NC(=O)c1cccc(Nc2ccc(C(=O)N=C3NCCCN3)cc2C2CC2)c1] |
| 103 | 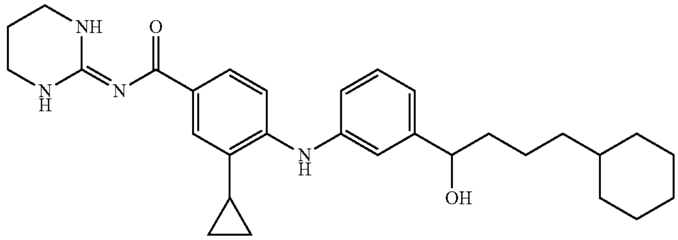 [SMILES: O=C(N=C1NCCCN1)c1ccc(Nc2cccc(C(O)CCCC3CCCCC3)c2)c(C2CC2)c1] |
| 104 | 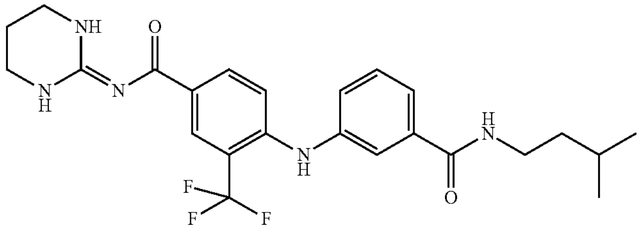 [SMILES: CC(C)CCNC(=O)c1cccc(Nc2ccc(C(=O)N=C3NCCCN3)cc2C(F)(F)F)c1] |
| 105 | 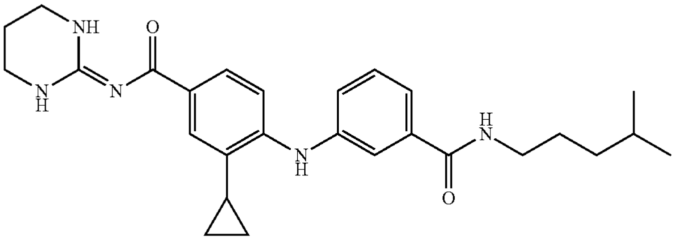 [SMILES: CC(C)CCCNC(=O)c1cccc(Nc2ccc(C(=O)N=C3NCCCN3)cc2C2CC2)c1] |

-continued
| (Ic) |
|---|
| 106 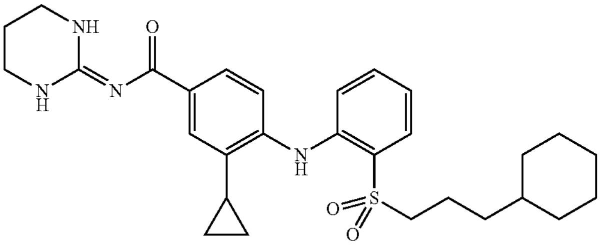 [SMILES: O=C(N=C1NCCCN1)c1ccc(Nc2ccccc2S(=O)(=O)CCCC2CCCCC2)c(C2CC2)c1] |
| 107 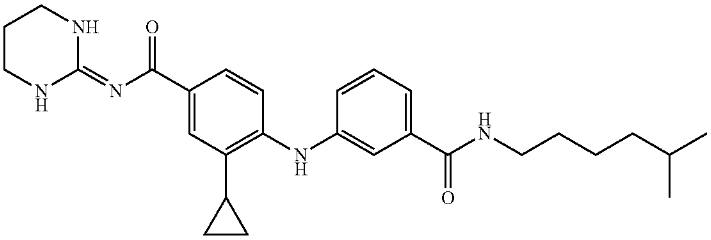 [SMILES: CC(C)CCCCNC(=O)c1cccc(Nc2ccc(C(=O)N=C3NCCCN3)cc2C2CC2)c1] |
| 108 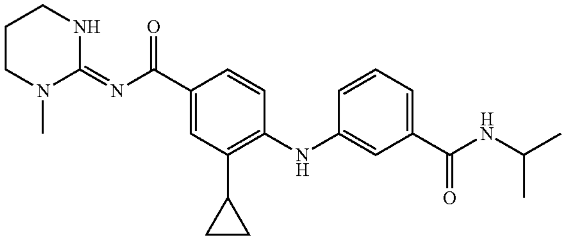 [SMILES: CC(C)NC(=O)c1cccc(Nc2ccc(C(=O)/N=C3\NCCCN3C)cc2C2CC2)c1] |
| 109 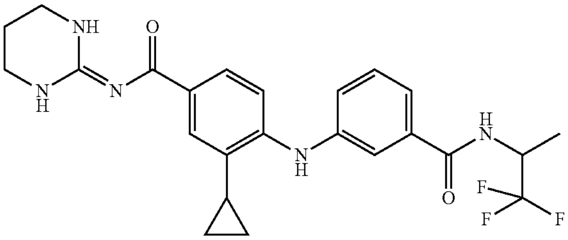 [SMILES: CC(NC(=O)c1cccc(Nc2ccc(C(=O)N=C3NCCCN3)cc2C2CC2)c1)C(F)(F)F] |
| 110 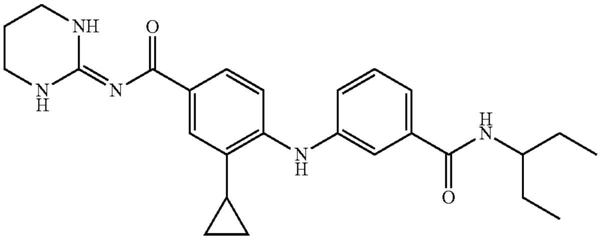 [SMILES: CCC(CC)NC(=O)c1cccc(Nc2ccc(C(=O)N=C3NCCCN3)cc2C2CC2)c1] |
| 111 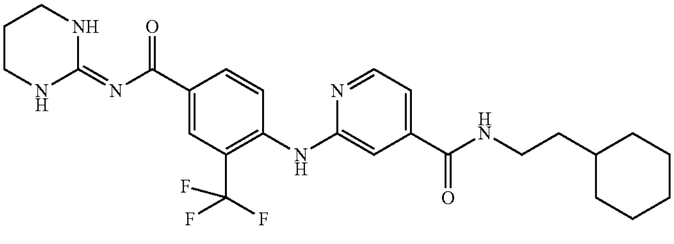 [SMILES: O=C(N=C1NCCCN1)c1ccc(Nc2cc(C(=O)NCCC3CCCCC3)ccn2)c(C(F)(F)F)c1] |

-continued
(Ic)
112
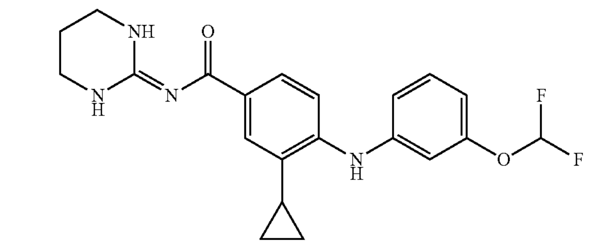 [SMILES: O=C(N=C1NCCCN1)c1ccc(Nc2cccc(OC(F)F)c2)c(C2CC2)c1]
113
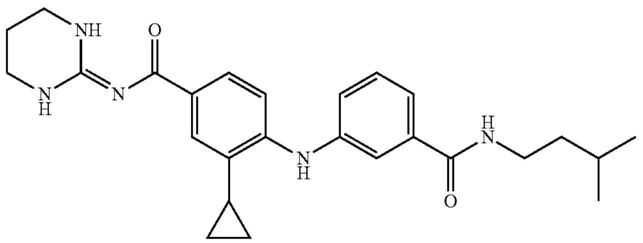 [SMILES: CC(C)CCNC(=O)c1cccc(Nc2ccc(C(=O)N=C3NCCCN3)cc2C2CC2)c1]
114
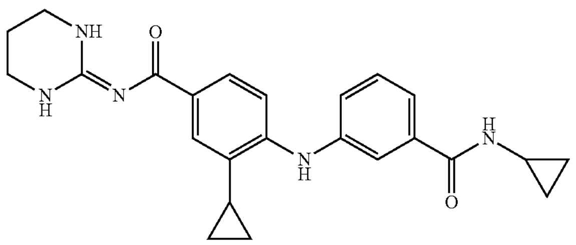 [SMILES: O=C(N=C1NCCCN1)c1ccc(Nc2cccc(C(=O)NC3CC3)c2)c(C2CC2)c1]
115
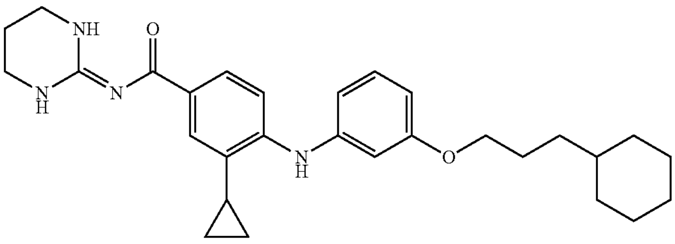 [SMILES: O=C(N=C1NCCCN1)c1ccc(Nc2cccc(OCCCC3CCCCC3)c2)c(C2CC2)c1]
116
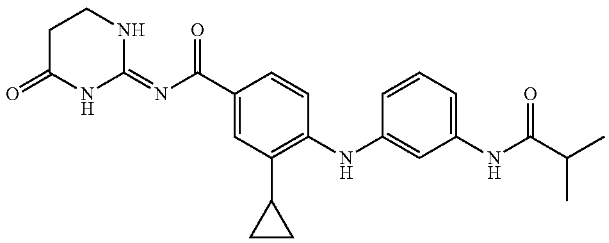 [SMILES: CC(C)C(=O)Nc1cccc(Nc2ccc(C(=O)/N=C3\NCCC(=O)N3)cc2C2CC2)c1]
117
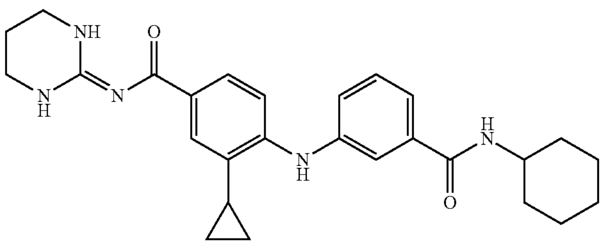 [SMILES: O=C(N=C1NCCCN1)c1ccc(Nc2cccc(C(=O)NC3CCCCC3)c2)c(C2CC2)c1]

-continued
| (Ic) |
| --- |
118 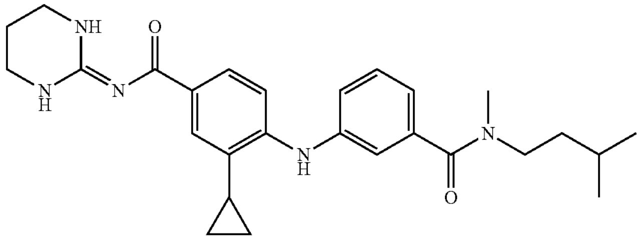 [SMILES: CC(C)CCN(C)C(=O)c1cccc(Nc2ccc(C(=O)N=C3NCCCN3)cc2C2CC2)c1]
119 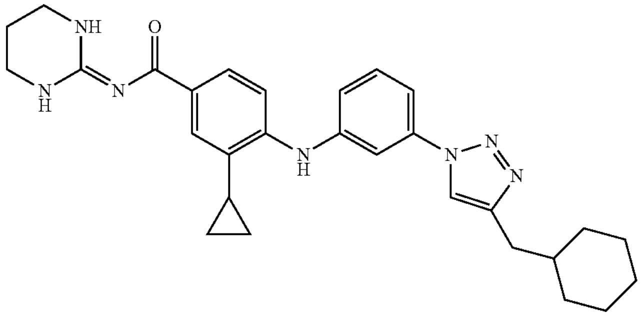 [SMILES: O=C(N=C1NCCCN1)c1ccc(Nc2cccc(-n3cc(CC4CCCCC4)nn3)c2)c(C2CC2)c1]
120 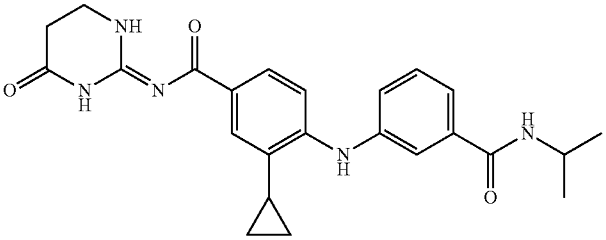 [SMILES: CC(C)NC(=O)c1cccc(Nc2ccc(C(=O)/N=C3\NCCC(=O)N3)cc2C2CC2)c1]
121 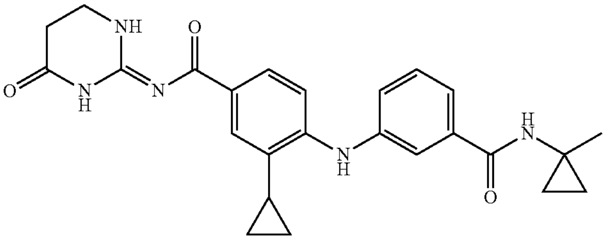 [SMILES: CC1(NC(=O)c2cccc(Nc3ccc(C(=O)/N=C4\NCCC(=O)N4)cc3C3CC3)c2)CC1]
122 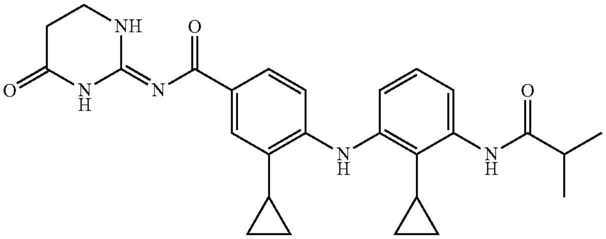 [SMILES: CC(C)C(=O)Nc1cccc(Nc2ccc(C(=O)/N=C3\NCCC(=O)N3)cc2C2CC2)c1C1CC1]
123 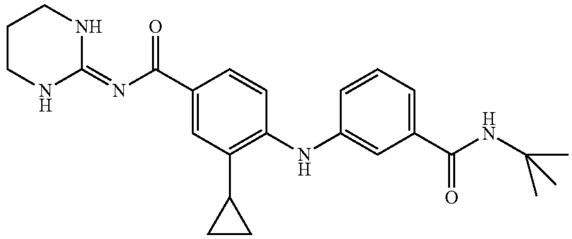 [SMILES: CC(C)(C)NC(=O)c1cccc(Nc2ccc(C(=O)N=C3NCCCN3)cc2C2CC2)c1]

-continued
| (Ic) |
| --- |
124 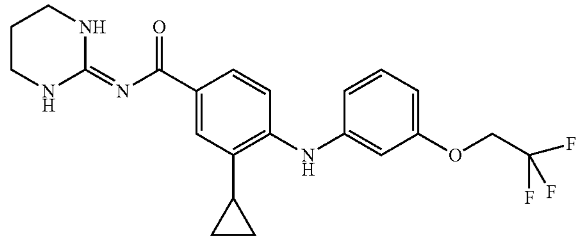 [SMILES: O=C(N=C1NCCCN1)c1ccc(Nc2cccc(OCC(F)(F)F)c2)c(C2CC2)c1]
125 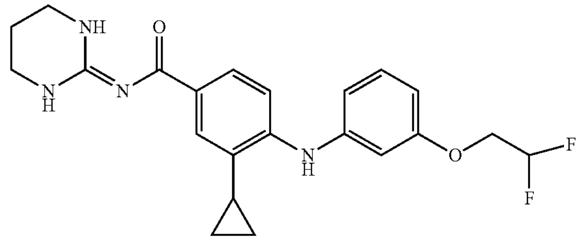 [SMILES: O=C(N=C1NCCCN1)c1ccc(Nc2cccc(OCC(F)F)c2)c(C2CC2)c1]
126 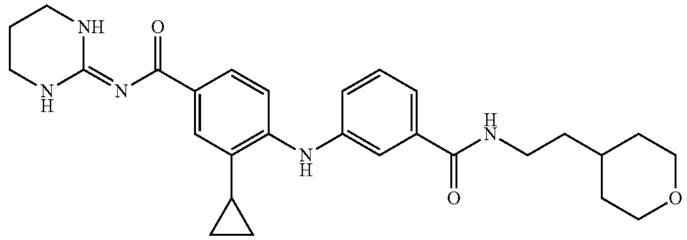 [SMILES: O=C(N=C1NCCCN1)c1ccc(Nc2cccc(C(=O)NCCC3CCOCC3)c2)c(C2CC2)c1]
127 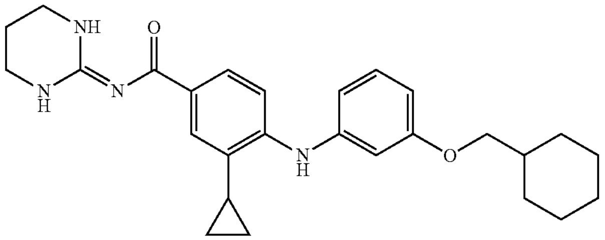 [SMILES: O=C(N=C1NCCCN1)c1ccc(Nc2cccc(OCC3CCCCC3)c2)c(C2CC2)c1]
128 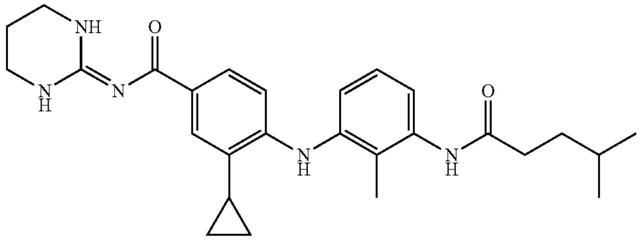 [SMILES: Cc1c(NC(=O)CCC(C)C)cccc1Nc1ccc(C(=O)N=C2NCCCN2)cc1C1CC1]
129 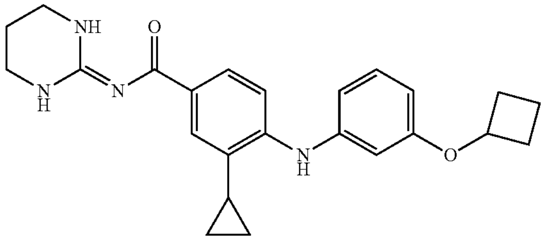 [SMILES: O=C(N=C1NCCCN1)c1ccc(Nc2cccc(OC3CCC3)c2)c(C2CC2)c1]

-continued
| (Ic) | |
|---|---|
| 130 | 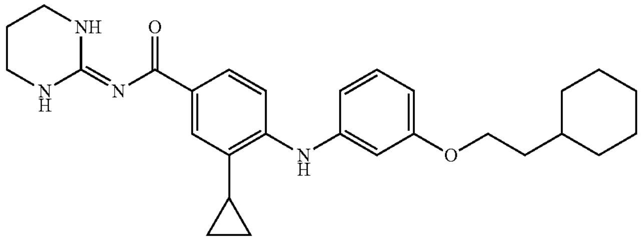 [SMILES: O=C(N=C1NCCCN1)c1ccc(Nc2cccc(OCCC3CCCCC3)c2)c(C2CC2)c1] |
| 131 | 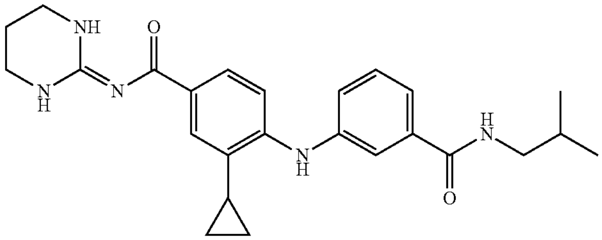 [SMILES: CC(C)CNC(=O)c1cccc(Nc2ccc(C(=O)N=C3NCCCN3)cc2C2CC2)c1] |
| 132 | 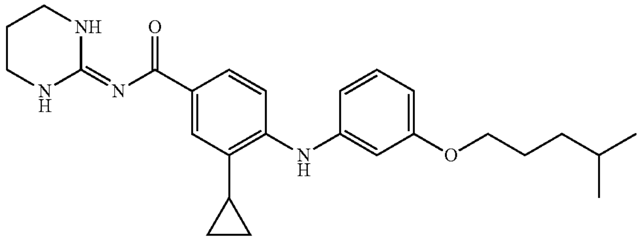 [SMILES: CC(C)CCCOc1cccc(Nc2ccc(C(=O)N=C3NCCCN3)cc2C2CC2)c1] |
| 133 | 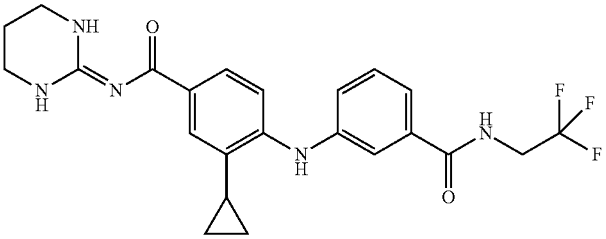 [SMILES: O=C(N=C1NCCCN1)c1ccc(Nc2cccc(C(=O)NCC(F)(F)F)c2)c(C2CC2)c1] |
| 134 | 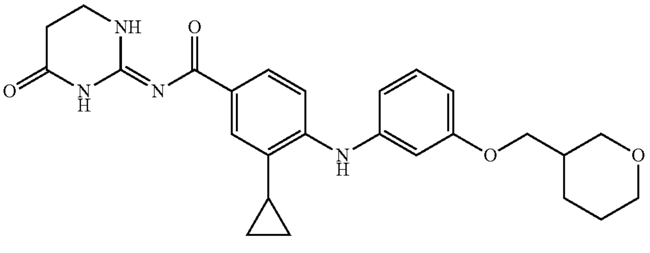 |
| 135 | 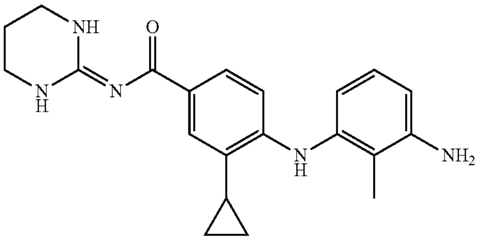 [SMILES: Cc1c(N)cccc1Nc1ccc(C(=O)N=C2NCCCN2)cc1C1CC1] |

-continued
(Ic)
136
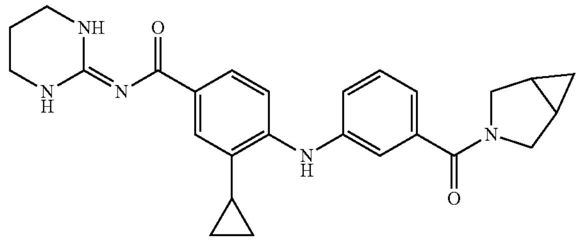 [SMILES: O=C(N=C1NCCCN1)c1ccc(Nc2cccc(C(=O)N3CC4CC4C3)c2)c(C2CC2)c1]
137
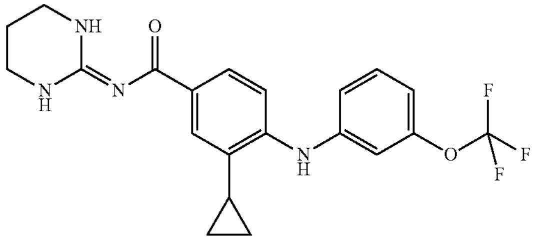 [SMILES: O=C(N=C1NCCCN1)c1ccc(Nc2cccc(OC(F)(F)F)c2)c(C2CC2)c1]
138
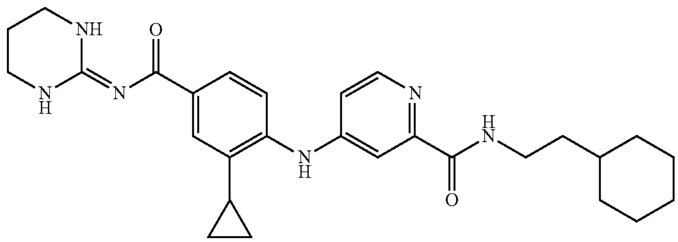 [SMILES: O=C(N=C1NCCCN1)c1ccc(Nc2ccnc(C(=O)NCCC3CCCCC3)c2)c(C2CC2)c1]
139
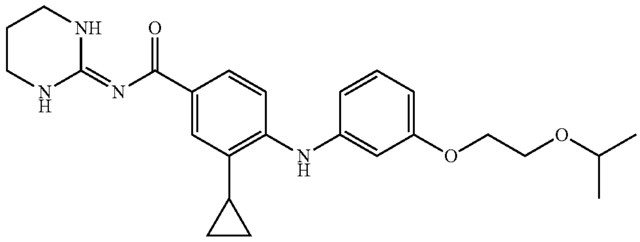
140
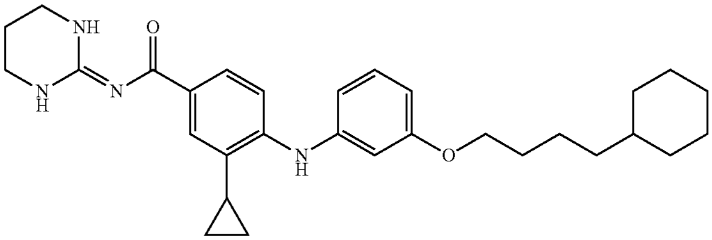 [SMILES: O=C(N=C1NCCCN1)c1ccc(Nc2cccc(OCCCCC3CCCCC3)c2)c(C2CC2)c1]
141
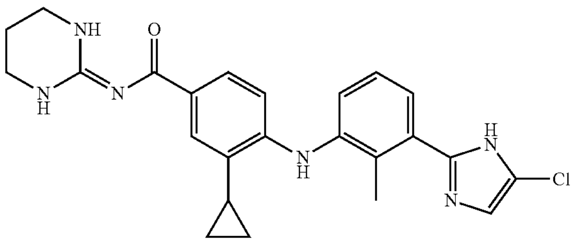 [SMILES: Cc1c(Nc2ccc(C(=O)N=C3NCCCN3)cc2C2CC2)cccc1-c1ncc(Cl)[nH]1]

-continued
| (Ic) |
|---|
142
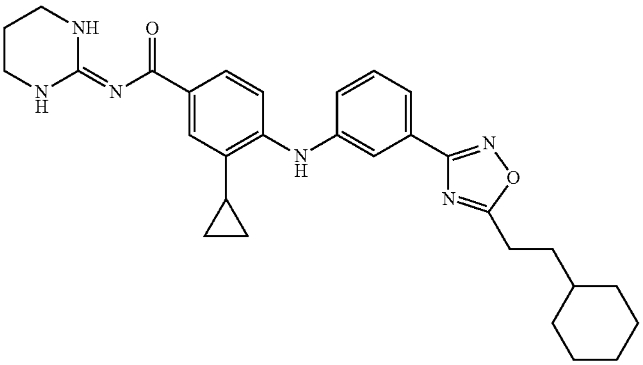 [SMILES: O=C(N=C1NCCCN1)c1ccc(Nc2cccc(-c3noc(CCC4CCCCC4)n3)c2)c(C2CC2)c1]
143
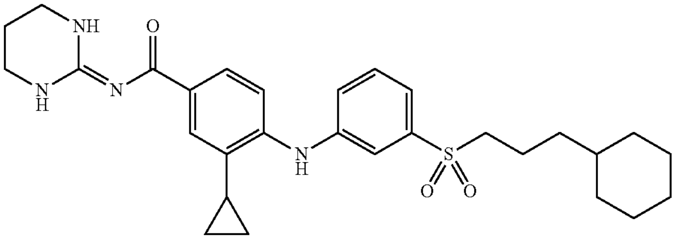 [SMILES: O=C(N=C1NCCCN1)c1ccc(Nc2cccc(S(=O)(=O)CCCC3CCCCC3)c2)c(C2CC2)c1]
144
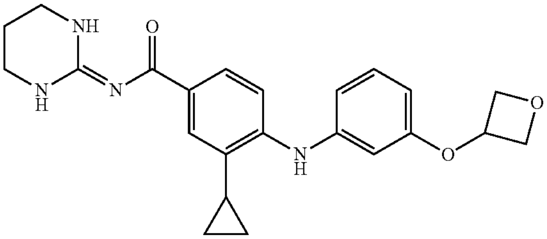 [SMILES: O=C(N=C1NCCCN1)c1ccc(Nc2cccc(OC3COC3)c2)c(C2CC2)c1]
145
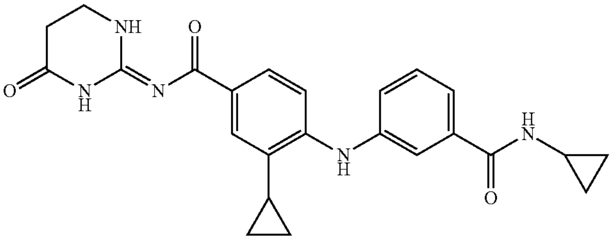 [SMILES: O=C1CCN/C(=N\C(=O)c2ccc(Nc3cccc(C(=O)NC4CC4)c3)c(C3CC3)c2)N1]
146
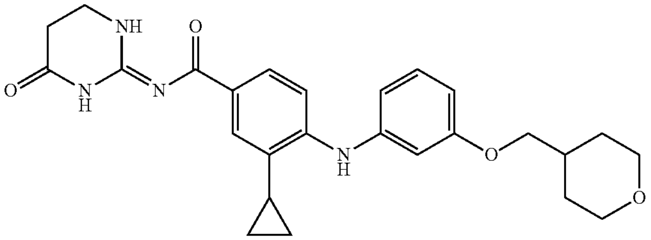 [SMILES: O=C1CCN/C(=N\C(=O)c2ccc(Nc3cccc(OCC4CCOCC4)c3)c(C3CC3)c2)N1]

-continued
| (Ic) |
| --- |
147 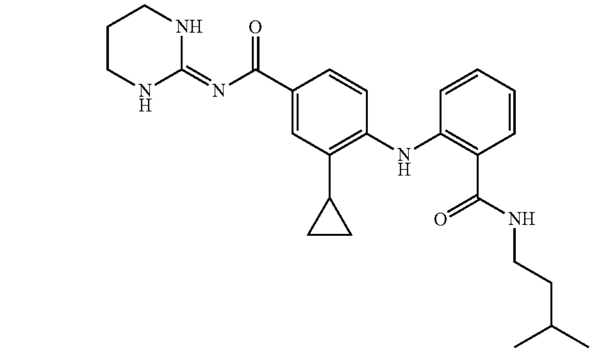 [SMILES: CC(C)CCNC(=O)c1ccccc1Nc1ccc(C(=O)N=C2NCCCN2)cc1C1CC1]
148 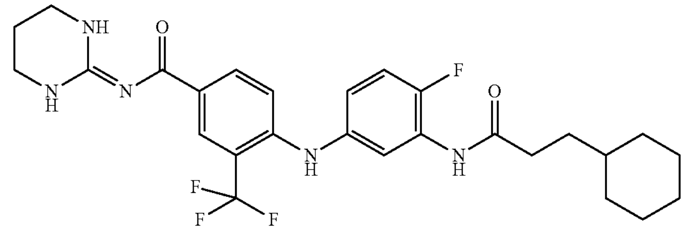 [SMILES: O=C(CCC1CCCCC1)Nc1cc(Nc2ccc(C(=O)N=C3NCCCN3)cc2C(F)(F)F)ccc1F]
149 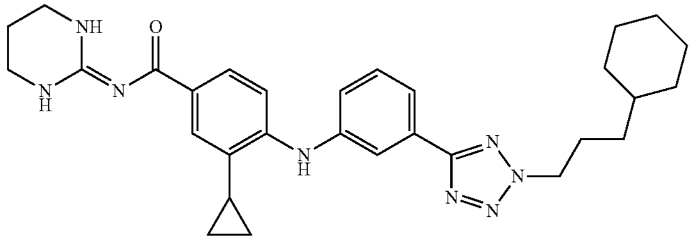 [SMILES: O=C(N=C1NCCCN1)c1ccc(Nc2cccc(-c3nnn(CCCC4CCCCC4)n3)c2)c(C2CC2)c1]
150 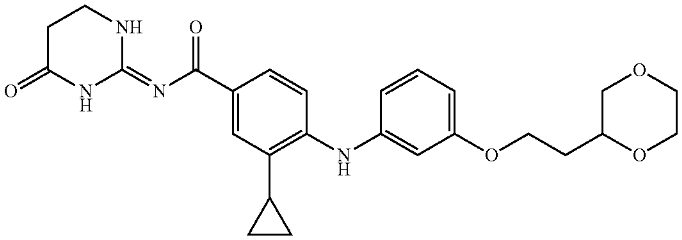 [SMILES: O=C1CCN/C(=N\C(=O)c2ccc(Nc3cccc(OCCC4COCCO4)c3)c(C3CC3)c2)N1]
151 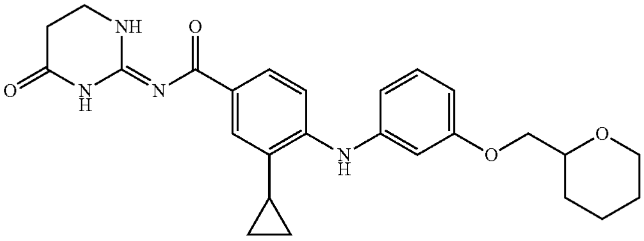 [SMILES: O=C1CCN/C(=N\C(=O)c2ccc(Nc3cccc(OCC4CCCCO4)c3)c(C3CC3)c2)N1]
152 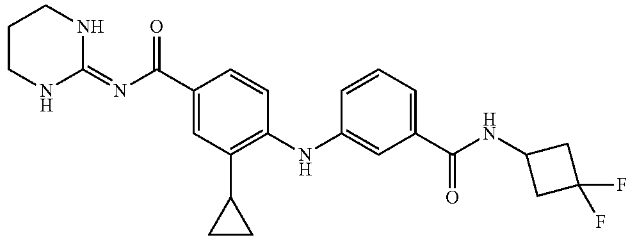 [SMILES: O=C(N=C1NCCCN1)c1ccc(Nc2cccc(C(=O)NC3CC(F)(F)C3)c2)c(C2CC2)c1]

-continued
| (Ic) |
|---|
153 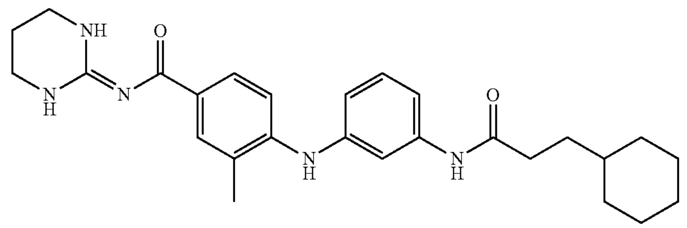 [SMILES: Cc1cc(C(=O)N=C2NCCCN2)ccc1Nc1cccc(NC(=O)CCC2CCCCC2)c1]
154 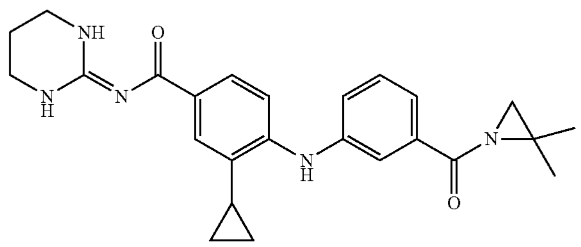 [SMILES: CC1(C)CN1C(=O)c1cccc(Nc2ccc(C(=O)N=C3NCCCN3)cc2C2CC2)c1]
155 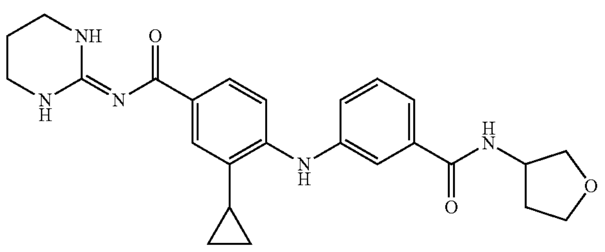 [SMILES: O=C(N=C1NCCCN1)c1ccc(Nc2cccc(C(=O)NC3CCOC3)c2)c(C2CC2)c1]
156 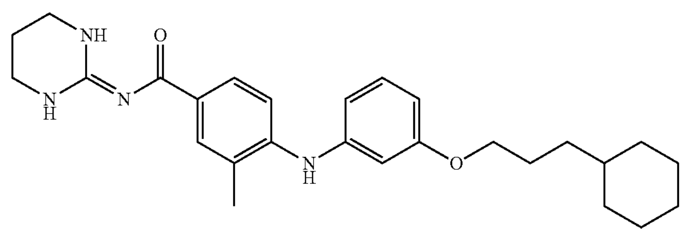 [SMILES: Cc1cc(C(=O)N=C2NCCCN2)ccc1Nc1cccc(OCCCC2CCCCC2)c1]
157 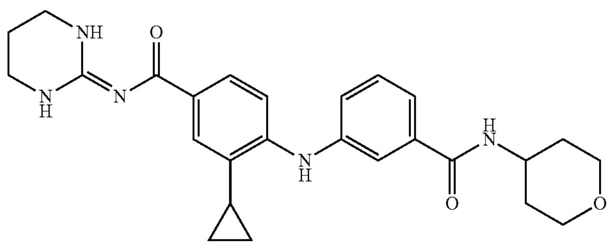 [SMILES: O=C(N=C1NCCCN1)c1ccc(Nc2cccc(C(=O)NC3CCOCC3)c2)c(C2CC2)c1]
158 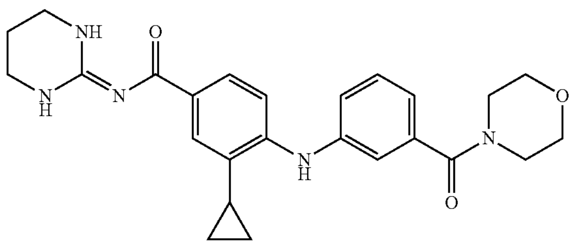 [SMILES: O=C(N=C1NCCCN1)c1ccc(Nc2cccc(C(=O)N3CCOCC3)c2)c(C2CC2)c1]

-continued
| (Ic) | |
|---|---|
| 159 | 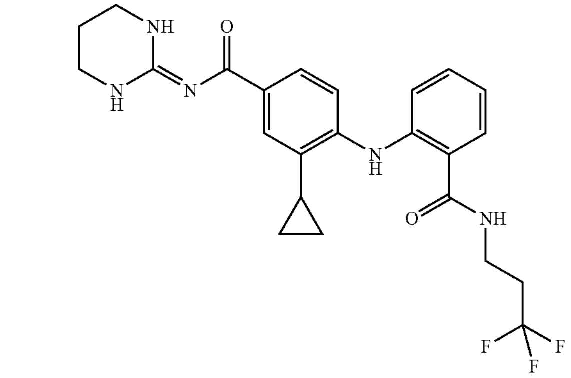 [SMILES: O=C(N=C1NCCCN1)c1ccc(Nc2ccccc2C(=O)NCCC(F)(F)F)c(C2CC2)c1] |
| 160 | 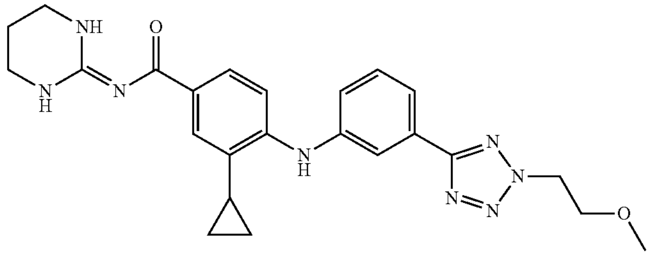 [SMILES: COCCn1nnc(-c2cccc(Nc3ccc(C(=O)N=C4NCCCN4)cc3C3CC3)c2)n1] |
| 161 | 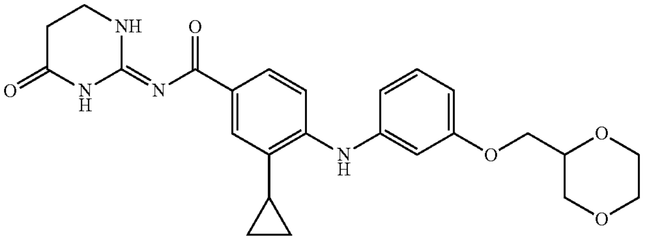 [SMILES: O=C1CCN/C(=N\C(=O)c2ccc(Nc3cccc(OCC4COCCO4)c3)c(C3CC3)c2)N1] |
| 162 | 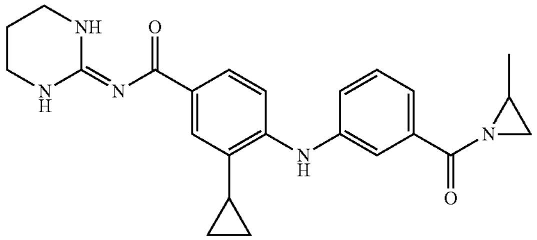 [SMILES: CC1CN1C(=O)c1cccc(Nc2ccc(C(=O)N=C3NCCCN3)cc2C2CC2)c1] |
| 163 | 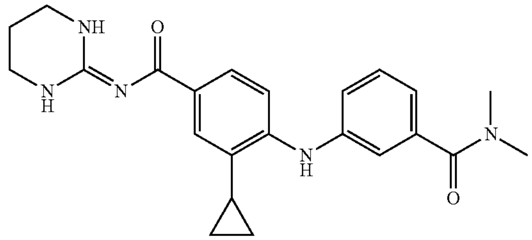 [SMILES: CN(C)C(=O)c1cccc(Nc2ccc(C(=O)N=C3NCCCN3)cc2C2CC2)c1] |

-continued
| (Ic) |
|---|
164
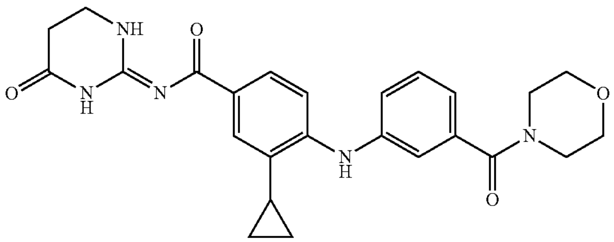 [SMILES: O=C1CCN/C(=N\C(=O)c2ccc(Nc3cccc(C(=O)N4CCOCC4)c3)c(C3CC3)c2)N1]
165
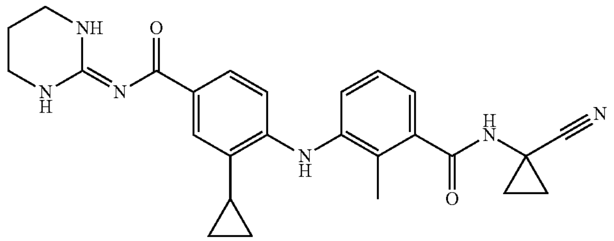 [SMILES: Cc1c(Nc2ccc(C(=O)N=C3NCCCN3)cc2C2CC2)cccc1C(=O)NC1(C#N)CC1]
166
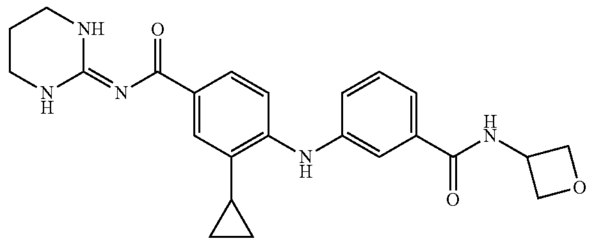 [SMILES: O=C(N=C1NCCCN1)c1ccc(Nc2cccc(C(=O)NC3COC3)c2)c(C2CC2)c1]
167
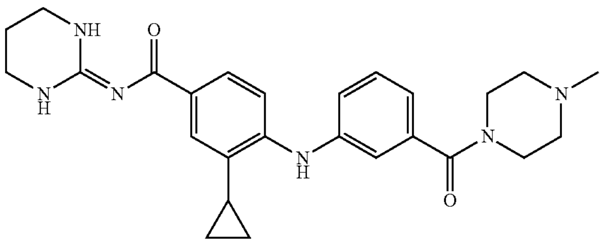 [SMILES: CN1CCN(C(=O)c2cccc(Nc3ccc(C(=O)N=C4NCCCN4)cc3C3CC3)c2)CC1]
168
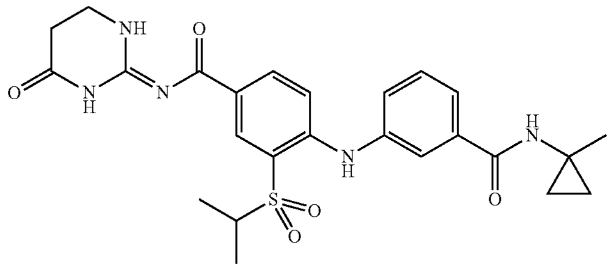 [SMILES: CC(C)S(=O)(=O)c1cc(C(=O)/N=C2\NCCC(=O)N2)ccc1Nc1cccc(C(=O)NC2(C)CC2)c1]
169
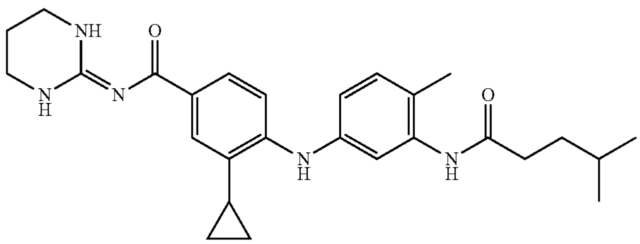 [SMILES: Cc1ccc(Nc2ccc(C(=O)N=C3NCCCN3)cc2C2CC2)cc1NC(=O)CCC(C)C]

-continued
| (Ic) |
|---|
170 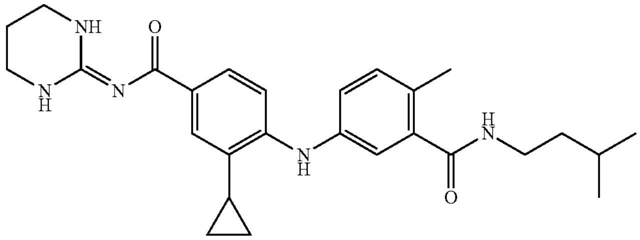 [SMILES: Cc1ccc(Nc2ccc(C(=O)N=C3NCCCN3)cc2C2CC2)cc1C(=O)NCCC(C)C]
171 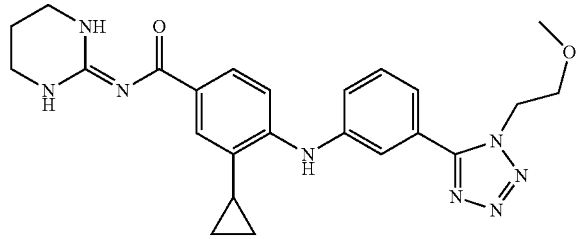 [SMILES: COCCn1nnnc1-c1cccc(Nc2ccc(C(=O)N=C3NCCCN3)cc2C2CC2)c1]
172 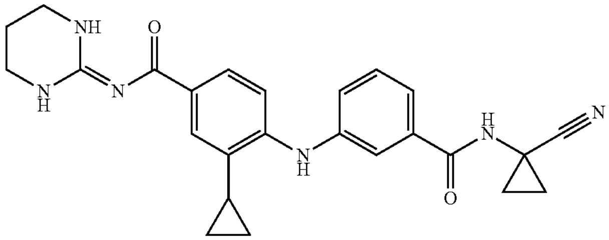 [SMILES: N#CC1(NC(=O)c2cccc(Nc3ccc(C(=O)N=C4NCCCN4)cc3C3CC3)c2)CC1]
173 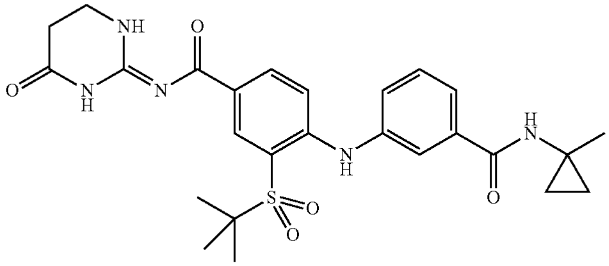 [SMILES: CC1(NC(=O)c2cccc(Nc3ccc(C(=O)/N=C4\NCCC(=O)N4)cc3S(=O)(=O)C(C)(C)C)c2)CC1]
174 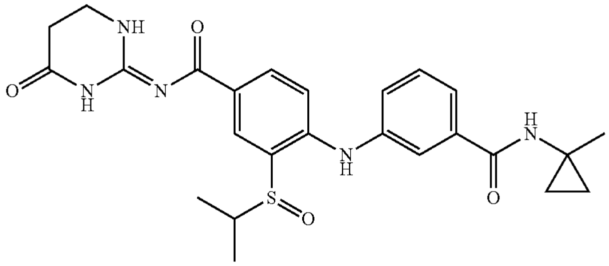 [SMILES: CC(C)S(=O)c1cc(C(=O)/N=C2\NCCC(=O)N2)ccc1Nc1cccc(C(=O)NC2(C)CC2)c1]
175 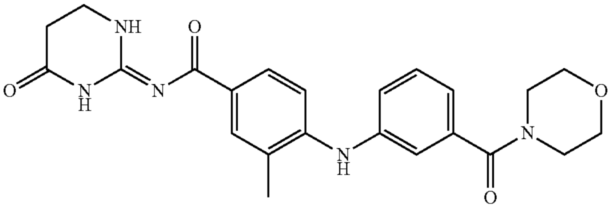 [SMILES: Cc1cc(C(=O)/N=C2\NCCC(=O)N2)ccc1Nc1cccc(C(=O)N2CCOCC2)c1]

-continued
| (Ic) | |
|---|---|
| 176 | 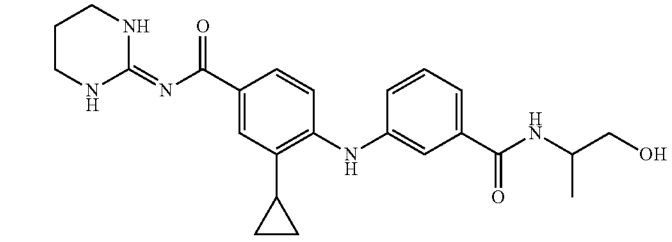 [SMILES: CC(CO)NC(=O)c1cccc(Nc2ccc(C(=O)N=C3NCCCN3)cc2C2CC2)c1] |
| 177 | 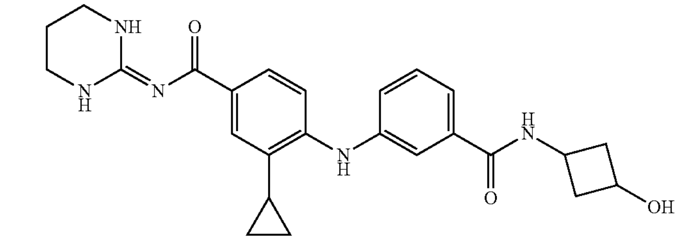 [SMILES: O=C(N=C1NCCCN1)c1ccc(Nc2cccc(C(=O)NC3CC(O)C3)c2)c(C2CC2)c1] |
| 178 | 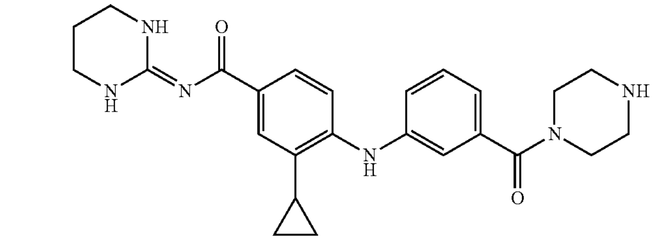 [SMILES: O=C(N=C1NCCCN1)c1ccc(Nc2cccc(C(=O)N3CCNCC3)c2)c(C2CC2)c1] |
| 179 | 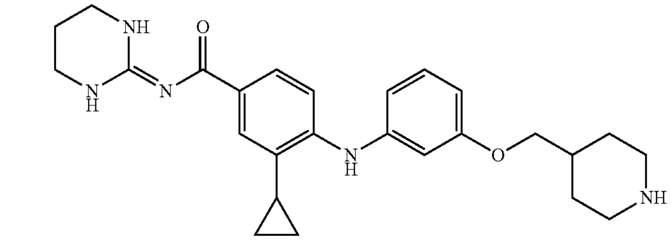 [SMILES: O=C(N=C1NCCCN1)c1ccc(Nc2cccc(OCC3CCNCC3)c2)c(C2CC2)c1] |
| 180 | 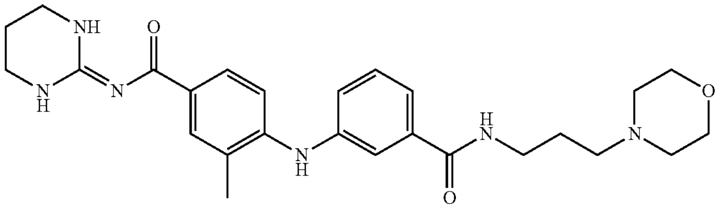 [SMILES: Cc1cc(C(=O)N=C2NCCCN2)ccc1Nc1cccc(C(=O)NCCCN2CCOCC2)c1] |
| | and |
| 181 | 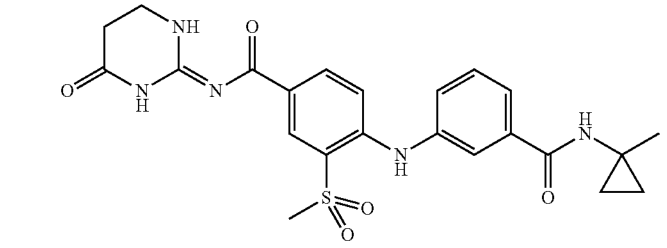 [SMILES: CC1(NC(=O)c2cccc(Nc3ccc(C(=O)/N=C4\NCCC(=O)N4)cc3S(C)(=O)=O)c2)CC1] |
or a pharmaceutically acceptable salt thereof; and at least one pharmaceutically acceptable excipient.

17. A process for the preparation of
a) a compound of formula (Ic) or a pharmaceutically acceptable salt thereof according to claim 1; or
b) a compound selected from 19-31 and 91-181
| (Ic) |
|---|
| 19 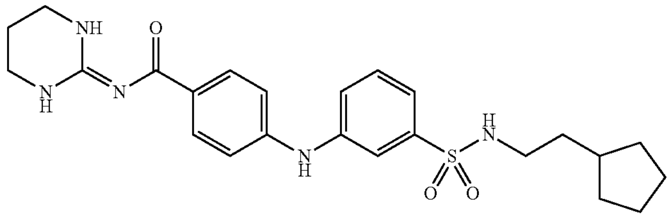 [SMILES: O=C(N=C1NCCCN1)c1ccc(Nc2cccc(S(=O)(=O)NCCC3CCCC3)c2)cc1] |
| 20 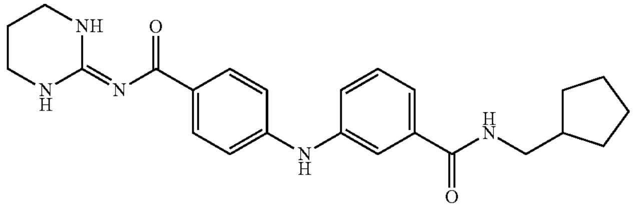 [SMILES: O=C(N=C1NCCCN1)c1ccc(Nc2cccc(C(=O)NCC3CCCC3)c2)cc1] |
| 21 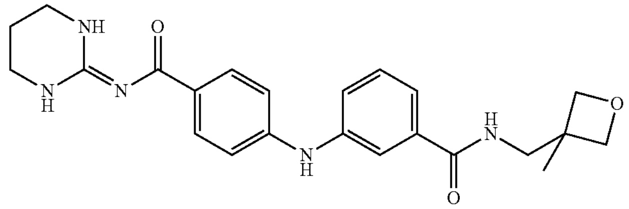 [SMILES: CC1(CNC(=O)c2cccc(Nc3ccc(C(=O)N=C4NCCCN4)cc3)c2)COC1] |
| 22 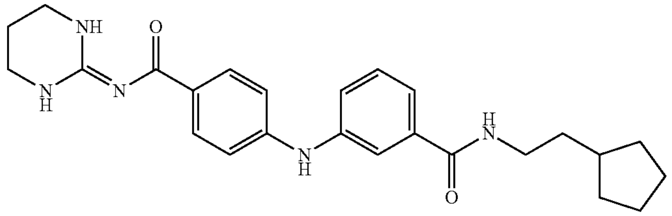 [SMILES: O=C(N=C1NCCCN1)c1ccc(Nc2cccc(C(=O)NCCC3CCCC3)c2)cc1] |
| 23 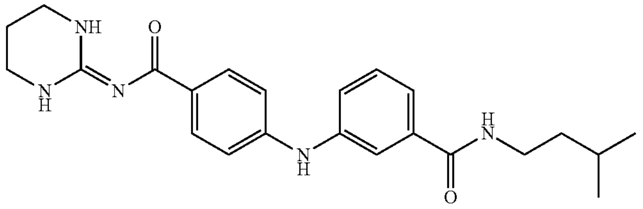 [SMILES: CC(C)CCNC(=O)c1cccc(Nc2ccc(C(=O)N=C3NCCCN3)cc2)c1] |
| 24 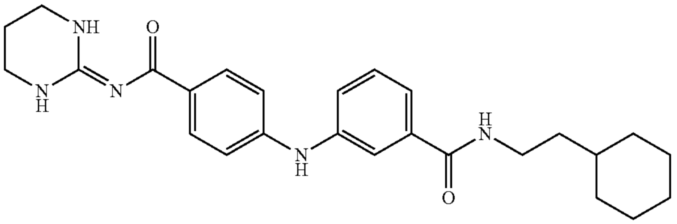 [SMILES: O=C(N=C1NCCCN1)c1ccc(Nc2cccc(C(=O)NCCC3CCCCC3)c2)cc1] |

-continued
| (Ic) |
|---|
| 25 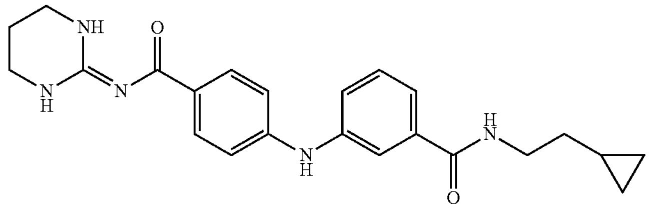 [SMILES: O=C(N=C1NCCCN1)c1ccc(Nc2cccc(C(=O)NCCC3CC3)c2)cc1] |
| 26 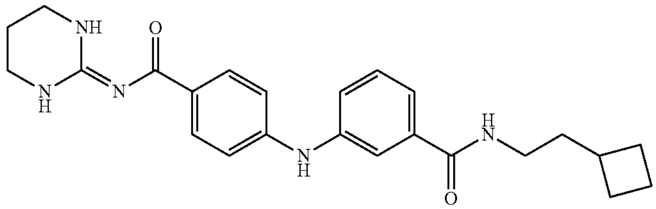 [SMILES: O=C(N=C1NCCCN1)c1ccc(Nc2cccc(C(=O)NCCC3CCC3)c2)cc1] |
| 27 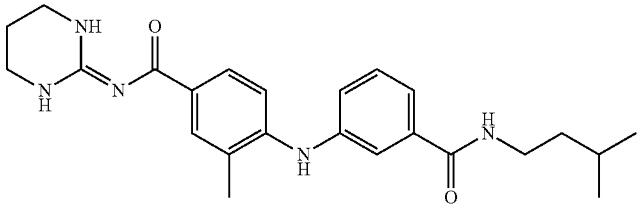 [SMILES: Cc1cc(C(=O)N=C2NCCCN2)ccc1Nc1cccc(C(=O)NCCC(C)C)c1] |
| 28 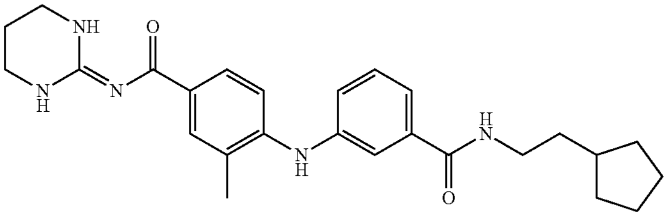 [SMILES: Cc1cc(C(=O)N=C2NCCCN2)ccc1Nc1cccc(C(=O)NCCC2CCCC2)c1] |
| 29 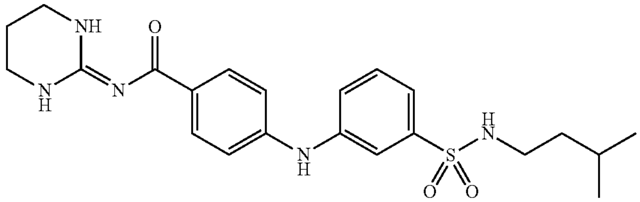 [SMILES: CC(C)CCNS(=O)(=O)c1cccc(Nc2ccc(C(=O)N=C3NCCCN3)cc2)c1] |
| 30 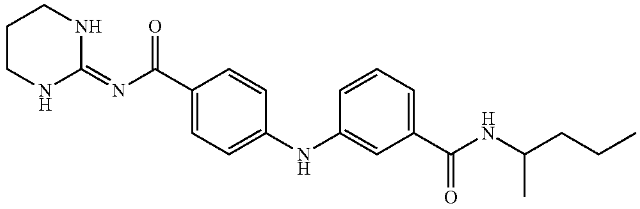 [SMILES: CCCC(C)NC(=O)c1cccc(Nc2ccc(C(=O)N=C3NCCCN3)cc2)c1] |
| 31 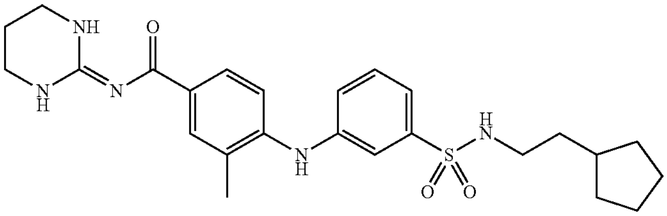 [SMILES: Cc1cc(C(=O)N=C2NCCCN2)ccc1Nc1cccc(S(=O)(=O)NCCC2CCCC2)c1] |

-continued
| (Ic) |
| --- |
91
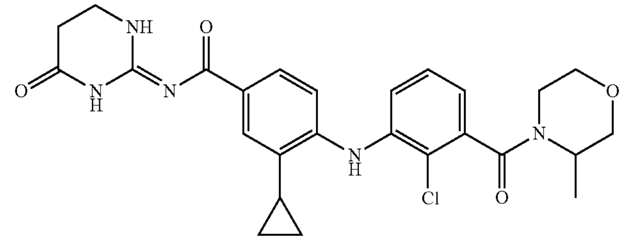 [SMILES: CC1COCCN1C(=O)c1cccc(Nc2ccc(C(=O)/N=C3\NCCC(=O)N3)cc2C2CC2)c1Cl]
92
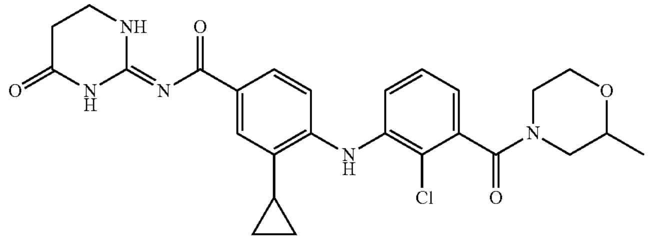 [SMILES: CC1CN(C(=O)c2cccc(Nc3ccc(C(=O)/N=C4\NCCC(=O)N4)cc3C3CC3)c2Cl)CCO1]
93
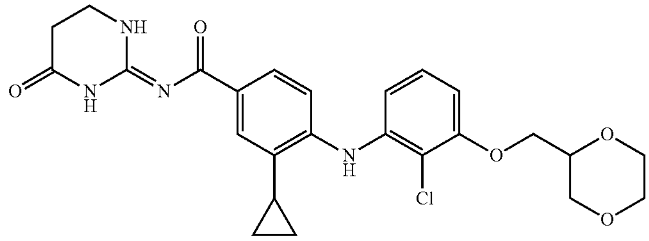 [SMILES: O=C1CCN/C(=N\C(=O)c2ccc(Nc3cccc(OCC4COCCO4)c3Cl)c(C3CC3)c2)N1]
94
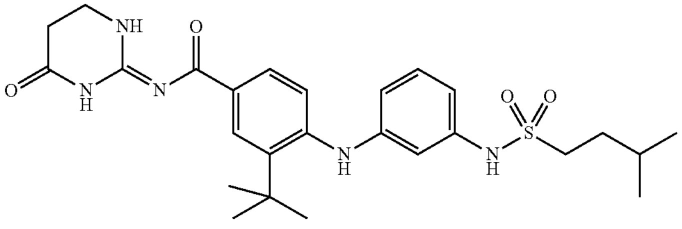 [SMILES: CC(C)CCS(=O)(=O)Nc1cccc(Nc2ccc(C(=O)/N=C3\NCCC(=O)N3)cc2C(C)(C)C)c1]
95
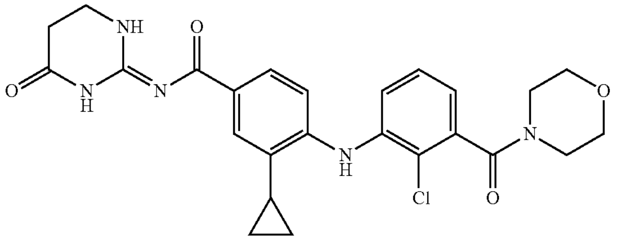 [SMILES: O=C1CCN/C(=N\C(=O)c2ccc(Nc3cccc(C(=O)N4CCOCC4)c3Cl)c(C3CC3)c2)N1]
96
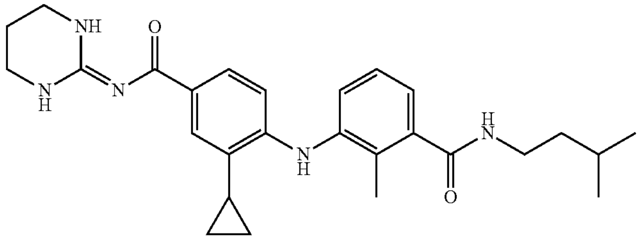 [SMILES: Cc1c(Nc2ccc(C(=O)N=C3NCCCN3)cc2C2CC2)cccc1C(=O)NCCC(C)C]

-continued
| (Ic) |
|---|
97
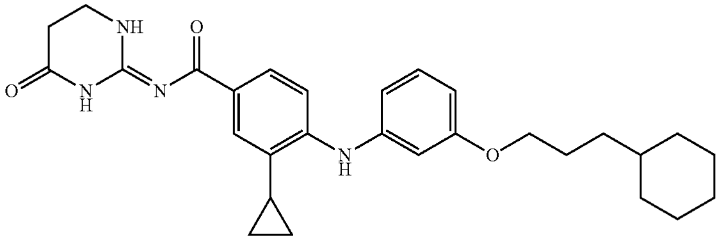 [SMILES: O=C1CCN/C(=N\C(=O)c2ccc(Nc3cccc(OCCCC4CCCCC4)c3)c(C3CC3)c2)N1]
98
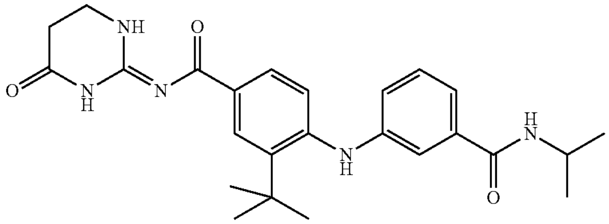 [SMILES: CC(C)NC(=O)c1cccc(Nc2ccc(C(=O)/N=C3\NCCC(=O)N3)cc2C(C)(C)C)c1]
99
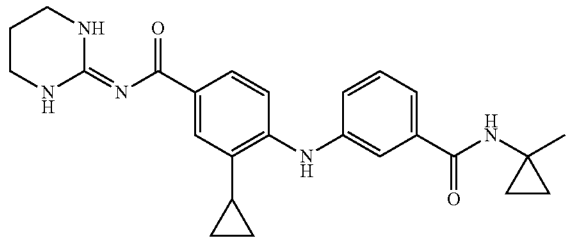 [SMILES: CC1(NC(=O)c2cccc(Nc3ccc(C(=O)N=C4NCCCN4)cc3C3CC3)c2)CC1]
100
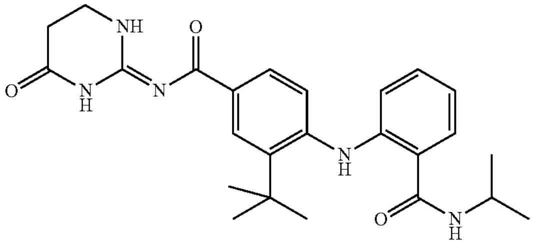 [SMILES: CC(C)NC(=O)c1ccccc1Nc1ccc(C(=O)/N=C2\NCCC(=O)N2)cc1C(C)(C)C]
101
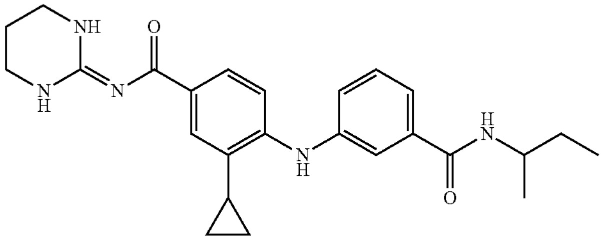 [SMILES: CCC(C)NC(=O)c1cccc(Nc2ccc(C(=O)N=C3NCCCN3)cc2C2CC2)c1]
102
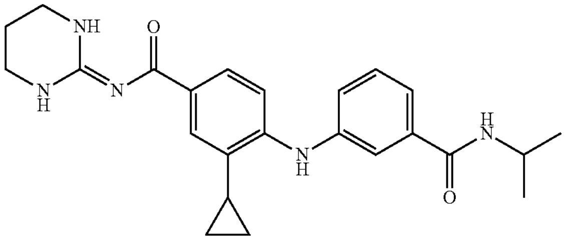 [SMILES: CC(C)NC(=O)c1cccc(Nc2ccc(C(=O)N=C3NCCCN3)cc2C2CC2)c1]

-continued
(Ic)
103
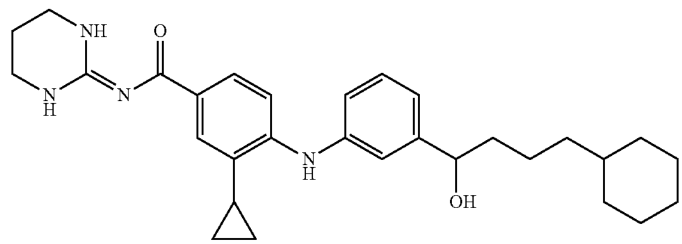 [SMILES: O=C(N=C1NCCCN1)c1ccc(Nc2cccc(C(O)CCCC3CCCCC3)c2)c(C2CC2)c1]
104
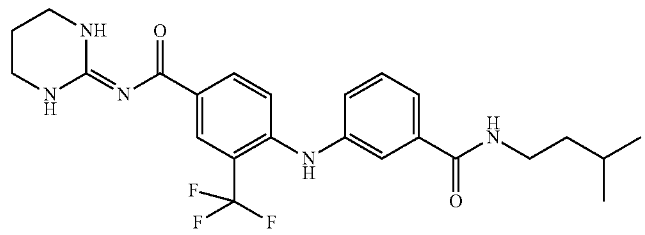 [SMILES: CC(C)CCNC(=O)c1cccc(Nc2ccc(C(=O)N=C3NCCCN3)cc2C(F)(F)F)c1]
105
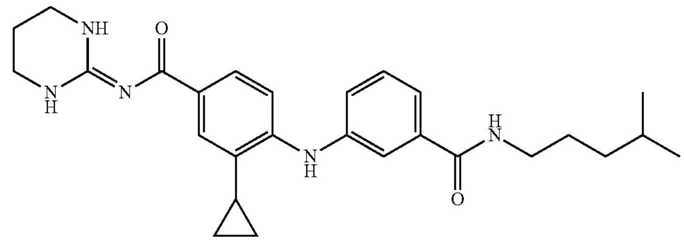 [SMILES: CC(C)CCCNC(=O)c1cccc(Nc2ccc(C(=O)N=C3NCCCN3)cc2C2CC2)c1]
106
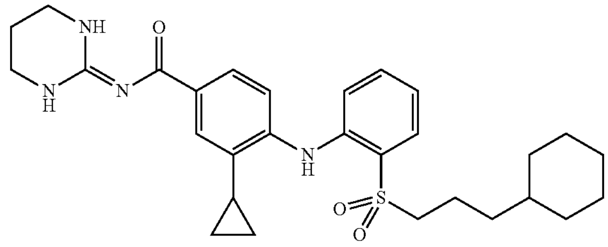 [SMILES: O=C(N=C1NCCCN1)c1ccc(Nc2ccccc2S(=O)(=O)CCCC2CCCCC2)c(C2CC2)c1]
107
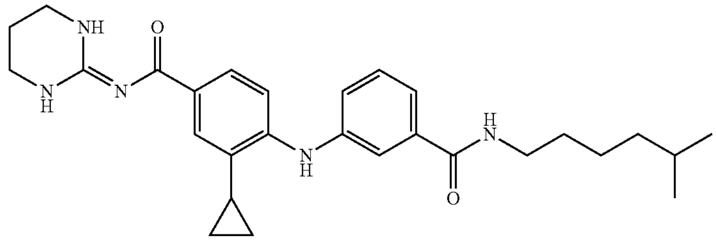 [SMILES: CC(C)CCCCNC(=O)c1cccc(Nc2ccc(C(=O)N=C3NCCCN3)cc2C2CC2)c1]
108
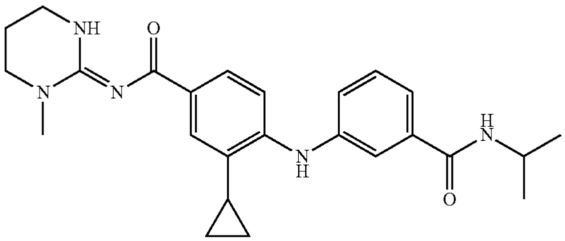 [SMILES: CC(C)NC(=O)c1cccc(Nc2ccc(C(=O)/N=C3\NCCCN3C)cc2C2CC2)c1]

-continued
| (Ic) |
|---|
109
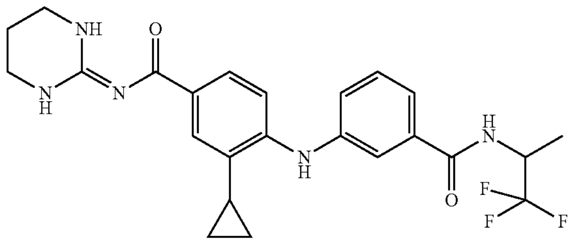 [SMILES: CC(NC(=O)c1cccc(Nc2ccc(C(=O)N=C3NCCCN3)cc2C2CC2)c1)C(F)(F)F]
110
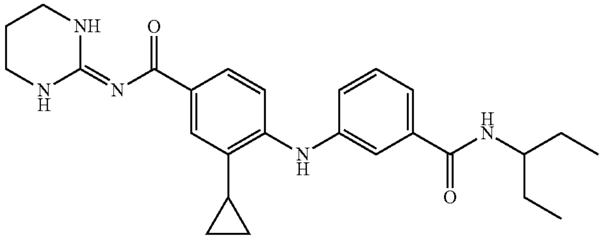 [SMILES: CCC(CC)NC(=O)c1cccc(Nc2ccc(C(=O)N=C3NCCCN3)cc2C2CC2)c1]
111
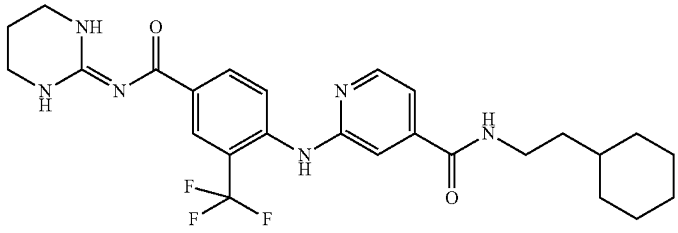 [SMILES: O=C(N=C1NCCCN1)c1ccc(Nc2cc(C(=O)NCCC3CCCCC3)ccn2)c(C(F)(F)F)c1]
112
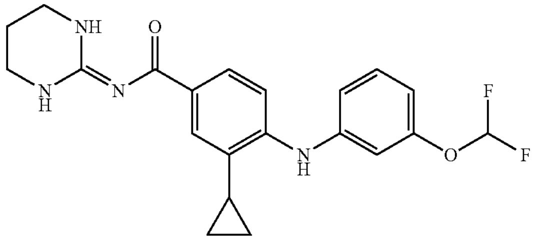 [SMILES: O=C(N=C1NCCCN1)c1ccc(Nc2cccc(OC(F)F)c2)c(C2CC2)c1]
113
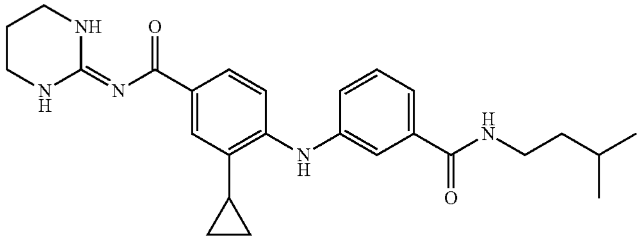
114
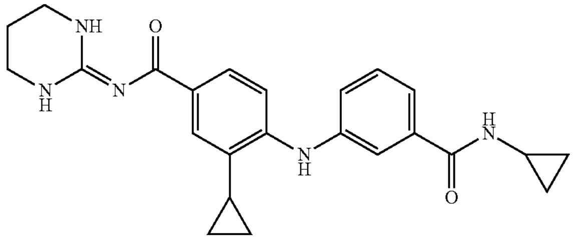 [SMILES: O=C(N=C1NCCCN1)c1ccc(Nc2cccc(C(=O)NC3CC3)c2)c(C2CC2)c1]

-continued
(Ic)
115
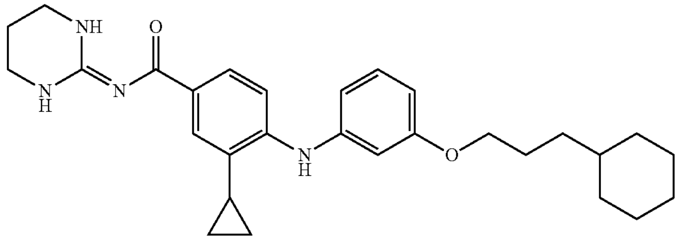 [SMILES: O=C(N=C1NCCCN1)c1ccc(Nc2cccc(OCCCC3CCCCC3)c2)c(C2CC2)c1]
116
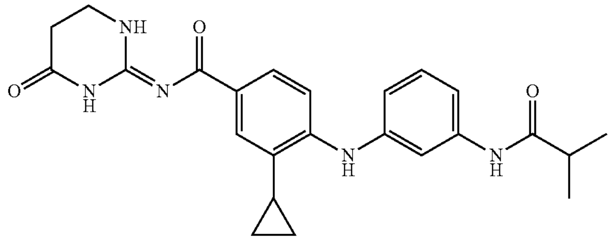 [SMILES: CC(C)C(=O)Nc1cccc(Nc2ccc(C(=O)/N=C3\NCCC(=O)N3)cc2C2CC2)c1]
117
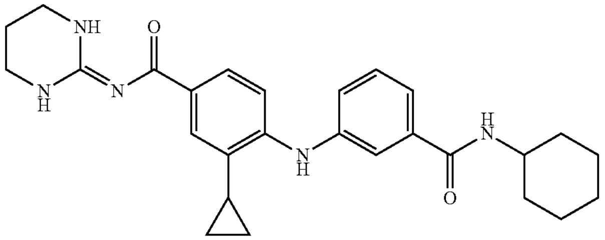 [SMILES: O=C(N=C1NCCCN1)c1ccc(Nc2cccc(C(=O)NC3CCCCC3)c2)c(C2CC2)c1]
118
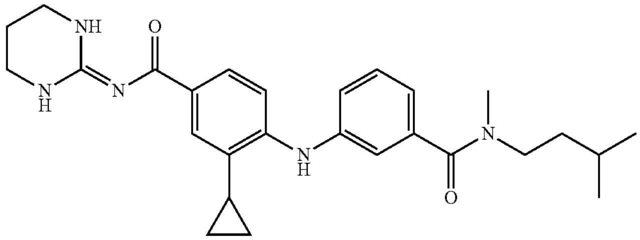 [SMILES: CC(C)CCN(C)C(=O)c1cccc(Nc2ccc(C(=O)N=C3NCCCN3)cc2C2CC2)c1]
119
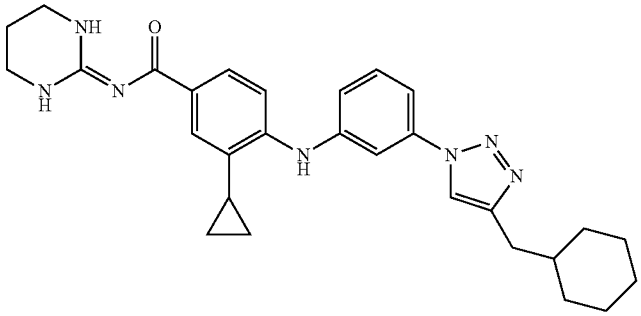 [SMILES: O=C(N=C1NCCCN1)c1ccc(Nc2cccc(-n3cc(CC4CCCCC4)nn3)c2)c(C2CC2)c1]
120
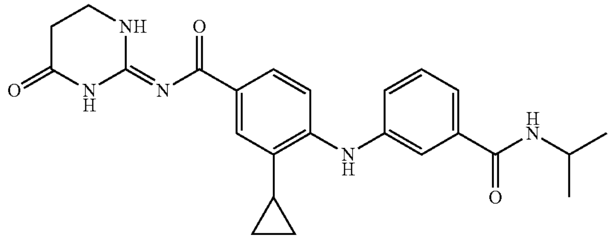 [SMILES: CC(C)NC(=O)c1cccc(Nc2ccc(C(=O)/N=C3\NCCC(=O)N3)cc2C2CC2)c1]

-continued
(Ic)
121
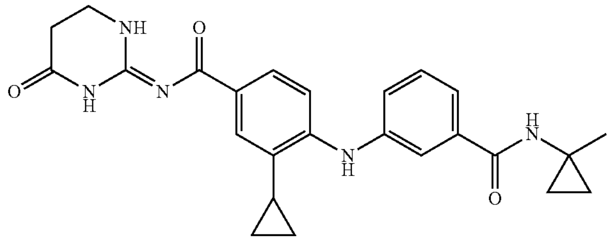 [SMILES: CC1(NC(=O)c2cccc(Nc3ccc(C(=O)/N=C4\NCCC(=O)N4)cc3C3CC3)c2)CC1]
122
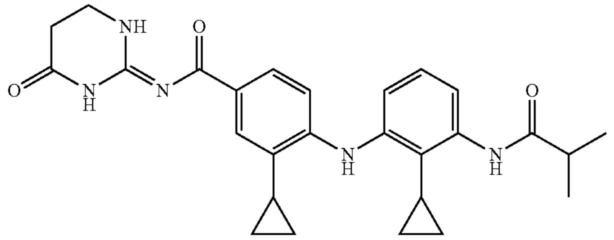 [SMILES: CC(C)C(=O)Nc1cccc(Nc2ccc(C(=O)/N=C3\NCCC(=O)N3)cc2C2CC2)c1C1CC1]
123
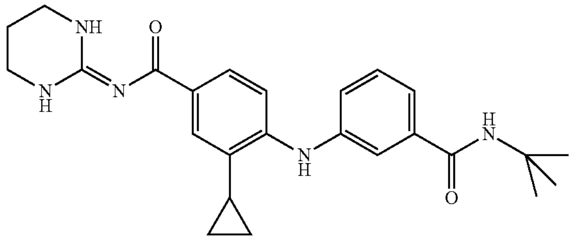
124
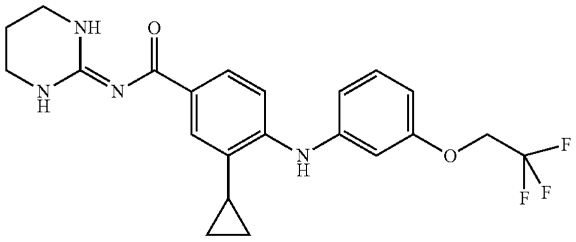 [SMILES: O=C(N=C1NCCCN1)c1ccc(Nc2cccc(OCC(F)(F)F)c2)c(C2CC2)c1]
125
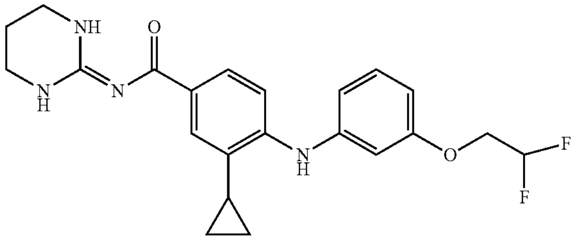 [SMILES: O=C(N=C1NCCCN1)c1ccc(Nc2cccc(OCC(F)F)c2)c(C2CC2)c1]
126
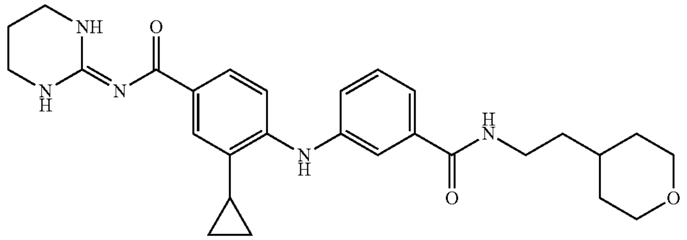 [SMILES: O=C(N=C1NCCCN1)c1ccc(Nc2cccc(C(=O)NCCC3CCOCC3)c2)c(C2CC2)c1]

-continued
| (Ic) |
|---|
127
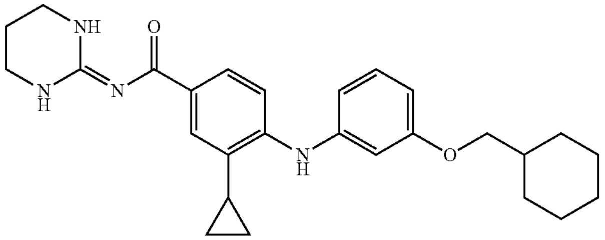 [SMILES: O=C(N=C1NCCCN1)c1ccc(Nc2cccc(OCC3CCCCC3)c2)c(C2CC2)c1]
128
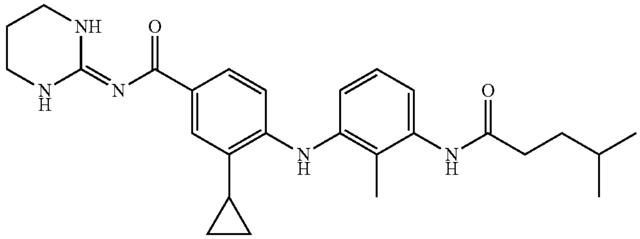 [SMILES: Cc1c(NC(=O)CCC(C)C)cccc1Nc1ccc(C(=O)N=C2NCCCN2)cc1C1CC1]
129
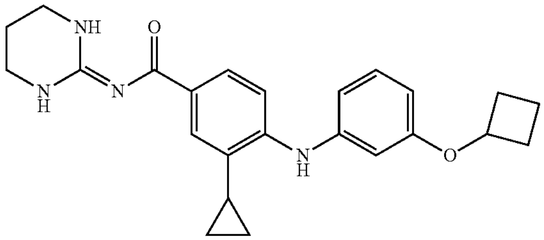 [SMILES: O=C(N=C1NCCCN1)c1ccc(Nc2cccc(OC3CCC3)c2)c(C2CC2)c1]
130
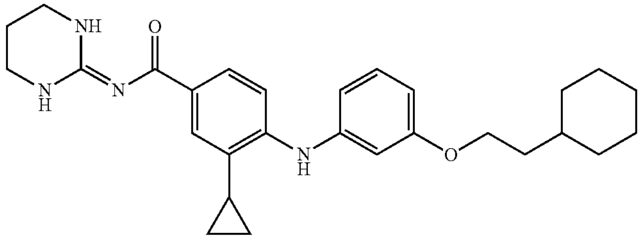 [SMILES: O=C(N=C1NCCCN1)c1ccc(Nc2cccc(OCCC3CCCCC3)c2)c(C2CC2)c1]
131
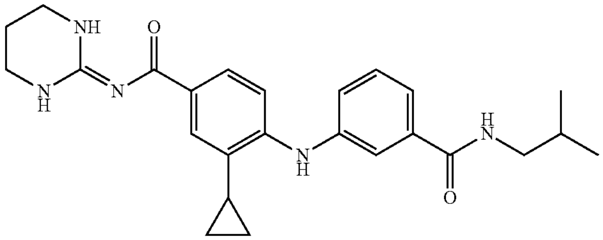 [SMILES: CC(C)CNC(=O)c1cccc(Nc2ccc(C(=O)N=C3NCCCN3)cc2C2CC2)c1]
132
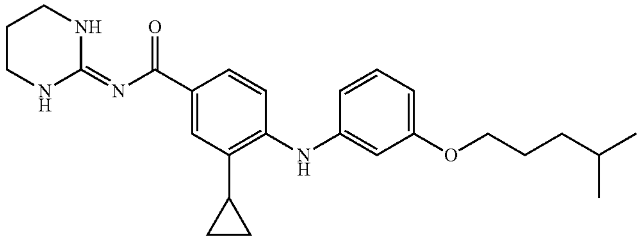

-continued
| (Ic) | |
|---|---|
| 133 | 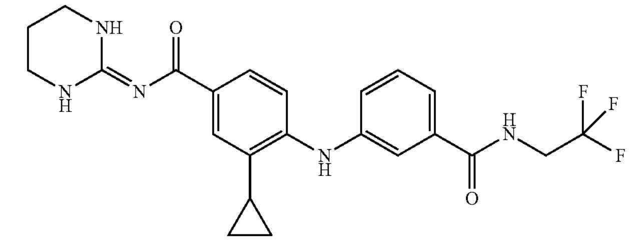 [SMILES: O=C(N=C1NCCCN1)c1ccc(Nc2cccc(C(=O)NCC(F)(F)F)c2)c(C2CC2)c1] |
| 134 | 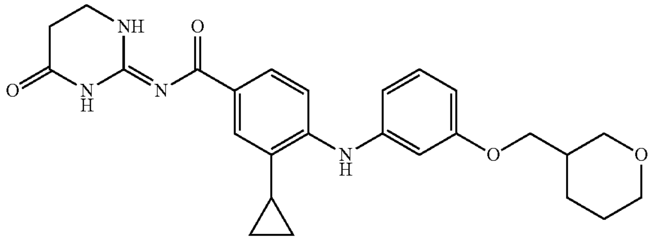 [SMILES: O=C1CCN/C(=N\C(=O)c2ccc(Nc3cccc(OCC4CCCOC4)c3)c(C3CC3)c2)N1] |
| 135 | 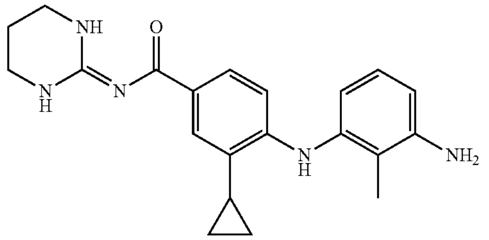 [SMILES: Cc1c(N)cccc1Nc1ccc(C(=O)N=C2NCCCN2)cc1C1CC1] |
| 136 | 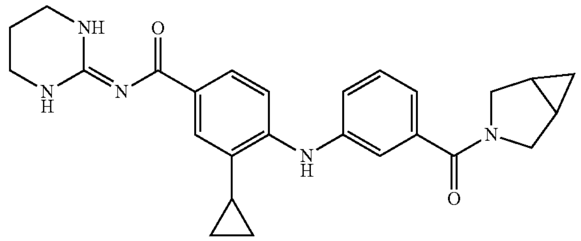 [SMILES: O=C(N=C1NCCCN1)c1ccc(Nc2cccc(C(=O)N3CC4CC4C3)c2)c(C2CC2)c1] |
| 137 | 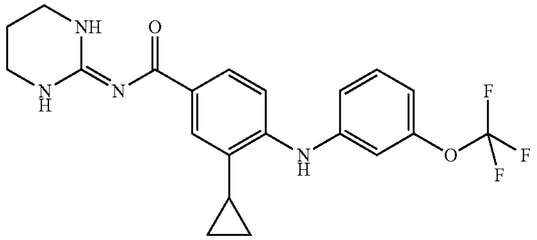 [SMILES: O=C(N=C1NCCCN1)c1ccc(Nc2cccc(OC(F)(F)F)c2)c(C2CC2)c1] |
| 138 | 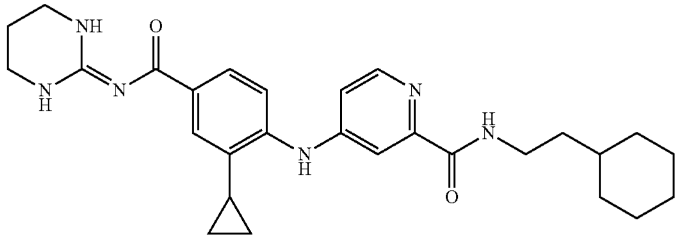 [SMILES: O=C(N=C1NCCCN1)c1ccc(Nc2ccnc(C(=O)NCCC3CCCCC3)c2)c(C2CC2)c1] |

-continued
(Ic)
139
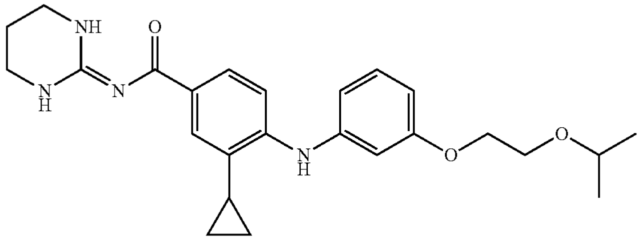
140
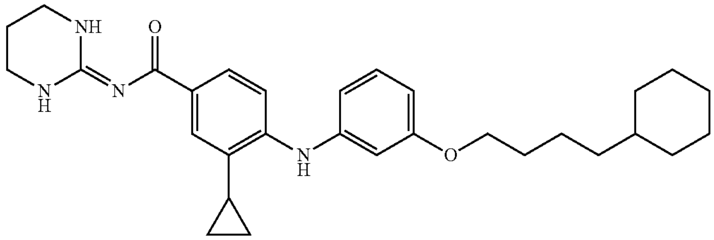 [SMILES: O=C(N=C1NCCCN1)c1ccc(Nc2cccc(OCCCCC3CCCCC3)c2)c(C2CC2)c1]
141
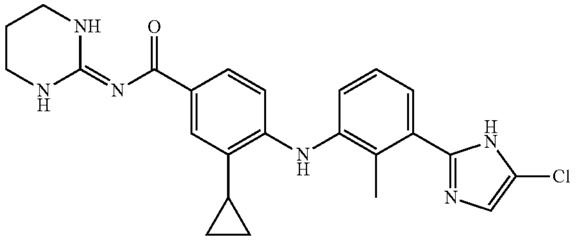 [SMILES: Cc1c(Nc2ccc(C(=O)N=C3NCCCN3)cc2C2CC2)cccc1-c1ncc(Cl)[nH]1]
142
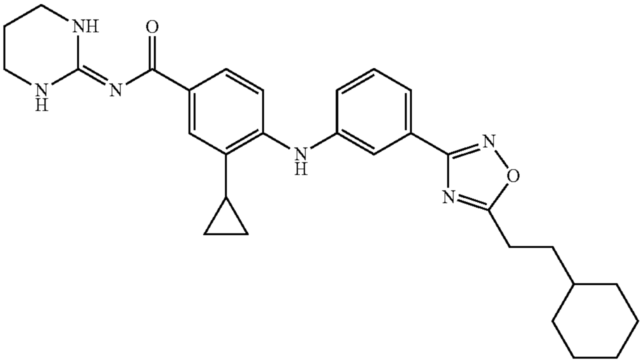 [SMILES: O=C(N=C1NCCCN1)c1ccc(Nc2cccc(-c3noc(CCC4CCCCC4)n3)c2)c(C2CC2)c1]
143
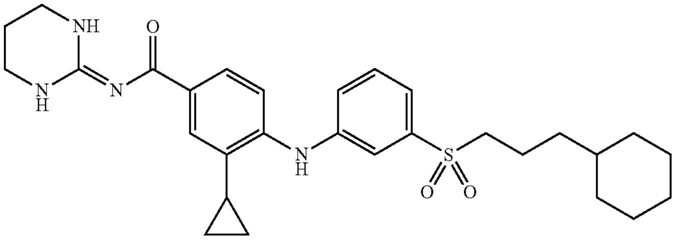 [SMILES: O=C(N=C1NCCCN1)c1ccc(Nc2cccc(S(=O)(=O)CCCC3CCCCC3)c2)c(C2CC2)c1]
144
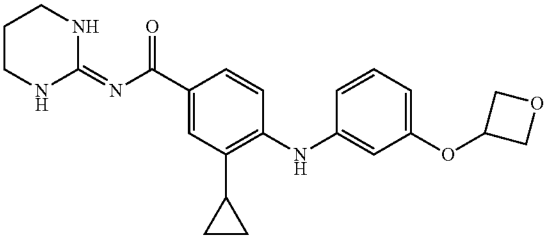 [SMILES: O=C(N=C1NCCCN1)c1ccc(Nc2cccc(OC3COC3)c2)c(C2CC2)c1]

-continued
| (Ic) |
| --- |
145 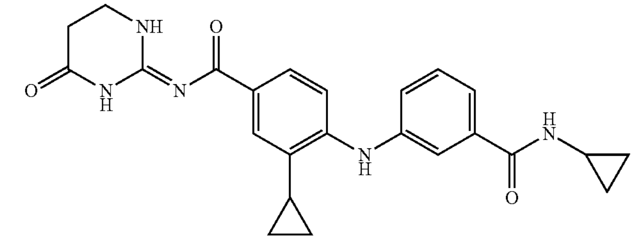 [SMILES: O=C1CCN/C(=N\C(=O)c2ccc(Nc3cccc(C(=O)NC4CC4)c3)c(C3CC3)c2)N1]
146 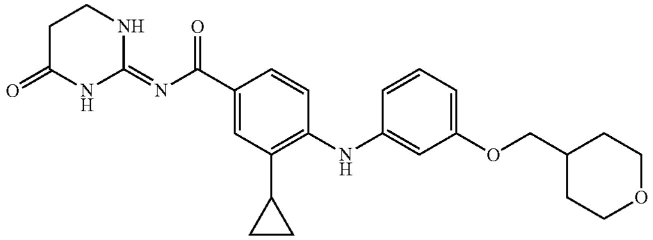 [SMILES: O=C1CCN/C(=N\C(=O)c2ccc(Nc3cccc(OCC4CCOCC4)c3)c(C3CC3)c2)N1]
147 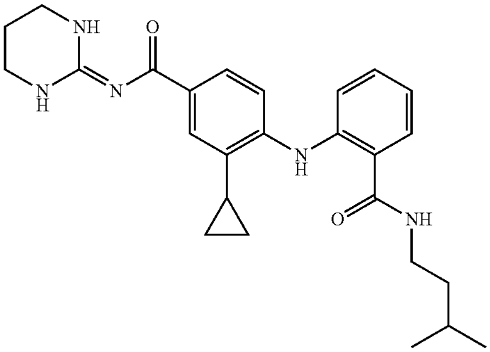 [SMILES: CC(C)CCNC(=O)c1ccccc1Nc1ccc(C(=O)N=C2NCCCN2)cc1C1CC1]
148 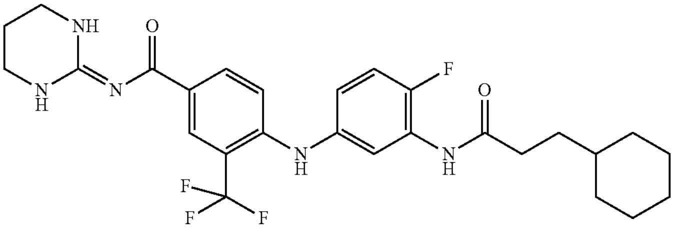 [SMILES: O=C(CCC1CCCCC1)Nc1cc(Nc2ccc(C(=O)N=C3NCCCN3)cc2C(F)(F)F)ccc1F]
149 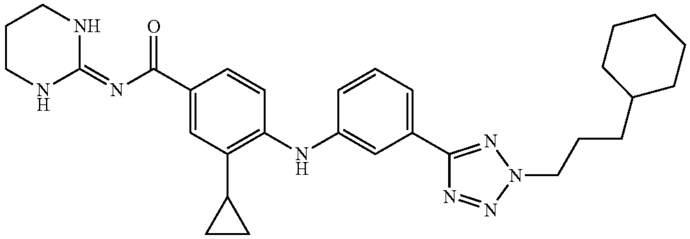 [SMILES: O=C(N=C1NCCCN1)c1ccc(Nc2cccc(-c3nnn(CCCC4CCCCC4)n3)c2)c(C2CC2)c1]

-continued
| (Ic) |
|---|
150
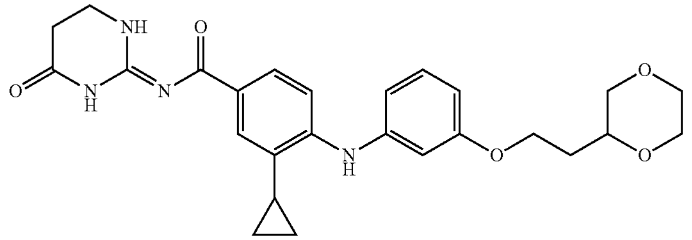 [SMILES: O=C1CCN/C(=N\C(=O)c2ccc(Nc3cccc(OCCC4COCCO4)c3)c(C3CC3)c2)N1]
151
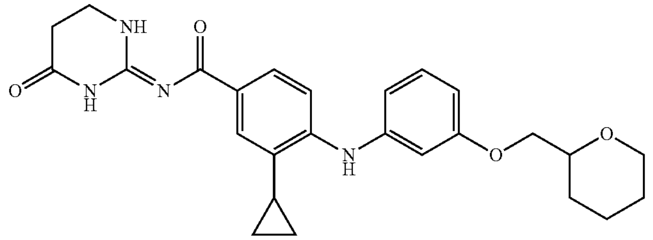 [SMILES: O=C1CCN/C(=N\C(=O)c2ccc(Nc3cccc(OCC4CCCCO4)c3)c(C3CC3)c2)N1]
152
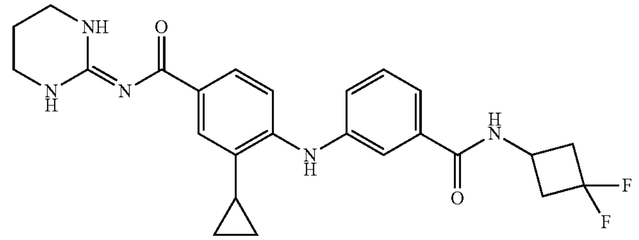 [SMILES: O=C(N=C1NCCCN1)c1ccc(Nc2cccc(C(=O)NC3CC(F)(F)C3)c2)c(C2CC2)c1]
153
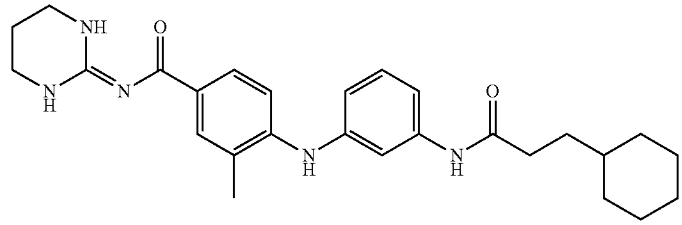 [SMILES: Cc1cc(C(=O)N=C2NCCCN2)ccc1Nc1cccc(NC(=O)CCC2CCCCC2)c1]
154
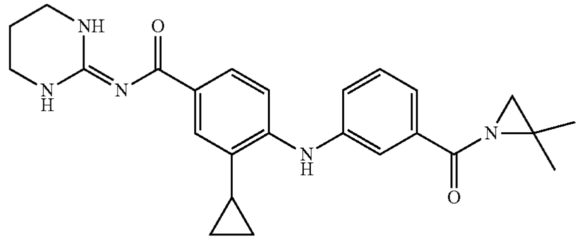 [SMILES: CC1(C)CN1C(=O)c1cccc(Nc2ccc(C(=O)N=C3NCCCN3)cc2C2CC2)c1]
155
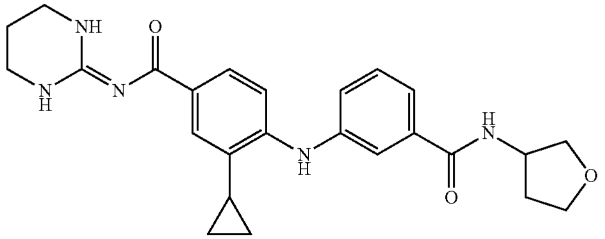 [SMILES: O=C(N=C1NCCCN1)c1ccc(Nc2cccc(C(=O)NC3CCOC3)c2)c(C2CC2)c1]

-continued
| (Ic) |
|---|
156 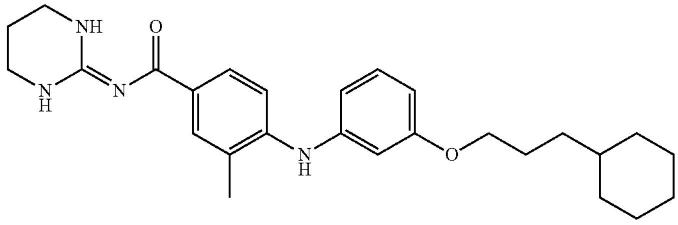 [SMILES: Cc1cc(C(=O)N=C2NCCCN2)ccc1Nc1cccc(OCCCC2CCCCC2)c1]
157 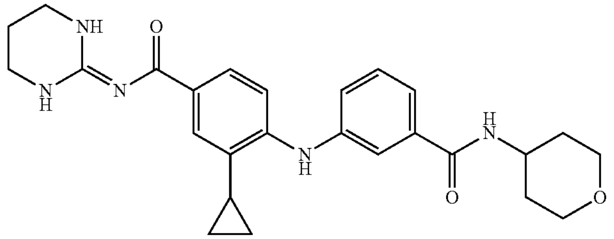 [SMILES: O=C(N=C1NCCCN1)c1ccc(Nc2cccc(C(=O)NC3CCOCC3)c2)c(C2CC2)c1]
158 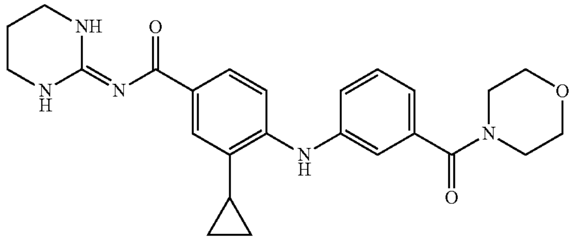 [SMILES: O=C(N=C1NCCCN1)c1ccc(Nc2cccc(C(=O)N3CCOCC3)c2)c(C2CC2)c1]
159 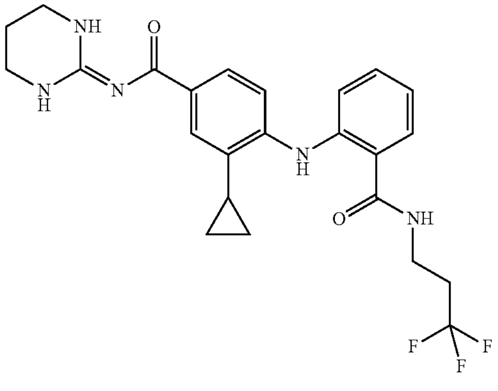 [SMILES: O=C(N=C1NCCCN1)c1ccc(Nc2ccccc2C(=O)NCCC(F)(F)F)c(C2CC2)c1]
160 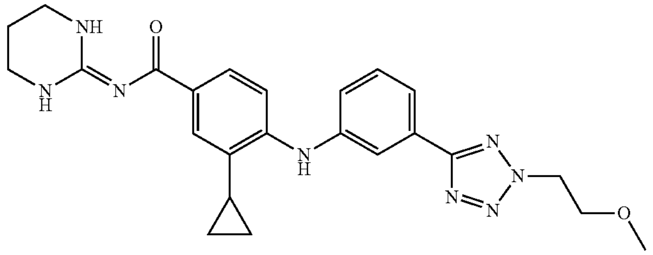 [SMILES: COCCn1nnc(-c2cccc(Nc3ccc(C(=O)N=C4NCCCN4)cc3C3CC3)c2)n1]

-continued
(Ic)
161
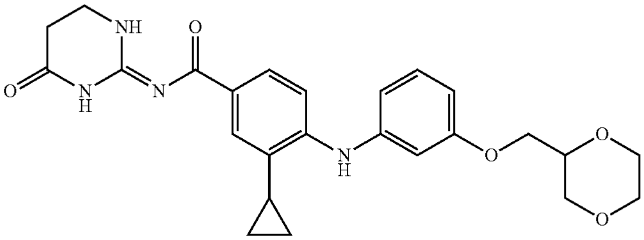 [SMILES: O=C1CCN/C(=N\C(=O)c2ccc(Nc3cccc(OCC4COCCO4)c3)c(C3CC3)c2)N1]
162
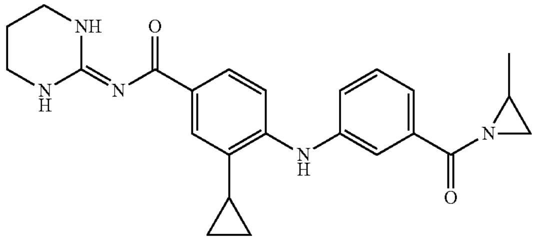 [SMILES: CC1CN1C(=O)c1cccc(Nc2ccc(C(=O)N=C3NCCCN3)cc2C2CC2)c1]
163
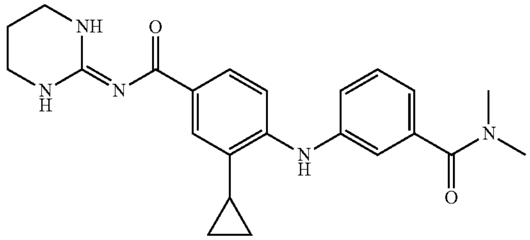 [SMILES: CN(C)C(=O)c1cccc(Nc2ccc(C(=O)N=C3NCCCN3)cc2C2CC2)c1]
164
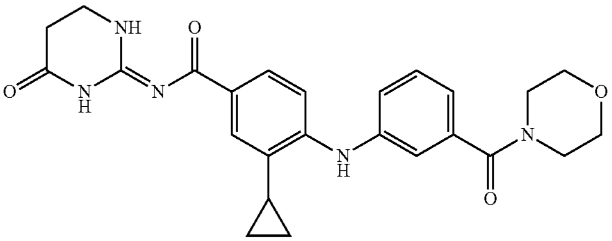 [SMILES: O=C1CCN/C(=N\C(=O)c2ccc(Nc3cccc(C(=O)N4CCOCC4)c3)c(C3CC3)c2)N1]
165
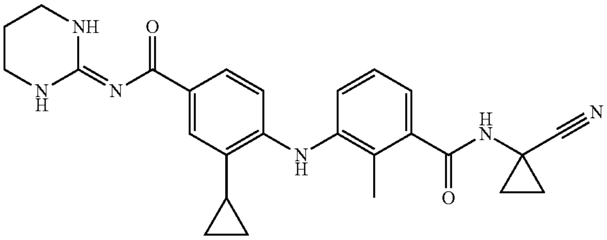 [SMILES: Cc1c(Nc2ccc(C(=O)N=C3NCCCN3)cc2C2CC2)cccc1C(=O)NC1(C#N)CC1]
166
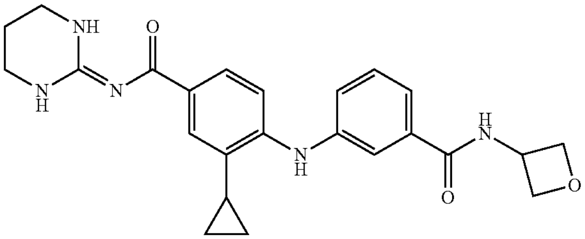 [SMILES: O=C(N=C1NCCCN1)c1ccc(Nc2cccc(C(=O)NC3COC3)c2)c(C2CC2)c1]

-continued
| (Ic) |
| --- |
167
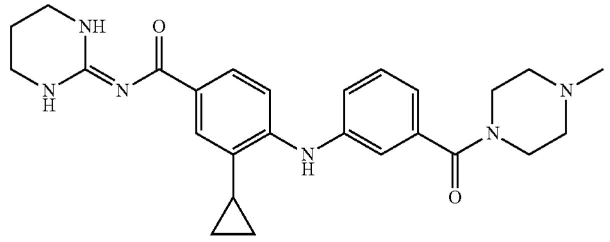 [SMILES: CN1CCN(C(=O)c2cccc(Nc3ccc(C(=O)N=C4NCCCN4)cc3C3CC3)c2)CC1]
168
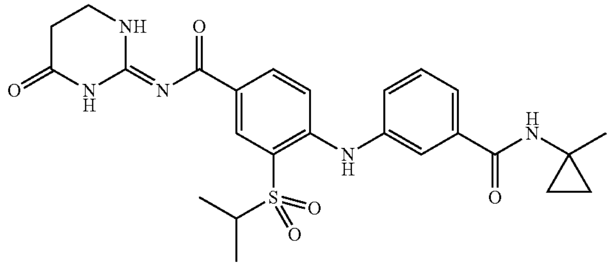 [SMILES: CC(C)S(=O)(=O)c1cc(C(=O)/N=C2\NCCC(=O)N2)ccc1Nc1cccc(C(=O)NC2(C)CC2)c1]
169
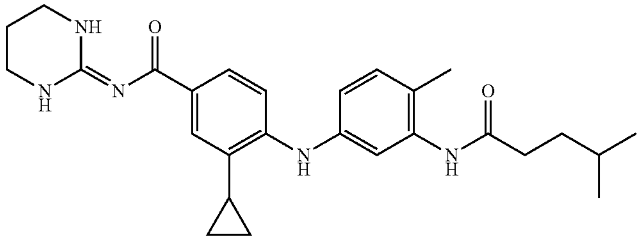 [SMILES: Cc1ccc(Nc2ccc(C(=O)N=C3NCCCN3)cc2C2CC2)cc1NC(=O)CCC(C)C]
170
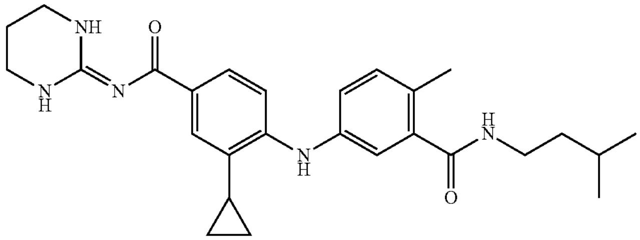 [SMILES: Cc1ccc(Nc2ccc(C(=O)N=C3NCCCN3)cc2C2CC2)cc1C(=O)NCCC(C)C]
171
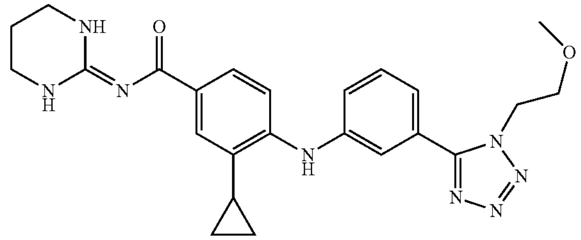 [SMILES: COCCn1nnnc1-c1cccc(Nc2ccc(C(=O)N=C3NCCCN3)cc2C2CC2)c1]
172
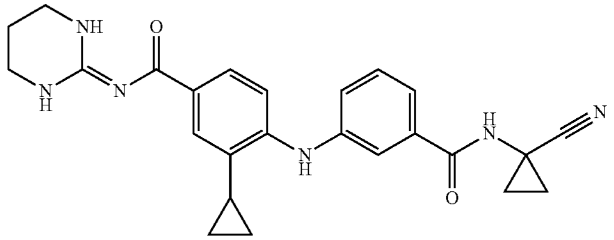 [SMILES: N#CC1(NC(=O)c2cccc(Nc3ccc(C(=O)N=C4NCCCN4)cc3C3CC3)c2)CC1]

-continued
| (Ic) |
|---|
173
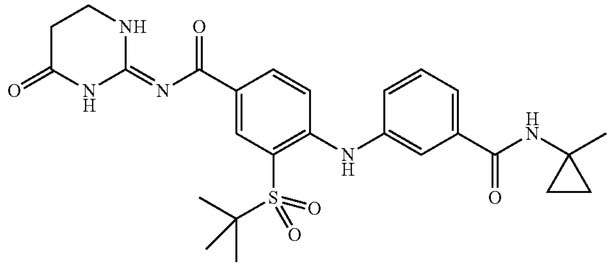 [SMILES: CC1(NC(=O)c2cccc(Nc3ccc(C(=O)/N=C4\NCCC(=O)N4)cc3S(=O)(=O)C(C)(C)C)c2)CC1]
174
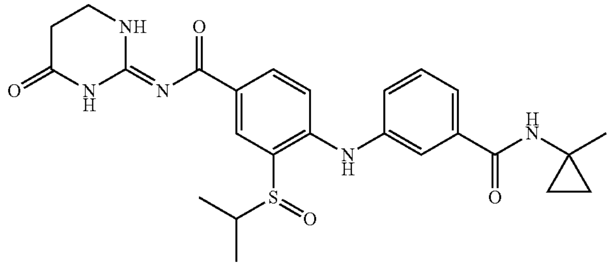 [SMILES: CC(C)S(=O)c1cc(C(=O)/N=C2\NCCC(=O)N2)ccc1Nc1cccc(C(=O)NC2(C)CC2)c1]
175
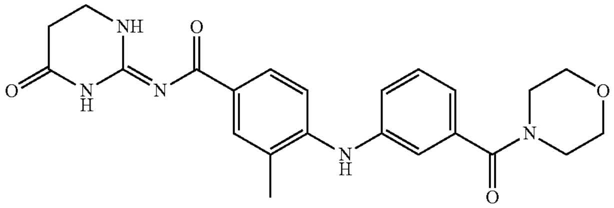 [SMILES: Cc1cc(C(=O)/N=C2\NCCC(=O)N2)ccc1Nc1cccc(C(=O)N2CCOCC2)c1]
176
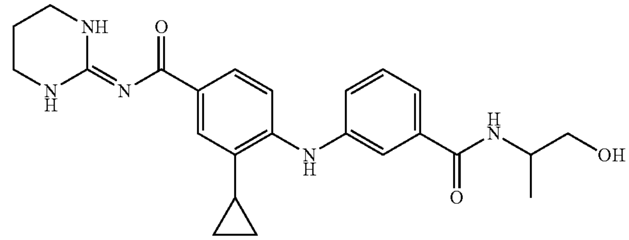 [SMILES: CC(CO)NC(=O)c1cccc(Nc2ccc(C(=O)N=C3NCCCN3)cc2C2CC2)c1]
177
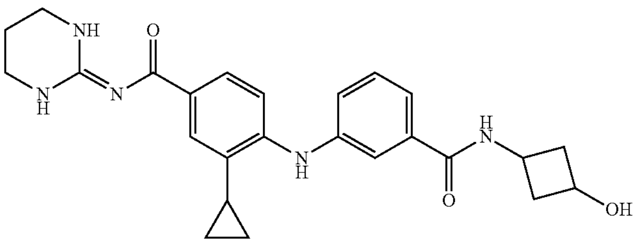 [SMILES: O=C(N=C1NCCCN1)c1ccc(Nc2cccc(C(=O)NC3CC(O)C3)c2)c(C2CC2)c1]
178
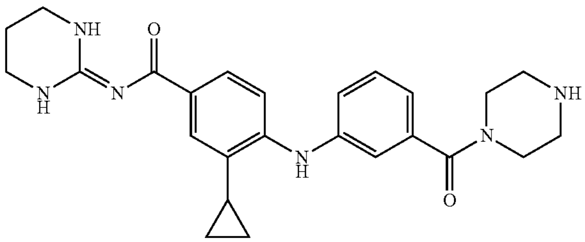 [SMILES: O=C(N=C1NCCCN1)c1ccc(Nc2cccc(C(=O)N3CCNCC3)c2)c(C2CC2)c1]

-continued (Ic)

179

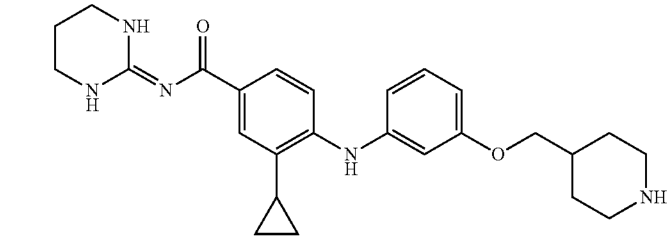 [SMILES: O=C(N=C1NCCCN1)c1ccc(Nc2cccc(OCC3CCNCC3)c2)c(C2CC2)c1]

180

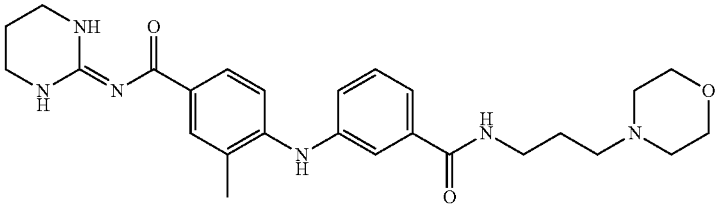 [SMILES: Cc1cc(C(=O)N=C2NCCCN2)ccc1Nc1cccc(C(=O)NCCCN2CCOCC2)c1]

and

181

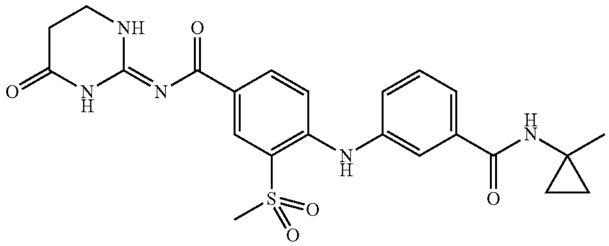 [SMILES: CC1(NC(=O)c2cccc(Nc3ccc(C(=O)/N=C4\NCCC(=O)N4)cc3S(C)(=O)=O)c2)CC1]

or a pharmaceutically acceptable salt thereof;

comprising:

coupling a compound of the formula (IIc)

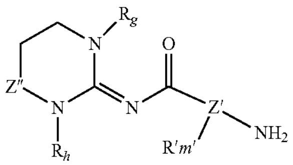

with a compound of the formula (IIIc)

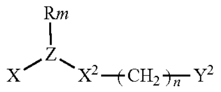

wherein, X is Cl, I, or Br, in the presence of an inorganic base, a diphosphine, and an organometallic catalyst, to obtain:

a) a compound of formula (Ic) or a pharmaceutically acceptable salt thereof according to claim 1; or b) a compound selected from 19-31 and 91-181, or a pharmaceutically acceptable salt thereof.

* * * * *